(12) United States Patent
Gish et al.

(10) Patent No.: US 10,308,713 B2
(45) Date of Patent: Jun. 4, 2019

(54) ANTI-CS1 ANTIBODIES AND ANTIBODY DRUG CONJUGATES

(71) Applicant: AbbVie Biotherapeutics Inc., Redwood City, CA (US)

(72) Inventors: Kurt C. Gish, Piedmont, CA (US); Han K. Kim, Redwood City, CA (US); Louie Naumovski, Los Altos, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 3 days.

(21) Appl. No.: 15/819,153

(22) Filed: Nov. 21, 2017

(65) Prior Publication Data

US 2018/0222979 A1 Aug. 9, 2018

Related U.S. Application Data

(62) Division of application No. 14/928,738, filed on Oct. 30, 2015, now Pat. No. 10,011,657.

(Continued)

(51) Int. Cl.
| | |
|---|---|
| *A61K 45/06* | (2006.01) |
| *C07K 16/28* | (2006.01) |
| *A61K 47/68* | (2017.01) |
| *A61K 31/454* | (2006.01) |
| *A61K 31/573* | (2006.01) |
| *A61K 31/69* | (2006.01) |
| *A61K 31/704* | (2006.01) |
| *A61K 39/395* | (2006.01) |
| *A61K 39/00* | (2006.01) |

(52) U.S. Cl.
CPC ........ *C07K 16/2806* (2013.01); *A61K 31/454* (2013.01); *A61K 31/573* (2013.01); *A61K 31/69* (2013.01); *A61K 31/704* (2013.01); *A61K 39/395* (2013.01); *A61K 45/06* (2013.01); *A61K 47/6803* (2017.08); *A61K 47/6813* (2017.08); *A61K 47/6851* (2017.08); *A61K 47/6867* (2017.08); *C07K 16/2803* (2013.01); *A61K 2039/505* (2013.01); *A61K 2300/00* (2013.01); *C07K 2317/24* (2013.01); *C07K 2317/34* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel |
| 4,444,887 A | 4/1984 | Hoffman |
| (Continued) | | |

FOREIGN PATENT DOCUMENTS

| | | |
|---|---|---|
| EP | 0239400 B1 | 8/1994 |
| EP | 0519596 B1 | 2/2005 |
| (Continued) | | |

OTHER PUBLICATIONS

Amir et al., 2003 "Self-Immolative Dendrimers," *Angew Chem Int Ed* 42:4494-4499.

(Continued)

*Primary Examiner* — Karl J Puttlitz
(74) *Attorney, Agent, or Firm* — Dechert LLP

(57) ABSTRACT

The present disclosure provides antibodies and antibody drug conjugates that bind human CS1 and their uses to treat subjects diagnosed with a plasma cell neoplasm, for example, multiple myeloma.

20 Claims, 46 Drawing Sheets

Figure 3A:
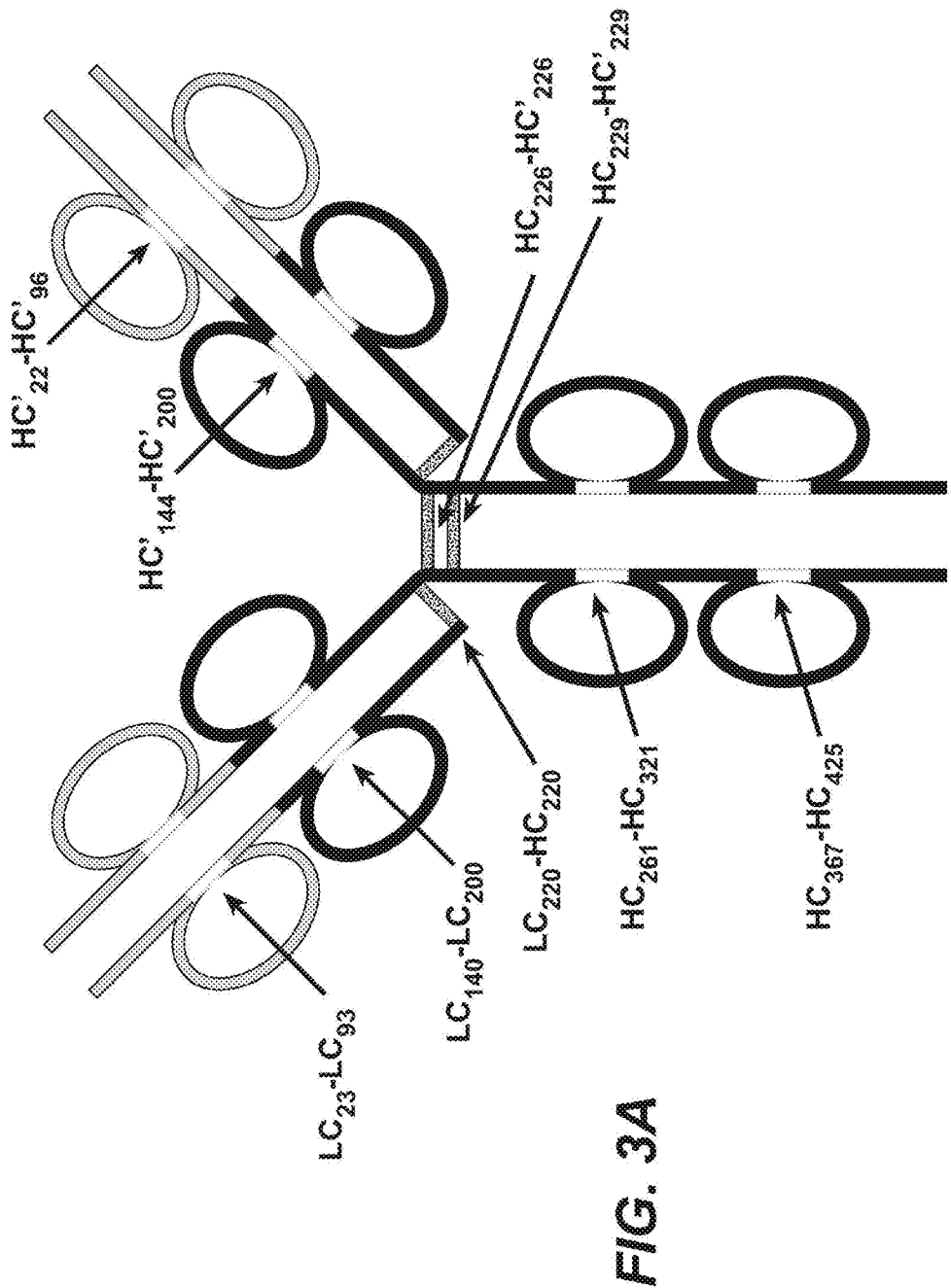

Specification includes a Sequence Listing.

Related U.S. Application Data

(60) Provisional application No. 62/073,824, filed on Oct. 31, 2014.

(56) References Cited

U.S. PATENT DOCUMENTS

| | | |
|---|---|---|
| 4,510,245 A | 4/1985 | Cousens |
| 4,634,665 A | 1/1987 | Axel |
| 4,716,111 A | 12/1987 | Osband |
| 4,816,397 A | 3/1989 | Boss |
| 4,816,567 A | 3/1989 | Cabilly |
| 4,968,615 A | 11/1990 | Koszinowski |
| 5,168,062 A | 12/1992 | Stinski |
| 5,179,017 A | 1/1993 | Axel |
| 5,225,539 A | 7/1993 | Winter |
| 5,413,923 A | 5/1995 | Kucherlapati |
| 5,530,101 A | 6/1996 | Queen |
| 5,545,806 A | 8/1996 | Lonberg |
| 5,565,332 A | 10/1996 | Hoogenboom |
| 5,569,825 A | 10/1996 | Lonberg |
| 5,585,089 A | 12/1996 | Queen |
| 5,625,126 A | 4/1997 | Lonberg |
| 5,633,425 A | 5/1997 | Lonberg |
| 5,658,570 A | 8/1997 | Newman |
| 5,661,016 A | 8/1997 | Lonberg |
| 5,681,722 A | 10/1997 | Newman |
| 5,693,761 A | 12/1997 | Queen |
| 5,693,762 A | 12/1997 | Queen |
| 5,693,780 A | 12/1997 | Newman |
| 5,807,715 A | 9/1998 | Morrison |
| 5,814,318 A | 9/1998 | Lonberg |
| 5,834,597 A | 11/1998 | Tso |
| 5,885,793 A | 3/1999 | Griffiths |
| 5,916,771 A | 6/1999 | Hori |
| 5,939,598 A | 8/1999 | Kucherlapati |
| 6,180,370 B1 | 1/2001 | Queen |
| 7,217,797 B2 | 5/2007 | Hinton |
| 7,223,837 B2 | 5/2007 | De Groot |
| 7,521,541 B2 | 4/2009 | Eigenbrot |
| 7,709,610 B2 | 5/2010 | Williams |
| 7,842,293 B2 | 11/2010 | Afar |
| 7,855,275 B2 | 12/2010 | Eigenbrot |
| 7,989,434 B2 | 8/2011 | Feng |
| 8,088,898 B2 | 1/2012 | Williams |
| 8,349,330 B2 | 1/2013 | Williams |
| 8,436,146 B2 | 5/2013 | Williams |
| 8,444,980 B2 | 5/2013 | Williams |
| 8,445,646 B2 | 5/2013 | Williams |
| 8,455,622 B2 | 6/2013 | McDonagh |
| 8,455,646 B2 | 6/2013 | Caligiuri |
| 8,461,306 B2 | 6/2013 | Williams |
| 8,535,678 B2 | 9/2013 | Law |
| 8,568,728 B2 | 10/2013 | Jeffrey |
| 8,632,772 B2 | 1/2014 | Anderson |
| 2005/0271615 A1 | 12/2005 | Shabat |
| 2006/0024296 A1 | 2/2006 | Williams |
| 2006/0116422 A1 | 6/2006 | De Groot |
| 2006/0134709 A1 | 6/2006 | Stavenhagen |
| 2007/0280931 A1 | 12/2007 | Chen |
| 2008/0025989 A1 | 1/2008 | Law |
| 2013/0280280 A1 | 10/2013 | Algate |
| 2013/0309256 A1 | 11/2013 | Lyon |

FOREIGN PATENT DOCUMENTS

| | | |
|---|---|---|
| WO | WO 1989/012624 | 12/1989 |
| WO | WO 1991/09967 | 7/1991 |
| WO | WO 1991/010741 | 7/1991 |
| WO | WO 1992/001047 | 1/1992 |
| WO | WO 1996/033735 | 10/1996 |
| WO | WO 1996/034096 | 10/1996 |
| WO | WO 1998/016654 | 4/1998 |
| WO | WO 1998/024893 | 6/1998 |
| WO | WO 1998/046645 | 10/1998 |
| WO | WO 1998/050433 | 11/1998 |
| WO | WO 2004/010957 A2 | 2/2004 |
| WO | WO 2004/100898 A2 | 11/2004 |
| WO | WO 2005/102387 A2 | 11/2005 |
| WO | WO 2005/123780 A2 | 12/2005 |
| WO | WO 2006/113909 A2 | 10/2006 |
| WO | WO 2007/089149 A2 | 8/2007 |
| WO | WO 2008/019376 A2 | 2/2008 |
| WO | WO 2008/019378 A1 | 2/2008 |
| WO | WO 2009/073445 A2 | 6/2009 |
| WO | WO 2010/068795 A2 | 6/2010 |
| WO | WO 2010/114940 A1 | 10/2010 |
| WO | WO 2010/138719 A1 | 12/2010 |
| WO | WO 2011/120053 A1 | 9/2011 |
| WO | WO 2012/163805 A1 | 12/2012 |
| WO | WO 2012/171020 A1 | 12/2012 |
| WO | WO 2013/085925 A1 | 6/2013 |
| WO | WO 2013/096901 A1 | 6/2013 |
| WO | WO 2013/130093 A1 | 9/2013 |
| WO | WO 2014/008375 A1 | 1/2014 |
| WO | WO 2014/055370 A1 | 4/2014 |
| WO | WO 2014/093379 A1 | 6/2014 |
| WO | WO 2014/093394 A1 | 6/2014 |
| WO | WO 2014/093640 A1 | 6/2014 |
| WO | WO 2014/100740 A1 | 6/2014 |

OTHER PUBLICATIONS

Axup et al., 2012 "Synthesis of site-specific entibody-drug conjugates using unnatural amino acids," *Proc Natl Acad Sci USA* 109:40:16101-16106.

Badescu et al., 2014 "Bridging Disulfides for Stable and Defined Antibody Drug Conjugates," *Bioconjug Chem* 25(6):1124-1136.

Burke et al., 2009 "Design, Synthesis, and Biological Evaluation of Antibody—Drug Conjugates Comprised of Potent Camptothecin Analogues," *Bioconjug Chem* 20(6):1242-1250.

Canfield et al., 1991 "The Binding Affinity of Human IgG for its High Affinity Fc Receptor Is Determined by Multiple Amino Acids in the $C_H2$ Domain and Is Modulated by the Hinge Region," *J Exp Med* 173:1483-1491.

Chari, 2008 "Targeted Cancer Therapy: Conferring Specificity to Cytotoxic Drugs," *Acc Chem Res* 41(1):98-107.

De Groot et al., 2003 "'Cascade-Release Dendrimers' Liberate All End Groups upon a Single Triggering Event in the Dendritic Core," *Angew Chem Int Ed* 42:4490-4494.

Doronina et al., 2003 "Development of potent monoclonal antibody auristatin conjugates for cancer therapy," *Nat Biotechnol* 21(7):778-784.

Doronina et al., 2006 "Enhanced Activity of Monomethylauristatin F through Monoclonal Antibody Delivery: Effects of Linker Technology on Efficacy and Toxicity," *Bioconjug Chem* 17(1):114-124.

Dubowchik et al., 1998 "Cathepsin B-sensitive dipeptide prodrugs. 1. A model study of structural requirements for efficient release of doxorubicin," *Bioorg Med Chem Lett* 8(23):3341-3346.

Ducry et al., 2010 "Antibody—Drug Conjugates: Linking Cytotoxic Payloads to Monoclonal Antibodies," *Bioconjug Chem* 21(1):5-13.

Durie et al., 1975 "A Clinical Staging System for Multiple Myeloma," *Cancer* 36:842-854.

Francisco et al., 2003 "cAC10-vcMMAE, an anti-CD30—monomethyl auristatin E conjugate with potent and selective antitumor activity," *Blood* 102(4):1458-1465.

Greipp et al., 2003 "Development of an International Prognostic Index (IPI) for Myeloma: Report of the International Myeloma Working Group," *Hematology J* 4(Suppl 1):P7.1 S42-S45.

Hamblett et al., 2004 "Effects of Drug Loading on the Antitumor Activity of Monoclonal Antibody Drug Conjugate," *Clin Cancer Res* 10:7063-7070.

Hollander et al., 2008 "Selection of Reaction Additives Used in the Preparation of Monomeric Antibody—Calicheamicin Conjugates," *Bioconjug Chem* 19:358-361.

Hsi et al., 2008 "CS1, a Potential New Therapeutic Antibody Target for the Treatment of Multiple Myeloma," *Clin Cancer Res* 14(9):2775-2784.

(56) References Cited

OTHER PUBLICATIONS

Huston et al., 1988 "Protein engineering of antibody binding sites: Recovery of specific activity in an anti-digoxin single-chain Fv analogue produced in *Escherichia coli*," *Proc Natl Acad Sci USA* 85:5879-5883.

Jeffrey et al., 2006 "Development and Properties of β-Glucuronide Linkers for Monoclonal Antibody-Drug Conjugates," *Bioconjug Chem* 17:831-840.

Jeffrey et al., 2007 "Minor groove binder antibody conjugates employing a water soluble β- glucuronide linker," *Bioorg Med Chem Lett* 17:2278-2280.

Jiang et al., 2005 "Synthesis and Complete Stereochemical Assignment of Psymberin/Irciniastatin A," *J Am Chem Soc* 127:11254-11255.

King et al., 2002 "Monoclonal Antibody Conjugates of Doxorubicin Prepared with Branched Peptide Linkers: Inhibition of Aggregation by Methoxytriethyleneglycol Chains," *J Med Chem* 45:4336-4343.

King et al., 2002 "Facile synthesis of maleimide bifunctional linkers," *Tetrahedron Letters* 43:1987-1990.

Kitson et al., 2013 "Antibody-Drug Conjugates (ADCs)—Biotherapeutic bullets," *Chemistry Today* 31(4):30-38.

Lonial et al., 2012 "Elotuzumab in Combination With Lenalidomide and Low-Dose Dexamethasone in Relapsed or Refractory Multiple Myeloma," *J Clin Oncol* 30(16):1953-1959.

Lonial et al., 2015 "Elotuzumab Therapy for Relapsed or Refractory Multiple Myeloma," *N Engl J Med* 373:621-631.

Lyon et al., 2014 "Self-hydrolyzing maleimides improve the stability and pharmacological properties of antibody-drug conjugates," *Nature Biotechnology* 32(10):1059-1065.

Miyakawa et al., 2004 "Establishment of a new model of human multiple myeloma using NOD/SCID/$\gamma_c^{null}$ (NOG) mice," *Biochemical and Biophysical Research Communications* 313(2):258-262.

Murray et al., 2013 "Cell-free translation of peptides and proteins: from high throughput screening to clinical production," *Current Opinion in Chemical Biology* 17:420-426.

Nolting, 2013 "Linker Technologies for Antibody-Drug Conjugates," *Methods Mol Biol* 1045:71-100.

Polson et al., 2007 "Antibody-drug conjugates targeted to CD79 for the treatment of non-Hodgkin lymphoma," *Blood* 110(2):616-623.

Pratt et al., 2007 "Immunodeficiency and immunotherapy in multiple myeloma," *British Journal of Haematology* 138:563-579.

Roguska et al., 1994 "Humanization of murine monoclonal antibodies through variable domain resurfacing," *Proc Natl Acad Sci USA* 91:969-973.

Shamis et al., 2004 "Bioactivation of Self-Immolative Dendritic Prodrugs by Catalytic Antibody 38C2," *J Am Chem Soc* 126:1726-1731.

Shields et al., 2002 "Lack of Fucose on Human IgG1 N-Linked Oligosaccharide Improves Binding to Human FcγRIII and Antibody-dependent Cellular Toxicity," *J Biol Chem* 277(30):26733-26740.

Shinkawa et al., 2003 "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J Biol Chem* 278(5):3466-3473.

Sun et al., 2002 "Syntheses of Dendritic Linkers Containing Chlorambucil Residues for the Preparation of Antibody-Multidrug Immunoconjugates," *Bioorg Med Chem Lett* 12:2213-2215.

Sun et al., 2003 "Enabling ScFvs as Multi-Drug Carriers: A Dendritic Approach," *Bioorg Med Chem Lett* 11:1761-1768.

Sutherland et al., 2013 "SGN-CD33A: a novel CD33-targeting antibody-drug conjugate using a pyrrolobenzodiazepine dimer is active in models of drug-resistant AML," *Blood* 122(8): 1455-1463.

Tai et al., 2008 "Anti-CS1 humanized monoclonal antibody HuLuc63 inhibits myeloma cell adhesion and induces antibody-dependent cellular cytotoxocity in the bone marrow milieu," *Blood* 112(4) : 1329-1337.

Toki et al., 2002 "Protease-Mediated Fragmentation of p-Amidobenzyl Ethers: A New Strategy for the Activation of Anticancer Prodrugs," *J Org Chem* 67:1866-1872.

Urlaub et al., 1980 "Isolation of Chinese hamster cell mutants deficient in dihydrofolate reductase activity," *Proc Natl Acad Sci USA* 77(7): 4216-4220.

Van Rhee et al., 2009 "Combinatorial efficacy of anti-CS1 monoclonal antibody elotuzumab (HuLuc63) and bortezomib against multiple myeloma," *Mol Cancer Ther* 8(9):2616-2624.

Wahl et al., 1983 "Improved Radioimaging and Tumor Localization with Monoclonal F(ab)$_2$," *J Nucl Med* 24:314-325.

Walker et al., 2002 "Synthesis of an Immunoconjugate of Camptothecin," *Bioorg Med Chem Lett* 12:217-219.

Walker et al., 2004 "Monoclonal antibody mediated intracellular targeting of tallysomycin $S_{10b}$," *Bioorg Med Chem Lett* 14:4323-4327.

Woo et al., 2013 "PDL241, a novel humanized monoclonal antibody, reveals CD319 as a therapeutic target for rheumatoid arthritis," *Arthritis Research & Therapy* 15:R207.

Yazaki et al., 2004 "Humanization of the anti-CEA T84.66 antibody based on crystal structure data," *Protein Engineering Design Selection* 17(5):481-489.

Zhao et al., 2011 "Synthesis and Evaluation of Hydrophilic Linkers for Antibody-Maytansinoid Conjugates," *J Med Chem* 54:3606-3623.

Zonder et al., 2012 "A phase 1, multicenter, open-label, dose escalation study of elotuzumab in patients with multiple myeloma," *Blood* 120(3):552-559.

Elkins et al., 2012 "FcRL5 as a Target of Antibody-Drug Conjugates for the Treatment of Multiple Myeloma," *Mol Cancer Ther* 11(10):2222-2232 (12 pages).

Goldmacher et al., 2011 "Antibody-drug conjugates: using monoclonal antibodies for delivery of cytotoxic payloads to cancer cells," *Ther Deliv* 2(3):397-416.

Sutherland et al., 2006 "Lysosomal Trafficking and Cysteine Protease Metabolism Confer Target-specific Cytotoxicity by Peptide-linked Anti-CD30-Auristatin Conjugates," *J Biol Chem* 281(15):10540-10547.

Tai et al., 2014 "Novel anti-B -cell maturation antigen antibody-drug conjugate (GSK2857916) selectively induces killing of multiple myeloma," *Blood* 123(20):3128-3138.

Teicher et al., 2011 "Antibody Conjugate Therapeutics: Challenges and Potential," *Clin Cancer Res* 17(20):6389-6397.

Anonymous: "Anti-SLAMF7 antibody ab172723," URL: http://www.abcam.com/SLAMF7-antibody-ab172723.pdf, retrieved on Feb. 5, 2016 (3 pages).

Anonymous: "Competitive inhibition," Wikipedia, the free encyclopedia, URL:http://en.wikipedia.org/wiki/Compeitive_inhibition, retrieved on Oct. 3, 2011 (5 pages).

huCS1 cDNA and Encoded huCS1 Polypeptide

```
atg gct ggt tcc cca aca tgc acc ctc atc tat atc ctt tgg cag ctc aca ggg tca
 M   A   G   S   P   T   C   T   L   I   Y   I   L   W   Q   L   T   G   S gca gcc tct gga ccc gtg aaa gag ctg gag gtc ggt tcc gtt ggc gcc gtg act ttc ccc
 A   A   S   G   P   V   K   E   L   E   V   G   S   V   G   A   V   T   F   P ctg aag tcc aaa gta aag caa gtt gac tct att gtc tgg acc ttc aac aca acc cct ctt
 L   K   S   K   V   K   Q   V   D   S   I   V   W   T   F   N   T   T   P   L gtc acc ata cag cca gaa ggg act ata gtc aag ctc agc aaa ctc tca cag ccc agt cag
 V   T   I   Q   P   E   G   T   I   V   K   L   S   K   L   S   Q   P   S   Q gta gac ttc cca gat gga ggc tac tcc ctg tac agc tgg tac aag gtc acc atg gtt ctg
 V   D   F   P   D   G   G   Y   S   L   Y   S   W   Y   K   V   T   M   G ggg atc tac tat gtg ggg ata tac tac gag cac cac ctg tca aag cct aaa gtc tgc atg
 G   I   Y   Y   V   G   I   Y   Y   E   H   H   L   S   K   P   K   V   C   M gtg ctg cat gtc tac gag tgt gtg ggg ata tac tac gag cac cac ctg tca aag cct aaa
 V   L   H   V   Y   E   C   V aag aat ggc acc tgg aag gcc ctg ggg caa gca gcc aat gag tgc atg gaa cat ggg gaa
 K   N   G   T   W   K   A   L   G   Q   A   A   N   E   C   M   E   H   G   E att tat acc tcc tat gtt gga ata tac tac ttc cat aat ggg tcc atc ctc
 I   Y   T   S   Y   V   G   E   S   H   N   G   S   I   L ccc atc tcc tgg aga tgg gga gaa agt gat atg acc ttc atc tgc gtt gcc agg aac cct
 P   I   S   W   R   W   G   E   S   D   M   T   F   I   C   V   A   R   N   P
```

FIG. 1A

```
gtc agc aga aac ttc tca agc ccc atc ctt gcc agg aag ctc tgt gaa ggt gct gct gat
 V   S   R   N   F   S   S   P   I   L   A   R   K   L   C   E   G   A   A   D gac cca gat tcc tcc atg gtc ctc atg ctc tgt ctc ttg gtg ctc ccc ctc ctg agt ctc
 D   P   D   S   S   M   V   L   M   L   C   L   L   V   L   P   L   L   S   L ttt gta ctg ggg cta ttt ctt tgg ttt ctg aaa gag aga caa gaa gag tac att gaa
 F   V   L   G   L   F   L   W   F   L   K   E   R   Q   E   E   Y   I   E gag aag aga gta gac aca atc cct cac act aat aga aag atg gaa aat ccc cac ctg ctc
 E   K   R   V   D   T   I   P   H   T   N   R   K   M   E   N   P   H   L   L aac acg gtt tac tcc act gtg gaa ata ccg cta ttt gcc tat gag aat gtt atc tag
 N   T   V   Y   S   T   V   E   I   P   L   F   A   Y   E   N   V   I   * acg atg cca gac aca cca agg cta ttt gcc tat gag aat gtt atc tag
 T   M   P   D   T   P   R   L   F   A   Y   E   N   V   I Signal peptide is dashed underlined
Ig Domain #1 is underlined
Ig Domain #2 is double underlined
Transmembrane domain is highlighted
```

FIG. 1B cmCS1 cDNA and Encoded cmCS1 Polypeptide

```
atg gct ggt tcc cca aca tgc ttc acc ttc atc tat atc ctt tgg cag ctc aca ggg tca
 M   A   G   S   P   T   C   F   T   F   I   Y   I   L   W   Q   L   T   G   S aca gcc tct gga tcc gtg aaa gag ctg gtc ggt tcc att ggt ggg gct gtg act ttc ccc
 T   A   S   G   S   V   K   E   L   V   G   S   I   G   G   A   V   T   F   P ctg aag tct gaa gta aag caa gtt gac tct att gtc tgg acc ttc aac aca acc act ctt
 L   K   S   E   V   K   Q   V   D   S   I   V   W   T   F   N   T   T   T   L gtc acc ata cag cca gaa ggg ggc cct atg ata gtg acc caa aat cgt aat aag gag aga
 V   T   I   Q   P   E   G   G   P   M   I   V   T   Q   N   R   N   K   E   R gta cac ttc cca gat gga ggc tat tcc ctg aag ctc agc aaa ctg aag aag aat gac tca
 V   H   F   P   D   G   G   Y   S   L   K   L   S   K   L   K   K   N   D   S ggg atc tac aat gtg gag ata tac agc tca tcc ctc cag gat ccc ttc acc cgg aag tat
 G   I   Y   N   V   E   I   Y   S   S   S   L   Q   D   P   F   T   R   K   Y gtc ctg cgt gtc tac gag cac cac ctg aca tcc aaa cct aaa gtc atg gaa cat ggg cta cag agt aat
 V   L   R   V   Y   E   H   H   L   T   S   K   P   K   V   M   E   H   G   L   Q   S   N aag aat ggc acc tgt gtg acc aat ctg aca ggg caa gca gtc aat gag tcc cat aat ggg tcc atc cta
 K   N   G   T   C   V   T   N   L   T   G   Q   A   V   N   E   S   H   N   G   S   I   L att tat acc tgg aga gga gaa agt gat atg aca ttc atc tgc act gtc agg aac cct
 I   Y   T   W   R   G   E   S   D   M   T   F   I   C   T   V   R   N   P ccc atc tcc tgg aga gga gaa agt gat atg acc ttc atc tgc act gtc agg aac cct
 P   I   S   W   R   G   E   S   D   M   T   F   I   C   T   V   R   N   P
```

FIG. 1C

```
gtc agc agc aac tcc tca agc ccc atc ctt gct gcc agg aag ctc tgt gaa ggt gct gct gat
 V   S   S   N   S   S   S   P   I   L   A   A   R   K   L   C   E   G   A   A   D gac tca gat tcc tcc atg gtc ctc ctg tgt ctc ttg gtg ccc ctc ctg agt ctc
 D   S   D   S   S   M   V   L   L   C   L   L   V   P   L   L   S   L ttt gta ctg ggg cta ttt ctt tgg ttt ctg aag aga aag ctc tgt caa gaa tcc att gaa
 F   V   L   G   L   F   L   W   F   L   K   R   K   L   C   Q   E   S   I   E ggg aag aga gcg gac att tgt cgg gaa act cct aac ata tgc ccc tat tct gga gag
 G   K   R   A   D   I   C   R   E   T   P   N   I   C   P   Y   S   G   E aac aca gag tat gac aca atc cct tac act aga aat aga act atc cca atg gaa gat gca gca
 N   T   E   Y   D   T   I   P   Y   T   R   N   R   T   I   P   M   E   D   A   A aat aca ctt tat tcc act gtg gaa ata cca aaa att gaa aat ccc cac tca ctg ctc
 N   T   L   Y   S   T   V   E   I   P   K   K   I   E   N   P   H   S   L   L acg atg cca gac aca cca agg cta ttt gcc cta ttt gag aat gtt atc tag
 T   M   P   D   T   P   R   L   F   A   L   F   E   N   V   I Signal peptide is dashed underlined
Ig Domain #1 is underlined
Ig Domain #2 is double underlined
Transmembrane domain is highlighted
```

FIG. 1D

Exemplary Anti-huCS1 Antibody V_H Chains

```
                     1           2           3           4
               1234567890  1234567890  1234567890  1234567890
Mu34C3V_H:     EVKLVESEGG  LVQPGSSMKL  SCTASGFTFS  DYYMAWVRQV
Hu34C3V_H.1:   EVQLVESGGG  LVQPGGSLRL  SCAASGFTFS  DYYMAWVRQA
Hu34C3V_H.1b:  EVQLVESGGG  LVQPGGSLRL  SCAASGFTFS  DYYMAWVRQA
Hu34C3V_HS55E: EVQLVESGGG  LVQPGGSLRL  SCAASGFTFS  DYYMAWVRQA
Mu31D2V_H:     EVKLVESEGG  LVQPGSSMKL  SCTASGFTFS  DYYMAWVRQV
Hu31D2V_H.1:   EVQLVESGGG  LVQPGGSLRL  SCAASGFTFS  DYYMAWVRQA
Hu31D2V_H.1a:  EVQLVESGGG  LVQPGGSLRL  SCAASGFTFS  DYYMAWVRQA
Mu27A12V_H:    EVKLVESEGG  LVQPGSSMKL  SCTASGFTFS  DYYMAWVRQV
Hu27A12V_H.1:  EVQLVESGGG  LVQPGGSLRL  SCAASGFTFS  DYYMAWVRQA
Hu27A12V_H.1b: EVQLVESGGG  LVQPGGSLRL  SCAASGFTFS  DYYMAWVRQA
Mu12D10V_H:    EVKLVESEGG  LVQPGSSMKL  SCTASGFTFS  DYFMAWVRQV
Mu14C11V_H:    EVKLVESEGG  LVQPGSSMKL  SCTASGFTFS  DYYMAWVRQV
Mu27H1V_H:     QVQLQQSGPE  LVKPGTSVNI  SCKASGYTFT  DHYINWVKQR 5           6           7           8
               1234567890  12a34567890  1234567890  1234567890
Mu34C3V_H:     PEKGLEWVAS  INYDGSSTYYL  DSLKSRFIIS  RDNAKNILFL
Hu34C3V_H.1:   PGKGLEWVAS  INYDGSSTYYL  DSLKSRFTIS  RDNAKNSLYL
Hu34C3V_H.1b:  PGKGLEWVAS  INYDGSSTYYV  DSVKGRFTIS  RDNAKNSLYL
Hu34C3V_HS55E: PGKGLEWVAS  INYDGESTYYV  DSVKGRFTIS  RDNAKNSLYL
MuD12V_H:      PEKGLEWVAD  INYDGGSTYYL  DSLKSRFIIS  RDNAKNILCL
Hu31D2V_H.1:   PGKGLEWVAD  INYDGGSTYYL  DSLKSRFTIS  RDNAKNSLYL
Hu31D2V_H.1a:  PGKGLEWVAD  INYDGGSTYYV  DSVKGRFTIS  RDNAKNSLYL
Mu27A12V_H:    PEKGLEWVAE  INYDGSSTYYL  DSLKSRFIIS  RDNAKNILYL
Hu27A12V_H.1:  PGKGLEWVAE  INYDGSSTYYL  DSLKSRFTIS  RDNAKNSLYL
Hu27A12V_H.1b: PGKGLEWVAE  INYDGSSTYYV  DSVKGRFTIS  RDNAKNSLYL
Mu12D10V_H:    PEKGLEWVAS  INYDGNSTYFL  DSLKSRFIIS  RDNAKNILYL
Mu14C11V_H:    PEKGLEWVAS  INYDGSSTYYL  DSLKSRFIIS  RDNAKNILYL
Mu27H1V_H:     PGQGLEWIGW  IFPGTGITYYN  ENFKGKATLT  VDKSSSTAYM
```

FIG. 2A

```
                                       1         1
                             9         0         1
                  12abc34567890 1234567890 1234567890 123
Mu34C3V_H:        QMNSLKSEDTATY YCARDRGYYF DYWGQGTTLT VSS
Hu34C3V_H.1:      QMNSLRAEDTAVY YCARDRGYYF DYWGQGTTVT VSS
Hu34C3V_H.1b:     QMNSLRAEDTAVY YCARDRGYYF DYWGQGTTVT VSS
Hu34C3V_HS55E:    QMNSLRAEDTAVY YCARDRGYYF DYWGQGTTVT VSS
Mu31D2V_H:        QMSSLKSEDTATY YCARDRGYYF DYWGQGTTLT VSS
Hu31D2V_H.1:      QMNSLRAEDTAVY YCARDRGYYF DYWGQGTLVT VSS
Hu31D2V_H.1a:     QMNSLRAEDTAVY YCARDRGYYF DYWGQGTLVT VSS
Mu27A12V_H:       QMSNLKSEDTATY YCARDRGFYF DYWGQGTTLT VSS
Hu27A12V_H.1:     QMNSLRAEDTAVY YCARDRGFYF DYWGQGTTVT VSS
Hu27A12V_H.1b:    QMNSLRAEDTAVY YCARDRGFYF DYWGQGTTVT VSS
Mu12D10V_H:       QMSSLKSEDTATY YCARDRGFYF DYWGQGTTLT VSS
Mu14C11V_H:       QMSGLKSEDTATY SCARDRGFYF DYWGQGTTLT VSS
Mu27H1V_H:        LLSSLTSEDSAVY FCARRGYGSF DYWGQGTTLT VSS
```

Bold underline = CDRs
Double underline = Hu germline changes
Highlighted = affinity-increasing mutations

FIG. 2B

Exemplary Anti-huCS1 Antibody V$_L$ Chains

```
                        1          2            3              4
                  1234567890 1234567890 1234567abcdef890 1234567890
Mu34C3V_L:        DVVMTQTPLS LPVSLGDQAS ISCRSSQSLVHS-NGN TYLHWYLQKP
Hu34C3V_L.1:      DIVMTQTPLS LSVTPGQPAS ISCRSSQSLVHS-NGN TYLHWYLQKP
Hu34C3V_L.1a:     DVVMTQTPLS LSVTPGQPAS ISCRSSQSLVHS-NGN TYLHWYLQKP
Hu34C3V_L.1b:     DVVMTQTPLS LSVTPGQPAS ISCRSSQSLVHS-NGN TYLHWYLQKP
Hu34C3V_LN30L:    DVVMTQTPLS LSVTPGQPAS ISCRSSQSLVHS-NGL TYLHWYLQKP
Mu31D2V_L:        DVVMTQTPLS LPVSLGDQAS ISCRSSQSLVHS-NGN TYLHWYLQKP
Hu31D2V_L.1:      DIVMTQSPLS LPVTPGEPAS ISCRSSQSLVHS-NGN TYLHWYLQKP
Hu31D2V_L.1a:     DVVMTQSPLS LPVTPGEPAS ISCRSSQSLVHS-NGN TYLHWYLQKP
Hu31D2V_L.1b:     DVVMTQSPLS LPVTPGEPAS ISCRSSQSLVHS-NGN TYLHWYLQKP
Mu27A12V_L:       DVVMTQTPLS LPVSLGDQAS ISCRSSQSLVHN-NGN TYLHWYLQKP
Hu27A12V_L.1:     DIVMTQTPLS LSVTPGQPAS ISCRSSQSLVHN-NGN TYLHWYLQKP
Hu27A12V_L.1a:    DVVMTQTPLS LSVTPGQPAS ISCRSSQSLVHN-NGN TYLHWYLQKP
Hu27A12V_L.1b:    DVVMTQTPLS LSVTPGQPAS ISCRSSQSLVHN-NGN TYLHWYLQKP
Mu12D10V_L:       DVVMTQTPLS LPVSLGDQAS ISCRFSQSLVHR-NGN TYLHWYLQKP
Mu14C11V_L:       DVVMTQTPLS LPVSLGDQAS ISCRSSQSLVHR-NGN TYLHWYLQKP
Mu27H1V_L:        DIVMTQSPSS LAMSVGQKVT MSCKSSQSLLNSSNQK NYLAWYLQKP 5          6          7          8
                  1234567890 1234567890 1234567890 1234567890
Mu34C3V_L:        GQSPKLLIYK VSNRFSGVPD RFSGSGSGTD FTLKISRVEA
Hu34C3V_L.1:      GQSPQLLIYK VSNRFSGVPD RFSGSGSGTD FTLKISRVEA
Hu34C3V_L.1a:     GQSPQLLIYK VSNRFSGVPD RFSGSGSGTD FTLKISRVEA
Hu34C3V_L.1b:     GQSPQLLIYK VSNRFSGVPD RFSGSGSGTD FTLKISRVEA
Hu34C3V_LN30L:    GQSPQLLIYK VSNRFSGVPD RFSGSGSGTD FTLKISRVEA
Mu31D2V_L:        GQSPKLLIYK VSNRFSGVPD RFSGSGSGTD FTLKISRVEA
Hu31D2V_L.1:      GQSPQLLIYK VSNRFSGVPD RFSGSGSGTD FTLKISRVEA
Hu31D2V_L.1a:     GQSPQLLIYK VSNRFSGVPD RFSGSGSGTD FTLKISRVEA
Hu31D2V_L.1b:     GQSPQLLIYK VSNRFSGVPD RFSGSGSGTD FTLKISRVEA
Mu27A12V_L:       GQSPKLLIYK VSNRFSGVPD RFSGSGSGTD FTLKISRVEA
Hu27A12V_L.1:     GQSPQLLIYK VSNRFSGVPD RFSGSGSGTD FTLKISRVEA
Hu27A12V_L.1a:    GQSPQLLIYK VSNRFSGVPD RFSGSGSGTD FTLKISRVEA
Hu27A12V_L.1b:    GQSPQLLIYK VSNRFSGVPD RFSGSGSGTD FTLKISRVEA
Mu12D10V_L:       GQSPKLLIYK VSNRFSGVPD RFSGSGSGTD FTLKISRVEA
Mu14C11V_L:       GQSPKLLIYK VSNRFSGVPD RFSGSGSGTD FTLKISRVEA
Mu27H1V_L:        GQSLKLMVYF AYTRESGVPD RFIGSGSGTD FTLTISSVQA
```

FIG. 2C

```
                                        1
                              9         0
                     1234567890 12345a67890 1234567
Mu34C3V_L:           EDLGVYFCSQ STHVPPFTFGG GTKLEIK
Hu34C3V_L.1:         EDVGVYYCSQ STHVPPFTFGG GTKVEIK
Hu34C3V_L.1a:        EDVGVYFCSQ STHVPPFTFGG GTKVEIK
Hu34C3V_L.1b:        EDVGVYYCSQ STHVPPFTFGG GTKVEIK
Hu34C3V_LN30L:       EDVGVYFCSQ STHVPPFTFGG GTKVEIK
Mu31D2V_L:           EDLGVYFCSQ STHVPPFTFGG GTKLEIK
Hu31D2V_L.1:         EDVGVYYCSQ STHVPPFTFGG GTKVEIK
Hu31D2V_L.1a:        EDVGVYFCSQ STHVPPFTFGG GTKVEIK
Hu31D2V_L.1b:        EDVGVYYCSQ STHVPPFTFGG GTKVEIK
Mu27A12V_L:          EDLGVYFCSQ STHVPPYTFGG GTKLEIK
Hu27A12V_L.1:        EDVGVYYCSQ STHVPPYTFGG GTKVEIK
Hu27A12V_L.1a:       EDVGVYFCSQ STHVPPYTFGG GTKVEIK
Hu27A12V_L.1b:       EDVGVYYCSQ STHVPPYTFGG GTKVEIK
Mu12D10V_L:          EDLGVYFCSQ STHVRPYTFGG GTKLEIR
Mu14C11V_L:          EDLGVYFCSQ STHVPPYTFGG GTKLEIK
Mu27H1V_L:           EDPADYFCQQ HYSSP-YTFGG GTKLEIK
```

Bold underline = CDRs
Highlighted = affinity-increasing mutations
*Bold, italic, dashed underline* = Mu FR back-mutation

FIG. 2D

Hu34C3 Light Chain

```
  1  Asp-Val-Val-Met-Thr-Gln-Thr-Pro-Leu-Ser-Leu-Ser-Val-Thr-Pro-Gly-Gln-Pro-Ala-Ser-
 21  Ile-Ser-Cys-Arg-Ser-Ser-Gln-Ser-Leu-Val-His-Ser-Asn-Gly-Asn-Thr-Tyr-Leu-His-Trp-
 41  Tyr-Leu-Gln-Lys-Pro-Gly-Gln-Ser-Pro-Gln-Leu-Leu-Ile-Tyr-Lys-Val-Ser-Asn-Arg-Phe-
 61  Ser-Gly-Val-Pro-Asp-Arg-Phe-Ser-Gly-Ser-Gly-Ser-Gly-Thr-Asp-Phe-Thr-Leu-Lys-Ile-
 81  Ser-Arg-Val-Glu-Ala-Glu-Asp-Val-Gly-Val-Tyr-Phe-Cys-Ser-Gln-Ser-Thr-His-Val-Pro-
101  Pro-Phe-Thr-Phe-Gly-Gly-Gly-Thr-Lys-Val-Glu-Ile-Lys-Arg-Thr-Val-Ala-Ala-Pro-Ser-
121  Val-Phe-Ile-Phe-Pro-Pro-Ser-Asp-Glu-Gln-Leu-Lys-Ser-Gly-Thr-Ala-Ser-Val-Val-Cys-
141  Leu-Leu-Asn-Asn-Phe-Tyr-Pro-Arg-Glu-Ala-Lys-Val-Gln-Trp-Lys-Val-Asp-Asn-Ala-Leu-
161  Gln-Ser-Gly-Asn-Ser-Gln-Glu-Ser-Val-Thr-Glu-Gln-Asp-Ser-Lys-Asp-Ser-Thr-Tyr-Ser-
181  Leu-Ser-Ser-Thr-Leu-Thr-Leu-Ser-Lys-Ala-Asp-Tyr-Glu-Lys-His-Lys-Val-Tyr-Ala-Cys-
201  Glu-Val-Thr-His-Gln-Gly-Leu-Ser-Ser-Pro-Val-Thr-Lys-Ser-Phe-Asn-Arg-Gly-Glu-Cys-
```

↔ Intrachain disulfide linkages

☐ Cysteine that forms interchain disulfides, potential conjugation sites after reduction

*FIG. 3B*

Hu34C3 Heavy Chain

```
  1  Glu-Val-Gln-Leu-Val-Glu-Ser-Gly-Gly-Gly-Leu-Val-Gln-Pro-Gly-Gly-Ser-Leu-Arg-Leu-
 21  Ser-Cys-Ala-Ala-Ser-Gly-Phe-Thr-Phe-Ser-Asp-Tyr-Tyr-Met-Ala-Trp-Val-Arg-Gln-Ala-
 41  Pro-Gly-Lys-Gly-Leu-Glu-Trp-Val-Ala-Ser-Ile-Asn-Tyr-Asp-Gly-Ser-Ser-Thr-Tyr-Tyr-
 61  Val-Asp-Ser-Val-Lys-Gly-Arg-Phe-Thr-Ile-Ser-Arg-Asn-Ala-Lys-Asn-Ser-Leu-Tyr-
 81  Leu-Gln-Met-Asn-Ser-Leu-Arg-Ala-Glu-Asp-Thr-Ala-Val-Tyr-Tyr-Cys-Ala-Arg-Asp-Arg-
101  Gly-Tyr-Tyr-Phe-Asp-Tyr-Trp-Gly-Gln-Gly-Thr-Thr-Val-Thr-Val-Ser-Ser-Ala-Ser-Thr-
121  Lys-Gly-Pro-Ser-Val-Phe-Pro-Leu-Ala-Pro-Ser-Ser-Lys-Ser-Thr-Ser-Gly-Gly-Thr-Ala-
141  Ala-Leu-Gly-Cys-Leu-Val-Lys-Asp-Tyr-Phe-Pro-Glu-Pro-Val-Thr-Val-Ser-Trp-Asn-Ser-
161  Gly-Ala-Leu-Thr-Ser-Gly-Val-His-Thr-Phe-Pro-Ala-Val-Leu-Gln-Ser-Ser-Gly-Leu-Tyr-
181  Ser-Leu-Ser-Ser-Val-Val-Thr-Val-Pro-Ser-Ser-Ser-Leu-Gly-Thr-Gln-Thr-Tyr-Ile-Cys-
201  Asn-Val-Asn-His-Lys-Pro-Ser-Asn-Thr-Lys-Val-Asp-Lys-Lys-Val-Glu-Pro-Lys-Ser-Cys-
221  Asp-Lys-Thr-His-Thr-Cys-Pro-Pro-Cys-Pro-Ala-Pro-Glu-Leu-Leu-Gly-Gly-Pro-Ser-Val-
241  Phe-Leu-Phe-Pro-Pro-Lys-Pro-Lys-Asp-Thr-Leu-Met-Ile-Ser-Arg-Thr-Pro-Glu-Val-Thr-
261  Cys-Val-Val-Val-Asp-Val-Ser-His-Glu-Asp-Pro-Glu-Val-Lys-Phe-Asn-Trp-Tyr-Val-Asp-
281  Gly-Val-Glu-Val-His-Asn-Ala-Lys-Thr-Lys-Pro-Arg-Glu-Glu-Gln-Tyr-Asn-Ser-Thr-Tyr-
301  Arg-Val-Val-Ser-Val-Leu-Thr-Val-Leu-His-Gln-Asp-Trp-Leu-Asn-Gly-Lys-Glu-Tyr-Lys-
321  Cys-Lys-Val-Ser-Asn-Lys-Ala-Leu-Pro-Ala-Pro-Ile-Glu-Lys-Thr-Ile-Ser-Lys-Ala-Lys-
341  Gly-Gln-Pro-Arg-Glu-Pro-Gln-Val-Tyr-Thr-Leu-Pro-Pro-Ser-Arg-Asp-Glu-Leu-Thr-Lys-
361  Asn-Gln-Val-Ser-Leu-Thr-Cys-Leu-Val-Lys-Gly-Phe-Tyr-Pro-Ser-Asp-Ile-Ala-Val-Glu-
381  Trp-Glu-Ser-Asn-Gly-Gln-Pro-Glu-Asn-Asn-Tyr-Lys-Thr-Thr-Pro-Pro-Val-Leu-Asp-Ser-
401  Asp-Gly-Ser-Phe-Phe-Leu-Tyr-Ser-Lys-Leu-Thr-Val-Asp-Lys-Ser-Arg-Trp-Gln-Gln-Gly-
421  Asn-Val-Phe-Ser-Cys-Ser-Val-Met-His-Glu-Ala-Leu-His-Asn-His-Tyr-Thr-Gln-Lys-Ser-
441  Leu-Ser-Leu-Ser-Pro-Gly-Lys-
```

↕ intrachain disulfide linkages

☐ Cysteines that form interchain disulfides, potential conjugation sites after reduction ⋯ N-linked glycosylation site

FIG. 3C

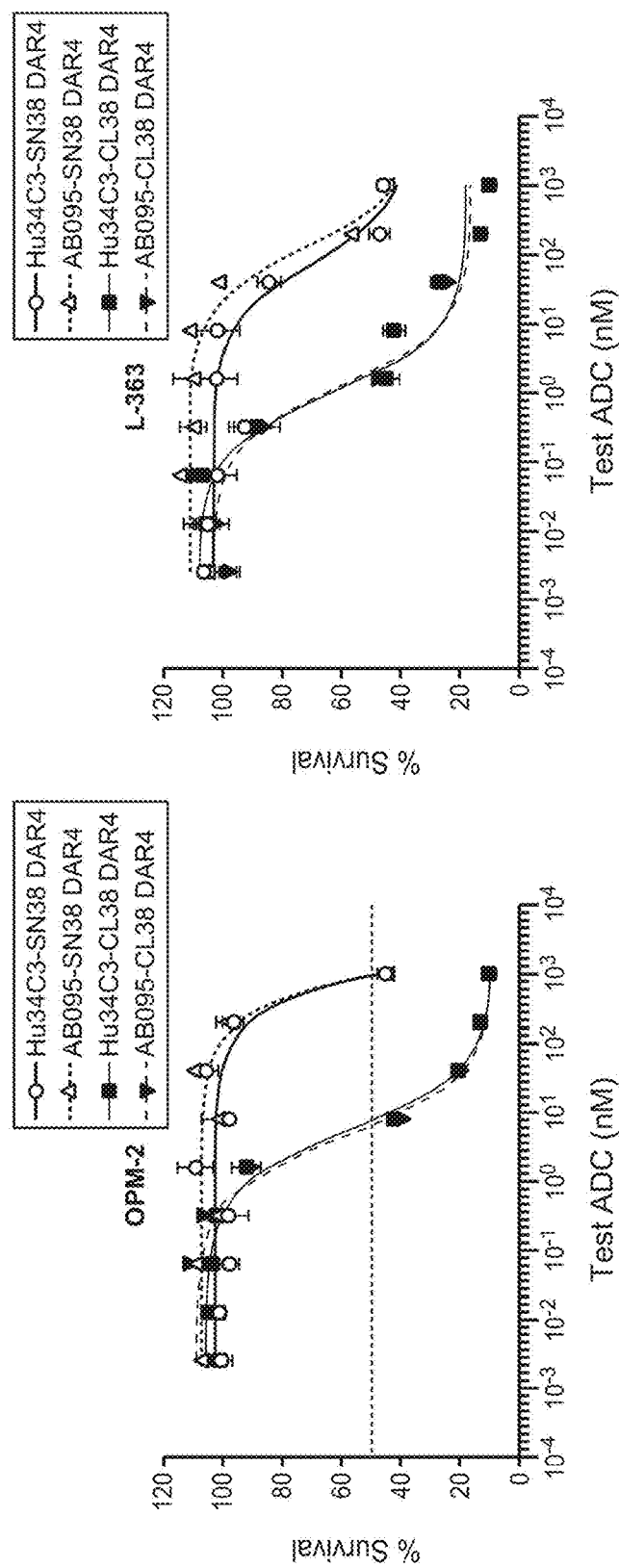

PDL241 V_H
QVQLVQSGAEVKKPGASVKVSCKASGYAFSSSWMNWVRQAPGQGLEWIGRIYPGDGDTKYNGKF KGKATLTADKSTSTAYMELSSLRSEDTAVYYCARSTMIATGAMDYWGQGTLVTVSS

PDL241 V_L
DIQMTQSPSSLSASVGDRVTITCKASQDVSTAVAWYQQKPGKAPKLLIYSASYRYTGVPDRFTG SGSGTDFTLTISSLQPEDFATYYCQQHYSTPPYTFGGGTKVEIKR

Elo V_H (SEQ ID NO:41 of US Patent No. 7,709,610)
EVQLVESGGGLVQPGGSLRLSCAASGFDFSRYWMSWVRQAPGKGLEWIGEINPDSSTINYAPSL KDKFIISRDNAKNSLYLQMNSLRAEDTAVYYCARPDGNYWYFDVWGQGTLVTVSS

Elo V_L (SEQ ID NO:44 of US Patent No. 7,709,610)
DIQMTQSPSSLSASVGDRVTITCKASQDVGIAVAWYQQKPGKVPKLLIYWASTRHTGVPDRFSG SGSGTDFTLTISSLQPEDVATYYCQQYSSYPYTFGQGTKVEIKR

Luc34 V_H (SEQ ID NO:7 of US Patent No.8,455,646)
QVQLQQSGAELARPGASVKLSCKASGYTFTSYWMQWVKQRPGQGLEWIGAIYPGDGDTRYTQKF KGKATLTADKSSSTAYMQLSSLASEDSAVYYCARGKVYYGSNPFAYWGQGTLVTVSA

Luc34 V_L (SEQ ID NO:8 of US Patent No.8,455,646)
DIQMTQSSSYLSVSLGGRVTITCKASDHINNWLAWYQQKPGNAPRLLISGATSLETGVPSRFSG SGSGKDYTLSITSLQTEDVATYYCQQYWSTPWTFGGGTKLEIKR

*FIG. 30*

ANTI-CS1 ANTIBODIES AND ANTIBODY DRUG CONJUGATES

1. CROSS REFERENCE TO RELATED APPLICATIONS

This application is a divisional under 35 U.S.C. § 121 of U.S. application Ser. No. 14/928,738, filed Oct. 30, 2015, which claims the benefit under 35 U.S.C. § 119(e) of U.S. Provisional Application No. 62/073,824, filed Oct. 31, 2014, the contents of each of which are incorporated herein in its entirety by reference thereto.

2. REFERENCE TO SEQUENCE LISTING

The instant application contains a Sequence Listing which has been submitted electronically in ASCII format and is hereby incorporated by reference in its entirety. Said ASCII copy, created on Oct. 22, 2015, is named 381493-838US (136841)_SL.txt and is 77,289 bytes in size.

3. FIELD

This present application pertains to, among other things, new anti-CS1 antibodies that bind an epitope different from known anti-CS1 antibodies, antibody drug conjugates ("ADCs") comprising the new anti-CS1 antibodies, compositions including the new antibodies and ADCs, methods of making the new antibodies and ADCs, and methods of using the new antibodies and ADCs to modulate biological processes and treat diseases.

4. BACKGROUND

Multiple myeloma ("MM") is an incurable malignancy arising from postgerminal mature B cells, characterized by an excess of monotypic plasma cells in the bone marrow and elevated levels of monoclonal immunoglobulins in the serum and/or urine (Lonial et al., 2012, J Clin Oncol 30:1953-1959). Common clinical sequelae include lytic bone lesions, fractures, myelosuppression, and renal failure. In the United States, the estimated annual diagnosed incidence is 20,000 (Lonial et al., 2012, J Clin Oncol 30:1953-1959). MM accounts for 15% of all hematologic malignancies and 2% of all malignancies (Lonial et al., 2012, J Clin Oncol 30:1953-1959). Advances in high-dose chemotherapy and stem cell transplantation have improved overall survival (OS) and event-free disease periods in MM (Lonial et al., 2012, J Clin Oncol 30:1953-1959), although relapses are inevitable. Newer therapeutic agents, such as proteasome inhibitors (currently approved: Velcade® (bortezomib), Kyprolis® (carfilzomib)), and the immunomodulatory drugs thalidomide, Revlimid® (lenalidomide), and Pomalyst® (pomalidomide) have demonstrated clinical benefit in patients with newly diagnosed, relapsed or refractory disease (Lonial et al., 2012, J Clin Oncol 30:1953-1959). Despite these therapeutic advances, long-term control of relapsed or refractory MM remains an unmet medical need for most MM patients. Progressive disease that is resistant to both immunomodulatory drugs (IMiDs) and proteasome inhibitors is associated with a particularly poor prognosis (Lonial et al., 2012, J Clin Oncol 30:1953-1959). As such, there remains an important need for additional novel therapies to augment existing first-generation agents and continue to improve patient outcome.

CS1 (also known as SLAMF7, CRACC, 19A, APEX-1, and FOAP12) is a cell surface glycoprotein that has emerged as a new target antigen for therapeutic antibodies in multiple myeloma (MM) (Lonial et al., 2012, J Clin Oncol 30:1953-1959). Elotuzumab is a humanized monoclonal immunoglobulin G1 antibody targeting CS1 (see, e.g., PCT publications WO 2004/100898, WO 2005/102387, WO 2008/019376, and WO 2008/019378; see also U.S. Pat. Nos. 8,088,898, 8,133,981, 8,008,450, 8,445,646, 8,349,330, 8,461,306, 8,444,980, 8,436,146, 7,709,610, 8,632,772, and 7,842,293). Elotuzumab has shown encouraging antimyeloma activity in preclinical studies when used alone or in combination with other approved agents. For example, elotuzumab and lenalidomide have certain complementary mechanisms of action. Lenalidomide has been shown to increase the number and anti-MM cytotoxic activity of NK cells (Lonial et al., 2012, J Clin Oncol 30:1953-1959). Elotuzumab acts primarily through NK cell-mediated ADCC (Lonial et al., 2012, J Clin Oncol 30:1953-1959). A Phase III clinical trial, ELOQUENT-2, evaluated the efficacy and safety of elotuzumab in combination with lenalidomide and dexamethasone, as compared with lenalidomide and dexamethasone alone, in patients with relapsed or refractory multiple myeloma. In patients with relapsed or refractory multiple myeloma, the addition of elotuzumab to lenalidomide and dexamethasone, as compared with lenalidomide and dexamethasone as control therapy, improved progression-free survival and the overall response rate, showing that direct activation and engagement of the innate immune system selectively to target myeloma cells can provide clinically meaningful and statistically significant improvements in treatment outcomes. Specifically, Kaplan-Meier curves for progression-free survival showed early and increasing separation between the two groups over time. Patients receiving elotuzumab had a relative reduction of 30% in the risk of disease progression or death as compared with the control group (Lonial et al., 2015, N Engl J Med, 373:621-631).

Although the results with elotuzumab are promising, there remains a need to identify novel therapies that do not exert their anti-myeloma effect primarily via NK cell-mediated ADCC (Zonder, 2012, Blood, 120:552-559), in part because MM patients with advanced disease often have an impaired immune system (Pratt, 2007, Br J Haematol 138:563-579). Therapies that work effectively with an impaired immune system would be desirable.

5. SUMMARY

In one aspect, the present disclosure provides new antibodies, and/or binding fragments, that specifically bind human CS1 ("HuCS1"; SEQ ID NO:1) at epitopes different from the epitopes bound by anti-CS1 antibodies reported in the literature, and in particular antibodies LucX (and its humanized version, PDL241), elotuzumab and Luc34.3.8 (see, e.g., PCT publications WO 2004/100898, WO 2005/102387, and Woo, et al., 2013, Arthritis Res Ther 15(6): R207). One of the new antibodies binds a unique epitope. This antibody exhibits superior anti-proliferation properties in vivo. Unlike elotuzumab, all of the new antibodies and binding fragments described herein cross react with cynomolgus CS1 ("CmCS1"; SEQ ID NO:3). This property is advantageous in that it permits safety testing in cynomolgus monkeys.

The new antibodies and/or binding fragments generally comprise a variable heavy ($V_H$) chain having three complementarity determining regions ("CDRs") referred to herein (in N→C order) as $V_H$CDR#1, $V_H$CDR#2, and $V_H$CDR#3, and a variable light ($V_L$) chain having three complementarity determining regions referred to herein (in N→C order) as $V_L$ CDR#1, $V_L$ CDR#2, and $V_L$ CDR#3. The amino acid sequences of the $V_H$ and $V_L$ regions of the heavy and light chains of a number of exemplary anti-CS1 antibodies have been determined, and their CDRs identified. With the exception of antibody Mu27H1, the sequences of the respective heavy and light chain CDRs of exemplary anti-CS1 antibodies disclosed herein exhibit a high degree of similarity. Accordingly, anti-CS1 antibodies comprising any combination of heavy chain CDRs and any combination of light chain CDRs, as well as any combination of $V_H$ and $V_L$ chains disclosed herein are contemplated. Specific exemplary embodiments of CDRs, $V_H$ chains and $V_L$ chains that may be incorporated into anti-CS1 antibodies, as well as specific exemplary embodiments of anti-CS1 antibodies that compete for binding HuCS1 with reference antibodies, are provided in the Detailed Description section.

The anti-CS1 antibodies described herein can be in the form of full-length antibodies, bispecific antibodies, dual variable domain antibodies, multiple chain or single chain antibodies, and/or binding fragments that specifically bind human CS1, including but not limited to Fab, Fab', (Fab')$_2$, Fv), scFv (single chain Fv), surrobodies (including surrogate light chain construct), single domain antibodies, camelized antibodies and the like. They also can be of, or derived from, any isotype, including, for example, IgA (e.g., IgA$_1$ or IgA$_2$), IgD, IgE, IgG (e.g. IgG$_1$, IgG$_2$, IgG$_3$ or IgG$_4$), or IgM. In some embodiments, the anti-CS1 antibody is an IgG (e.g. IgG$_1$, IgG$_2$, IgG$_3$ or IgG$_4$). Anti-CS1 antibodies can be of human or non-human origin. Examples of non-human origin include but are not limited to mammalian origin (e.g., simians, rodents, goats, and rabbits).

The anti-CS1 antibodies and/or binding fragments described herein may also include modifications and/or mutations that alter the properties of the antibodies and/or fragments, such as those that increase half-life, increase or decrease ADCC, etc., as is known in the art.

For some uses, it is desirable to have anti-CS1 antibodies with high affinity to HuCS1; for other uses, affinity is not important. For certain uses, such as therapeutic uses, an affinity of at least about 100 nM is desirable. For applications in which specific affinities are desired, anti-CS1 antibodies specifically bind HuCS1 with an affinity of at least about 100 nM, or even higher, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or greater. Affinity of anti-CS1 antibodies can be determined using techniques well known in the art or described herein, such as for example, ELISA, isothermal titration calorimetry (ITC), BIAcore, or fluorescent polarization assay.

In another aspect, the disclosure provides antibody-drug conjugates (ADCs) comprising cytotoxic and/or cytostatic agents linked by way of linkers to an anti-CS1 antibody and/or binding fragment as disclosed herein. The cytotoxic and/or cytostatic agents may be any agents known to inhibit the growth and/or replication of and/or kill cells, and in particular cancer and/or tumor cells. Numerous agents having cytotoxic and/or cytostatic properties are known in the literature. Non-limiting examples of classes of cytotoxic and/or cytostatic agents include, by way of example and not limitation, alkylating agents, DNA intercalating agents (e.g., groove binding agents such as minor groove binders), topoisomerase I inhibitors, topoisomerase II inhibitors, cell cycle modulators, kinase inhibitors, protein synthesis inhibitors, histone deacetylase inhibitors, mitochondria inhibitors, RNA/DNA antimetabolites and antimitotic agents. Any of these agents, or other cytotoxic and/or cytostatic agents, that include or that may be modified to include a site of attachment to an antibody may be included in the ADCs disclosed herein. In a specific embodiment, the cytotoxic and/or cytostatic agent is an antimitotic agent. In another specific embodiment, is an auristatin, for example, monomethyl auristatin E ("MMAE") or monomethyl auristatin F ("MMAF").

The linkers linking the cytotoxic and/or cytostatic agents to the antibody of an ADC may be long, short, flexible, rigid, hydrophilic or hydrophobic in nature, or may comprise segments have different characteristics, such as segments of flexibility, segments of rigidity, etc. The linker may be chemically stable to extracellular environments, for example, chemically stable in the blood stream, or may include linkages that are not stable and release the cytotoxic and/or cytostatic agents in the extracellular milieu. In some embodiments, the linker includes linkages that are designed to release the cytotoxic and/or cytostatic agents upon internalization of the ADC within the cell. In some specific embodiments, the linker includes linkages designed to cleave and/or immolate or otherwise breakdown specifically or non-specifically inside cells. A wide variety of linkers useful for linking drugs to antibodies in the context of ADCs are known in the art. Any of these linkers, as well as other linkers, may be used to link the cytotoxic and/or cytostatic agents to the antibody of the ADCs described herein.

The number of cytotoxic and/or cytostatic agents linked to the antibody of an ADC can vary (called the "drug-to-antibody ratio," or "DAR"), and will be limited only by the number of available attachment sites on the antibody and the number of agents linked to a single linker. Typically, a linker will link a single cytotoxic and/or cytostatic agent to the antibody of an ADC. In embodiments of ADCs that include more than a single cytotoxic or cytostatic agent, each agent may be the same or different. As long as the ADC does not exhibit unacceptable levels of aggregation under the conditions of use and/or storage, ADCs with DARs of twenty, or even higher, are contemplated. In some embodiments, the ADCs described herein may have a DAR in the range of about 1-10, 1-8, 1-6, or 1-4. In certain specific embodiments, the ADCs may have a DAR of 2, 3 or 4.

In some embodiments, the ADCs are compounds according to structural formula (I):

[D-L-XY]$_n$-Ab     (I)

or salts thereof, where each "D" represents, independently of the others, a cytotoxic and/or cytostatic agent; each "L" represents, independently of the others, a linker; "Ab" represents an anti-CS1 antigen binding moiety, such as an anti-CS1 antibody or binding fragment described herein; each "XY" represents a linkage formed between a functional group $R^x$ on the linker and a "complementary" functional group $R^y$ on the antibody, and n represents the DAR of the ADC. In one specific embodiment, each "D" is the same, each "L" is the same, and "Ab" is an antibody or binding fragment. In a specific embodiment, the ADCs are compounds according to structural formula (I) in which "D" is an auristatin, for example MMAE or MMAF, "L" is a linker cleavable by a lysosomal enzyme, "XY" is linkage formed between a maleimide and a sulfydryl group, "Ab" is antibody Hu34C3 or a binding fragment thereof, and n is 2, 3 or 4.

In another aspect, the present disclosure provides compositions including the anti-CS1 antibodies and/or ADCs described herein. The compositions generally comprise one or more anti-CS1 antibodies, binding fragments and/or ADCs as described herein, and/or salts thereof, and one or more excipients, carriers or diluents. The compositions may be formulated for pharmaceutical use, or other uses. In one specific embodiment, the composition is formulated for pharmaceutical use and comprises anti-CS1 antibody Hu34C3, or a pharmaceutically acceptable salt thereof, and one or more pharmaceutically acceptable excipients, carriers or diluents. In another specific embodiment, the composition is formulated for pharmaceutical use and comprises an ADC according to structural formula (I) or a pharmaceutically acceptable salt thereof in which "D" is an auristatin, for example MMAE or MMAF, "L" is a linker cleavable by a lysosomal enzyme, "Ab" is antibody Hu34C3 or a binding fragment thereof, and n is 2, 3 or 4, and one or more pharmaceutically acceptable excipients, carriers or diluents.

Compositions formulated for pharmaceutical use may be packaged in bulk form suitable for multiple administrations, or may be packaged in the form of unit doses suitable for a single administration. Whether packaged in bulk or in the form of unit doses, the composition may be presented in dry form, such as a lyophilate, or in liquid form. Unit dosage liquid compositions may be conveniently packaged in the form of syringes pre-filled with a quantity of antibody or ADC suitable for a single administration.

Also provided are polynucleotides encoding the new anti-CS1 antibodies described herein, host cells transformed or transfected with the polynucleotides, and methods of making the various anti-CS1 antibodies and ADCs described herein.

The anti-CS1 antibodies, binding fragments and ADCs bind CS1 on cells expressing CS1, such as plasma and multiple myeloma cells, and inhibit proliferation and/or induce cell death. Accordingly, in another aspect, the present disclosure provides methods of treating subjects, such as human subjects, diagnosed with a plasma cell neoplasm, e.g., multiple myeloma. The method generally involves administering to the subject an amount of an anti-CS1 antibody, binding fragment and/or ADC described herein effective to provide therapeutic benefit. The subject may be diagnosed with Monoclonal Gammopathy of Undetermined Significance (MGUS), plasmacytoma, smoldering-asymptomatic multiple myeloma, or symptomatic multiple myeloma. The plasma cell neoplasm, e.g., multiple myeloma, may be newly diagnosed, or may be relapsed, or relapsed and refractory. An anti-CS1 antibody and/or binding fragment is typically administered as an intravenous infusion at doses ranging from 0.5 to 20 mg/kg, from once a week to once a month. An anti-CS1 ADC is typically administered as an intravenous infusion at doses ranging from 0.15 mg/kg to 10 mg/kg administered once a week, once every 2 weeks, once every 3 weeks, or once a month.

The anti-CS1 antibodies, binding fragments and/or ADCs may be administered as single therapeutic agents (monotherapy) or adjunctively with or to therapeutic agents typically, but not necessarily, those used for the treatment of a plasma cell neoplasm, e.g, MM. Depending on the therapeutic agent, the anti-CS1 antibody, binding fragment or ADC may be administered once a week, once every 2 weeks, once every 3 weeks, to once a month. Therapeutic agents typically will be used at their approved dose, route of administration, and frequency of administration, but may be used at lower dosages.

The ADCs may be administered via a variety of routes or modes of administration, including but not limited to, intravenous infusion and/or injection and subcutaneous injection. The amount administered will depend upon the route of administration, the dosing schedule, the stage of cancer being treated, and other parameters such as the age and weight of the patient, as is well known in the art. Specific exemplary dosing schedules expected to provide therapeutic benefit are provided in the Detailed Description.

The anti-CS1 antibody elotuzumab has shown significant promise in treating multiple myeloma in clinical studies when administered adjunctive to or with current standards of care, such as lenalidomide and dexamethasone. Based on data presented herein, it is expected that the anti-CS1 ADCs described herein will provide therapeutic benefit to subjects diagnosed with multiple myeloma when administered as monotherapy.

6. BRIEF DESCRIPTION OF THE FIGURES

FIGS. 1A and 1B provide the amino acid sequence of human CS1 (SEQ ID NO:1), as well as an encoding polynucleotide sequence (SEQ ID NO:2). The signal peptide is indicated with a dashed underline; the Ig domain #1 is underlined; the Ig domain #2 is double-underlined and the transmembrane domain is highlighted.

FIGS. 1C and 1D provide the amino acid sequence of cynomolgus CS1 (SEQ ID NO:3), as well as an encoding polynucleotide sequence (SEQ ID NO:4). The signal peptide is indicated with a dashed underline; the Ig domain #1 is underlined; the Ig domain #2 is double-underlined and the transmembrane domain is highlighted.

FIGS. 2A and 2B provide amino acid sequences of $V_H$ chains of various antibodies described herein. The CDR sequences are shown in bolded, underlined text according to the Kabat numbering system (which is illustrated). Human germline changes within CDRs are double-underlined; mutations that increase affinity as compared to Hu34C3 are highlighted. FIGS. 2A and 2B disclose SEQ ID NOS: 5, 7, 8, 12, 14, 16, 17, 21, 23, 24, 28, 30, and 32, respectively, in order of appearance.

FIGS. 2C and 2D provide amino acid sequences of $V_L$ chains of various antibodies described herein. The CDR sequences are shown in bolded, underlined text, according to the Kabat numbering system (which is illustrated). Human germline changes within CDRs are double-underlined; mutations that increase affinity as compared to Hu34C3 are highlighted and murine framework back-mutations are shown in bolded, italicized, dashed-underlined text. FIGS. 2C and 2D disclose SEQ ID NOS: 6, 9, 10, 11, 13, 15, 18, 19, 20, 22, 25, 26, 27, 29, 31, and 33, respectively, in order of appearance.

FIG. 3A is a cartoon illustrating the disulfide bridging in antibody Hu34C3. Variable regions of the heavy and light chains are illustrated in grey; constant regions in black. Intrachain disulfide bridges are illustrated in white; interchain disulfide bridges in stippled black. The numbers refer to the position of the amino acid within the chain, where the amino acids are numbered consecutively (in the N→C direction) from 1-220 (light chain) or 1-447 (heavy chain). One or more of the interchain disulfide bridges may be reduced to yield sulfhydryl groups, which may be used for conjugation of drugs in ADCs described herein.

FIG. 3B provides a cartoon illustrating the predicted amino acid sequence of the light chain of antibody Hu34C3 (SEQ ID NO:35). Cys residues involved in intrachain disulfide bridges, as well as Cys residues that form intrachain disulfide bridges and provide potential attachment sites for drugs in ADCs, are illustrated. Underlined residues indicate those corresponding to the constant region.

FIG. 3C provides a cartoon illustrating the predicted amino acid sequence of the heavy chain of antibody Hu34C3

(SEQ ID NO:34). Cys residues involved in intrachain disulfide bridges, as well as Cys residues that form intrachain disulfide bridges and provide potential attachment sites for drugs in ADCs, are illustrated. Also shown is an N-linked glycosylation site (Asn-297). Underlined residues indicate those corresponding to the constant region.

Figure 4:
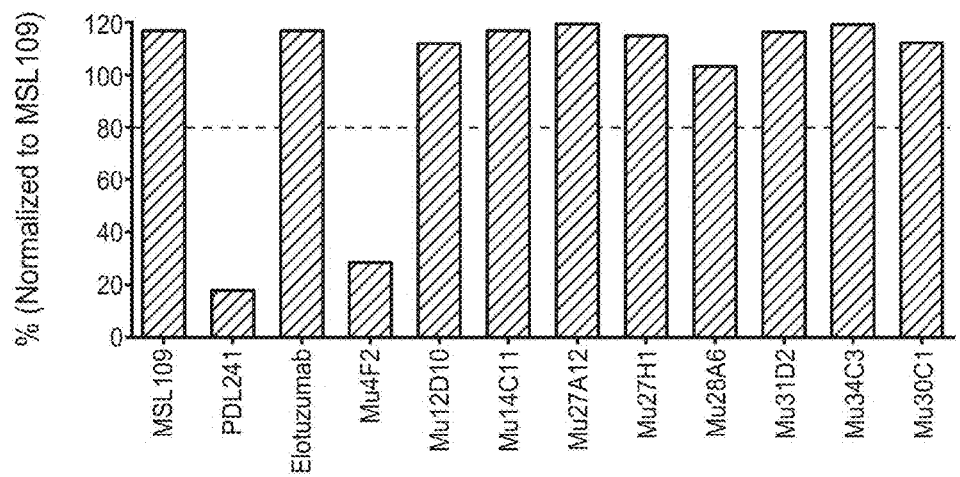

FIG. 4 provides a graph illustrating that exemplary new anti-CS1 antibodies do not compete with, and hence bind an epitope of human CS1 different from, the epitope bound by antibody PDL241.

Figure 5:
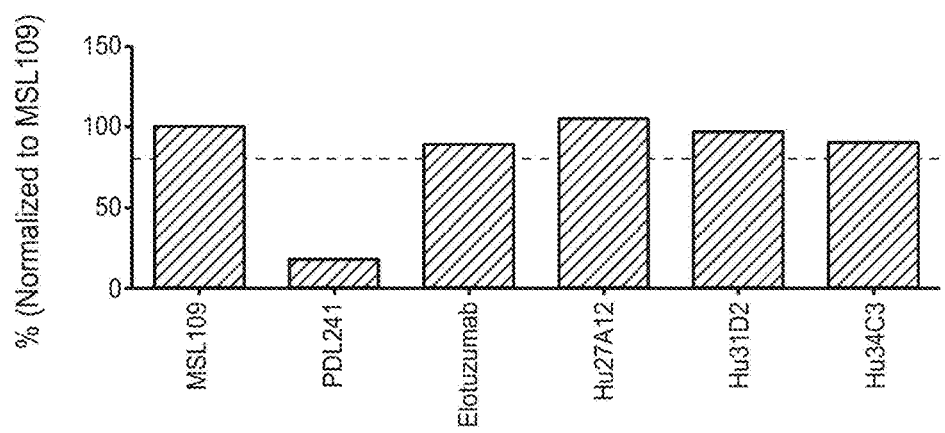

FIG. 5 provides a graph illustrating that exemplary humanized anti-CS1 antibodies do not compete with, and hence bind an epitope of human CS1 different from, the epitope bound by antibody PDL241.

Figure 6:
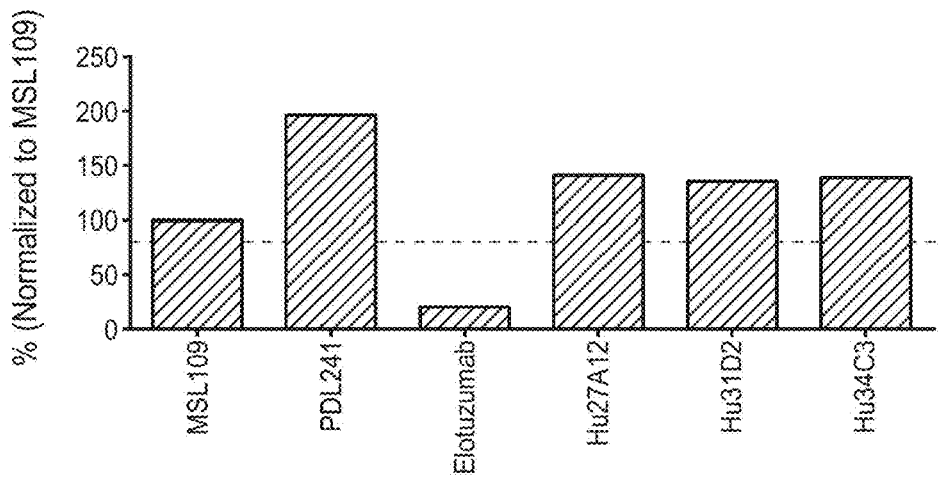

FIG. 6 provides a graph illustrating that exemplary humanized anti-CS1 antibodies do not compete with, and hence bind an epitope of human CS1 different from, the epitope bound by antibody elotuzumab.

Figure 7:
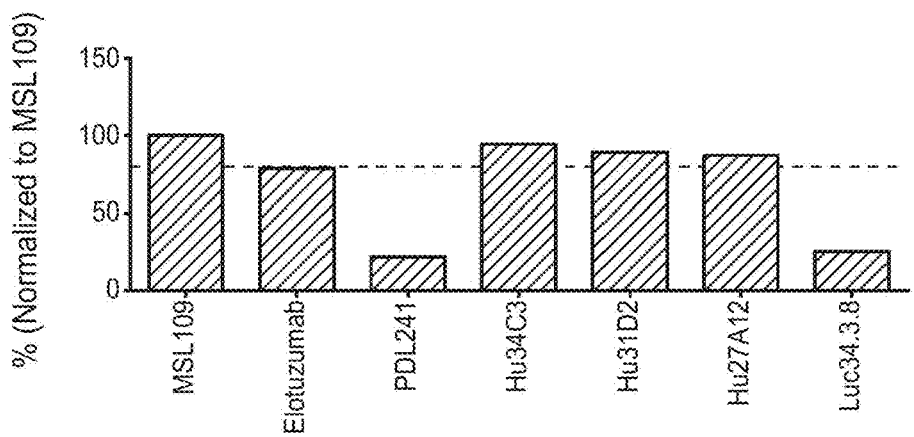

FIG. 7 provides a graph illustrating that exemplary humanized anti-CS1 antibodies do not compete with, and hence bind an epitope of human CS1 different from, the epitope bound by antibody Luc34.3.8.

Figure 8:
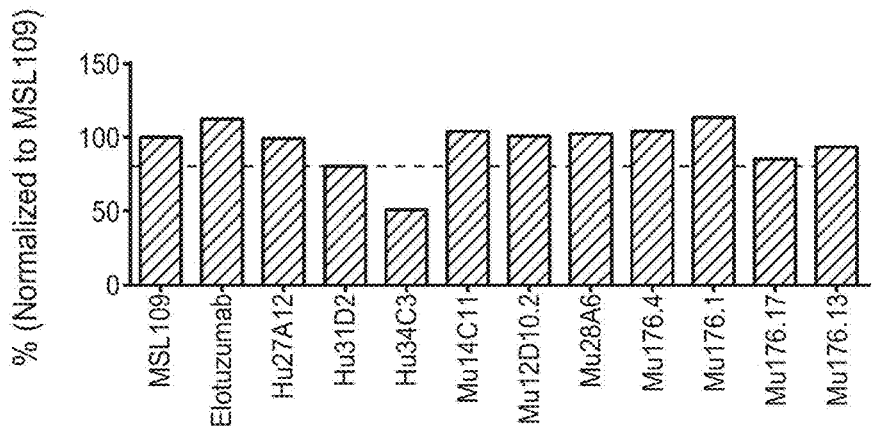

FIG. 8 provides a graph illustrating that humanized anti-CS1 antibody Hu34C3 binds a unique epitope.

Figure 9A:
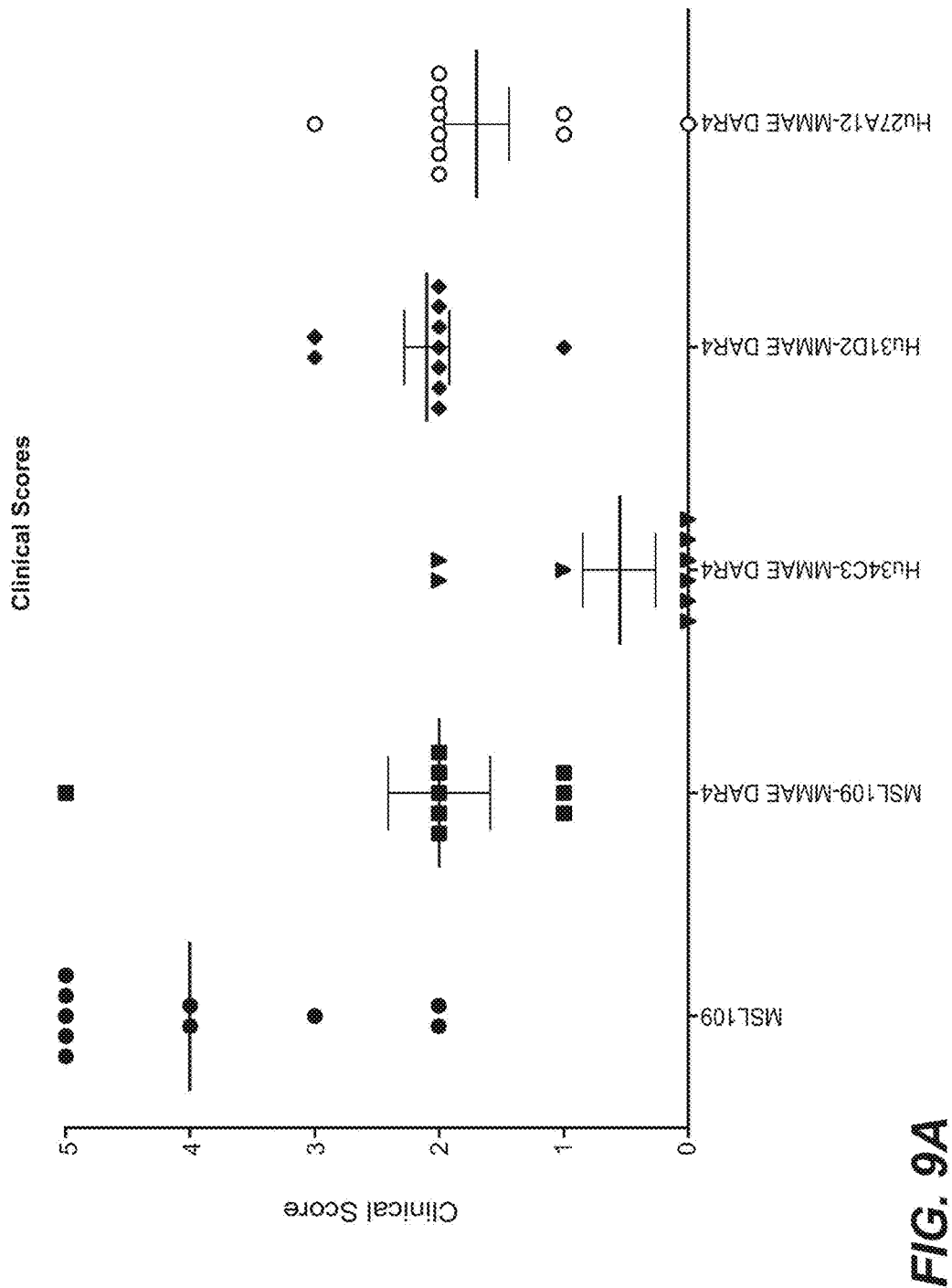
Figure 9B:
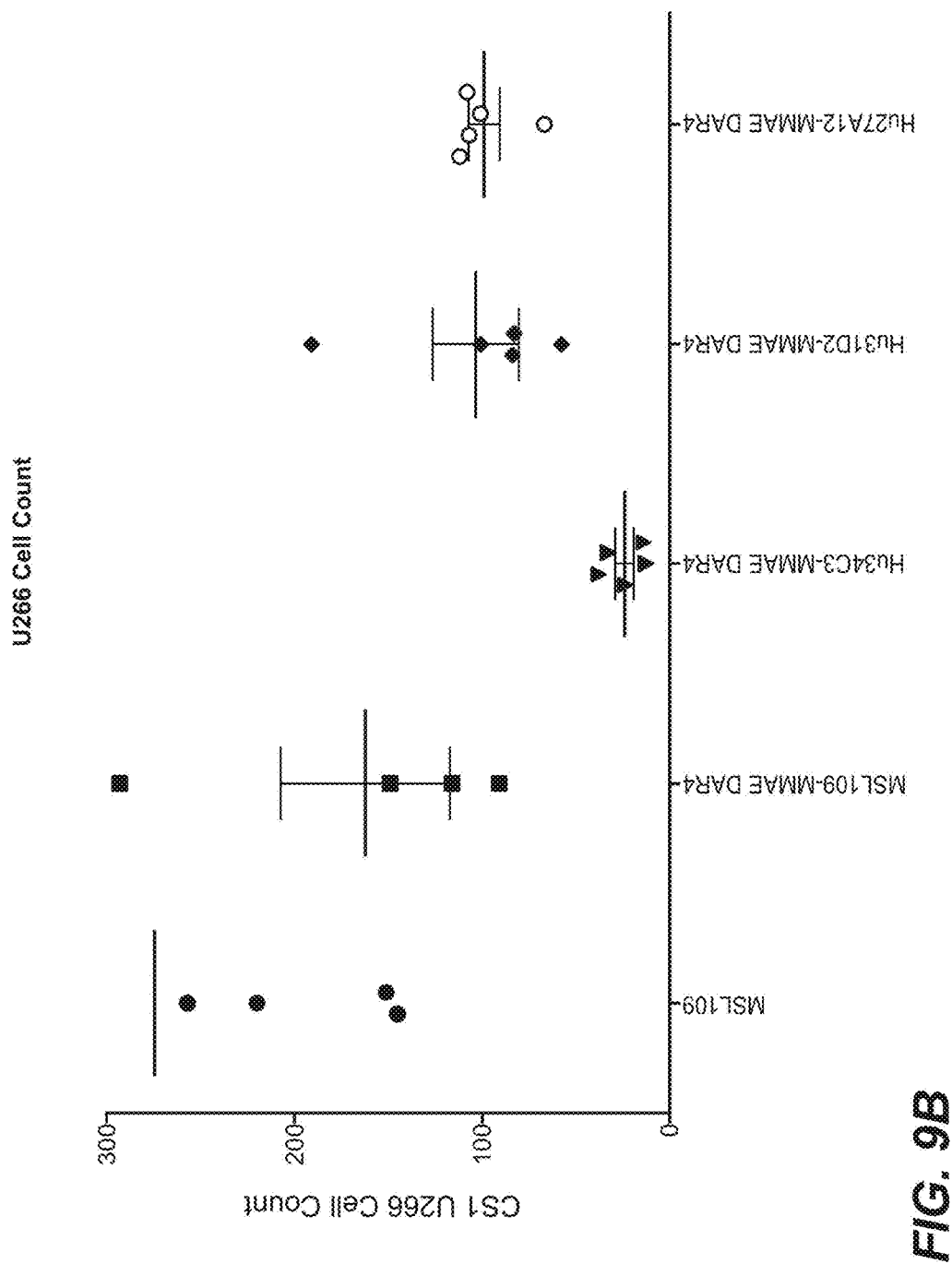

FIG. 9A and FIG. 9B provide graphs illustrating that MMAE ADCs of exemplary humanized anti-CS1 antibodies are effective in vivo in a U266 xenograft model.

Figure 10:
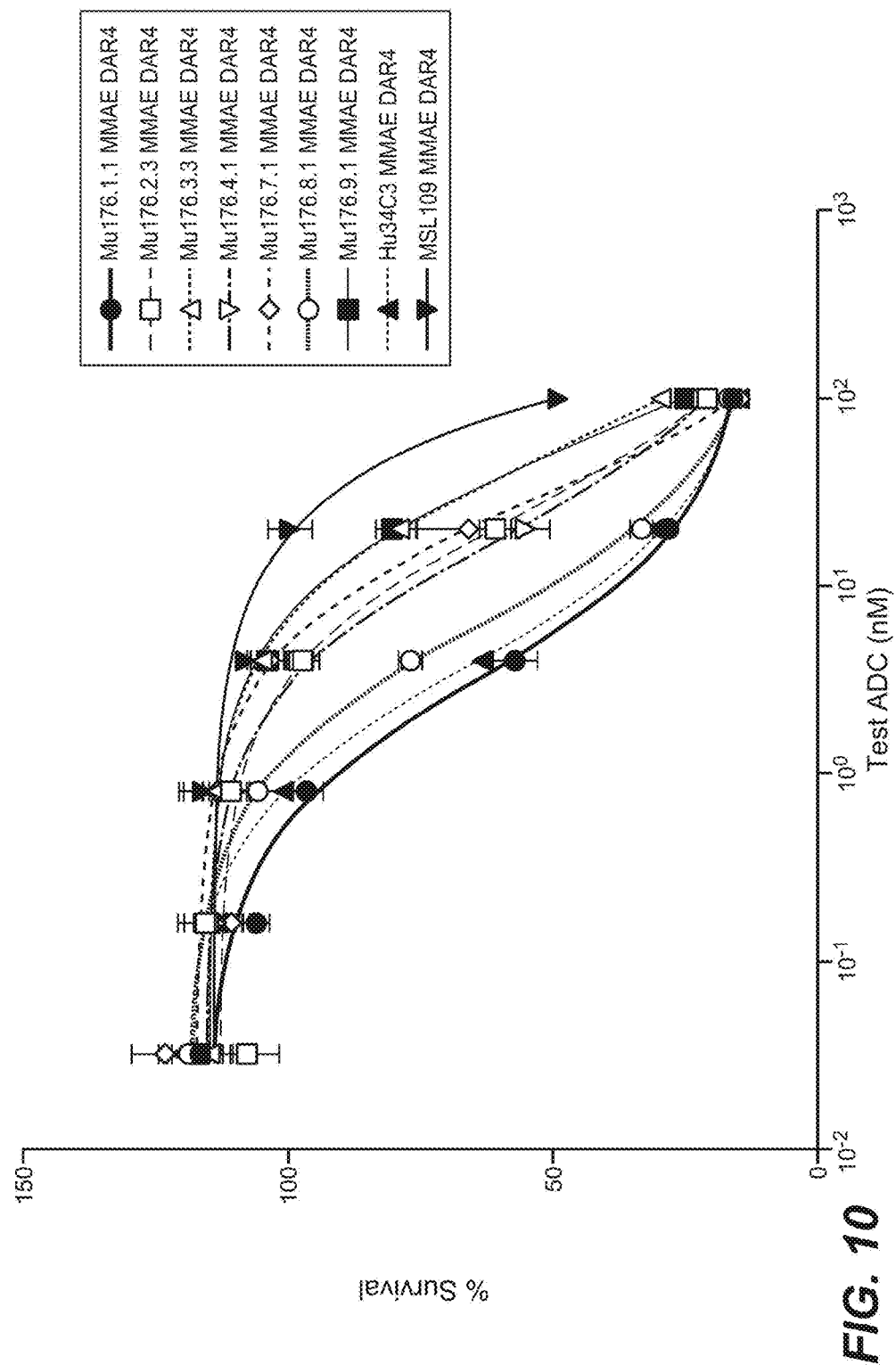

FIG. 10 provides a graph illustrating that an ADC comprising exemplary humanized anti-CS1 antibody Hu34C3 is more effective in vitro than ADCs comprising other anti-CS1 antibodies.

Figure 11:
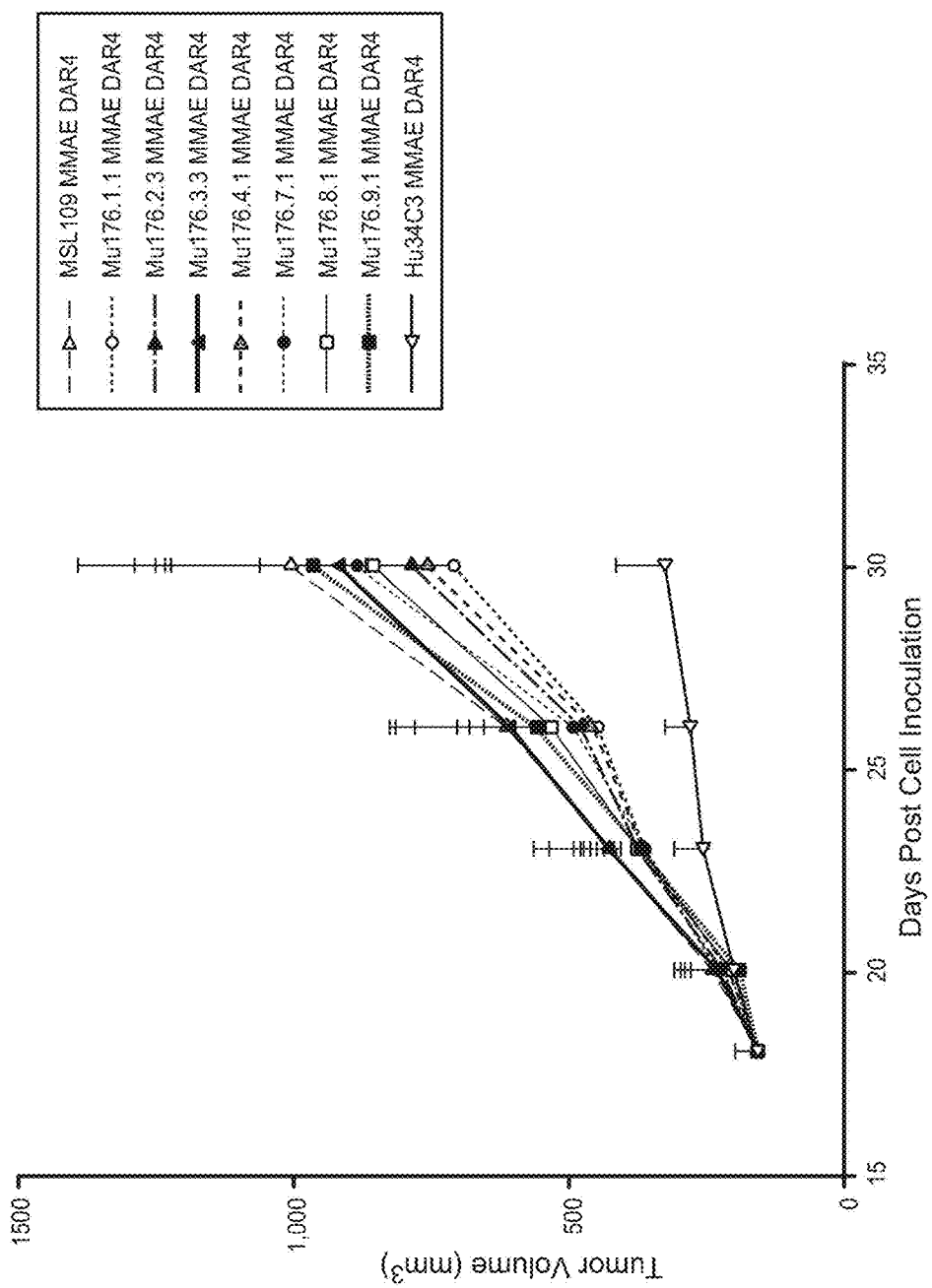

FIG. 11 provides a graph illustrating that an ADC comprising exemplary humanized anti-CS1 antibody Hu34C3 is more potent in vivo than ADCs comprising other anti-CS1 antibodies.

Figure 12:
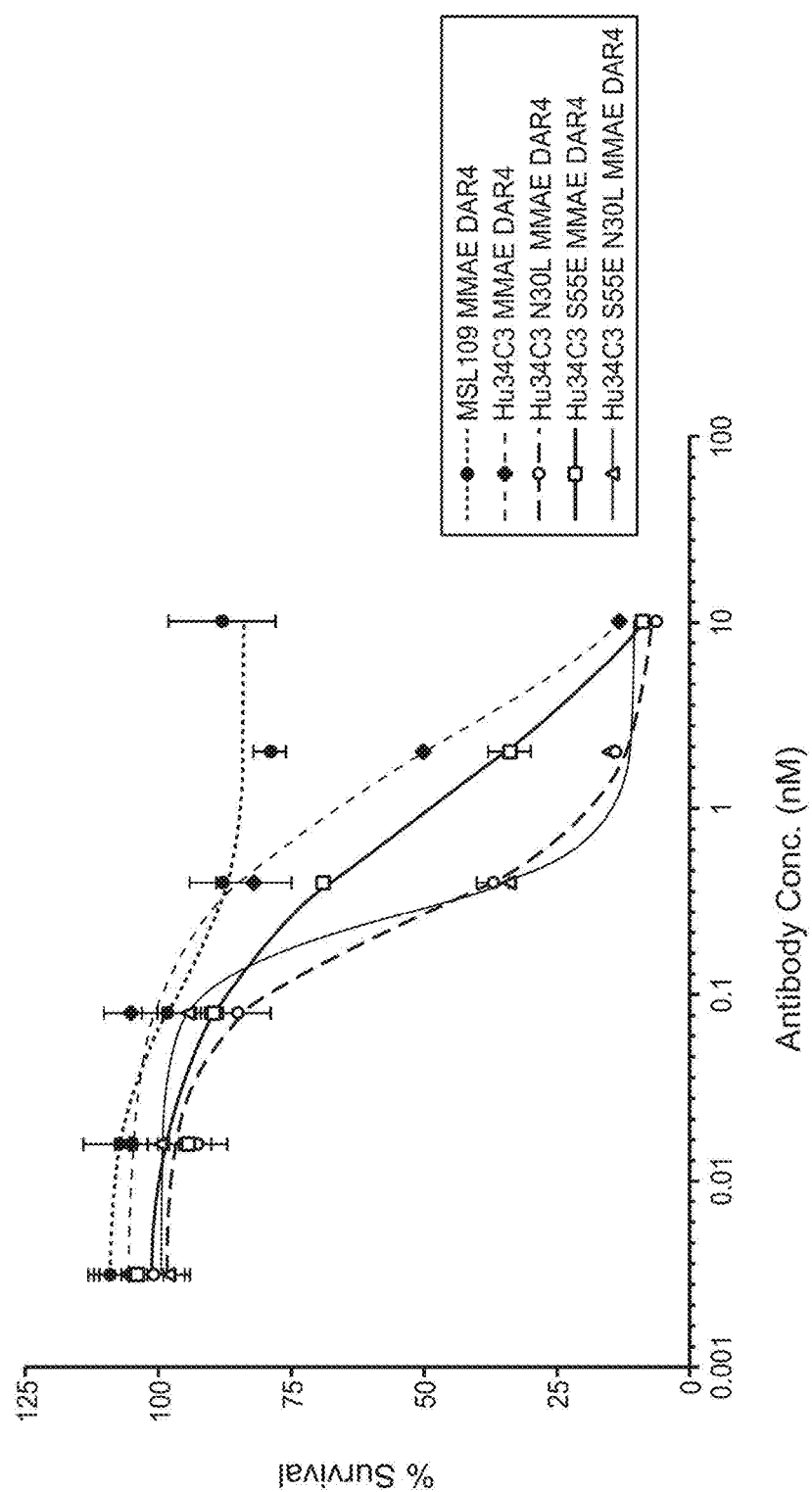

FIG. 12 provides a graph illustrating the in vitro anti-proliferation activities of ADCs comprising mutants of antibody Hu34C3 having increased affinity for HuCS1 as compared to Hu34C3.

Figure 13:
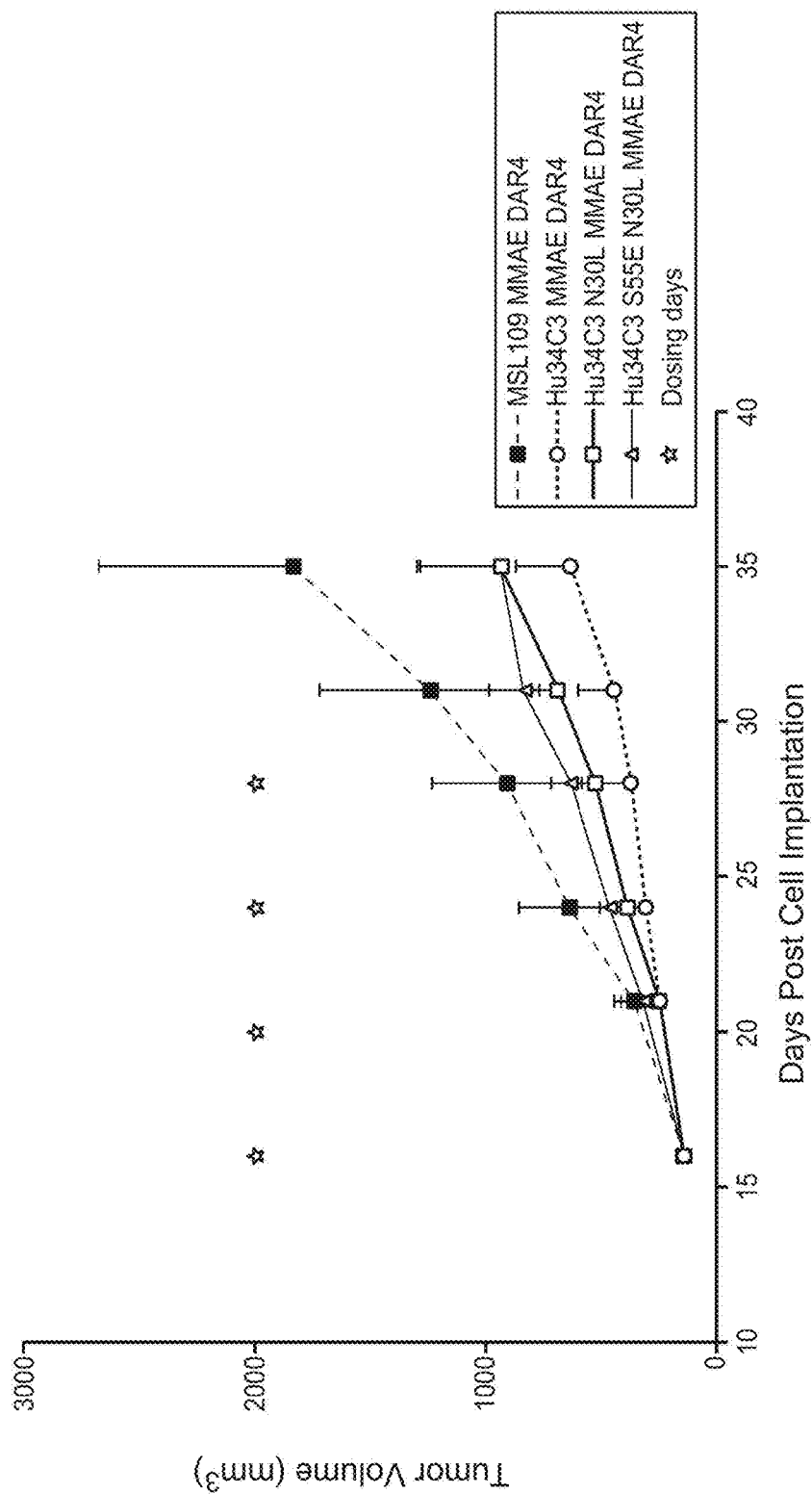

FIG. 13 provides a graph illustrating the in vivo anti-tumor activities of ADCs comprising mutants of antibody Hu34C3 having increased affinity for HuCS1 as compared to Hu34C3.

Figure 14A:
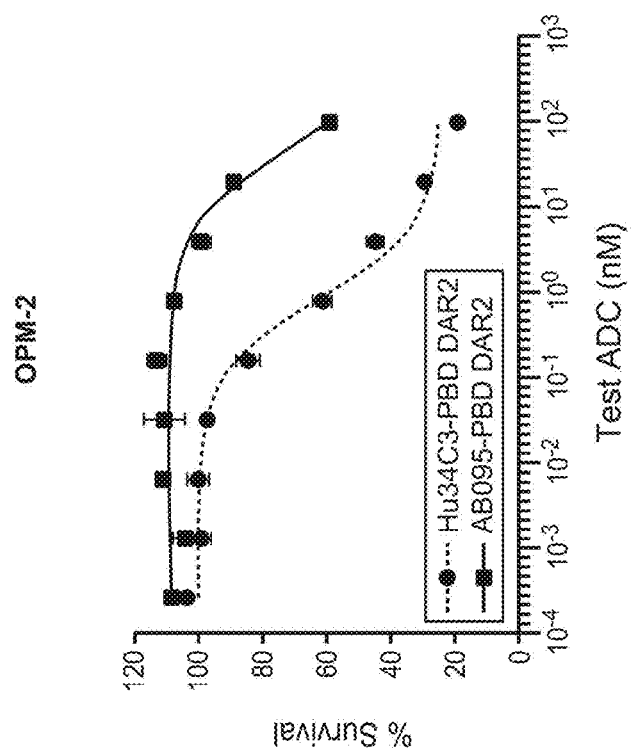

FIG. 14A provides a graph illustrating the in vitro anti-proliferation activities of ADCs comprising antibody Hu34C3 and a pyrrolobenzodiazepine in OPM-2 cells.

Figure 14B:
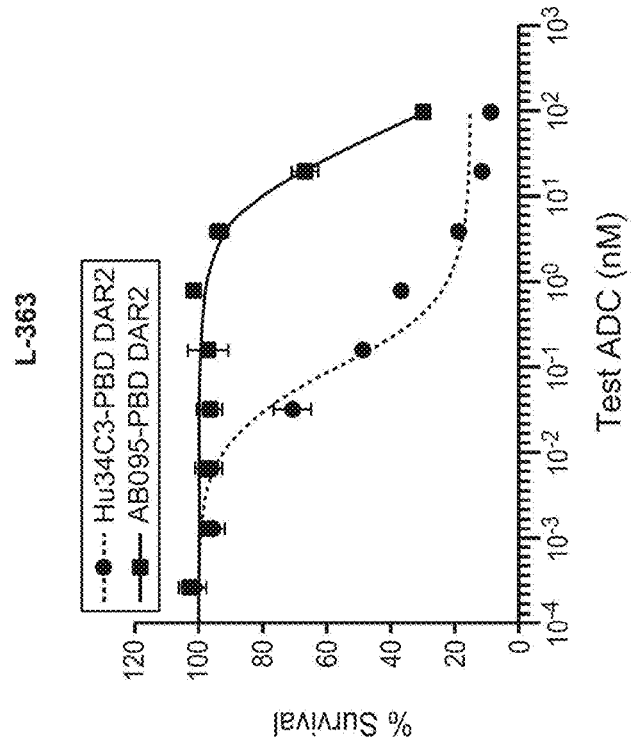

FIG. 14B provides a graph illustrating the in vitro anti-proliferation activities of ADCs comprising antibody Hu34C3 and a pyrrolobenzodiazepine in L-363 cells.

Figure 14D:
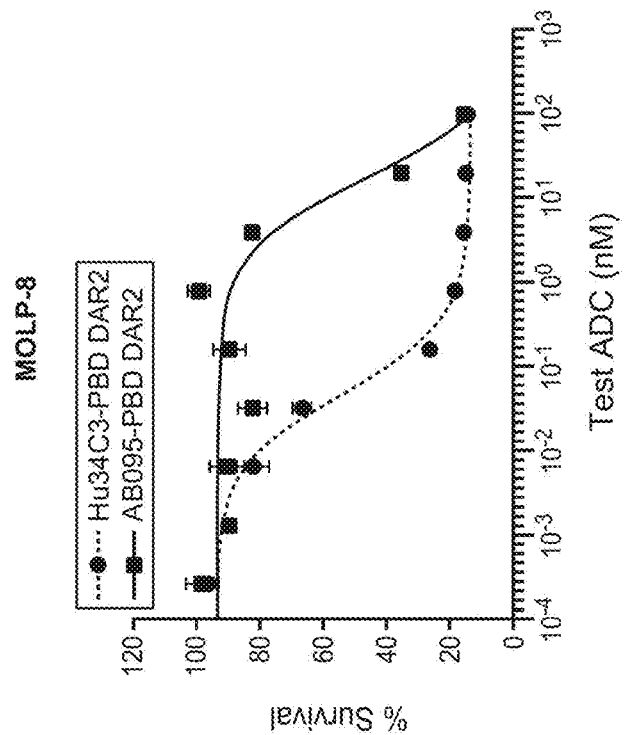
Figure 14C:
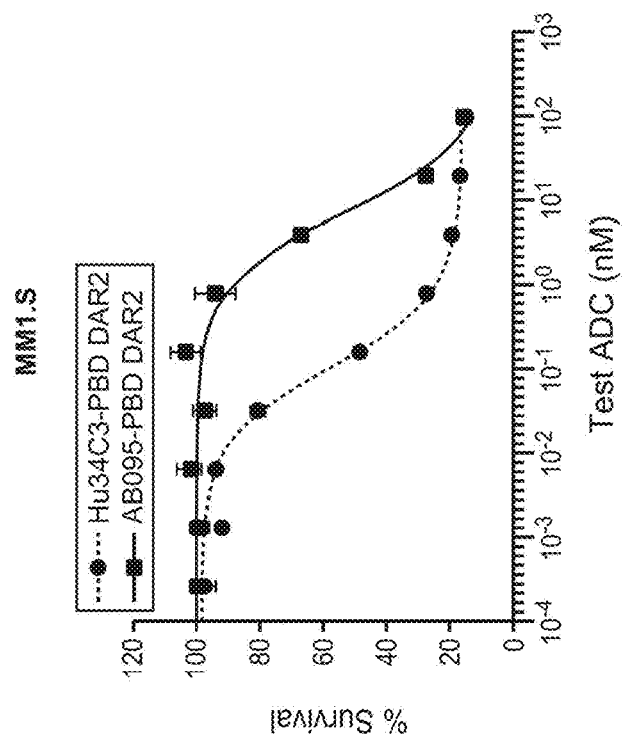

FIG. 14C provides a graph illustrating the in vitro anti-proliferation activities of ADCs comprising antibody Hu34C3 and a pyrrolobenzodiazepine in MM1.S cells.

FIG. 14D provides a graph illustrating the in vitro anti-proliferation activities of ADCs comprising antibody Hu34C3 and a pyrrolobenzodiazepine in MOLP-8 cells.

Figure 15:
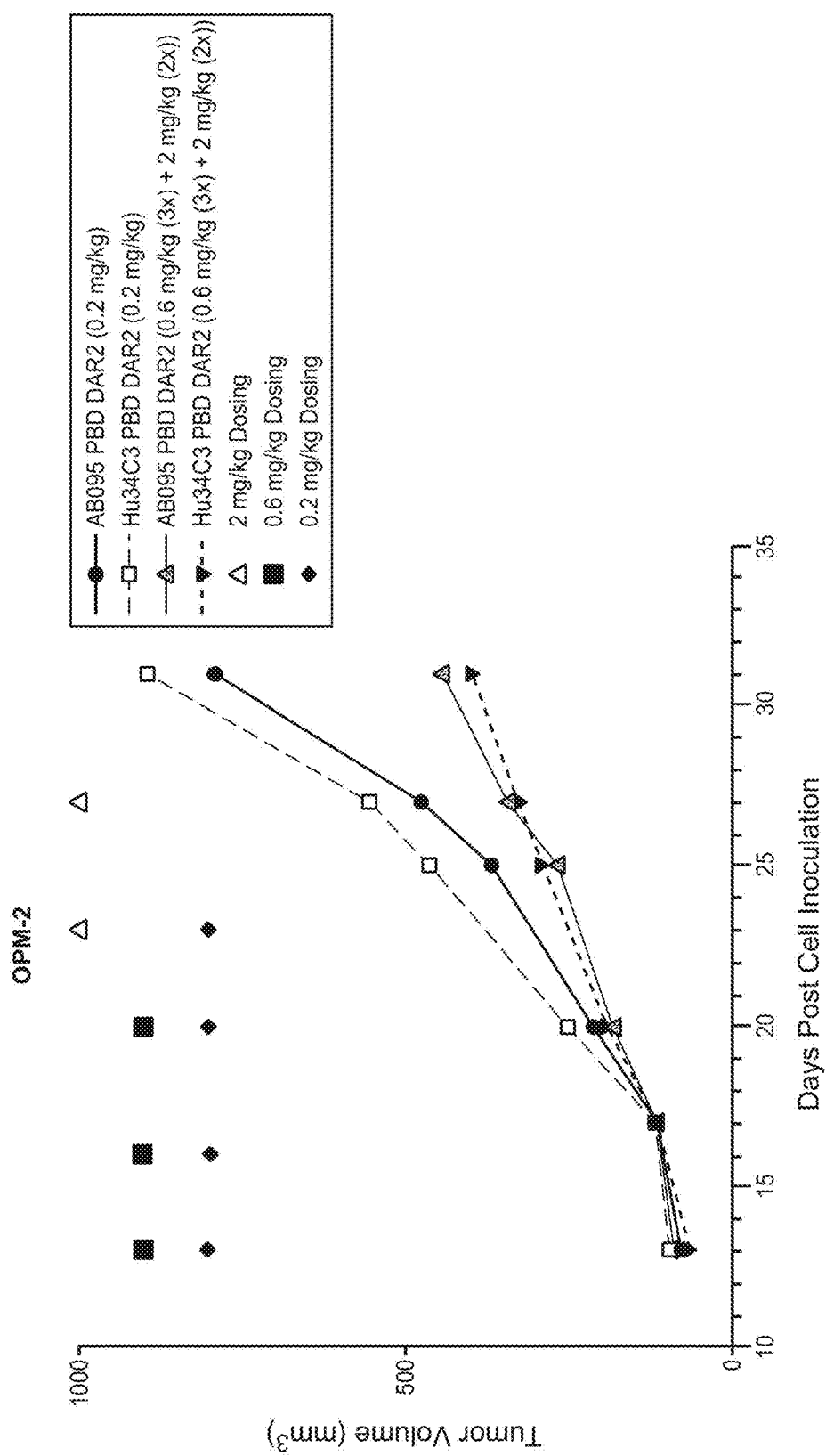

FIG. 15 provides a graph illustrating the in vivo anti-tumor activities of ADCs comprising the antibody Hu34C3 and a pyrrolobenzodiazepine in an OPM-2 xenograft.

Figure 16B:
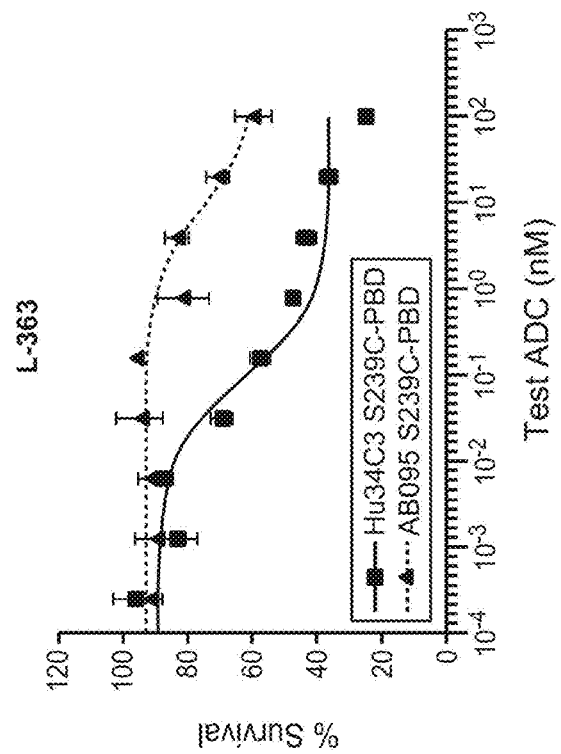
Figure 16A:
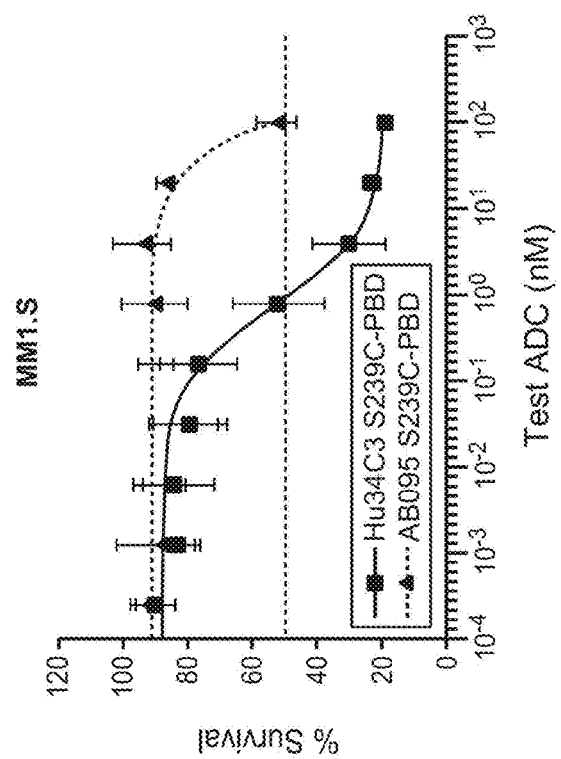

FIG. 16A provides a graph illustrating the in vitro anti-proliferation activities of ADCs comprising a S239C mutant of antibody Hu34C3 and a pyrrolobenzodiazepine in MM1.S cells.

FIG. 16B provides a graph illustrating the in vitro anti-proliferation activities of ADCs comprising a S239C mutant of antibody Hu34C3 and a pyrrolobenzodiazepine in L-363 cells.

FIG. 17A provides a graph illustrating the in vitro anti-proliferation activities of ADCs comprising the antibody Hu34C3 and a topoisomerase I inhibitor in OPM-2 cells.

FIG. 17B provides a graph illustrating the in vitro anti-proliferation activities of ADCs comprising the antibody Hu34C3 and a topoisomerase I inhibitor in L-363 cells.

Figure 18:
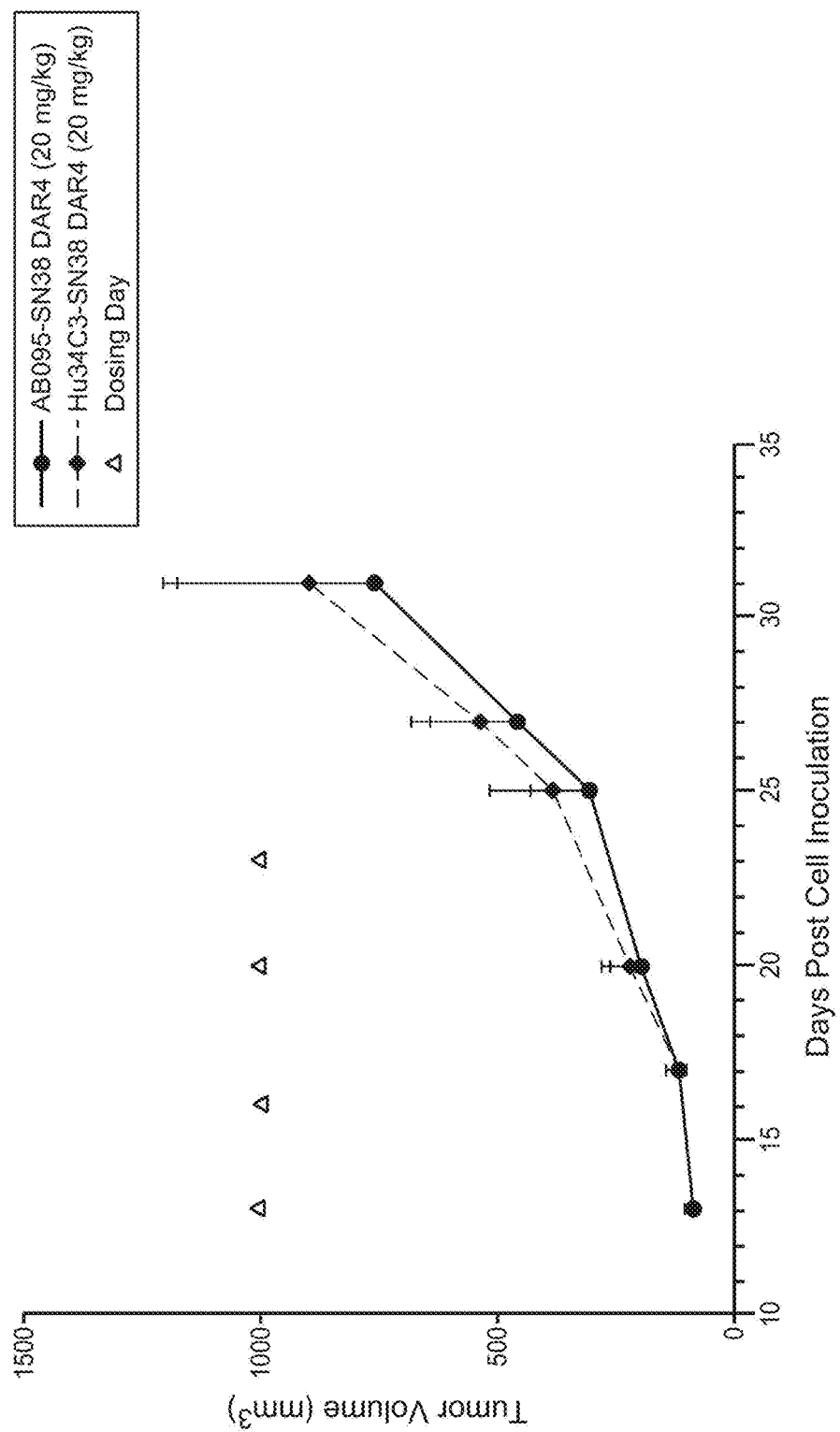

FIG. 18 provides a graph illustrating the in vivo anti-tumor activities of ADCs comprising the antibody Hu34C3 and a topoisomerase I inhibitor in an OPM-2 xenograft.

Figure 19A:
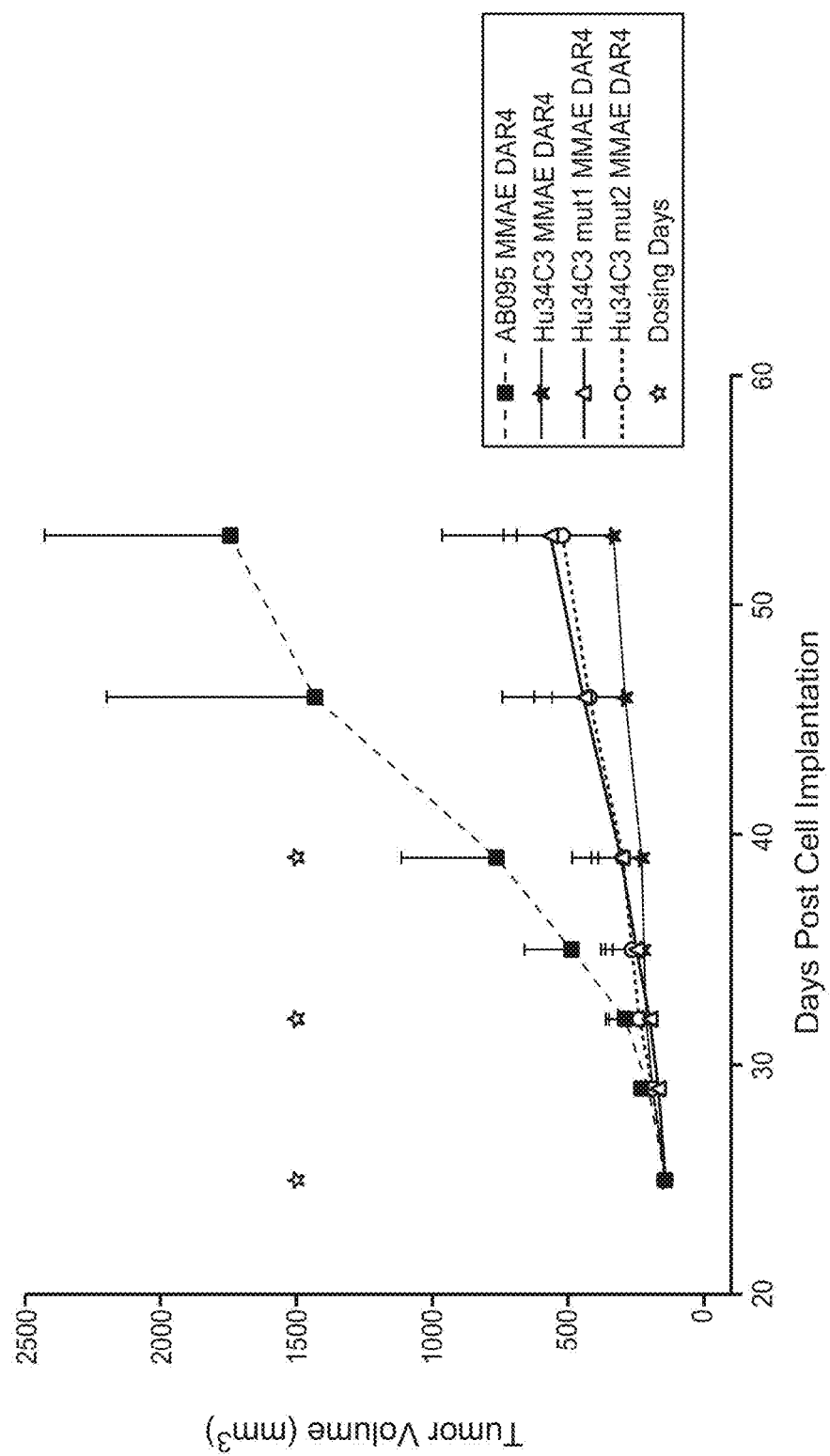
Figure 19B:
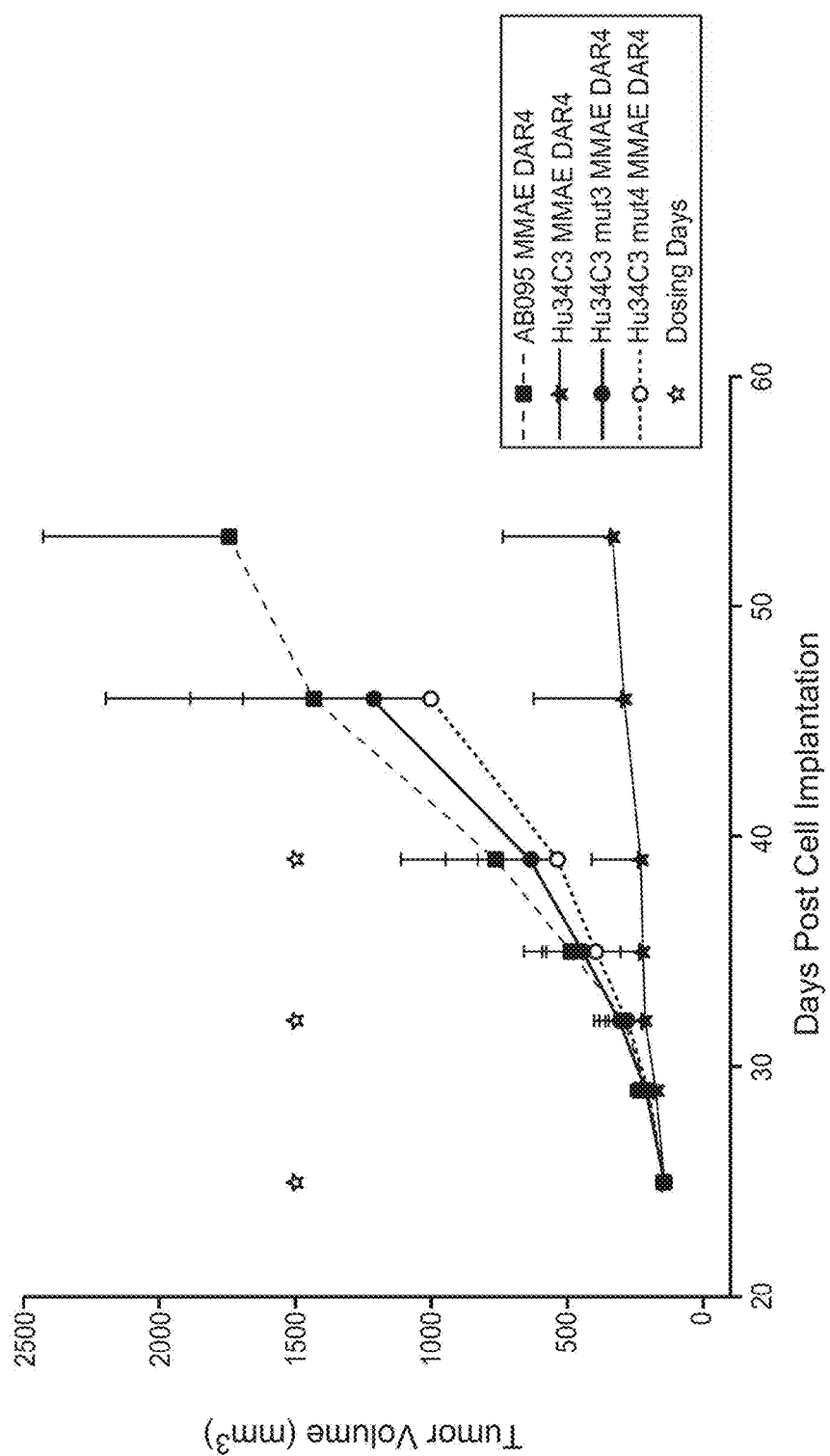

FIG. 19A and FIG. 19B provide graphs illustrating in vivo anti-tumor activity of ADCs comprising Fc mutants of Hu34C3 having lower ADCC, increased half life and/or reduced pinocytosis, as compared to Hu34C3.

Figure 20:
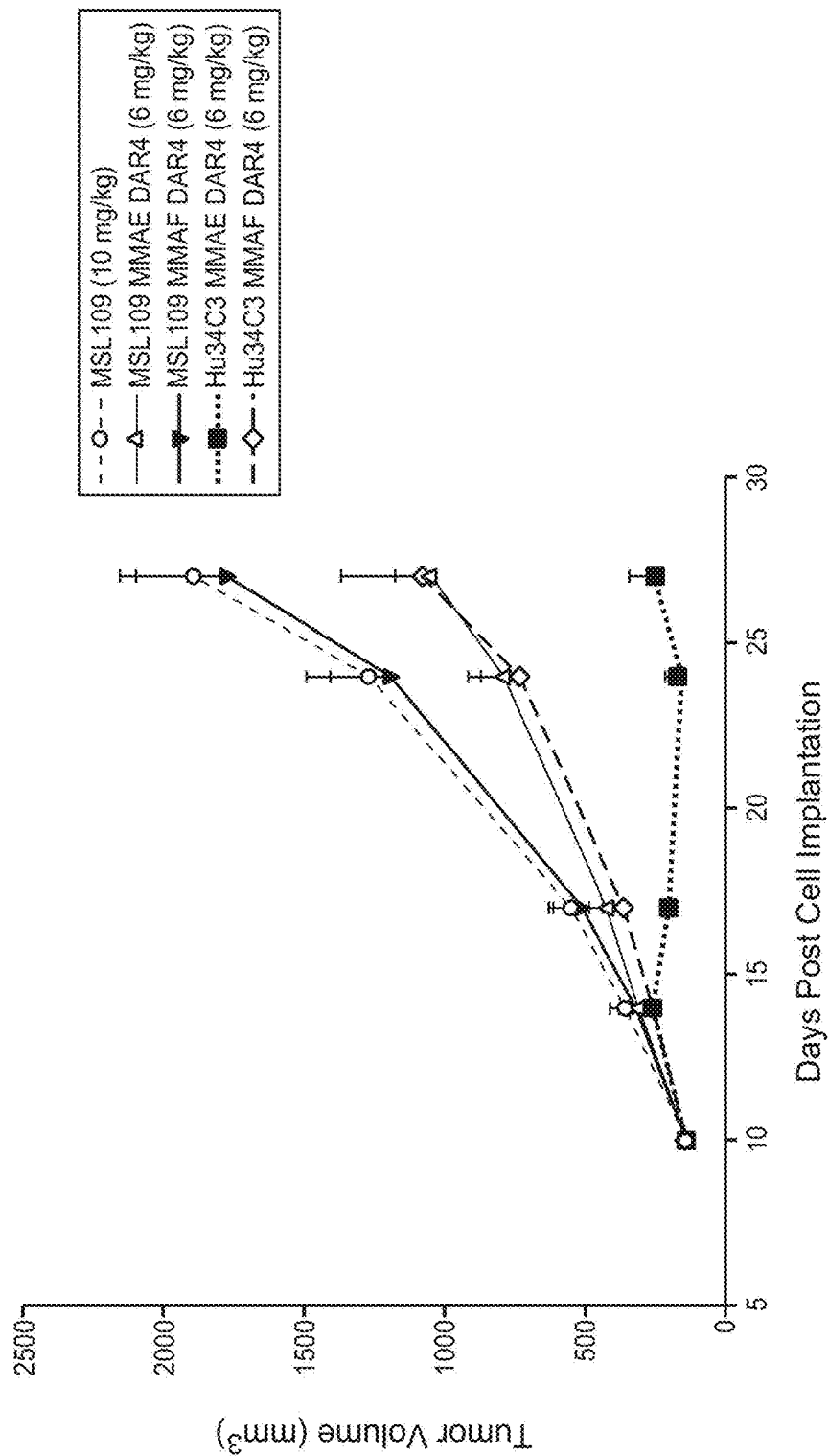

FIG. 20 provides a graph illustrating that MMAE ADCs of Hu34C3 are surprisingly more effective in vivo than corresponding MMAF ADCs.

Figure 21:
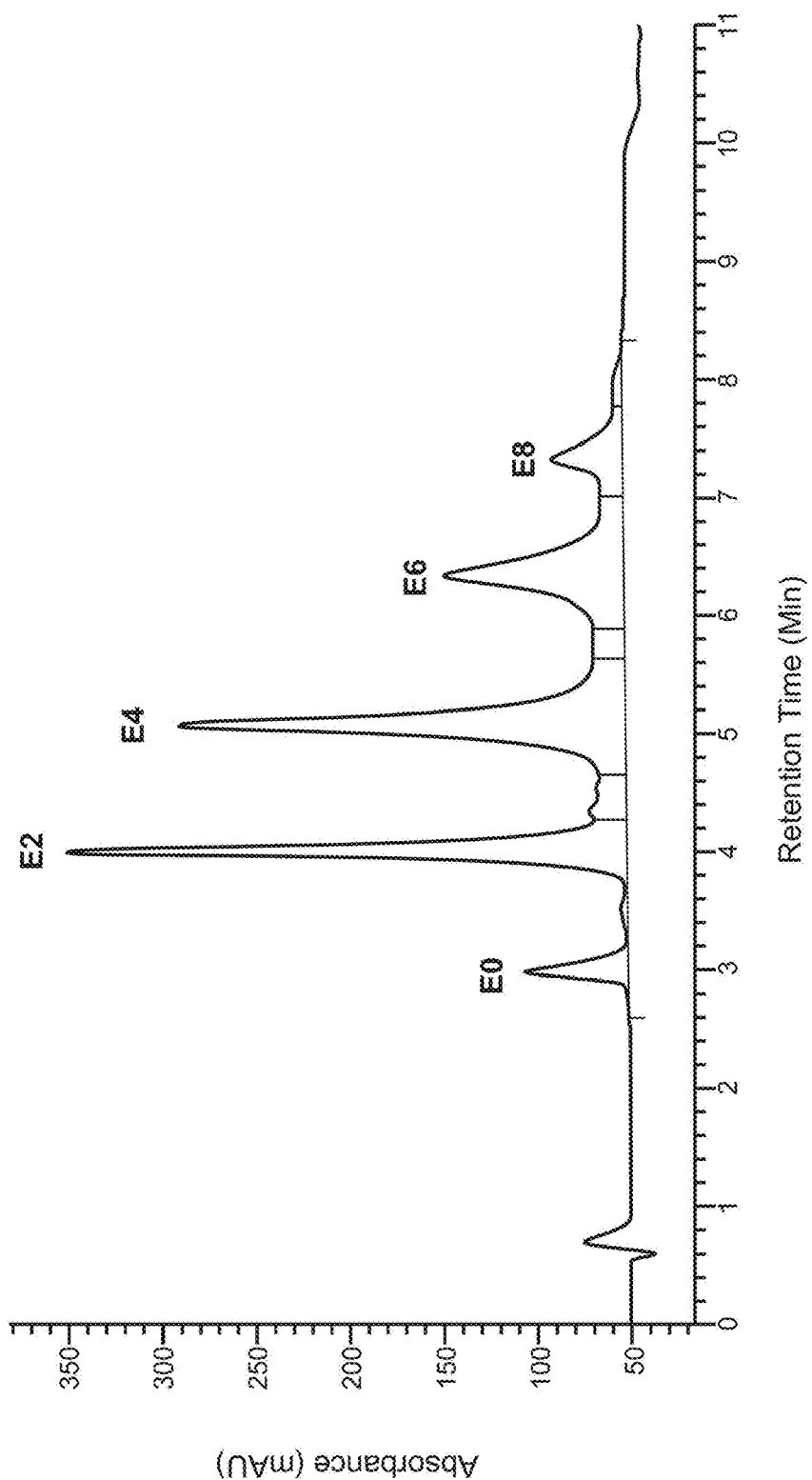

FIG. 21 is a graph illustrating chromatographic resolution of a crude preparation of an MMAE ADC conjugate of Hu34C3 loaded to an average DAR4. Retention times of the various Hu34C3 ADC peaks containing zero MMAE molecules per antibody ("E0"), two MMAE molecules per antibody ("E2"), four MMAE molecules per antibody ("E4"), six MMAE molecules per antibody ("E6") and eight MMAE molecules per antibody ("E8") are shown on the X-axis.

Figure 22A:
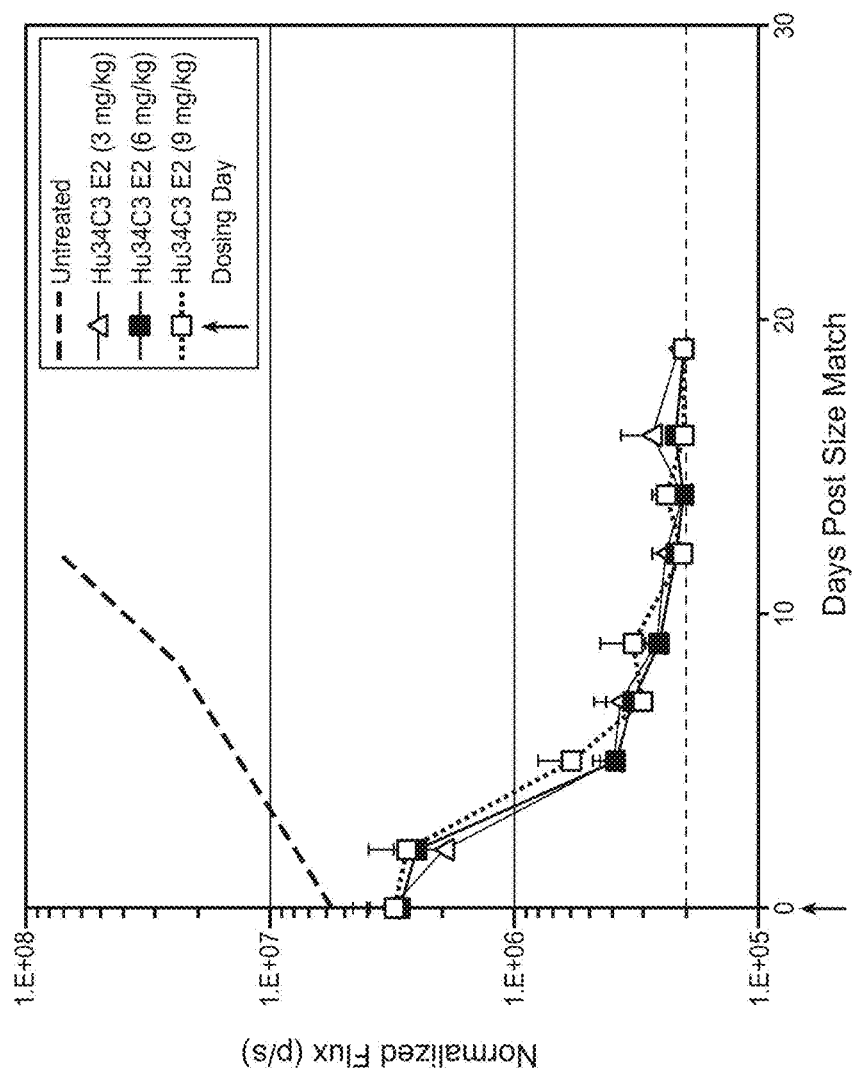
Figure 22B:
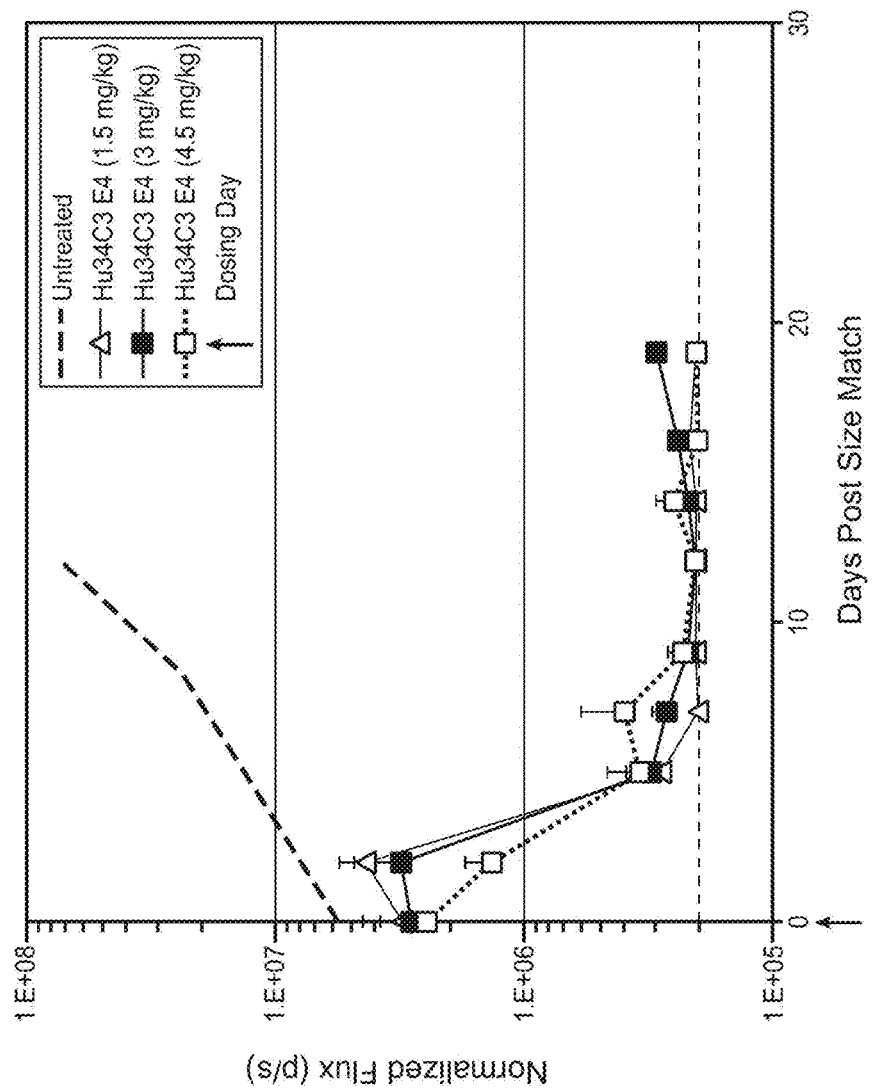

FIG. 22A and FIG. 22B provide graphs comparing the in vivo activity of enriched ADCs Hu34C3-MMAE E2 and Hu34C3-MMAE E4.

Figure 23A:
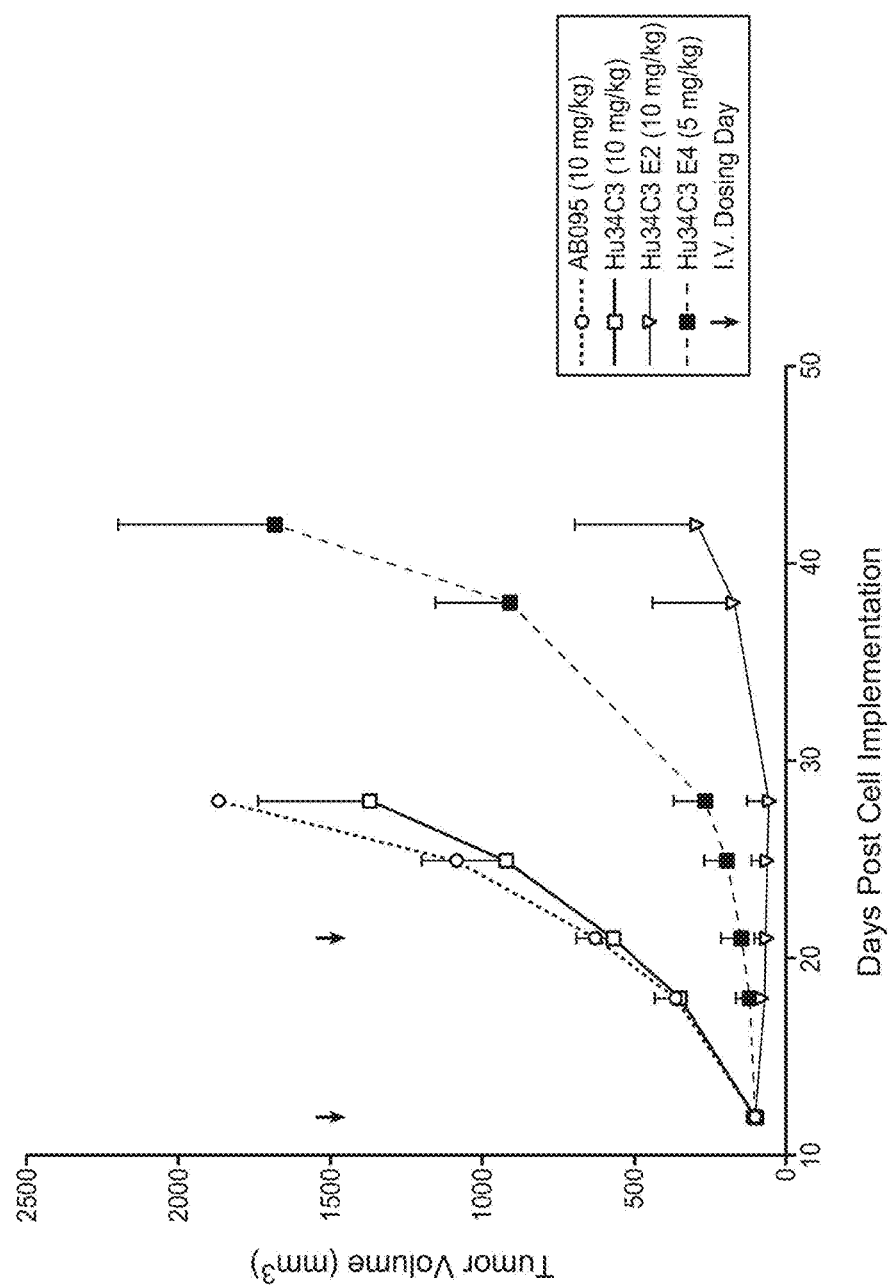
Figure 23B:
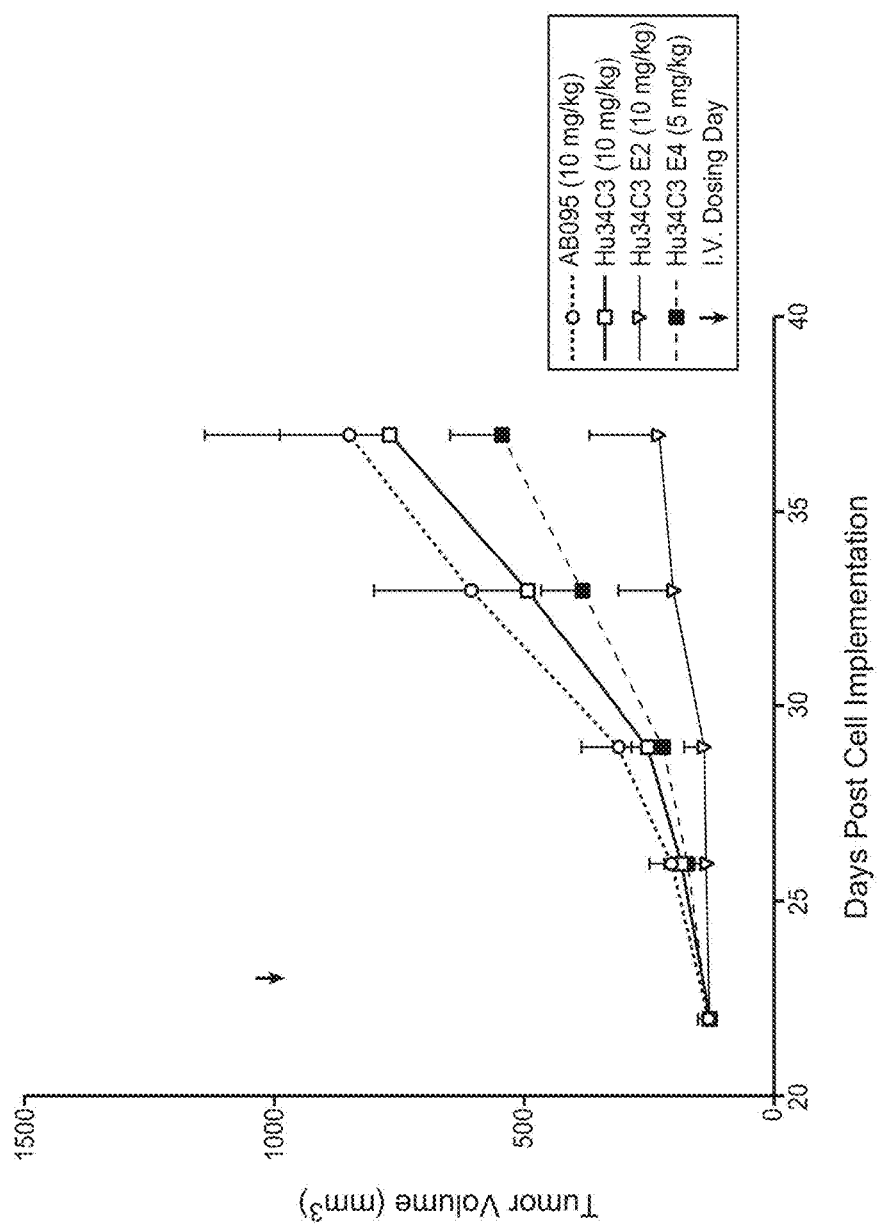
Figure 23C:
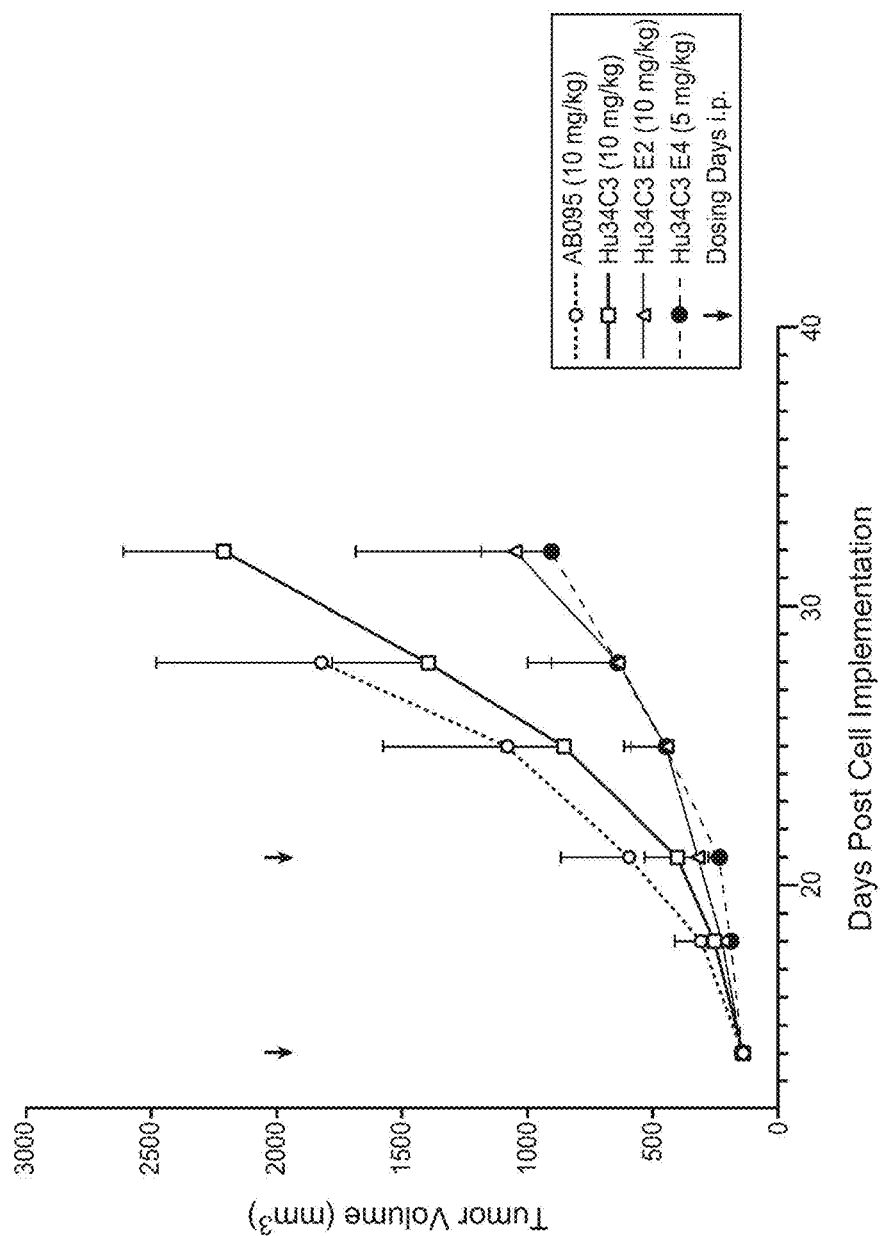

FIGS. 23A-23C provide graphs comparing the in vivo activity of enriched ADCs Hu34C3-MMAE E2 and Hu34C3-MMAE E4 in three animal models, the L-363 model (FIG. 23A), the MM1.S model (FIG. 23B) and the MOLP-8 xenograft model (FIG. 23C).

Figure 24A:
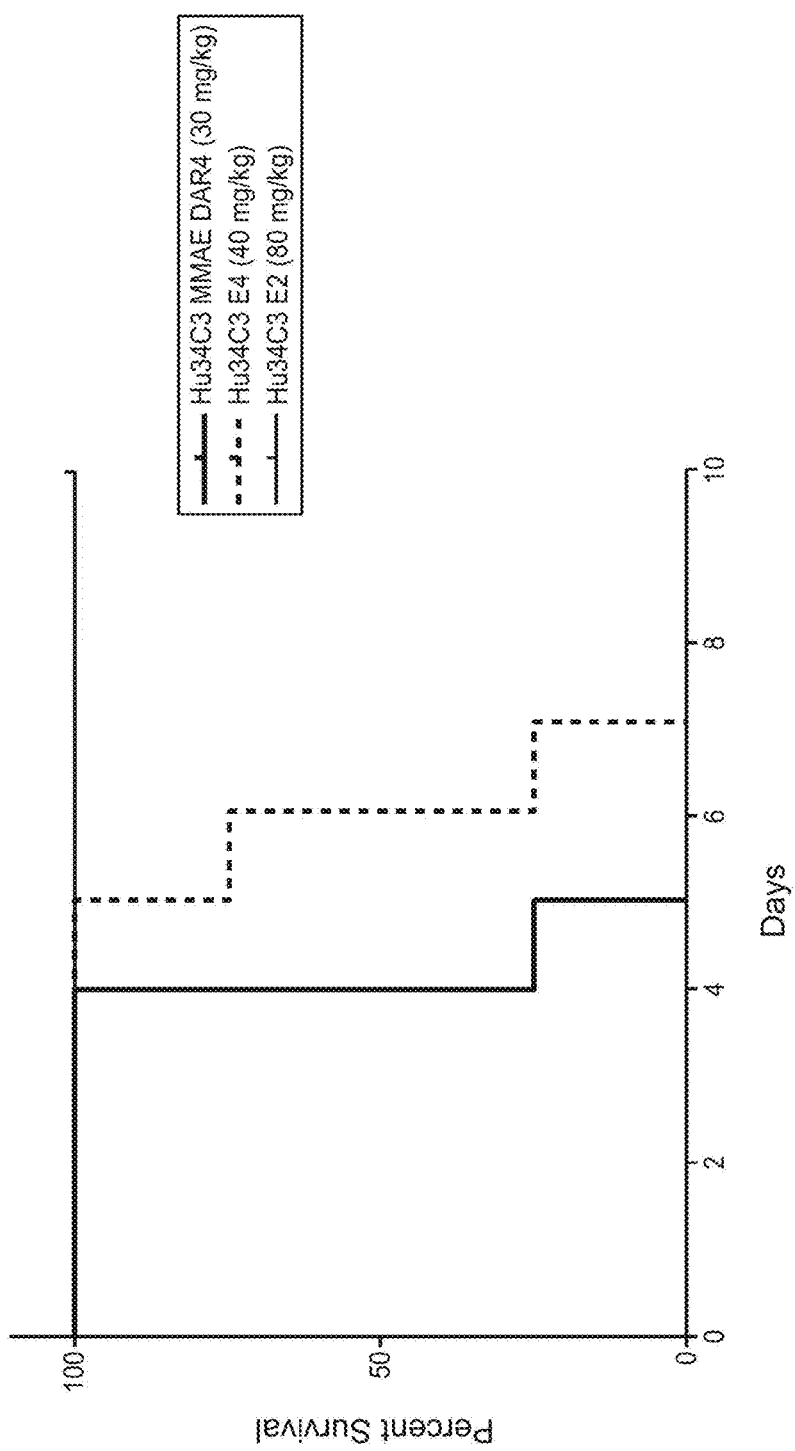
Figure 24B:
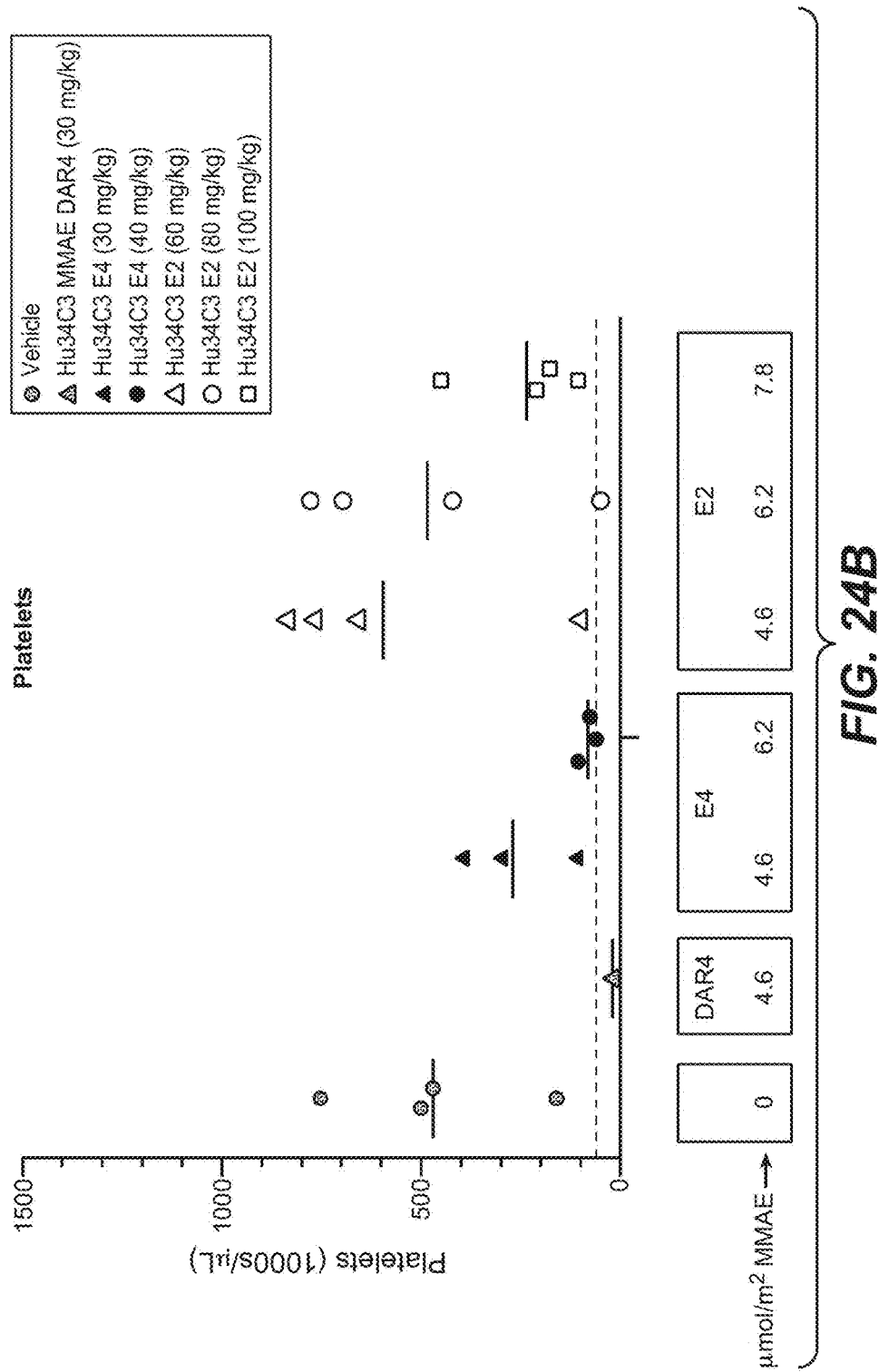
Figure 24C:
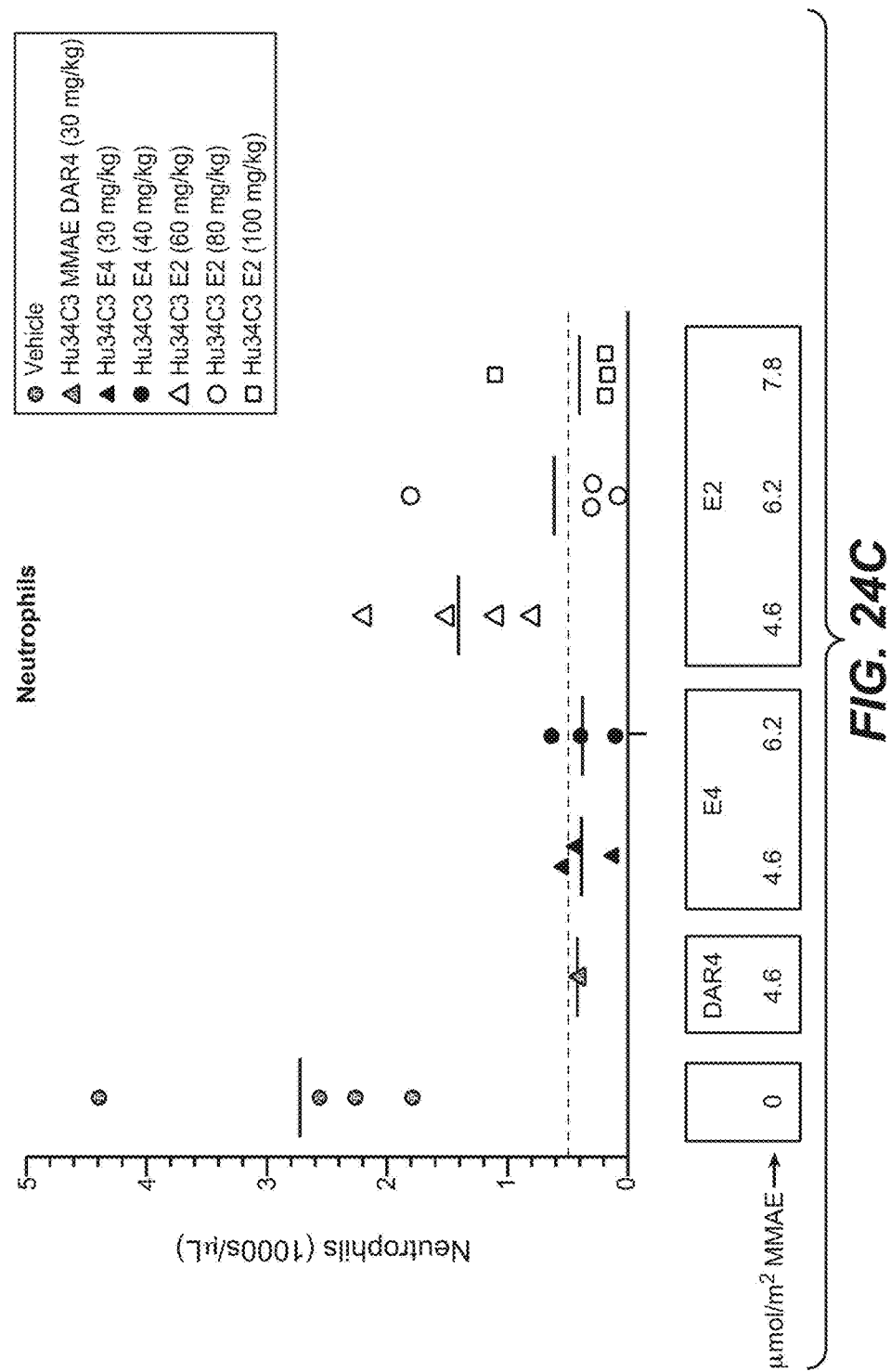
Figure 24D:
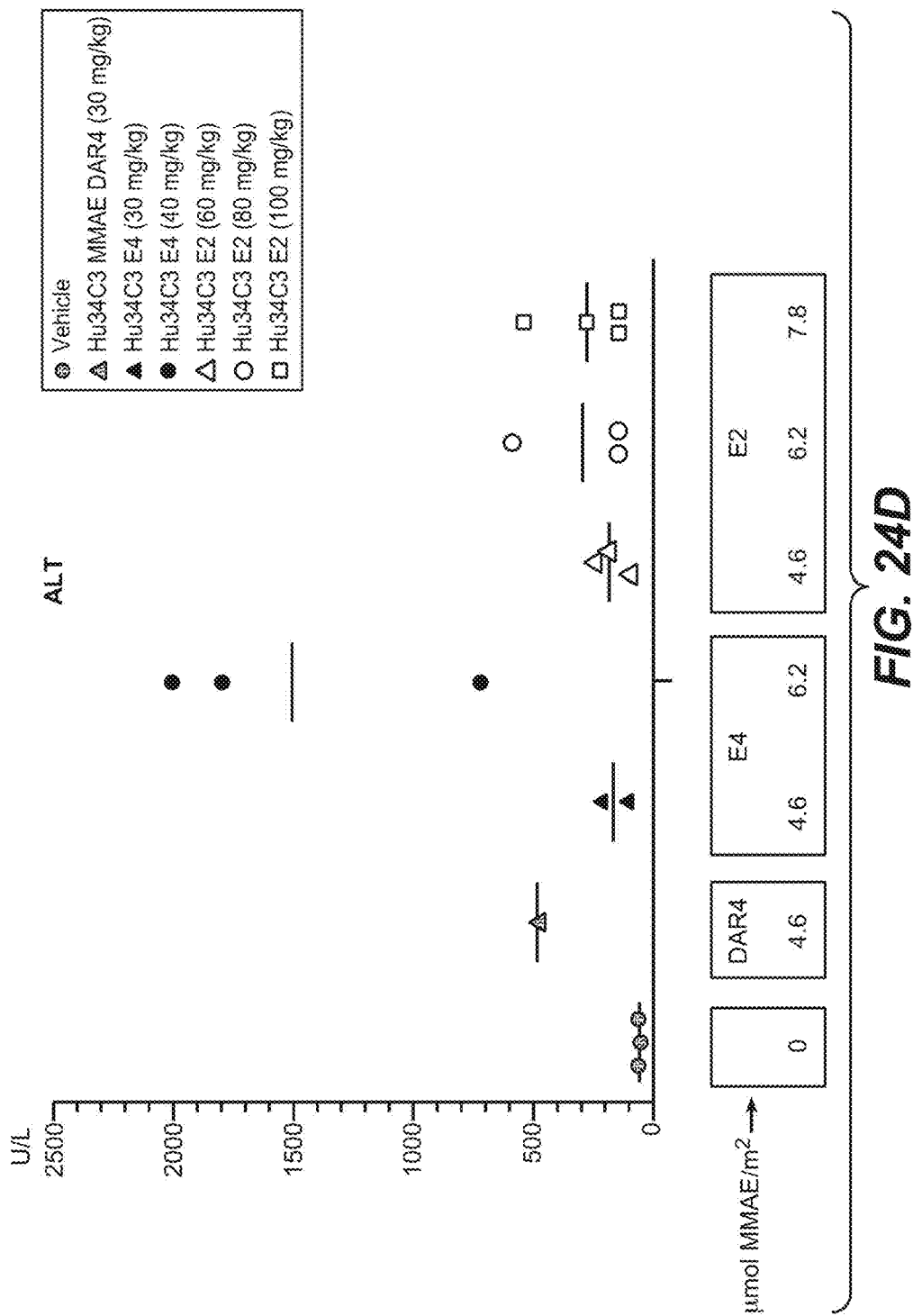

FIGS. 24A-24D provide graphs showing that ADC Hu34C3-MMAE E2 is less toxic than Hu34C3-MMAE E4 in rats (FIG. 24A) and better tolerated (FIG. 24B, FIG. 24C, and FIG. 24D).

Figure 25:
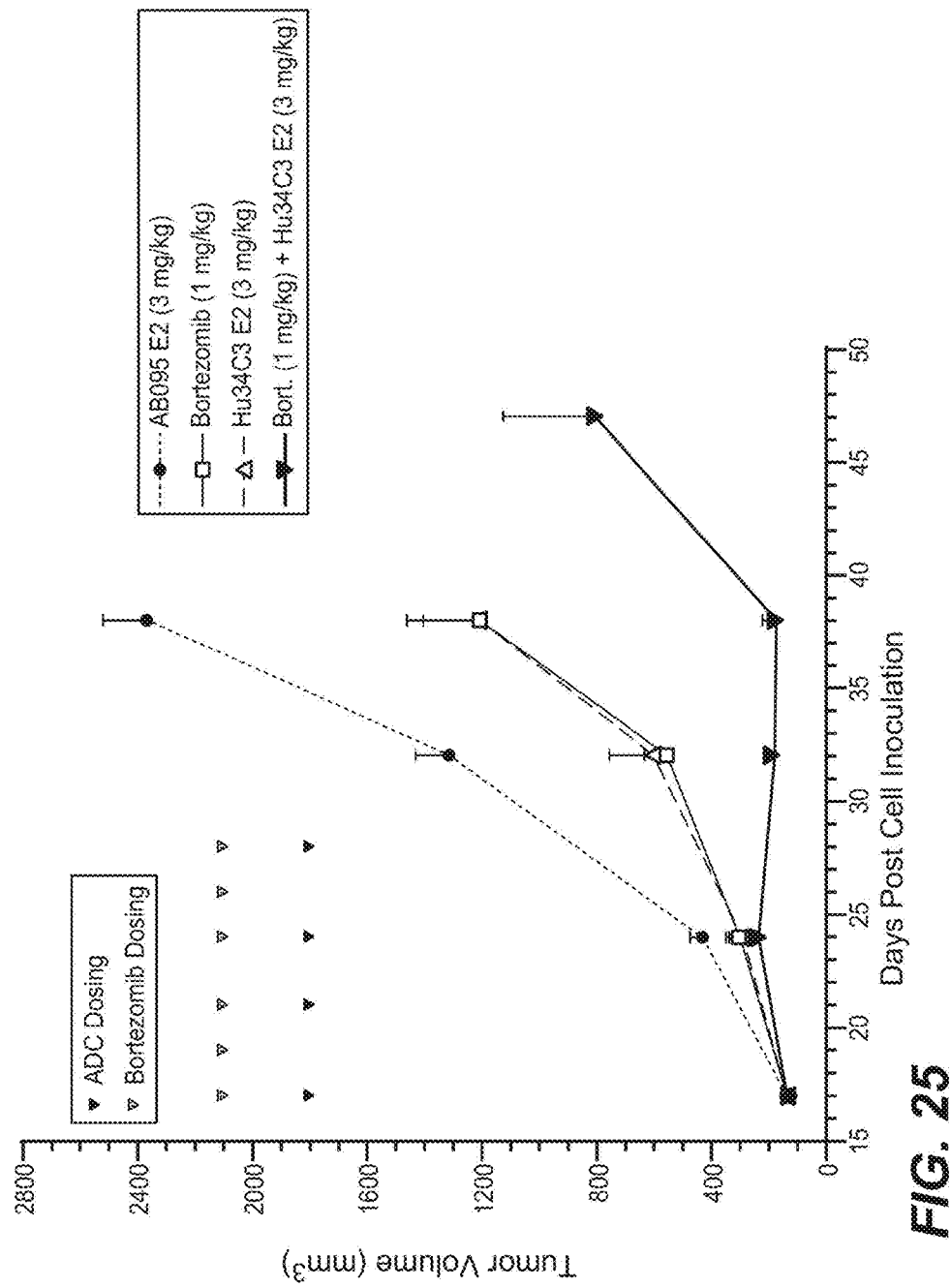

FIG. 25 provides a graph showing growth inhibition of OPM-2 xenografts by ADC Hu34C3-MMAE E2 alone and in combination with bortezomib in effector cell negative mice.

Figure 26A:
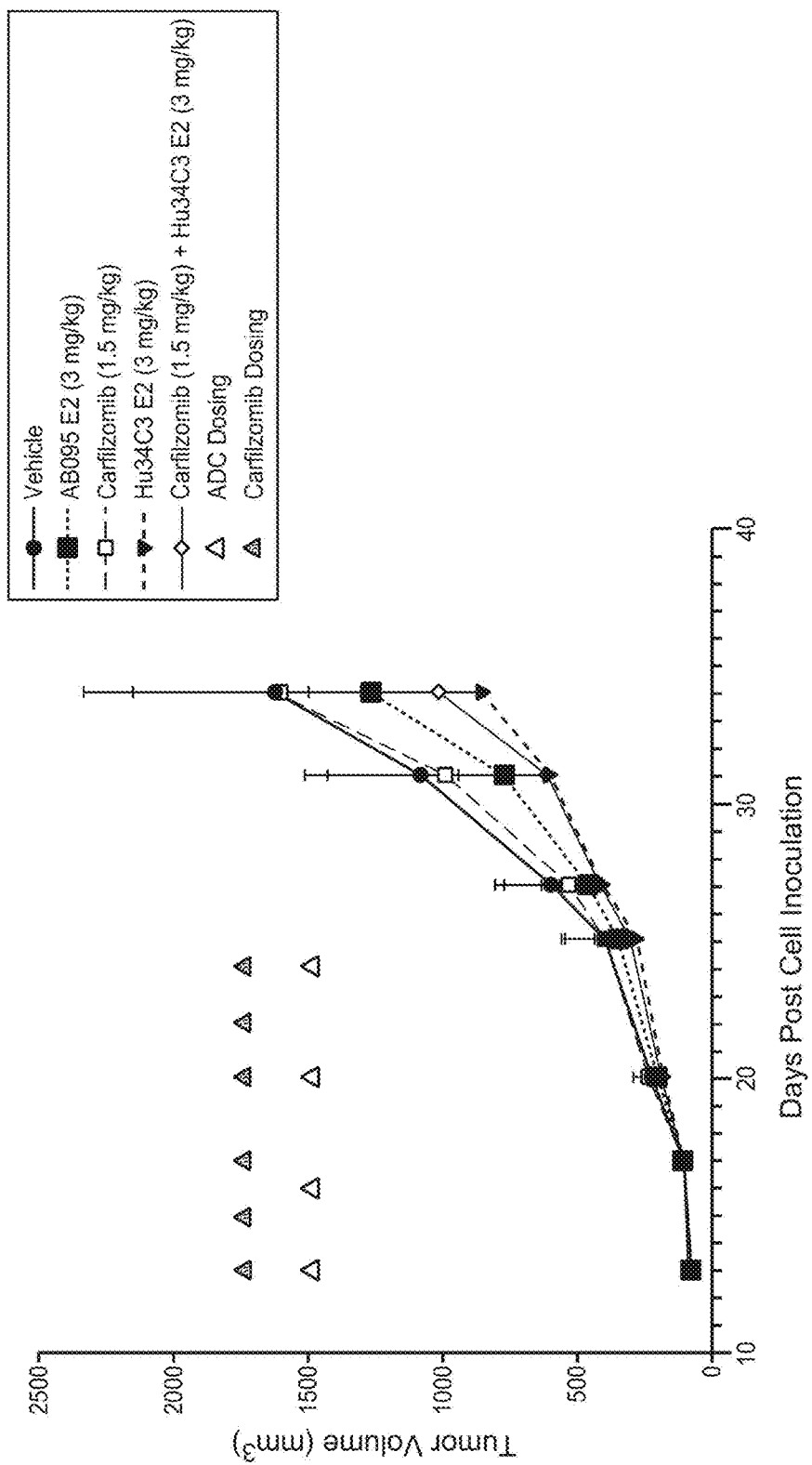
Figure 26B:
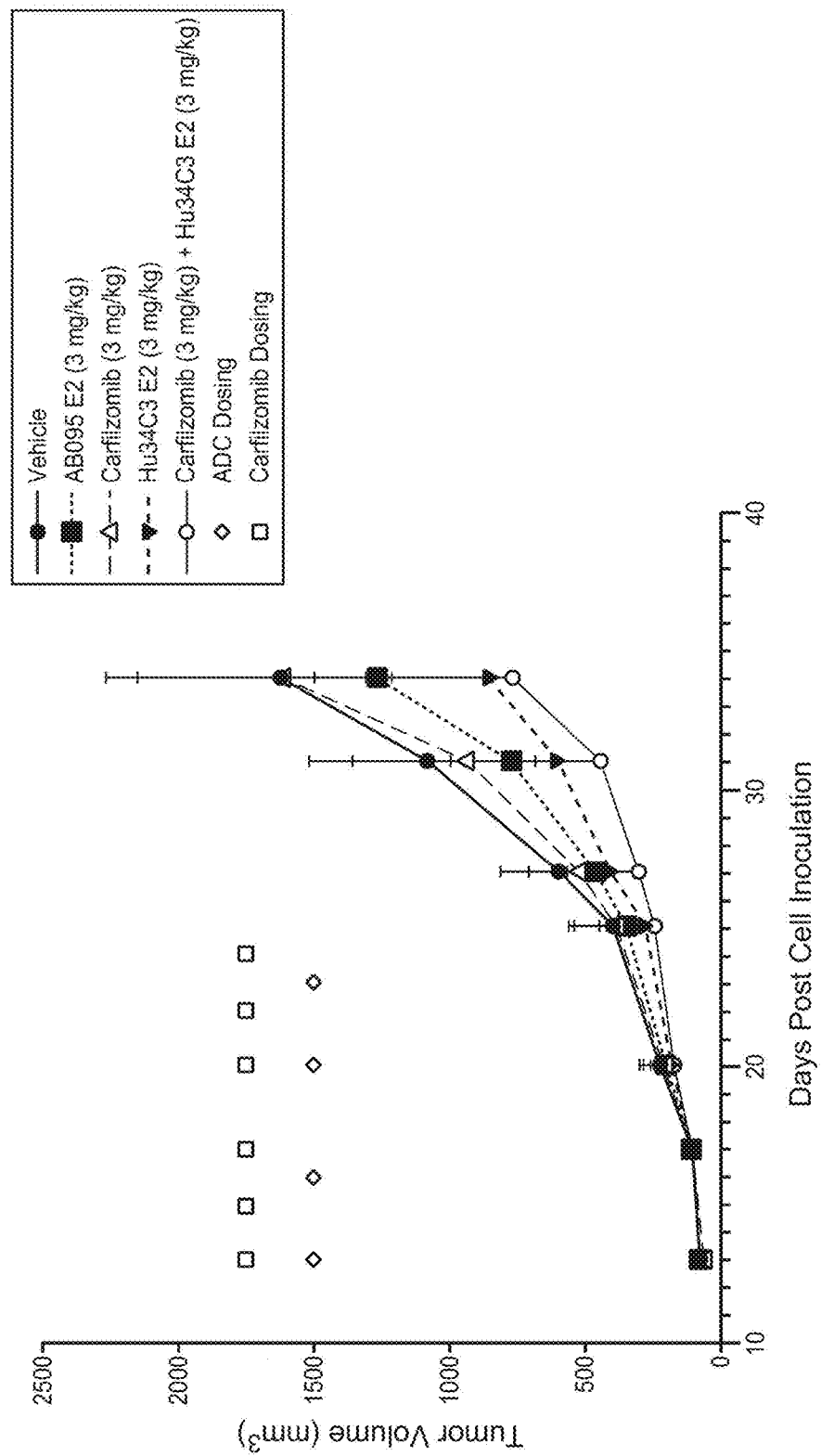

FIG. 26A and FIG. 26B provide graphs showing growth inhibition of OPM-2 xenografts by ADC Hu34C3-MMAE E2 alone and in combination with carfilzomib in effector cell negative mice. FIG. 26A provides a graph showing the results with carfilzomib at 1.5 mg/kg dosing. FIG. 26B provides a graph showing the results with carfilzomib at 3 mg/kg dosing.

Figure 27:
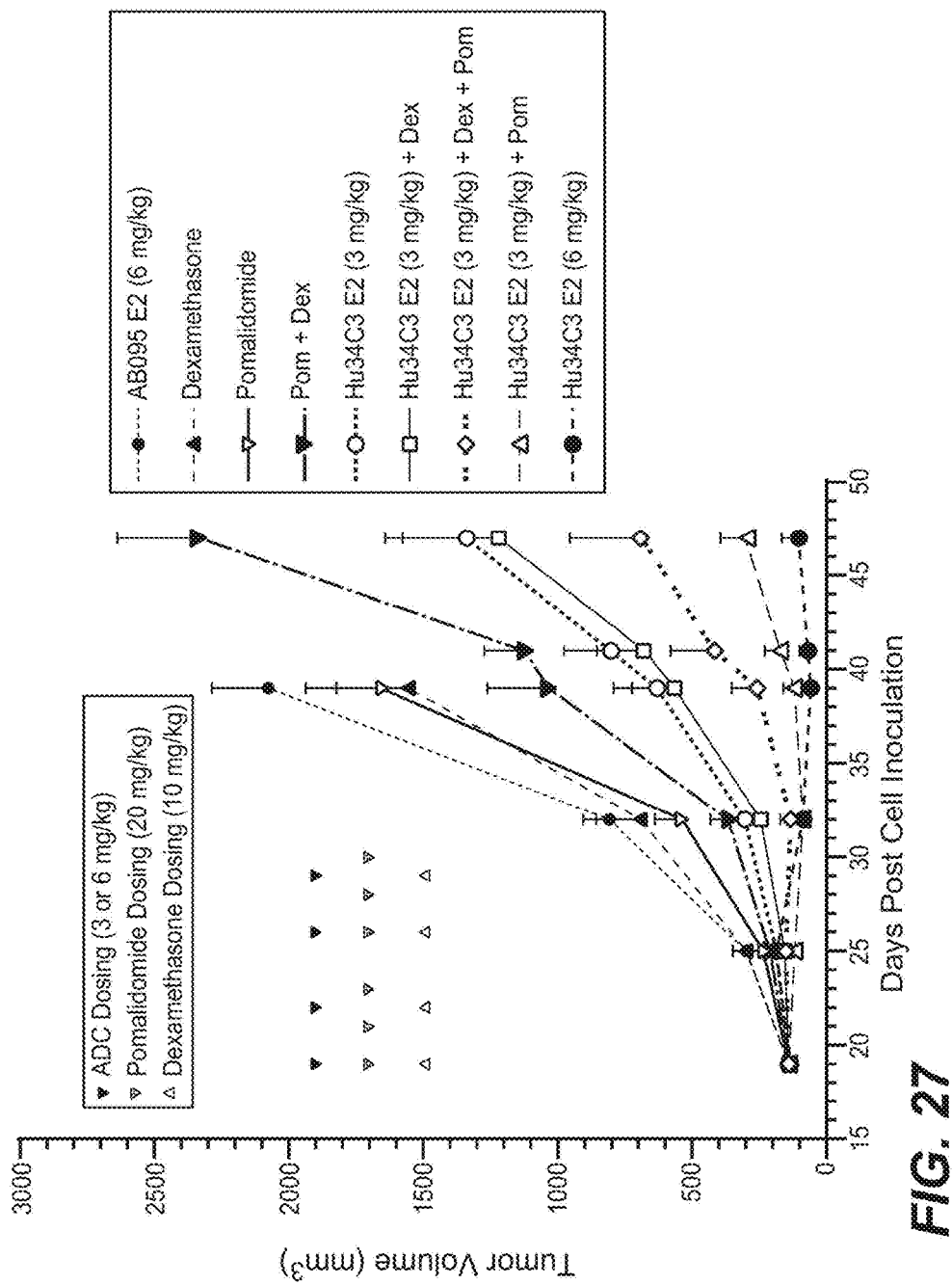

FIG. 27 provides a graph showing growth inhibition of OPM-2 xenografts by ADC Hu34C3-MMAE E2 alone and in combination with pomalidomide and/or dexamethasone in effector cell negative mice.

Figure 28:
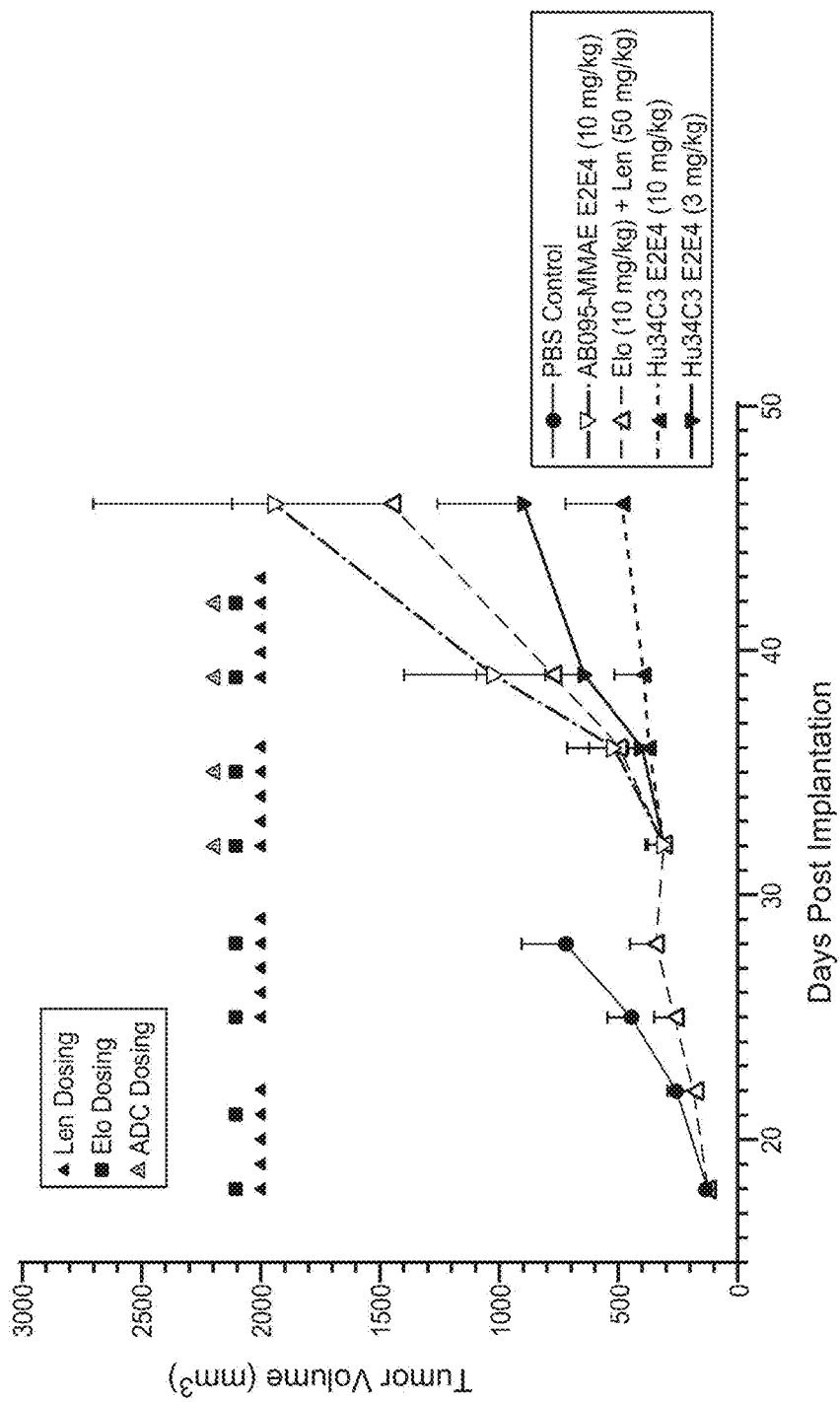

FIG. 28 provides a graph showing growth inhibition of L-363 xenografts by different doses of ADC Hu34C3-MMAE E2 in effector cell negative mice pre-treated with a combination of elotuzumab and lenalidomide.

Figure 29:
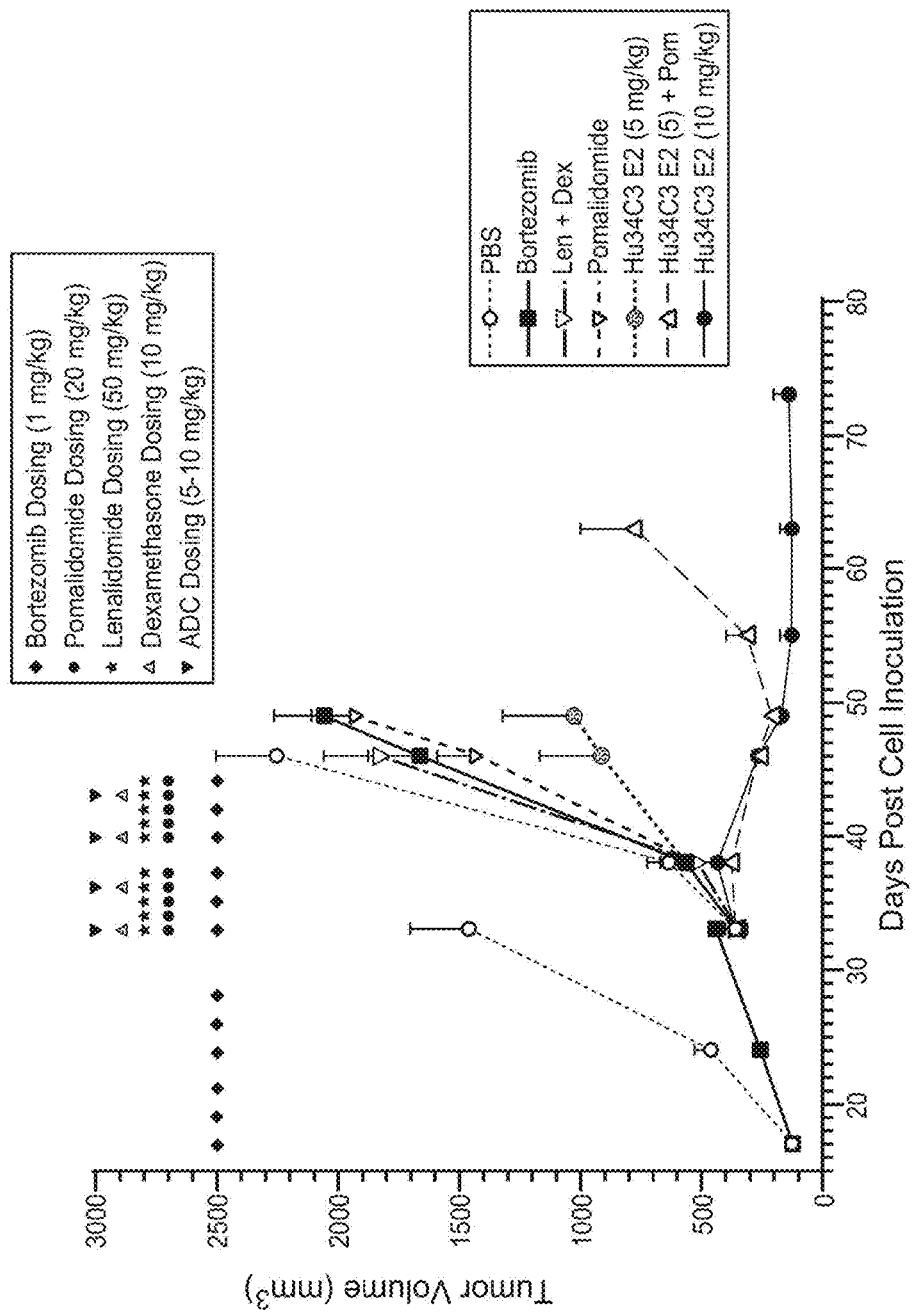

FIG. 29 provides a graph illustrating the anti-tumor activity of ADC Hu34C3-MMAE E2 alone and adjunctive to bortezomib, pomalidomide and/or lenalidomide and dexamethasone.

FIG. 30 provides $V_H$ and $V_L$ sequences for antibodies PDL241 (SEQ ID NO:38 and SEQ ID NO:39, respectively), elotuzumab (SEQ ID NO:36 and SEQ ID NO:37, respectively), and Luc34.3.8 (SEQ ID NO:40 and SEQ ID NO:41, respectively). Bold underline regions indicate CDRs.

Figure 31:
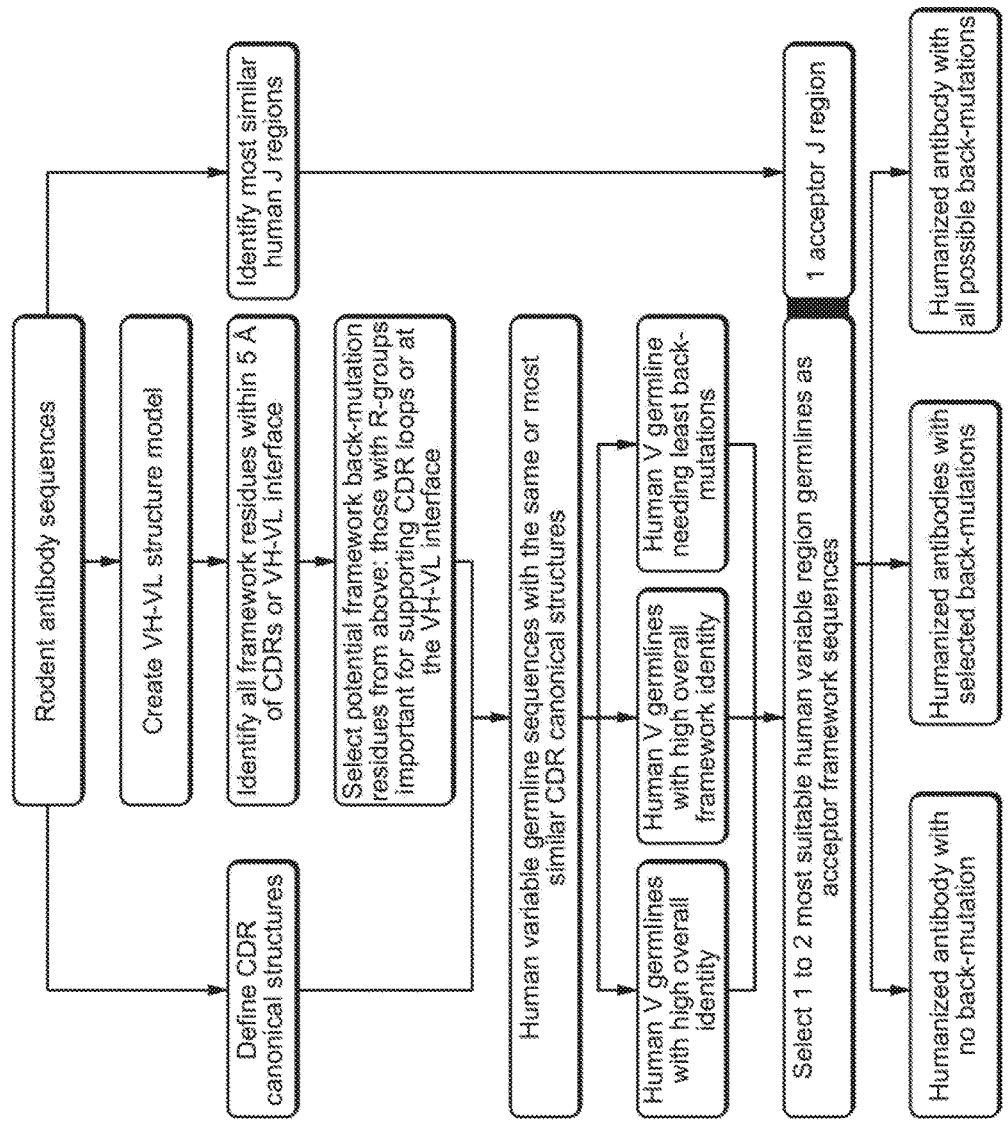

FIG. 31 provides a flow chart showing the antibody humanization process.

7. DETAILED DESCRIPTION

The present disclosure concerns antibodies that specifically bind HuCS1 and that are cross-reactive with CmCS1, ADCs comprising the antibodies, compositions comprising the antibodies and/or ADCs, polynucleotides encoding the anti-CS1 antibodies, host cells capable of producing the anti-CS1 antibodies, methods of making the anti-CS1 antibodies and ADCs, and various methods of using the anti-CS1 antibodies ADCs.

As will be appreciated by skilled artisans, antibodies and/or binding fragments are "modular" in nature. Throughout the disclosures, various specific embodiments of the various "modular" comprising the antibodies and/or binding fragments are described. As specific non-binding examples, various specific embodiments of $V_H$ CDRs, $V_H$ chains, $V_L$ CDRs and $V_L$ chains are described. It is intended that all of the specific embodiments may be combined with each other as though each specific combination were explicitly described.

The ADCs disclosed herein are "modular" in nature. Throughout the instant disclosure, various specific embodiments of the various "modules" comprising the ADCs are described. As specific non-limiting examples, specific embodiments of antibodies, linkers, and cytotoxic and/or cytostatic agents that may comprise the ADCs are described. It is intended that all of the specific embodiments described may be combined with each other as though each specific combination were explicitly described individually.

It will also be appreciated by skilled artisans that the various anti-CS1 antibodies and ADCs described herein may be in the form of salts, and in some specific embodiments, pharmaceutically acceptable salts. The anti-CS1 antibodies and/or ADCs of the disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as a bromide, chloride, or fluoride.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, etc. Base addition salts include those derived from inorganic bases, such as ammonium and alkali or alkaline earth metal hydroxides, carbonates, bicarbonates, and the like.

7.1. Abbreviations

The antibodies, binding fragments, ADCs and polynucleotides described herein are, in many embodiments, described by way of their respective polypeptide or polynucleotide sequences. Unless indicated otherwise, polypeptide sequences are provided in N→C orientation; polynucleotide sequences in 5'→3' orientation. For polypeptide sequences, the conventional three or one-letter abbreviations for the genetically encoded amino acids are used, as noted in TABLE 1, below.

TABLE 1

Encoded Amino Acid Abbreviations

| Amino Acid | Three Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Certain sequences are defined by structural formulae specifying amino acid residues belonging to certain classes (e.g., aliphatic, hydrophobic, etc.). The various classes to which the genetically encoded amino acids belong as used herein are noted in TABLE 2, below. Some amino acids may belong to more than one class. Cysteine, which contains a sulfhydryl group, and proline, which is conformationally constrained, are not assigned classes.

TABLE 2

Encoded Amino Acid Classes

| Class | Amino Acids |
|---|---|
| Aliphatic | A, I, L, V |
| Aromatic | F, Y, W |
| Non-Polar | M, A, I, L, V |
| Polar | N, Q, S, T |
| Basic | H, K, R |
| Acidic | D, E |
| Small | A, G |

The abbreviations used for the various exemplary and other antibodies disclosed herein are provided in TABLE 3, below:

TABLE 3

Antibody Abbreviations

| Clone/Name | Abbreviation | $V_H$ Sequence (FIG. 2A) | | $V_L$ Sequence (FIG. 2B) | |
|---|---|---|---|---|---|
| CS1.AD159.4F2 | Mu4F2 | Not sequenced | | Not sequenced | |
| CS1.AD159.34C3 | Mu34C3 | Mu34C3$V_H$ | SEQ ID NO: 5 | Mu34C3$V_L$ | SEQ ID NO: 6 |
| CS1.AD159.31D2 | Mu31D2 | Mu31D2$V_H$ | SEQ ID NO: 14 | Mu31D2$V_L$ | SEQ ID NO: 15 |
| CS1.AD159.27A12 | Mu27A12 | Mu27A12$V_H$ | SEQ ID NO: 21 | Mu27A12$V_L$ | SEQ ID NO: 22 |
| CS1.AD159.12D10 | Mu12D10 | Mu12D10$V_H$ | SEQ ID NO: 28 | Mu12D10$V_L$ | SEQ ID NO: 29 |
| CS1.AD159.12D10.2 | Mu12D10.2 | Not sequenced | | Not sequenced | |

TABLE 3-continued

Antibody Abbreviations

| Clone/Name | Abbreviation | $V_H$ Sequence (FIG. 2A) | | $V_L$ Sequence (FIG. 2B) | |
|---|---|---|---|---|---|
| CS1.AD159.14C11 | Mu14C11 | Mu14C11$V_H$ | SEQ ID NO: 30 | Mu14C11$V_L$ | SEQ ID NO: 31 |
| CS1.AD159.27H1 | Mu27H1 | Mu27H1$V_H$ | SEQ ID NO: 32 | Mu27H1$V_L$ | SEQ ID NO: 33 |
| CS1.AD159.28A6 | Mu28A6 | 3 variants; not sequenced | | 3 variants; not sequenced | |
| CS1.AD159.30C1 | Mu30C1 | Not sequenced | | Not sequenced | |
| CS1.AD176.1 | Mu176.1 | Not sequenced | | Not sequenced | |
| CS1.AD176.1.1 | Mu176.1.1 | Not sequenced | | Not sequenced | |
| CS1.AD176.2.3 | Mu176.2.3 | Not sequenced | | Not sequenced | |
| CS1.AD176.3.3 | Mu176.3.3 | Not sequenced | | Not sequenced | |
| CS1.AD176.4 | Mu176.4 | Not sequenced | | Not sequenced | |
| CS1.AD176.4.1 | Mu176.4.1 | Not sequenced | | Not sequenced | |
| CS1.AD176.7.1 | Mu176.7.1 | Not sequenced | | Not sequenced | |
| CS1.AD176.8.1 | Mu176.8.1 | Not sequenced | | Not sequenced | |
| CS1.AD176.9.1 | Mu176.9.1 | Not sequenced | | Not sequenced | |
| CS1.AD176.13 | Mu176.13 | Not sequenced | | Not sequenced | |
| CS1.AD176.17 | Mu176.17 | Not sequenced | | Not sequenced | |
| HuCS1.34C3 | Hu34C3 | Hu34C3$V_H$.1b | SEQ ID NO: 8 | Hu34C3$V_L$.1a | SEQ ID NO: 10 |
| Hu34C3 S55E | Hu34C3 S55E | Hu34C3$V_H$S55E | SEQ ID NO: 12 | Hu34C3$V_L$.1a | SEQ ID NO: 10 |
| Hu34C3 N30L | Hu34C3 N30L | Hu34C3$V_H$.1b | SEQ ID NO: 8 | Hu34C3$V_L$N30L | SEQ ID NO: 13 |
| Hu34C3 S55E/N30L | Hu34C3 S55E/N30L | Hu34C3$V_H$S55E | SEQ ID NO: 12 | Hu34C3$V_L$N30L | SEQ ID NO: 13 |
| HuCS1.31D2.2 | Hu31D2 | Hu31D2$V_H$.1 | SEQ ID NO: 16 | Hu31D2$V_L$.1a | SEQ ID NO: 19 |
| HuCS1.27A12 | Hu27A12 | Hu27A12$V_H$.1b | SEQ ID NO: 24 | Hu27A12$V_L$.1a | SEQ ID NO: 26 |

7.2. Definitions

Unless otherwise defined herein, scientific and technical terms used in connection with the present disclosure shall have the meanings that are commonly understood by those of ordinary skill in the art.

As used herein, "elotuzumab" refers to the monoclonal humanized IgG$_1$ antibody disclosed as "HuLuc63" in U.S. Pat. No. 7,709,610 (the "'610 patent"). The sequence of the $V_H$ chain is disclosed as SEQ ID NO:41 in the '610 patent; the sequence of the $V_L$ chain as SEQ ID NO:44 in the '610 patent. These sequences are illustrated in FIG. 30.

As used herein, "PDL241" refers to the monoclonal humanized IgG$_1$ antibody derived from the antibody disclosed as LucX in US Pub. No. 2006/0024296. The sequences of the $V_H$ and $V_L$ chains are illustrated in FIG. 30.

As used herein, "Luc34.3.8" refers to the murine monoclonal IgG$_1$ antibody described as "Luc34" in U.S. Pat. No. 8,445,646 (the "646 patent"). The sequence of the $V_H$ chain is disclosed as SEQ ID NO:7 in the '646 patent; the sequence of the $V_L$ chain as SEQ ID NO:8 in the '646 patent. These sequences are illustrated in FIG. 30.

7.3. Anti-CS1 Antibodies

One aspect of the disclosure concerns new anti-CS1 antibodies that specifically bind human HuCS1 (SEQ ID NO:1) at epitopes different from the epitopes bound by anti-CS1 antibodies reported in the literature, and specifically bind epitopes different from the epitopes bound by PDL241, elotuzumab and Luc34.3.8. Moreover, unlike elotuzumab, the new antibodies are cross-reactive with CmCS1, which provides the advantage of being able to test or confirm their biological properties in cynomolgus monkeys.

As used herein, the term "antibody" (Ab) refers to an immunoglobulin molecule that specifically binds to, or is immunologically reactive with, a particular antigen—here, HuCS1. The anti-CS1 antibodies of the disclosure bind to HuCS1 and inhibit proliferation of cells expressing CS1, and in some instances are cytotoxic to cells expressing CS1. Anti-CS1 antibodies of the disclosure comprise complementarity determining regions (CDRs), also known as hypervariable regions, in both the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies. See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al. unless otherwise indicated.

Using methods described in Example 1, infra, numerous antibodies that bind HuCS1 and that are cross-reactive with CmCS1 have been identified. Moreover, several anti-CS1 antibodies having good affinity for HuCS1 and good anti-tumor activity in vitro and/or in vivo assays have been identified, and the sequences of their CDRs and variable heavy and light chains have been determined. Sequence of the $V_H$ chains, $V_L$ chains and CDRs are provided in FIG. 2. As evidenced in competition assays, all of the antibodies bind epitopes that are different from epitopes bound by anti-CS1 antibodies reported in the literature, and in particular epitopes bound by PDL241, elotuzumab and Luc34.3.8. Antibody Mu34C3 and its humanized counterpart Hu34C3 bind an epitope that is unique.

The antibodies of the disclosure may be polyclonal, monoclonal, genetically engineered, and/or otherwise modified in nature, including but not limited to chimeric antibodies, humanized antibodies, human antibodies, primatized antibodies, single chain antibodies, bispecific antibodies, dual-variable domain antibodies, etc. In various embodiments, the antibodies comprise all or a portion of a constant region of an antibody. In some embodiments, the constant region is an isotype selected from: IgA (e.g., IgA$_1$ or IgA$_2$), IgD, IgE, IgG (e.g., IgG$_1$, IgG$_2$, IgG$_3$ or IgG$_4$), and IgM. In specific embodiments, the antibodies described herein comprise an IgG$_1$ constant region isotyope.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of the anti-CS1 antibodies in humans, chimeric, primatized, humanized, or human antibodies can suitably be used.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816397, which are incorporated herein by reference in their entireties.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and U.S. Pat. No. 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

"Human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

"Primatized antibodies" comprise monkey variable regions and human constant regions. Methods for producing primatized antibodies are known in the art. See, e.g., U.S. Pat. Nos. 5,658,570; 5,681,722; and 5,693,780, which are incorporated herein by reference in their entireties.

Anti-CS1 antibodies of the disclosure include both full-length (intact) antibody molecules, as well as binding fragments that are capable of specifically binding HuCS1. Examples of antibody binding fragments include by way of example and not limitation, Fab, Fab', F(ab')$_2$, Fv fragments, single chain Fv fragments and single domain fragments.

An Fab fragment contains the constant domain of the light chain and the first constant domain (CH$_1$) of the heavy chain. Fab' fragments differ from Fab fragments by the addition of a few residues at the carboxyl terminus of the heavy chain CH$_1$ domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_2$ fragments lack the Fc fragment of intact antibody, clear more rapidly from the circulation of animals, and may have less non-specific tissue binding than an intact antibody (see, e.g., Wahl et al., 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site.

"Single-chain Fv" or "scFv" antibody binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for target binding.

"Single domain antibodies" are composed of a single $V_H$ or $V_L$ domains which exhibit sufficient affinity to HuCS1. In a specific embodiment, the single domain antibody is a camelized antibody (See, e.g., Riechmann, 1999, Journal of Immunological Methods 231:25-38).

The anti-CS1 antibodies of the disclosure may also be bispecific antibodies. Bispecific antibodies are monoclonal, often human or humanized, antibodies that have binding specificities for two different epitopes on the same or different antigen. In the present disclosure, one of the binding specificities can be directed towards CS1, the other can be for any other antigen, e.g., for a cell-surface protein, receptor, receptor subunit, tissue-specific antigen, virally derived protein, virally encoded envelope protein, bacterially derived protein, or bacterial surface protein, etc.

The anti-CS1 antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (See, e.g., Wolfson, 2006, Chem. Biol. 13(10):1011-2).

The anti-CS1 antibodies or binding fragments may be antibodies or fragments whose sequences have been modified to alter at least one constant region-mediated biological effector function. For example, in some embodiments, an anti-CS1 antibody may be modified to reduce at least one constant region-mediated biological effector function relative to the unmodified antibody, e.g., reduced binding to the Fc receptor (FcγR). FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147: 2657-2662). Reduction in FcγR binding ability of the antibody can also reduce other effector functions which rely on FcγR interactions, such as opsonization, phagocytosis and antigen-dependent cellular cytotoxicity ("ADCC").

The anti-CS1 antibody or binding fragment described herein include antibodies and/or binding fragments that have been modified to acquire or improve at least one constant region-mediated biological effector function relative to an unmodified antibody, e.g., to enhance FcγR interactions (See, e.g., US 2006/0134709). For example, an anti-CS1 antibody of the disclosure can have a constant region that binds FcγRIIA, FcγRIIB and/or FcγRIIIA with greater affinity than the corresponding wild type constant region.

Thus, antibodies of the disclosure may have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (shown in FIG. 4 of U.S. Pat. No. 5,834,597) in which residue 236 is deleted and residues 234, 235 and 237 (using EU numbering) are substituted with alanines.

In some embodiments, the anti-CS1 antibodies of the disclosure have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

In yet another aspect, the anti-CS1 antibodies or binding fragments include modifications that increase or decrease their binding affinities to the fetal Fc receptor, FcRn, for example, by mutating the immunoglobulin constant region segment at particular regions involved in FcRn interactions (see, e.g., WO 2005/123780). In particular embodiments, an anti-CS1 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which is incorporated herein by reference. Such mutations increase binding to FcRn, which protects the antibody from degradation and increases its half-life.

In yet other aspects, an anti-CS1 antibody has one or more amino acids inserted into one or more of its hypervariable regions, for example as described in Jung and Plückthun, 1997, Protein Engineering 10:9, 959-966; Yazaki et al., 2004, Protein Eng. Des Sel. 17(5):481-9. Epub 2004 Aug. 17; and U.S. Pat. App. No. 2007/0280931.

Anti-CS1 antibodies and/or binding fragments with high affinity for HuCS1 may desirable for therapeutic and diagnostic uses. Accordingly, the present disclosure contemplates antibodies having a high binding affinity to HuCS1. In specific embodiments, the anti-CS1 antibodies that bind HuCS1 with an affinity of at least about 100 nM, but may exhibit higher affinity, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind HuCS1 with an affinity in the range of about 1 pM to about 100 nM, or an affinity ranging between any of the foregoing values.

Affinity of anti-CS1 antibodies for HuCS1 can be determined using techniques well known in the art or described herein, such as for example, but not by way of limitation, ELISA, isothermal titration calorimetry (ITC), BIAcore, or fluorescent polarization assay.

In some embodiments, the amino acid sequences of the CDRs of an anti-CS1 antibody and/or binding fragment are as follows:

| CDR | Sequence (N→C) | Identifier |
|---|---|---|
| VH CDR#1: | DYX₁MA, where:<br>X₁ is an aromatic residue, preferably Y or F. | (SEQ ID NO: 50) |
| VH CDR#2: | X₂INYDGX₃STYX₄X₅DSX₆KX₇, where:<br>X₂ is a polar or acid residue, preferably S, D or E;<br>X₃ is a polar, non-polar or acidic residue, preferably S, E, G or N;<br>X₄ is an aromatic residue, preferably Y or F;<br>X₅ is an aliphatic residue, preferably V or L;<br>X₆ is an aliphatic residue, preferably V or L; and<br>X₇ is a small residue, preferably G or S. | (SEQ ID NO: 51) |
| VH CDR#3: | DRGX₈YFDY, where:<br>X₈ is an aromatic residue, preferably Y or F. | (SEQ ID NO: 52) |
| VL CDR#1: | RX₉SQSLVHX₁₀NGX₁₁TYLH, where:<br>X₉ is a polar or aromatic residue, preferably S or F;<br>X₁₀ is a polar or basic residue, preferably S, N or R; and<br>X₁₁ is a polar or aliphatic residue, preferably N or L. | (SEQ ID NO: 53) |
| VL CDR#2: | KVSNRFS | (SEQ ID NO: 121) |
| VL CDR#3: | SQSTHVPPX₁₂T, where:<br>X₁₂ is an aromatic residue, preferably F or Y. | (SEQ ID NO: 54) |

In some embodiments, the amino acid sequences of the CDRs of an anti-CS1 antibody and/or binding fragment are selected from the following sequences:

| CDR | Sequence (N→C) | Identifier |
|---|---|---|
| VH CDR#1: | DYYMA | (SEQ ID NO: 100) |
| | DYFMA | (SEQ ID NO: 101) |
| | DHYIN | (SEQ ID NO: 102) |
| VH CDR#2: | SINYDGSSTYYLDSLKS | (SEQ ID NO: 103) |
| | SINYDGSSTYYVDSVKG | (SEQ ID NO: 104) |
| | SINYDGESTYYVDSVKG | (SEQ ID NO: 105) |
| | DINYDGGSTYYLDSLKS | (SEQ ID NO: 106) |
| | EINYDGSSTYYLDSLKS | (SEQ ID NO: 107) |
| | EINYDGSSTYYVDSVKG | (SEQ ID NO: 108) |
| | SINYDGNSTYFLDSLKS | (SEQ ID NO: 109) |
| | WIFPGTGITYYNENFKG | (SEQ ID NO: 110) |
| VH CDR#3: | DRGYYFDY | (SEQ ID NO: 111) |
| | DRGFYFDY | (SEQ ID NO: 112) |
| | RGYGSFDY | (SEQ ID NO: 113) |
| VL CDR#1: | RSSQSLVHSNGNTYLH | (SEQ ID NO: 114) |
| | RSSQSLVHSNGLTYLH | (SEQ ID NO: 115) |
| | RSSQSLVHSNGNTYLH | (SEQ ID NO: 116) |
| | RSSQSLVHNNGNTYLH | (SEQ ID NO: 117) |
| | RFSQSLVHRNGNTYLH | (SEQ ID NO: 118) |
| | RSSQSLVHRNGNTYLH | (SEQ ID NO: 119) |
| | KSSQSLLNSSNQKNYLA | (SEQ ID NO: 120) |
| VL CDR#2: | KVSNRFS | (SEQ ID NO: 121) |
| | FAYTRES | (SEQ ID NO: 122) |
| VL CDR#3: | SQSTHVPPFT | (SEQ ID NO: 123) |
| | SQSTHVPPYT | (SEQ ID NO: 124) |
| | SQSTHVRPYT | (SEQ ID NO: 125) |
| | QQHYSSPYT | (SEQ ID NO: 126) |

In some embodiments, each CDR of an anti-CS1 antibody and/or binding fragment, independently of the others, is selected to correspond in sequence to the respective CDR of an antibody provided in TABLE 3.

In some embodiments, an anti-CS1 antibody and/or binding fragment is an IgG₁ and comprises a V_H chain corresponding in sequence to any one of SEQ ID NOS:5, 14, 21, 28, 30 or 32; and a V_L chain corresponding in sequence to any one of SEQ ID NOS:6, 15, 22, 29, 31 or 33. In some embodiments, an anti-CS1 antibody and/or binding fragment is an IgG₁ and comprises a V_H chain corresponding in sequence to SEQ ID NO:5 and a V_L chain corresponding in sequence to SEQ ID NO:6. In some embodiments, an anti-CS1 antibody and/or binding fragment is an IgG₁ and comprises a V_H chain corresponding in sequence to SEQ ID NO:14 and a V_L chain corresponding in sequence to SEQ ID NO:15. In some embodiments, an anti-CS1 antibody and/or binding fragment is an IgG₁ and comprises a V_H chain corresponding in sequence to SEQ ID NO:21 and a V_L chain corresponding in sequence to SEQ ID NO:22. In some embodiments, an anti-CS1 antibody and/or binding fragment is an IgG₁ and comprises a V_H chain corresponding in sequence to SEQ ID NO:28 and a V_L chain corresponding in sequence to SEQ ID NO:29. In some embodiments, an anti-CS1 antibody and/or binding fragment is an IgG₁ and comprises a V_H chain corresponding in sequence to SEQ ID NO:30 and a V_L chain corresponding in sequence to SEQ ID NO:31. In some embodiments, an anti-CS1 antibody and/or binding fragment is an IgG₁ and comprises a V_H chain corresponding in sequence to SEQ ID NO:32 and a V_L chain corresponding in sequence to SEQ ID NO:33. In some embodiments, an anti-CS1 antibody is an IgG, and has a V_H and V_L corresponding in sequence the V_H and V_L of an antibody provided in TABLE 3.

In some embodiments, an anti-CS1 antibody and/or binding fragment is suitable for administration to humans. In a specific embodiment, the anti-CS1 antibody is humanized. In another specific embodiment, the amino acid sequences of the CDRs of the anti-CS1 antibody and/or binding fragment are selected from:

| CDR | Sequence (N→C) | Identifier |
|---|---|---|
| VH CDR#1: | DYYMA | (SEQ ID NO: 100) |
| VH CDR#2: | SINYDGSSTYYVDSVKG | (SEQ ID NO: 104) |
| | SINYDGESTYYVDSVKG | (SEQ ID NO: 105) |

-continued

| CDR | Sequence (N→C) | Identifier |
|---|---|---|
| | DINYDGGSTYYLDSLKS | (SEQ ID NO: 106) |
| | EINYDGSSTYYVDSVKG | (SEQ ID NO: 108) |
| VH CDR#3: | DRGYYFDY | (SEQ ID NO: 111) |
| | DRGFYFDY | (SEQ ID NO: 112) |
| VL CDR#1: | RSSQSLVHSNGNTYLH | (SEQ ID NO: 114) |
| | RSSQSLVHSNGLTYLH | (SEQ ID NO: 115) |
| | RSSQSLVHNNGNTYLH | (SEQ ID NO: 117) |
| VL CDR#2: | KVSNRFS | (SEQ ID NO: 121) |
| VL CDR#3: | SQSTHVPPFT | (SEQ ID NO: 123) |
| | SQSTHVPPYT | (SEQ ID NO: 124) |

In some embodiments, an anti-CS1 antibody and/or binding fragment is an IgG$_1$ and comprises a V$_H$ chain corresponding in sequence to any one of SEQ ID NOS:7, 8, 12, 16, 17, 23 or 24 and a V$_L$ chain corresponding in sequence to any one of SEQ ID NOS:9, 10, 11, 13, 18, 19, 20, 25, 26 or 27. In some embodiments, and anti-CS1 antibody and/or binding fragment is an IgG$_1$ and comprises a V$_H$ chain corresponding in sequence to SEQ ID NO:8 and a V$_L$ chain corresponding in sequence to SEQ ID NO:10 In some embodiments, and anti-CS1 antibody and/or binding fragment is an IgG$_1$ and comprises a V$_H$ chain corresponding in sequence to SEQ ID NO:12 and a V$_L$ chain corresponding in sequence to SEQ ID NO:13. In some embodiments, an anti-CS1 antibody and/or binding fragment is an IgG$_1$ and comprises a V$_H$ chain corresponding in sequence to SEQ ID NO:16 and a V$_L$ chain corresponding in sequence to SEQ ID NO:19. In some embodiments, an anti-CS1 antibody and/or binding fragment is an IgG, and comprises a V$_L$ chain having a sequence corresponding to SEQ ID NO:24 and a V$_L$ sequence corresponding to SEQ ID NO:27.

In some embodiments, the anti-CS1 antibodies and/or binding fragments compete for binding human CS1 on cells expressing CS1 in in vitro assays with a reference antibody. The reference antibody may be any of the anti-CS1 antibodies described herein. In some embodiments, the reference antibody is an antibody provided in TABLE 3. In specific embodiments, the reference antibody is selected from antibody CS1.AD159.34C3 ("Mu34C3"); antibody CS1.AD159.31D2 ("Mu31D2"); antibody CS1.AD159.27A12 ("Mu27A12"); antibody CS1.AD159.12D10 ("Mu12D10"); antibody CS1.AD159.14C11 ("Mu14C11"); antibody CS1.AD159.27H1 ("Mu27H1"); antibody CS1.AD159.28A6 ("Mu28A6"); and antibody CS1.AD15930C1 ("Mu30C1"). In some embodiments, the reference antibody is a humanized version of an antibody provided in TABLE 3. In some embodiments, the reference antibody is a humanized version of Mu34C3, Mu27A12, Mu12D10, Mu14C11, Mu27A12, Mu12D10, Mu14C11, Mu27H1, Mu28A6 or Mu30C1. In a specific embodiment, the reference antibody is Hu34C3.

Assays for competition include, but are not limited to, a radioactive material labeled immunoassay (RIA), an enzyme-linked immunosorbent assay (ELISA), a sandwich ELISA fluorescence activated cell sorting (FACS) assays and Biacore assays.

In conducting an antibody competition assay between a reference antibody and a test antibody (irrespective of species or isotype), one may first label the reference with a detectable label, such as a fluorophore, biotin or an enzymatic (or even radioactive) label to enable subsequent identification. In this case, cells expressing HuCS1 are incubated with unlabeled test antibody, labeled reference antibody is added, and the intensity of the bound label is measured. If the test antibody competes with the labeled reference antibody by binding to an overlapping epitope, the intensity will be decreased relative to a control reaction carried out without test antibody.

In a specific embodiment of this assay, the concentration of labeled reference antibody that yields 80% of maximal binding ("conc$_{80\%}$") under the assay conditions (e.g., a specified density of cells) is first determined, and a competition assay carried out with 10× conc$_{80\%}$ of unlabeled test antibody and conc$_{80\%}$ of labeled reference antibody.

The inhibition can be expressed as an inhibition constant, or K$_i$, which is calculated according to the following formula:

$$K_i = IC_{50}/(1+[\text{reference Ab concentration}]/K_d),$$

where IC$_{50}$ is the concentration of test antibody that yields a 50% reduction in binding of the reference antibody and K$_d$ is the dissociation constant of the reference antibody, a measure of its affinity for HuCS1. Antibodies that compete with anti-CS1 antibodies disclosed herein can have a K$_i$ from 10 pM to 10 nM under assay conditions described herein.

In various embodiments, a test antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

A specific assay and assay conditions useful for assessing whether an antibody competes for binding HuCS1 with a reference antibody as described herein is provided in Example 6, supra.

7.4. Polynucleotides Encoding the Anti-CS1 Antibodies, Expression Systems and Methods of Making the Antibodies The present disclosure encompasses nucleic acid molecules encoding immunoglobulin light and heavy chain genes for anti-CS1 antibodies, vectors comprising such nucleic acids, and host cells capable of producing the anti-CS1 antibodies of the disclosure.

An anti-CS1 of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

To generate nucleic acids encoding such anti-CS1 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference).

Once DNA fragments encoding anti-CS1 antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CHI, $CH_2$, $CH_3$ and, optionally, $CH_4$). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the $V_H$-encoding DNA can be operatively linked to another DNA molecule encoding only the heavy chain CHI constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region. To create a scFv gene, the $V_H$- and $V_L$-encoding DNA fragments are operatively linked to another fragment encoding a flexible linker, e.g., encoding the amino acid sequence $(Gly_4\text{-}Ser)_3$ (SEQ ID NO:127), such that the $V_H$ and $V_L$ sequences can be expressed as a contiguous single-chain protein, with the $V_L$ and $V_H$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-CS1 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-CS1 antibody-related light or heavy chain sequences, the expression vector can already carry antibody constant region sequences. For example, one approach to converting the anti-CS1 monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE—dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-CS1 antibody of this disclosure.

Recombinant DNA technology can also be used to remove some or all of the DNA encoding either or both of the light and heavy chains that is not necessary for binding to HuCS1. The molecules expressed from such truncated DNA molecules are also encompassed by the antibodies of the disclosure.

For recombinant expression of an anti-CS1 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-hCS1 antibody, further alterations or mutations can be introduced into the coding sequence, for example to generate nucleic acids encoding antibodies with different CDR sequences, antibodies with reduced affinity to the Fc receptor, or antibodies of different subclasses.

The anti-CS1 antibodies of the disclosure can also be produced by chemical synthesis (e.g., by the methods described in Solid Phase Peptide Synthesis, 2nd ed., 1984 The Pierce Chemical Co., Rockford, Ill.). Variant antibodies can also be generated using a cell-free platform (See, e.g., Chu et al., Biochemia No. 2, 2001 (Roche Molecular Biologicals) and Murray et al., 2013, Current Opinion in Chemical Biology, 17:420-426).

Once an anti-CS1 antibody of the disclosure has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-CS1 antibodies of the present disclosure and/or binding fragments can be fused to heterologous polypeptide sequences described herein or otherwise known in the art to facilitate purification.

Once isolated, the anti-CS1 antibody can, if desired, be further purified, e.g., by high performance liquid chromatography (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

7.5. Anti-CS1 Antibody Drug Conjugates

Another aspect of the disclosure concerns antibody drug conjugates (ADCs) including the anti-CS1 antibodies described herein. The ADCs generally comprise an anti-CS1 antibody and/or binding fragment as described herein having one or more cytotoxic and/or cytostatic agents linked thereto by way of one or more linkers. In specific embodiments, the ADCs are compounds according to structural formula (I):

$$[D\text{-}L\text{-}XY]_n\text{-}Ab \tag{I}$$

or salts thereof, where each "D" represents, independently of the others, a cytotoxic and/or cytostatic agent ("drug"); each "L" represents, independently of the others, a linker; "Ab" represents an anti-CS1 antigen binding moiety, such as an anti-CS1 antibody or binding fragment described herein; each "XY" represents a linkage formed between a functional group $R^x$ on the linker and a "complementary" functional group $R^y$ on the antibody, and n represents the number of drugs linked to, or drug-to-antibody ratio (DAR), of the ADC.

Specific embodiments of the various antibodies (Ab) that can comprise the ADCs include the various embodiments of anti-CS1 antibodies and/or binding fragments described above.

In some specific embodiments of the ADCs and/or salts of structural formula (I), each D is the same and/or each L is the same.

Specific embodiments of cytotoxic and/or cytostatic agents (D) and linkers (L) that can comprise the ADCs described herein, as well as the number of cytotoxic and/or cytostatic agents linked to the ADCs, are described in more detail below.

7.5.1. Cytotoxic and/or Cytostatic Agents

The cytotoxic and/or cytostatic agents may be any agents known to inhibit the growth and/or replication of and/or kill cells, and in particular cancer and/or tumor cells. Numerous agents having cytotoxic and/or cytostatic properties are known in the literature. Non-limiting examples of classes of cytotoxic and/or cytostatic agents include, by way of example and not limitation, radionuclides, alkylating agents, topoisomerase I inhibitors, topoisomerase II inhibitors, DNA intercalating agents (e.g., groove binding agents such as minor groove binders), RNA/DNA antimetabolites, cell cycle modulators, kinase inhibitors, protein synthesis inhibitors, histone deacetylase inhibitors, mitochondria inhibitors, and antimitotic agents.

Specific non-limiting examples of agents within certain of these various classes are provided below.

Alkylating Agents: asaley ((L-Leucine, N—[N-acetyl-4-[bis-(2-chloroethyl)amino]-DL-phenylalanyl]-, ethylester; NSC 167780; CAS Registry No. 3577897)); AZQ ((1,4-cyclohexadiene-1,4-dicarbamic acid, 2, 5-bis(1-aziridinyl)-3,6-dioxo-, diethyl ester; NSC 182986; CAS Registry No. 57998682)); BCNU ((N,N'-Bis(2-chloroethyl)-N-nitrosourea; NSC 409962; CAS Registry No. 154938)); busulfan (1,4-butanediol dimethanesulfonate; NSC 750; CAS Registry No. 55981); (carboxyphthalato)platinum (NSC 27164; CAS Registry No. 65296813); CBDCA ((cis-(1,1-cyclobutanedicarboxylato)diammineplatinum(II)); NSC 241240; CAS Registry No. 41575944)); CCNU ((N-(2-chloroethyl)-N'-cyclohexyl-N-nitrosourea; NSC 79037; CAS Registry No. 13010474)); CHIP (iproplatin; NSC 256927); chlorambucil (NSC 3088; CAS Registry No. 305033); chlorozotocin ((2-[[[(2-chloroethyl) nitrosoamino]carbonyl]amino]-2-deoxy-D-glucopyranose; NSC 178248; CAS Registry No. 54749905)); cis-platinum (cisplatin; NSC 119875; CAS Registry No. 15663271); clomesone (NSC 338947; CAS Registry No. 88343720); cyanomorpholinodoxorubicin (NCS 357704; CAS Registry No. 88254073); cyclodisone (NSC 348948; CAS Registry No. 99591738); dianhydrogalactitol (5,6-diepoxydulcitol; NSC 132313; CAS Registry No. 23261203); fluorodopan ((5-[(2-chloroethyl)-(2-fluoroethyl)amino]-6-methyl-uracil; NSC 73754; CAS Registry No. 834913); hepsulfam (NSC 329680; CAS Registry No. 96892578); hycanthone (NSC 142982; CAS Registry No. 23255938); melphalan (NSC 8806; CAS Registry No. 3223072); methyl CCNU ((1-(2-chloroethyl)-3-(trans-4-methylcyclohexane)-1-nitrosourea; NSC 95441; 13909096); mitomycin C (NSC 26980; CAS Registry No. 50077); mitozolamide (NSC 353451; CAS Registry No. 85622953); nitrogen mustard ((bis(2-chloroethyl) methylamine hydrochloride; NSC 762; CAS Registry No. 55867); PCNU ((1-(2-chloroethyl)-3-(2,6-dioxo-3-piperidyl)-1-nitrosourea; NSC 95466; CAS Registry No. 13909029)); piperazine alkylator ((1-(2-chloroethyl)-4-(3-chloropropyl)-piperazine dihydrochloride; NSC 344007)); piperazinedione (NSC 135758; CAS Registry No. 41109802); pipobroman ((N,N'-bis(3-bromopropionyl) piperazine; NSC 25154; CAS Registry No. 54911)); porfiromycin (N-methylmitomycin C; NSC 56410; CAS Registry No. 801525); spirohydantoin mustard (NSC 172112; CAS Registry No. 56605164); teroxirone (triglycidylisocyanurate; NSC 296934; CAS Registry No. 2451629); tetraplatin (NSC 363812; CAS Registry No. 62816982); thio-tepa (N,N',N"-tri-1,2-ethanediylthio phosphoramide; NSC 6396; CAS Registry No. 52244); triethylenemelamine (NSC 9706; CAS Registry No. 51183); uracil nitrogen mustard (desmethyldopan; NSC 34462; CAS Registry No. 66751); Yoshi-864 ((bis(3-mesyloxy propyl)amine hydrochloride; NSC 102627; CAS Registry No. 3458228).

Topoisomerase I Inhibitors: camptothecin (NSC 94600; CAS Registry No. 7689-03-4); various camptothecin derivatives and analogs (for example, NSC 100880, NSC 603071, NSC 107124, NSC 643833, NSC 629971, NSC 295500, NSC 249910, NSC 606985, NSC 74028, NSC 176323, NSC 295501, NSC 606172, NSC 606173, NSC 610458, NSC 618939, NSC 610457, NSC 610459, NSC 606499, NSC 610456, NSC 364830, and NSC 606497); morpholinisoxorubicin (NSC 354646; CAS Registry No. 89196043); SN-38 (NSC 673596; CAS Registry No. 86639-52-3).

Topoisomerase II Inhibitors: doxorubicin (NSC 123127; CAS Registry No. 25316409); amonafide (benzisoquinolinedione; NSC 308847; CAS Registry No. 69408817); m-AMSA ((4'-(9-acridinylamino)-3'-methoxymethanesulfonanilide; NSC 249992; CAS Registry No. 51264143)); anthrapyrazole derivative ((NSC 355644); etoposide (VP-16; NSC 141540; CAS Registry No. 33419420); pyrazoloacridine ((pyrazolo[3,4,5-kl]acridine-2(6H)-propanamine, 9-methoxy-N, N-dimethyl-5-nitro-, monomethanesulfonate; NSC 366140; CAS Registry No. 99009219); bisantrene hydrochloride (NSC 337766; CAS Registry No. 71439684); daunorubicin (NSC 821151; CAS Registry No. 23541506); deoxydoxorubicin (NSC 267469; CAS Registry No. 63950061); mitoxantrone (NSC 301739; CAS Registry No. 70476823); menogaril (NSC 269148; CAS Registry No. 71628961); N,N-dibenzyl daunomycin (NSC 268242; CAS Registry No. 70878512); oxanthrazole (NSC 349174; CAS Registry No. 105118125); rubidazone (NSC 164011; CAS Registry No. 36508711); teniposide (VM-26; NSC 122819; CAS Registry No. 29767202).

DNA Intercalating Agents: anthramycin (CAS Registry No. 4803274); chicamycin A (CAS Registry No. 89675376); tomaymycin (CAS Registry No. 35050556); DC-81 (CAS Registry No. 81307246); sibiromycin (CAS Registry No. 12684332); pyrrolobenzodiazepine derivative (CAS Registry No. 945490095); SGD-1882 ((S)-2-(4-aminophenyl)-7-methoxy-8-(3-(((S)-7-methoxy-2-(4-methoxyphenyl)-5-oxo-5,11a-dihydro-1H-benzo[e]pyrrolo[1,2-a][1,4]diazepin-8-yl)oxy)propoxy)-1H-benzo[e]pyrrolo[1,2-a][1,4]diazepin-5(11aH)-one); SG2000 (SJG-136; (11aS,11a'S)-8,8'-(propane-1,3-diylbis(oxy))bis(7-methoxy-2-methylene-2,3-dihydro-1H-benzo[e]pyrrolo[1,2-a][1,4]diazepin-5(11 aH)-one); NSC 694501; CAS Registry No. 232931576).

RNA/DNA Antimetabolites: L-alanosine (NSC 153353; CAS Registry No. 59163416); 5-azacytidine (NSC 102816; CAS Registry No. 320672); 5-fluorouracil (NSC 19893; CAS Registry No. 51218); acivicin (NSC 163501; CAS Registry No. 42228922); aminopterin derivative N-[2-chloro-5-[[(2, 4-diamino-5-methyl-6-quinazolinyl)methyl]amino]benzoyl] L-aspartic acid (NSC 132483); aminopterin derivative N-[4-[[(2, 4-diamino-5-ethyl-6-quinazolinyl)methyl]amino]benzoyl] L-aspartic acid (NSC 184692); aminopterin derivative N-[2-chloro-4-[[(2, 4-diamino-6-pteridinyl)methyl]amino]benzoyl] L-aspartic acid monohydrate (NSC 134033); an antifo (($N^\alpha$-(4-amino-4-deoxypteroyl)-$N^\gamma$-hemiphthaloyl-L-omithine; NSC 623017)); Baker's soluble antifol (NSC 139105; CAS Registry No. 41191042); dichlorallyl lawsone ((2-(3, 3-dichloroallyl)-3-hydroxy-1,4-naphthoquinone; NSC 126771; CAS Registry No. 36417160); brequinar (NSC 368390; CAS Registry No. 96201886); ftorafur ((pro-drug; 5-fluoro-1-(tetrahydro-2-furyl)-uracil; NSC 148958; CAS Registry No. 37076689); 5,6-dihydro-5-azacytidine (NSC 264880; CAS Registry No. 62402317); methotrexate (NSC 740; CAS Registry No. 59052); methotrexate derivative (N-[[4-[[(2, 4-diamino-6-pteridinyl)methyl]methylamino]-1-naphthalenyl]carbonyl] L-glutamic acid; NSC 174121); PALA ((N-(phosphonoacetyl)-L-aspartate; NSC 224131; CAS Registry No. 603425565); pyrazofurin (NSC 143095; CAS Registry No. 30868305); trimetrexate (NSC 352122; CAS Registry No. 82952645).

DNA Antimetabolites: 3-HP (NSC 95678; CAS Registry No. 3814797); 2'-deoxy-5-fluorouridine (NSC 27640; CAS Registry No. 50919); 5-HP (NSC 107392; CAS Registry No. 19494894); α-TGDR (α-2'-deoxy-6-thioguanosine; NSC 71851 CAS Registry No. 2133815); aphidicolin glycinate (NSC 303812; CAS Registry No. 92802822); ara C (cytosine arabinoside; NSC 63878; CAS Registry No. 69749); 5-aza-2'-deoxycytidine (NSC 127716; CAS Registry No. 2353335); β-TGDR (β-2'-deoxy-6-thioguanosine; NSC 71261; CAS Registry No. 789617); cyclocytidine (NSC 145668; CAS Registry No. 10212256); guanazole (NSC 1895; CAS Registry No. 1455772); hydroxyurea (NSC 32065; CAS Registry No. 127071); inosine glycodialdehyde (NSC 118994; CAS Registry No. 23590990); macbecin II (NSC 330500; CAS Registry No. 73341738); pyrazoloimidazole (NSC 51143; CAS Registry No. 6714290); thioguanine (NSC 752; CAS Registry No. 154427); thiopurine (NSC 755; CAS Registry No. 50442).

Cell Cycle Modulators: silibinin (CAS Registry No. 22888-70-6); epigallocatechin gallate (EGCG; CAS Registry No. 989515); procyanidin derivatives (e.g., procyanidin A1 [CAS Registry No. 103883030], procyanidin B1 [CAS Registry No. 20315257], procyanidin B4 [CAS Registry No. 29106512], arecatannin B1 [CAS Registry No. 79763283]); isoflavones (e.g., genistein [4',5,7-trihydroxyisoflavone; CAS Registry No. 446720], daidzein [4',7-dihydroxyisoflavone, CAS Registry No. 486668]; indole-3-carbinol (CAS Registry No. 700061); quercetin (NSC 9219; CAS Registry No. 117395); estramustine (NSC 89201; CAS Registry No. 2998574); nocodazole (CAS Registry No. 31430189); podophyllotoxin (CAS Registry No. 518285); vinorelbine tartrate (NSC 608210; CAS Registry No. 125317397); cryptophycin (NSC 667642; CAS Registry No. 124689652).

Kinase Inhibitors: afatinib (CAS Registry No. 850140726); axitinib (CAS Registry No. 319460850); ARRY-438162 (binimetinib) (CAS Registry No. 606143899); bosutinib (CAS Registry No. 380843754); cabozantinib (CAS Registry No. 1140909483); ceritinib (CAS Registry No. 1032900256); crizotinib (CAS Registry No. 877399525); dabrafenib (CAS Registry No. 1195765457); dasatinib (NSC 732517; CAS Registry No. 302962498); erlotinib (NSC 718781; CAS Registry No. 183319699); everolimus (NSC 733504; CAS Registry No. 159351696); fostamatinib (NSC 745942; CAS Registry No. 901119355); gefitinib (NSC 715055; CAS Registry No. 184475352); ibrutinib (CAS Registry No. 936563961); imatinib (NSC 716051; CAS Registry No. 220127571); lapatinib (CAS Registry No. 388082788); lenvatinib (CAS Registry No. 857890392); mubritinib (CAS 366017096); nilotinib (CAS Registry No. 923288953); nintedanib (CAS Registry No. 656247175); palbociclib (CAS Registry No. 571190302); pazopanib (NSC 737754; CAS Registry No. 635702646); pegaptanib (CAS Registry No. 222716861); ponatinib (CAS Registry No. 1114544318); rapamycin (NSC 226080; CAS Registry No. 53123889); regorafenib (CAS Registry No. 755037037); AP 23573 (ridaforolimus) (CAS Registry No. 572924540); INCB018424 (ruxolitinib) (CAS Registry No. 1092939177); ARRY-142886 (selumetinib) (NSC 741078; CAS Registry No. 606143-52-6); sirolimus (NSC 226080; CAS Registry No. 53123889); sorafenib (NSC 724772; CAS Registry No. 475207591); sunitinib (NSC 736511; CAS Registry No. 341031547); tofacitinib (CAS Registry No. 477600752); temsirolimus (NSC 683864; CAS Registry No. 163635043); trametinib (CAS Registry No. 871700173); vandetanib (CAS Registry No. 443913733); vemurafenib (CAS Registry No. 918850465l); SU6656 (CAS Registry No. 330161870); CEP-701 (lesaurtinib) (CAS Registry No. 111358884); XL019 (CAS Registry No. 945755566); PD-325901 (CAS Registry No. 391210109); PD-98059 (CAS Registry No. 167869218); ATP-competitive TORC1/TORC2 inhibitors including PI-103 (CAS Registry No. 371935749), PP242 (CAS Registry No. 1092351671), PP30 (CAS Registry No. 1092788094), Torin 1 (CAS Registry No. 1222998368), LY294002 (CAS Registry No. 154447366), XL-147 (CAS Registry No. 934526893), CAL-120 (CAS Registry No. 870281348), ETP-45658 (CAS Registry No. 1198357797), PX 866 (CAS Registry No. 502632668), GDC-0941 (CAS Registry No. 957054307), BGT226 (CAS Registry No. 1245537681), BEZ235 (CAS Registry No. 915019657), XL-765 (CAS Registry No. 934493762).

Protein Synthesis Inhibitors: acriflavine (CAS Registry No. 65589700); amikacin (NSC 177001; CAS Registry No. 39831555); arbekacin (CAS Registry No. 51025855); astromicin (CAS Registry No. 55779061); azithromycin (NSC 643732; CAS Registry No. 83905015); bekanamycin (CAS Registry No. 4696768); chlortetracycline (NSC 13252; CAS Registry No. 64722); clarithromycin (NSC 643733; CAS Registry No. 81103119); clindamycin (CAS Registry No. 18323449); clomocycline (CAS Registry No. 1181540); cycloheximide (CAS Registry No. 66819); dactinomycin (NSC 3053; CAS Registry No. 50760); dalfopristin (CAS Registry No. 112362502); demeclocycline (CAS Registry No. 127333); dibekacin (CAS Registry No. 34493986); dihydrostreptomycin (CAS Registry No. 128461); dirithromycin (CAS Registry No. 62013041); doxycycline (CAS Registry No. 17086281); emetine (NSC 33669; CAS Registry No. 483181); erythromycin (NSC 55929; CAS Registry No. 114078); flurithromycin (CAS Registry No. 83664208); framycetin (neomycin B; CAS Registry No. 119040); gentamycin (NSC 82261; CAS Registry No. 1403663); glycylcyclines, such as tigecycline (CAS Registry No. 220620097); hygromycin B (CAS Registry No. 31282049); isepamicin (CAS Registry No. 67814760); josamycin (NSC 122223; CAS Registry No. 16846245); kanamycin (CAS Registry No. 8063078); ketolides such as telithromycin (CAS Registry No. 191114484), cethromycin (CAS Registry No. 205110481), and solithromycin (CAS Registry No. 760981837); lincomycin (CAS Registry No. 154212); lymecycline (CAS Registry No. 992212); meclocycline (NSC 78502; CAS Registry No. 2013583); metacycline (rondomycin; NSC 356463; CAS Registry No. 914001); midecamycin (CAS Registry No. 35457808); minocycline (NSC 141993; CAS Registry No. 10118908); miocamycin (CAS Registry No. 55881077); neomycin (CAS Registry No. 119040); netilmicin (CAS Registry No. 56391561); oleandomycin (CAS Registry No. 3922905); oxazolidinones, such as eperezolid (CAS Registry No. 165800044), linezolid (CAS Registry No. 165800033), posizolid (CAS Registry No. 252260029), radezolid (CAS Registry No. 869884786), ranbezolid (CAS Registry No. 392659380), sutezolid (CAS Registry No. 168828588), tedizolid (CAS Registry No. 856867555); oxytetracycline (NSC 9169; CAS Registry No. 2058460); paromomycin (CAS Registry No. 7542372); penimepicycline (CAS Registry No. 4599604); peptidyl transferase inhibitors, e.g., chloramphenicol (NSC 3069; CAS Registry No. 56757) and derivatives such as azidamfenicol (CAS Registry No. 13838089), florfenicol (CAS Registry No. 73231342), and thiamphenicol (CAS Registry No. 15318453), and pleuromutilins such as retapamulin (CAS Registry No. 224452668), tiamulin (CAS Registry No. 55297955), valnemulin (CAS Registry No. 101312929); pirlimycin (CAS Registry No. 79548735); puromycin (NSC 3055; CAS Registry No. 53792); quinupristin (CAS Registry No. 120138503); ribostamycin (CAS Registry No. 53797356); rokitamycin (CAS Registry No. 74014510); rolitetracycline (CAS Registry No. 751973); roxithromycin (CAS Registry No. 80214831); sisomicin (CAS Registry No. 32385118); spectinomycin (CAS Registry No. 1695778); spiramycin (CAS Registry No. 8025818); streptogramins such as pristinamycin (CAS Registry No. 270076603), quinupristin/dalfopristin (CAS Registry No. 126602899), and virginiamycin (CAS Registry No. 11006761); streptomycin (CAS Registry No. 57921); tetracycline (NSC 108579; CAS Registry No. 60548); tobramycin (CAS Registry No. 32986564); troleandomycin (CAS Registry No. 2751099); tylosin (CAS Registry No. 1401690); verdamicin (CAS Registry No. 49863481).

Histone deacetylase inhibitors: abexinostat (CAS Registry No. 783355602); belinostat (NSC 726630; CAS Registry No. 414864009); chidamide (CAS Registry No. 743420022); entinostat (CAS Registry No. 209783802); givinostat (CAS Registry No. 732302997); mocetinostat (CAS Registry No. 726169739); panobinostat (CAS Registry No. 404950807); quisinostat (CAS Registry No. 875320299); resminostat (CAS Registry No. 864814880); romidepsin (CAS Registry No. 128517077); sulforaphane (CAS Registry No. 4478937); thioureidobutyronitrile (Kevetrin™; CAS Registry No. 6659890); valproic acid (NSC 93819; CAS Registry No. 99661); vorinostat (NSC 701852; CAS Registry No. 149647789); ACY-1215 (rocilinostat; CAS Registry No. 1316214524); CUDC-101 (CAS Registry No. 1012054599); CHR-2845 (tefinostat; CAS Registry No. 914382608); CHR-3996 (CAS Registry No. 1235859138); 4SC-202 (CAS Registry No. 910462430); CG200745 (CAS Registry No. 936221339); SB939 (pracinostat; CAS Registry No. 929016966).

Mitochondria Inhibitors: pancratistatin (NSC 349156; CAS Registry No. 96281311); rhodamine-123 (CAS Registry No. 63669709); edelfosine (NSC 324368; CAS Registry No. 70641519); d-alpha-tocopherol succinate (NSC 173849; CAS Registry No. 4345033); compound 11β (CAS Registry No. 865070377); aspirin (NSC 406186; CAS Registry No. 50782); ellipticine (CAS Registry No. 519233); berberine (CAS Registry No. 633658); cerulenin (CAS Registry No. 17397896); GX015-070 (Obatoclax®; 1H-Indole, 2-(2-((3,5-dimethyl-1H-pyrrol-2-yl)methylene)-3-methoxy-2H-pyrrol-5-yl)-; NSC 729280; CAS Registry No. 803712676); celastrol (tripterine; CAS Registry No. 34157830); metformin (NSC 91485; CAS Registry No. 1115704); Brilliant green (NSC 5011; CAS Registry No. 633034); ME-344 (CAS Registry No. 1374524556).

Antimitotic Agents: allocolchicine (NSC 406042); auristatins, such as MMAE (monomethyl auristatin E; CAS Registry No. 474645-27-7) and MMAF (monomethyl auristatin F; CAS Registry No. 745017-94-1; halichondrin B (NSC 609395); colchicine (NSC 757; CAS Registry No. 64868); cholchicine derivative (N-benzoyl-deacetyl benzamide; NSC 33410; CAS Registry No. 63989753); dolastatin 10 (NSC 376128; CAS Registry No 110417-88-4); maytansine (NSC 153858; CAS Registry No. 35846-53-8); rhozoxin (NSC 332598; CAS Registry No. 90996546); taxol (NSC 125973; CAS Registry No. 33069624); taxol derivative ((2'-N-[3-(dimethylamino)propyl]glutaramate taxol; NSC 608832); thiocolchicine (3-demethylthiocolchicine; NSC 361792); trityl cysteine (NSC 49842; CAS Registry No. 2799077); vinblastine sulfate (NSC 49842; CAS Registry No. 143679); vincristine sulfate (NSC 67574; CAS Registry No. 2068782).

Any of these agents that include or that may be modified to include a site of attachment to an antibody may be included in the ADCs disclosed herein.

In a specific embodiment, the cytotoxic and/or cytostatic agent is an antimitotic agent.

In another specific embodiment, the cytotoxic and/or cytostatic agent is an auristatin, for example, monomethyl auristatin E ("MMAE") or monomethyl auristatin F ("MMAF").

7.5.2. Linkers

In the ADCs described herein, the cytotoxic and/or cytostatic agents are linked to the antibody by way of linkers. The linker linking a cytotoxic and/or cytostatic agent to the antibody of an ADC may be short, long, hydrophobic, hydrophilic, flexible or rigid, or may be composed of segments that each independently have one or more of the above-mentioned properties such that the linker may include segments having different properties. The linkers may be polyvalent such that they covalently link more than one agent to a single site on the antibody, or monovalent such that covalently they link a single agent to a single site on the antibody.

As will be appreciated by skilled artisans, the linkers link cytotoxic and/or cytostatic agents to the antibody by forming a covalent linkage to the cytotoxic and/or cytostatic agent at one location and a covalent linkage to antibody at another. The covalent linkages are formed by reaction between functional groups on the linker and functional groups on the agents and antibody. As used herein, the expression "linker" is intended to include (i) unconjugated forms of the linker that include a functional group capable of covalently linking the linker to a cytotoxic and/or cytostatic agent and a functional group capable of covalently linking the linker to an antibody; (ii) partially conjugated forms of the linker that includes a functional group capable of covalently linking the linker to an antibody and that is covalently linked to a cytotoxic and/or cytostatic agent, or vice versa; and (iii) fully conjugated forms of the linker that is covalently linked to both a cytotoxic and/or cytostatic agent and an antibody. In some specific embodiments of linkers and ADCs described herein, as well as synthons used to conjugate linker-agents to antibodies, moieties comprising the functional groups on the linker and covalent linkages formed between the linker and antibody are specifically illustrated as $R^x$ and XY, respectively.

The linkers are preferably, but need not be, chemically stable to conditions outside the cell, and may be designed to cleave, immolate and/or otherwise specifically degrade inside the cell. Alternatively, linkers that are not designed to specifically cleave or degrade inside the cell may be used. Choice of stable versus unstable linker may depend upon the toxicity of the cytotoxic and/or cytostatic agent. For agents that are toxic to normal cells, stable linkers are preferred. Agents that are selective or targeted and have lower toxicity to normal cells may utilize, chemical stability of the linker to the extracellular milieu is less important. A wide variety of linkers useful for linking drugs to antibodies in the context of ADCs are known in the art. Any of these linkers, as well as other linkers, may be used to link the cytotoxic and/or cytostatic agents to the antibody of the ADCs described herein.

Exemplary polyvalent linkers that may be used to link many cytotoxic and/or cytostatic agents to a single antibody molecule are described, for example, in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the content of which are incorporated herein by reference in their entireties. For example, the Fleximer linker technology developed by Mersana et al. has the potential to enable high-DAR ADCs with good physicochemical properties. As shown below, the Mersana technology is based on incorporating drug molecules into a solubilizing poly-acetal backbone via a sequence of ester bonds. The methodology renders highly-loaded ADCs (DAR up to 20) while maintaining good physicochemical properties.

Additional examples of dendritic type linkers can be found in US 2006/116422; US 2005/271615; de Groot et al (2003) Angew. Chem. Int. Ed. 42:4490-4494; Amir et al (2003) Angew. Chem. Int. Ed. 42:4494-4499; Shamis et al (2004) J. Am. Chem. Soc. 126:1726-1731; Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990, each of which is incorporated herein by reference.

Exemplary monovalent linkers that may be used are described, for example, in Nolting, 2013, Antibody-Drug Conjugates, Methods in Molecular Biology 1045:71-100; Kitson et al., 2013, CROs/CMOs—Chemica Oggi—Chemistry Today 31(4):30-38; Ducry et al., 2010, Bioconjugate Chem. 21:5-13; Zhao et al., 2011, J. Med. Chem. 54:3606-3623; U.S. Pat. Nos. 7,223,837; 8,568,728; 8,535,678; and WO2004010957, each of which is incorporated herein by reference.

By way of example and not limitation, some cleavable and noncleavable linkers that may be included in the ADCs described herein are described below.

7.5.2.1. Cleavable Linkers

In certain embodiments, the linker selected is cleavable in vivo. Cleavable linkers may include chemically or enzymatically unstable or degradable linkages. Cleavable linkers generally rely on processes inside the cell to liberate the drug, such as reduction in the cytoplasm, exposure to acidic conditions in the lysosome, or cleavage by specific proteases or other enzymes within the cell. Cleavable linkers generally incorporate one or more chemical bonds that are either chemically or enzymatically cleavable while the remainder of the linker is noncleavable. In certain embodiments, a linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing linkers are the acidic environment of endosomes and lysosomes, while the disulfide containing linkers are reduced in the cytosol, which contains high thiol concentrations, e.g., glutathione. In certain embodiments, the plasma stability of a linker comprising a chemically labile group may be increased by introducing steric hindrance using substituents near the chemically labile group.

Acid-labile groups, such as hydrazone, remain intact during systemic circulation in the blood's neutral pH environment (pH 7.3-7.5) and undergo hydrolysis and release the drug once the ADC is internalized into mildly acidic endosomal (pH 5.0-6.5) and lysosomal (pH 4.5-5.0) compartments of the cell. This pH dependent release mechanism has been associated with nonspecific release of the drug. To increase the stability of the hydrazone group of the linker, the linker may be varied by chemical modification, e.g., substitution, allowing tuning to achieve more efficient release in the lysosome with a minimized loss in circulation.

Hydrazone-containing linkers may contain additional cleavage sites, such as additional acid-labile cleavage sites and/or enzymatically labile cleavage sites. ADCs including exemplary hydrazone-containing linkers include the following structures:

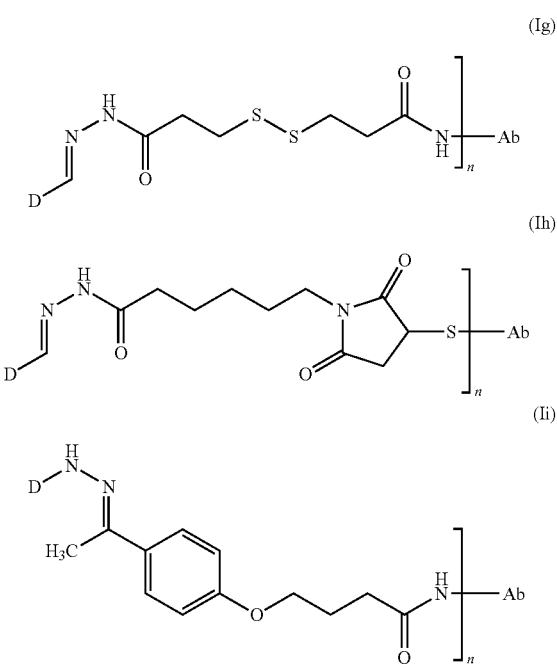

wherein D and Ab represent the cytotoxic and/or cytostatic agent (drug) and Ab, respectively, and n represents the number of drug-linkers linked to the antibody. In certain linkers such as linker (Ig), the linker comprises two cleavable groups—a disulfide and a hydrazone moiety. For such linkers, effective release of the unmodified free drug requires acidic pH or disulfide reduction and acidic pH. Linkers such as (Ih) and (Ii) have been shown to be effective with a single hydrazone cleavage site.

Additional linkers which remain intact during systemic circulation and undergo hydrolysis and release the drug when the ADC is internalized into acidic cellular compartments include carbonates. Such linkers can be useful in cases where the cytotoxic and/or cytostatic agent can be covalently attached through an oxygen.

Other acid-labile groups that may be included in linkers include cis-aconityl-containing linkers. cis-Aconityl chemistry uses a carboxylic acid juxtaposed to an amide bond to accelerate amide hydrolysis under acidic conditions.

Cleavable linkers may also include a disulfide group. Disulfides are thermodynamically stable at physiological pH and are designed to release the drug upon internalization inside cells, wherein the cytosol provides a significantly more reducing environment compared to the extracellular environment. Scission of disulfide bonds generally requires the presence of a cytoplasmic thiol cofactor, such as (reduced) glutathione (GSH), such that disulfide-containing linkers are reasonably stable in circulation, selectively releasing the drug in the cytosol. The intracellular enzyme protein disulfide isomerase, or similar enzymes capable of cleaving disulfide bonds, may also contribute to the preferential cleavage of disulfide bonds inside cells. GSH is reported to be present in cells in the concentration range of 0.5-10 mM compared with a significantly lower concentration of GSH or cysteine, the most abundant low-molecular weight thiol, in circulation at approximately 5 μM. Tumor cells, where irregular blood flow leads to a hypoxic state, result in enhanced activity of reductive enzymes and therefore even higher glutathione concentrations. In certain embodiments, the in vivo stability of a disulfide-containing linker may be enhanced by chemical modification of the linker, e.g., use of steric hinderance adjacent to the disulfide bond.

ADCs including exemplary disulfide-containing linkers include the following structures:

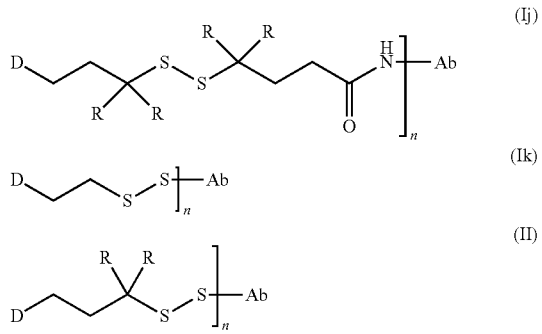

wherein D and Ab represent the drug and antibody, respectively, n represents the number of drug-linkers linked to the antibody and R is independently selected at each occurrence from hydrogen or alkyl, for example. In certain embodiments, increasing steric hinderance adjacent to the disulfide bond increases the stability of the linker. Structures such as (Ij) and (Il) show increased in vivo stability when one or more R groups is selected from a lower alkyl such as methyl.

Another type of cleavable linker that may be used is a linker that is specifically cleaved by an enzyme. Such linkers are typically peptide-based or include peptidic regions that act as substrates for enzymes. Peptide based linkers tend to be more stable in plasma and extracellular milieu than chemically labile linkers. Peptide bonds generally have good serum stability, as lysosomal proteolytic enzymes have very low activity in blood due to endogenous inhibitors and the unfavorably high pH value of blood compared to lysosomes. Release of a drug from an antibody occurs specifically due to the action of lysosomal proteases, e.g., cathepsin and plasmin. These proteases may be present at elevated levels in certain tumor cells.

In exemplary embodiments, the cleavable peptide is selected from tetrapeptides such as Gly-Phe-Leu-Gly (SEQ ID NO:128), Ala-Leu-Ala-Leu (SEQ ID NO:129) or dipeptides such as Val-Cit, Val-Ala, Met-(D)Lys, Asn-(D)Lys, Val-(D)Asp, Phe-Lys, Ile-Val, Asp-Val, His-Val, NorVal-(D) Asp, Ala-(D)Asp 5, Met-Lys, Asn-Lys, Ile-Pro, Me3Lys-Pro, PhenylGly-(D)Lys, Met-(D)Lys, Asn-(D)Lys, Pro-(D) Lys, Met-(D)Lys, Asn-(D)Lys, AM Met-(D)Lys, Asn-(D) Lys, AW Met-(D)Lys, and Asn-(D)Lys. In certain embodiments, dipeptides are preferred over longer polypeptides due to hydrophobicity of the longer peptides.

A variety of dipeptide-based cleavable linkers useful for linking drugs such as doxorubicin, mitomycin, camptothecin, pyrrolobenzodiazepine, tallysomycin and auristatin/auristatin family members to antibodies have been described (see, Dubowchik et al., 1998, *J. Org. Chem.* 67:1866-1872; Dubowchik et al., 1998, *Bioorg. Med. Chem. Lett.* 8(21): 3341-3346; Walker et al., 2002, *Bioorg. Med. Chem. Lett.* 12:217-219; Walker et al., 2004, *Bioorg. Med. Chem. Lett.* 14:4323-4327; Sutherland et al., 2013, *Blood* 122: 1455-1463; and Francisco et al., 2003, *Blood* 102:1458-1465, of each of which is incorporated herein by reference). All of these dipeptide linkers, or modified versions of these dipeptide linkers, may be used in the ADCs described herein. Other dipeptide linkers that may be used include those found in ADCs such as Seattle Genetics' Brentuximab Vendotin SGN-35 (Adcetris™), Seattle Genetics SGN-75 (anti-CD-70, Val-Cit-monomethyl auristatin F (MMAF), Seattle Genetics SGN-CD33A (anti-CD-33, Val-Ala-(SGD-1882)), Celldex Therapeutics glembatumumab (CDX-011) (anti-NMB, Val-Cit-monomethyl auristatin E (MMAE), and Cytogen PSMA-ADC (PSMA-ADC-1301) (anti-PSMA, Val-Cit-MMAE).

Enzymatically cleavable linkers may include a self-immolative spacer to spatially separate the drug from the site of enzymatic cleavage. The direct attachment of a drug to a peptide linker can result in proteolytic release of an amino acid adduct of the drug, thereby impairing its activity. The use of a self-immolative spacer allows for the elimination of the fully active, chemically unmodified drug upon amide bond hydrolysis.

One self-immolative spacer is the bifunctional para-aminobenzyl alcohol group, which is linked to the peptide through the amino group, forming an amide bond, while amine containing drugs may be attached through carbamate functionalities to the benzylic hydroxyl group of the linker (PABC). The resulting prodrugs are activated upon protease-mediated cleavage, leading to a 1,6-elimination reaction releasing the unmodified drug, carbon dioxide, and remnants of the linker group. The following scheme depicts the fragmentation of p-amidobenzyl ether and release of the drug:

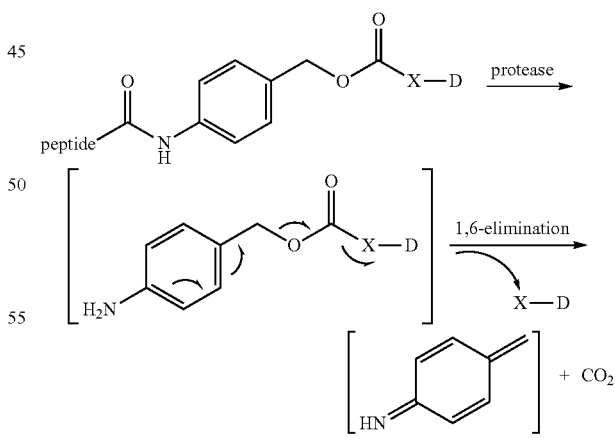

wherein X-D represents the unmodified drug.

Heterocyclic variants of this self-immolative group have also been described. See for example, U.S. Pat. No. 7,989, 434, incorporated herein by reference.

In some embodiments, the enzymatically cleavable linker is a ß-glucuronic acid-based linker. Facile release of the drug may be realized through cleavage of the ß-glucuronide glycosidic bond by the lysosomal enzyme ß-glucuronidase. This enzyme is present abundantly within lysosomes and is overexpressed in some tumor types, while the enzyme activity outside cells is low. ß-Glucuronic acid-based linkers may be used to circumvent the tendency of an ADC to undergo aggregation due to the hydrophilic nature of ß-glucuronides. In some embodiments, ß-glucuronic acid-based linkers are preferred as linkers for ADCs linked to hydrophobic drugs. The following scheme depicts the release of the drug from and ADC containing a ß-glucuronic acid-based linker:

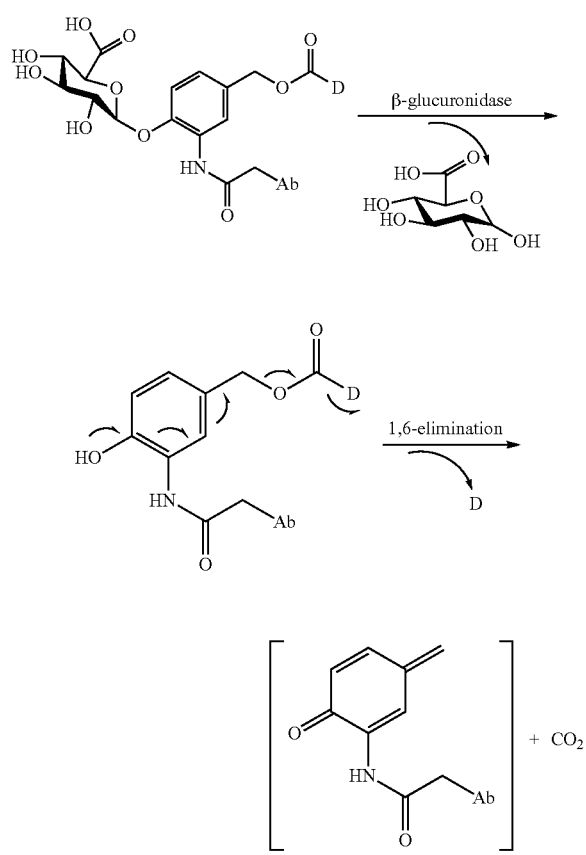

A variety of cleavable ß-glucuronic acid-based linkers useful for linking drugs such as auristatins, camptothecin and doxorubicin analogues, CBI minor-groove binders, and psymberin to antibodies have been described (see, see Nolting, Chapter 5 "Linker Technology in Antibody-Drug Conjugates," In: *Antibody-Drug Conjugates: Methods in Molecular Biology*, vol. 1045, pp. 71-100, Laurent Ducry (Ed.), Springer Science & Business Medica, LLC, 2013; Jeffrey et al., 2006, *Bioconjug. Chem.* 17:831-840; Jeffrey et al., 2007, *Bioorg. Med. Chem. Lett.* 17:2278-2280; and Jiang et al., 2005, *J Am. Chem. Soc.* 127:11254-11255, each of which is incorporated herein by reference). All of these ß-glucuronic acid-based linkers may be used in the ADCs described herein.

Additionally, cytotoxic and/or cytostatic agents containing a phenol group can be covalently bonded to a linker through the phenolic oxygen. One such linker, described in WO 2007/089149, relies on a methodology in which a diamino-ethane "SpaceLink" is used in conjunction with traditional "PABO"-based self-immolative groups to deliver phenols. The cleavage of the linker is depicted schematically below, where D represents a cytotoxic and/or cytostatic agent having a phenolic hydroxyl group.

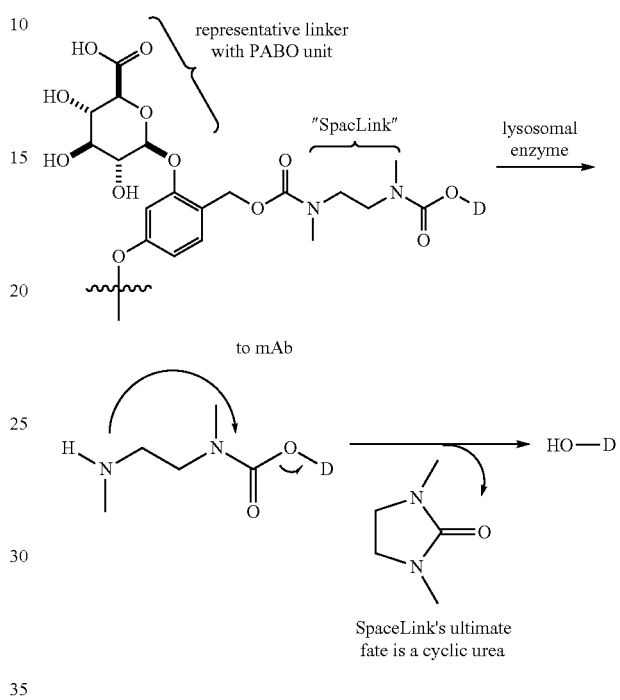

Cleavable linkers may include noncleavable portions or segments, and/or cleavable segments or portions may be included in an otherwise non-cleavable linker to render it cleavable. By way of example only, polyethylene glycol (PEG) and related polymers may include cleavable groups in the polymer backbone. For example, a polyethylene glycol or polymer linker may include one or more cleavable groups such as a disulfide, a hydrazone or a dipeptide.

Other degradable linkages that may be included in linkers include ester linkages formed by the reaction of PEG carboxylic acids or activated PEG carboxylic acids with alcohol groups on a biologically active agent, wherein such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

In certain embodiments, the linker comprises an enzymatically cleavable peptide moiety, for example, a linker comprising structural formula (IVa) or (IVb):

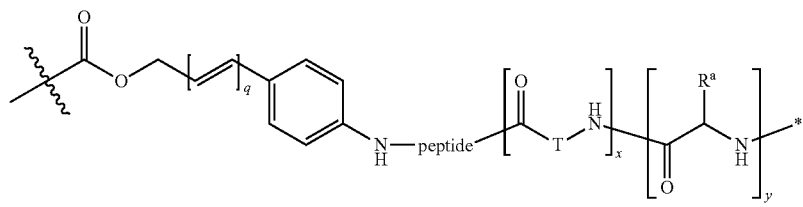

(IVa)

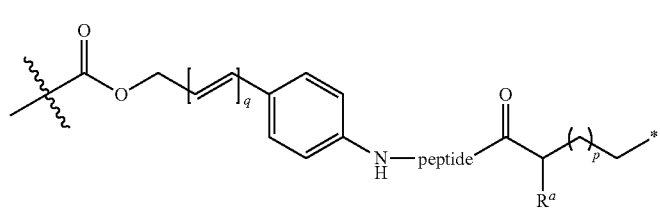

(IVb)

or a salt thereof, wherein:

peptide represents a peptide (illustrated C→N and not showing the carboxy and amino "termini") cleavable by a lysosomal enzyme;

T represents a polymer comprising one or more ethylene glycol units or an alkylene chain, or combinations thereof;

$R^a$ is selected from hydrogen, alkyl, sulfonate and methyl sulfonate;

p is an integer ranging from 0 to 5;

q is 0 or 1;

x is 0 or 1;

y is 0 or 1;

✓ represents the point of attachment of the linker to a cytotoxic and/or cytostatic agent; and \* represents the point of attachment to the remainder of the linker.

In certain embodiments, the peptide is selected from a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Val-Lys; Ala-Lys; Phe-Cit; Leu-Cit; Ile-Cit; Phe-Arg; and Trp-Cit. In certain embodiments, the dipeptide is selected from: Cit-Val; and Ala-Val.

Specific exemplary embodiments of linkers according to structural formula (IVa) that may be included in the ADCs described herein include the linkers illustrated below (as illustrated, the linkers include a group suitable for covalently linking the linker to an antibody):

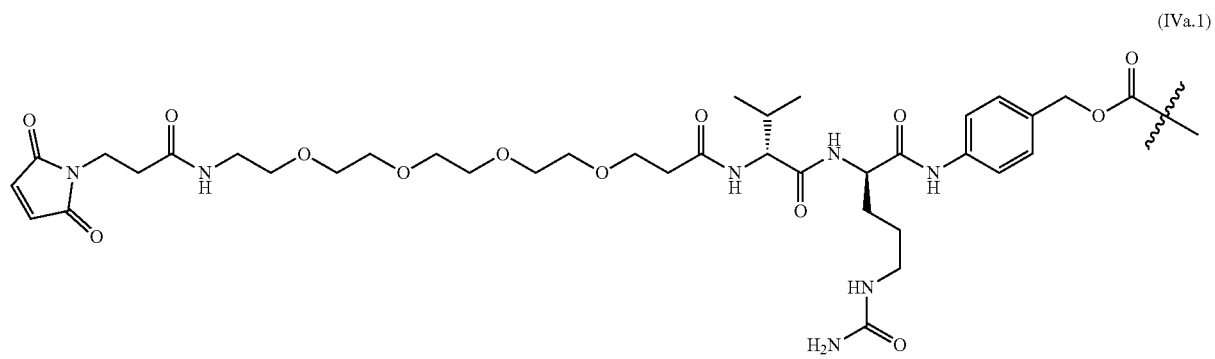

(IVa.1)

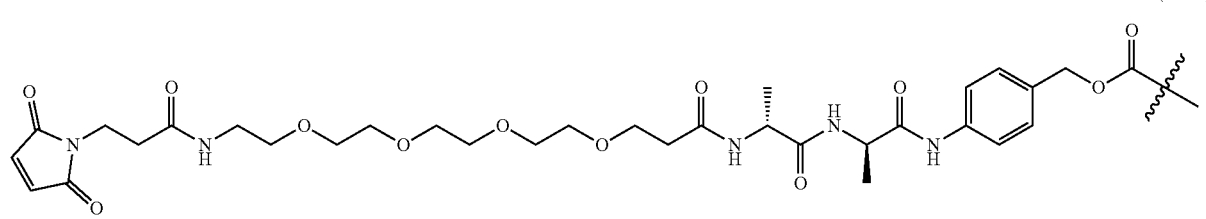

(IVa.2)

-continued
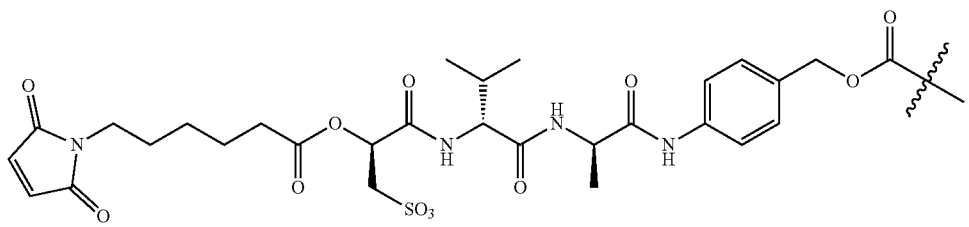
(IVa.3)
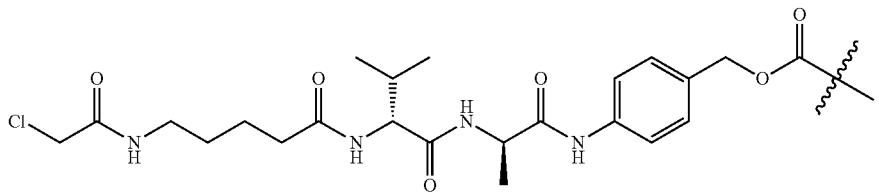
(IVa.4)
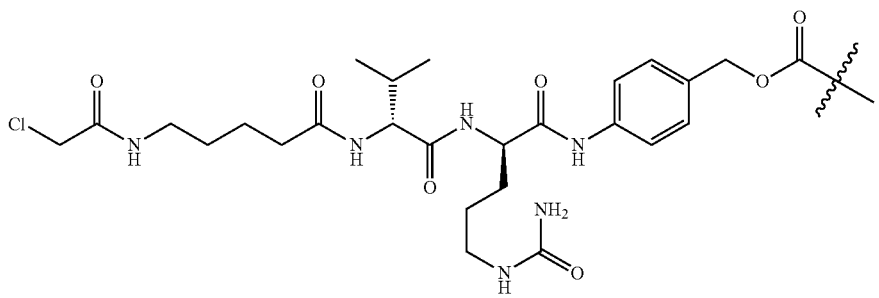
(IVa.5)
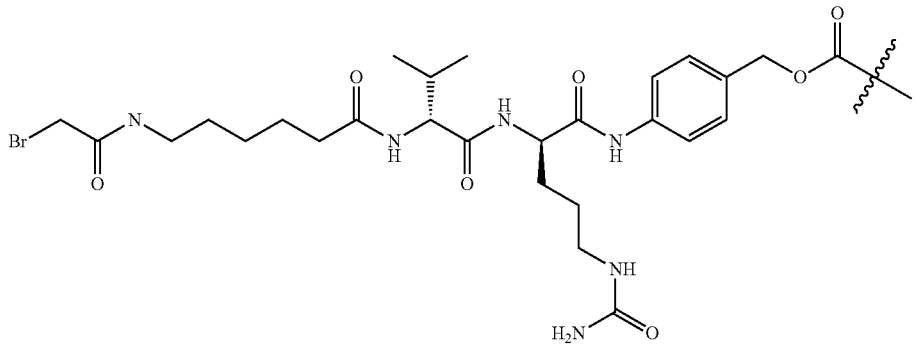
(IVa.6)
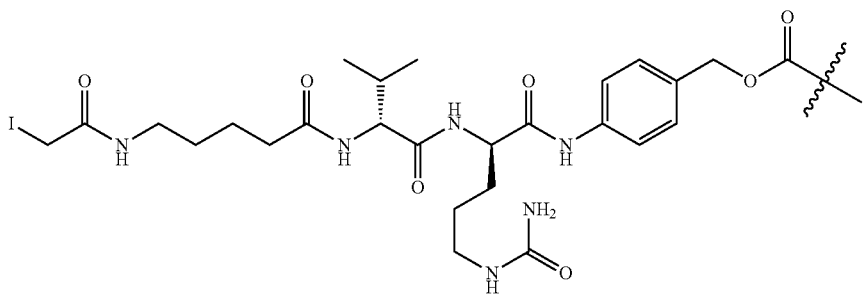
(IVa.7)
Specific exemplary embodiments of linkers according to structural formula (IVb) that may be included in the ADCs described herein include the linkers illustrated below (as illustrated, the linkers include a group suitable for covalently linking the linker to an antibody):

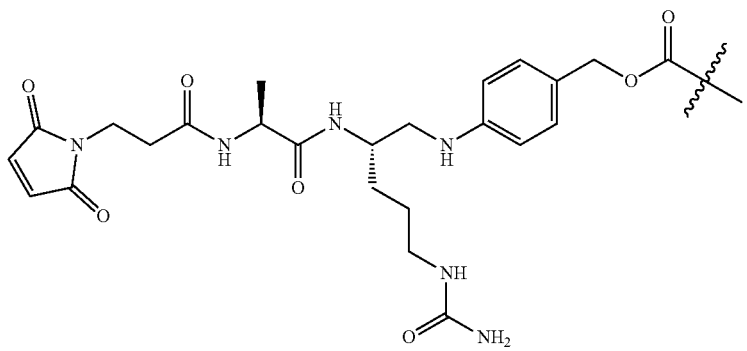
(IVb.1)
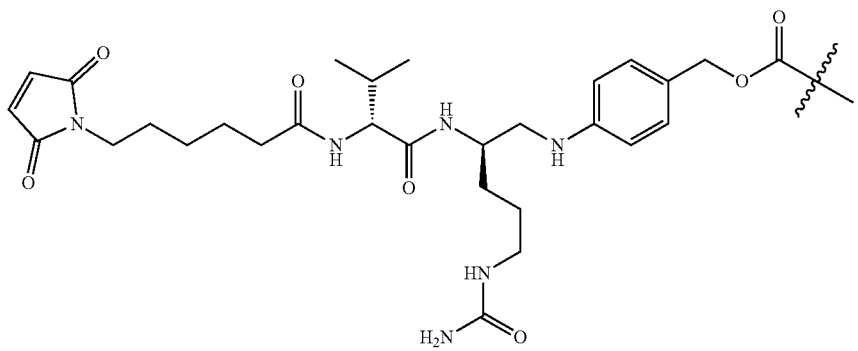
(IVb.2)
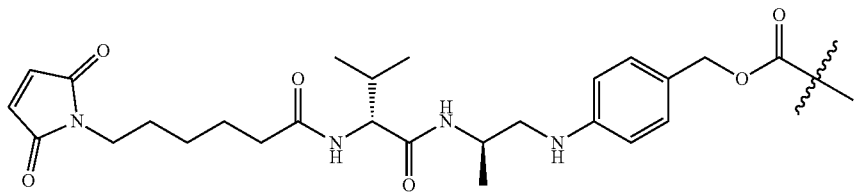
(IVb.3)
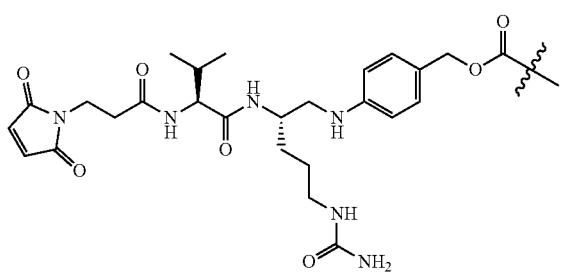
(IVb.4)
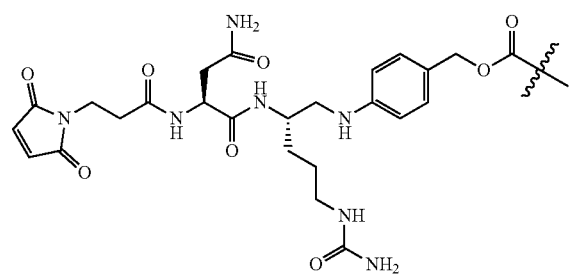
(IVb.5)
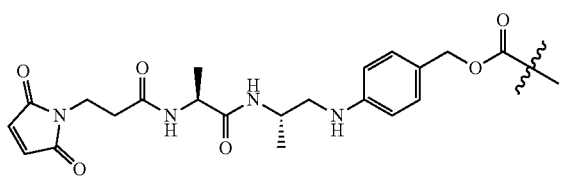
(IVb.6)
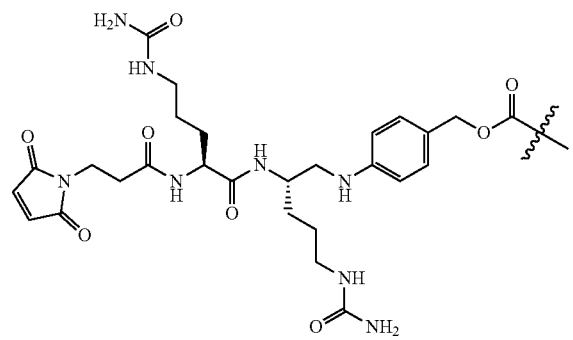
(IVb.7)

(IVb.8)
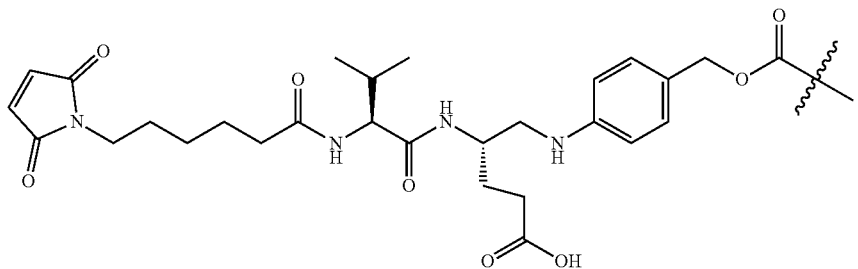
(IVb.9)
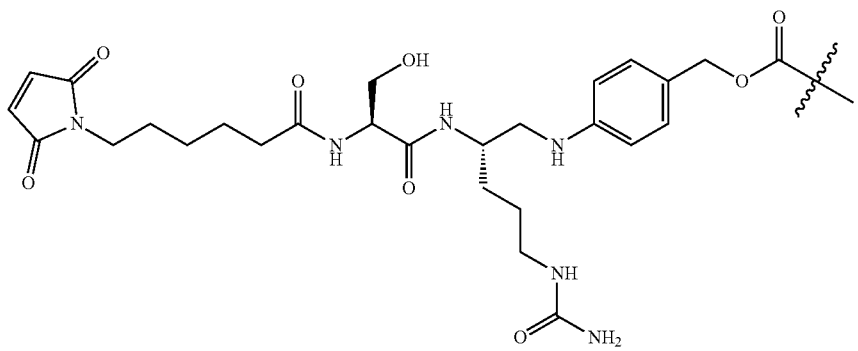
(IVb.10)
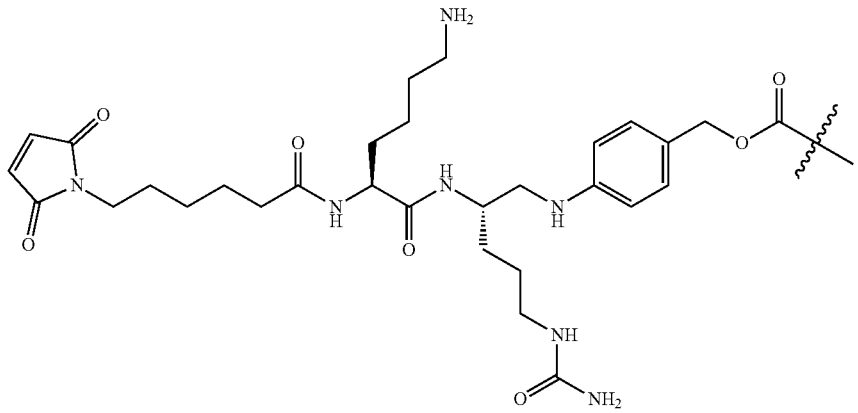
(IVb.11) (IVb.12)
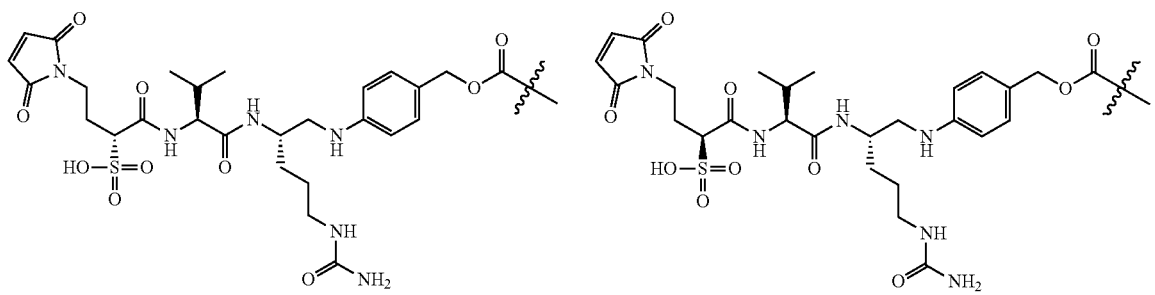

-continued
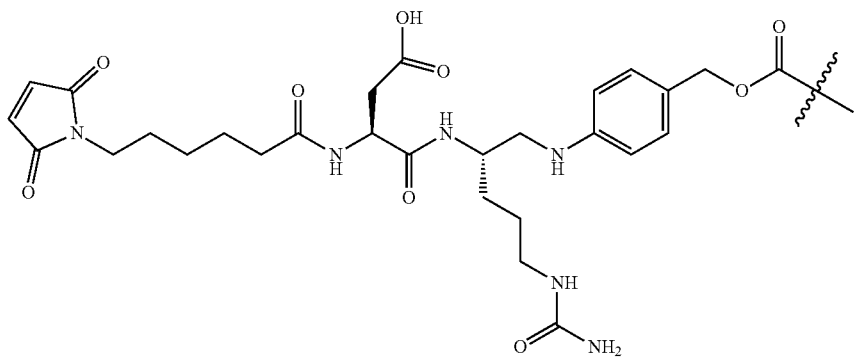
(IVb.13)
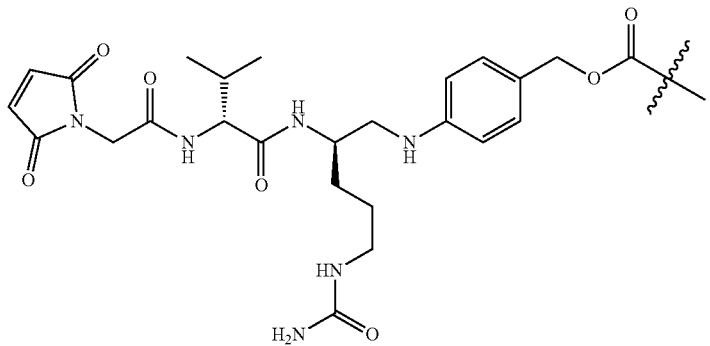
(IVb.14)
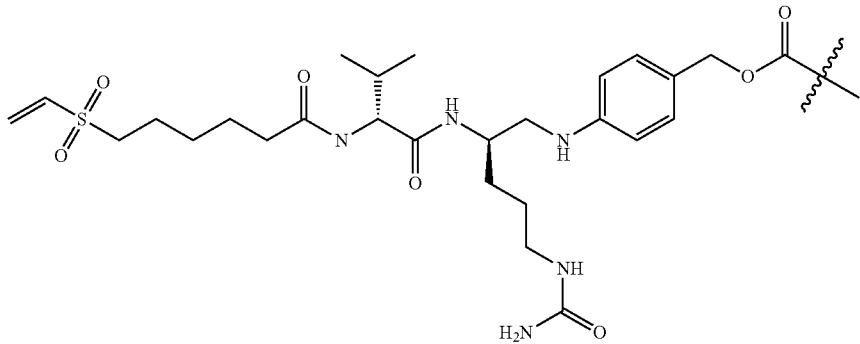
(IVb.15)
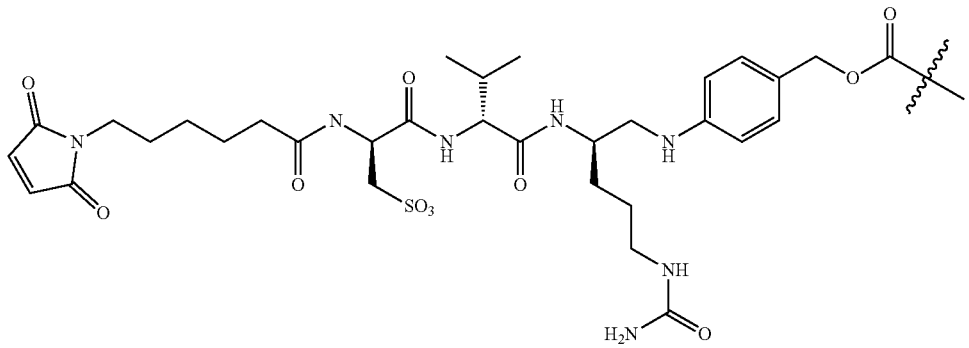
(IVb.16)

(IVb.17)

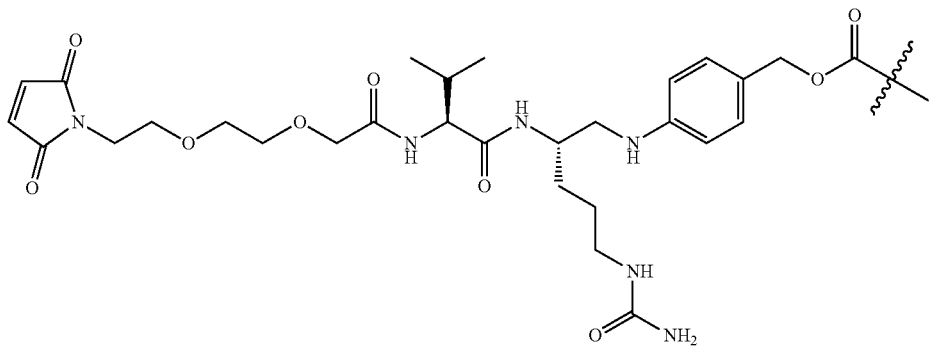

(IVb.18)

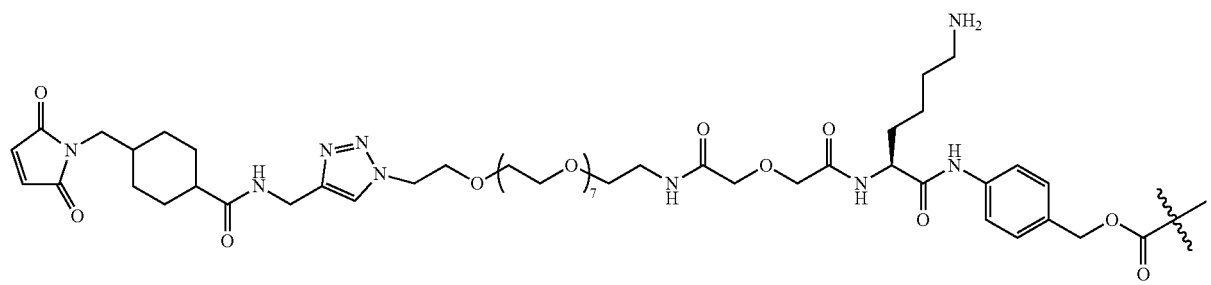

(IVb.19)

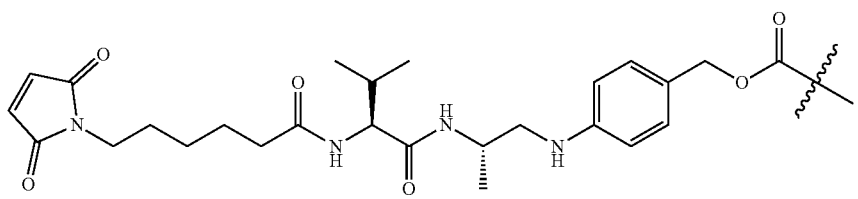

In certain embodiments, the linker comprises an enzymatically cleavable peptide moiety, for example, a linker comprising structural formula (IVc) or (IVd):

(IVc)

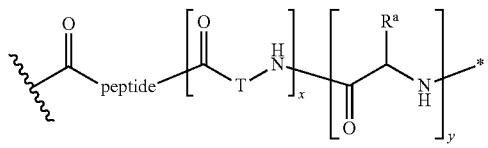

(IVd)

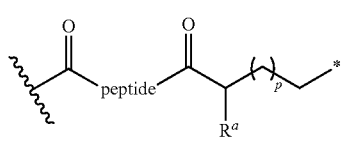

or a salt thereof, wherein:
peptide represents a peptide (illustrated C→N and not showing the carboxy and amino "termini") cleavable by a lysosomal enzyme;
T represents a polymer comprising one or more ethylene glycol units or an alkylene chain, or combinations thereof;
$R^a$ is selected from hydrogen, alkyl, sulfonate and methyl sulfonate;
p is an integer ranging from 0 to 5;
q is 0 or 1;
x is 0 or 1;
y is 0 or 1;
✦ represents the point of attachment of the linker to a cytotoxic and/or cytostatic agent; and
* represents the point of attachment to the remainder of the linker.

Specific exemplary embodiments of linkers according to structural formula (IVc) that may be included in the ADCs described herein include the linkers illustrated below (as illustrated, the linkers include a group suitable for covalently linking the linker to an antibody):

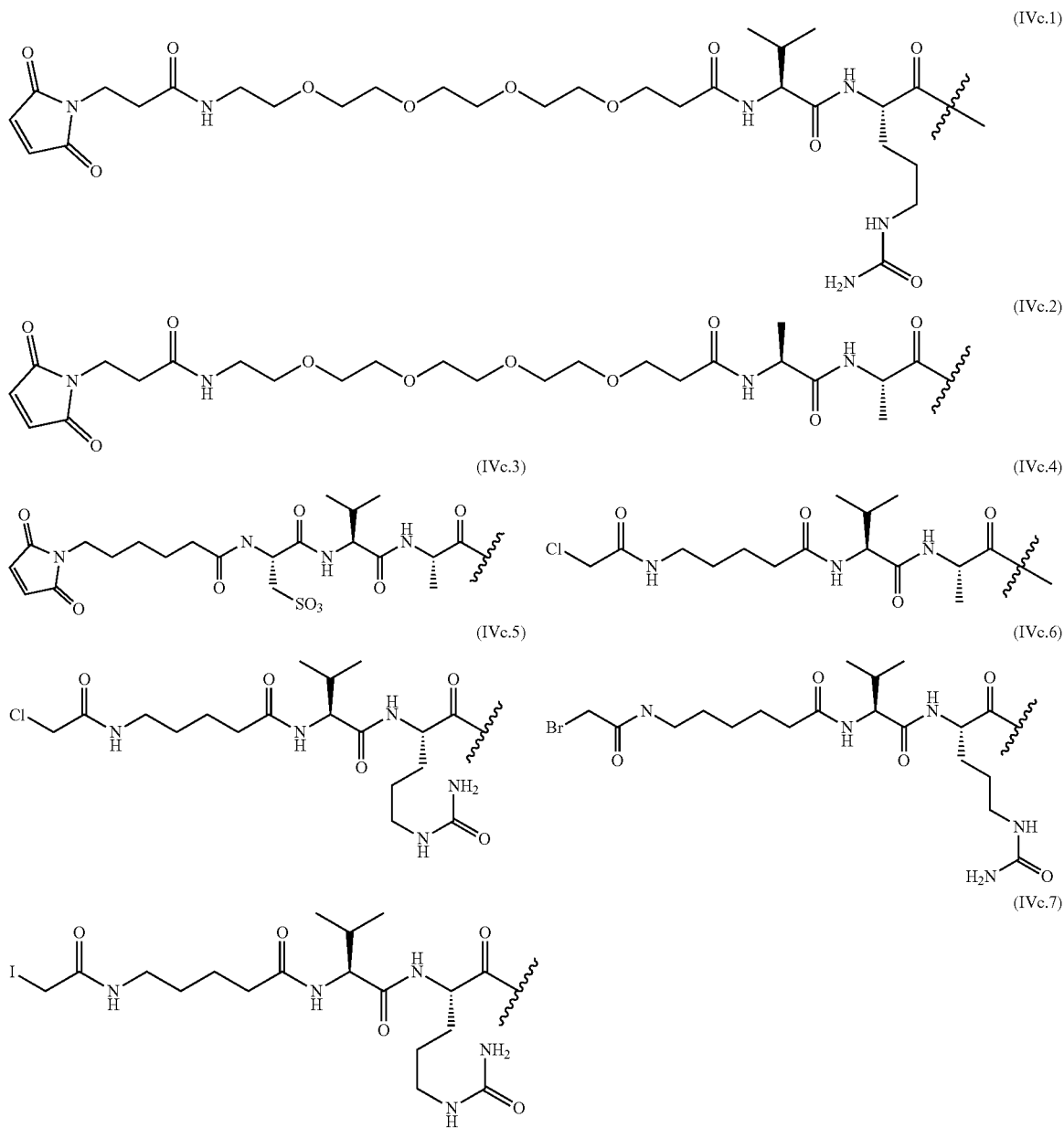
Specific exemplary embodiments of linkers according to structural formula (IVd) that may be included in the ADCs described herein include the linkers illustrated below (as illustrated, the linkers include a group suitable for covalently linking the linker to an antibody):
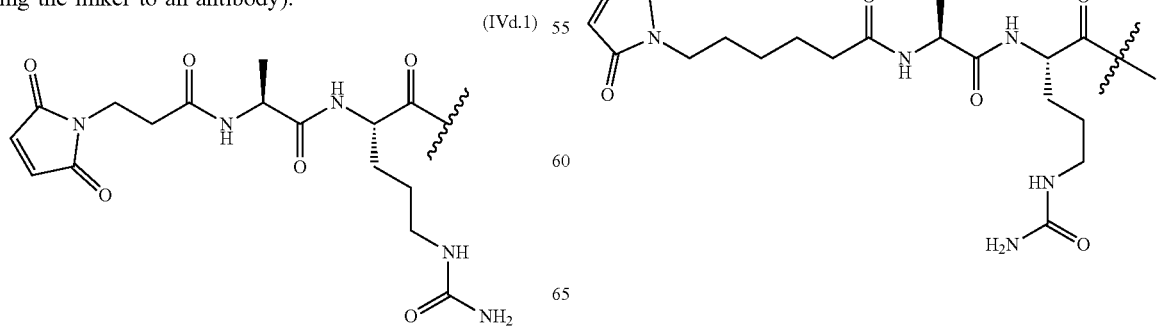
-continued (IVd.3)
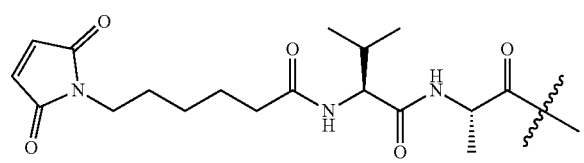
(IVd.4)
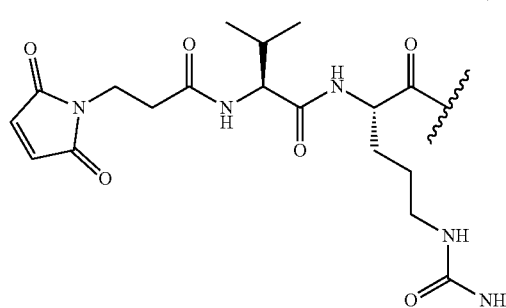
(IVd.5)
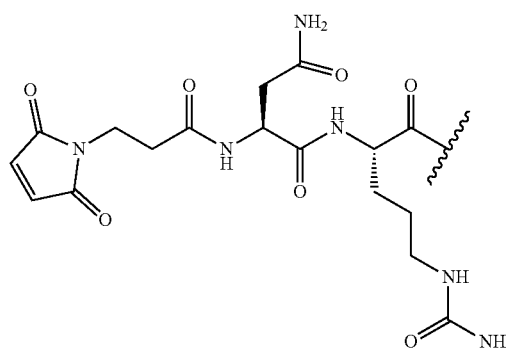
(IVd.6)
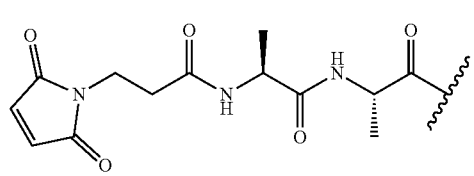
(IVd.7)
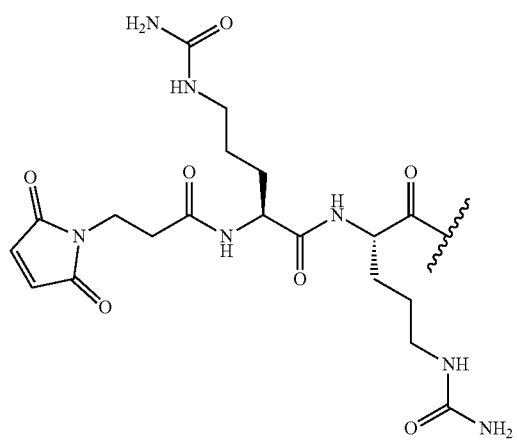
(IVd.8)
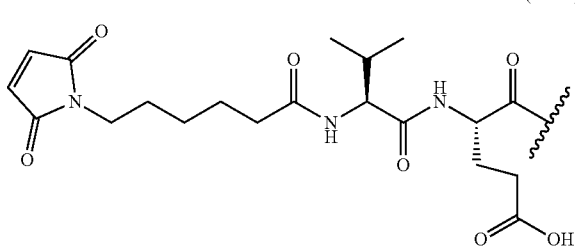
(IVd.9)
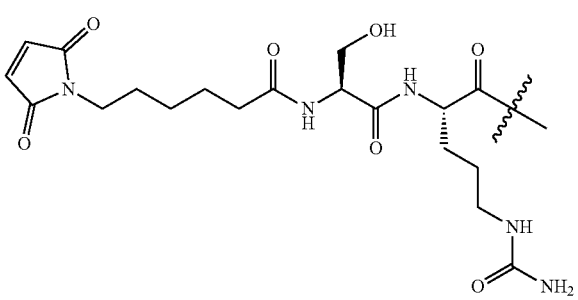
(IVd.10)
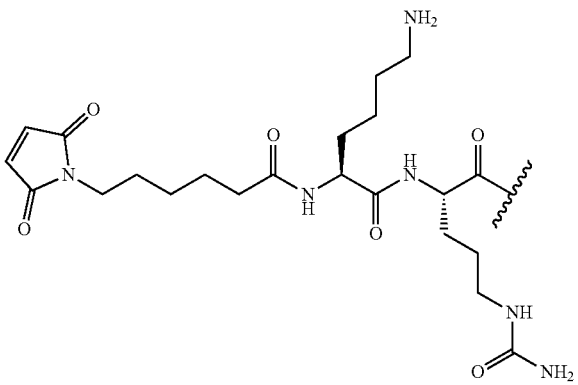
(IVd.11)
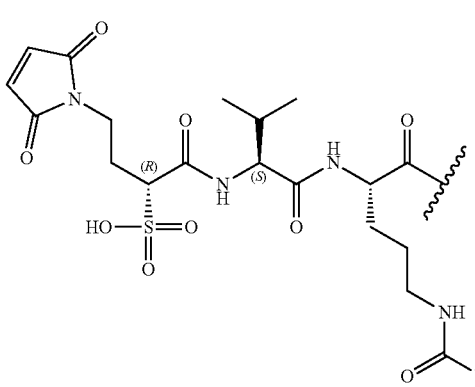

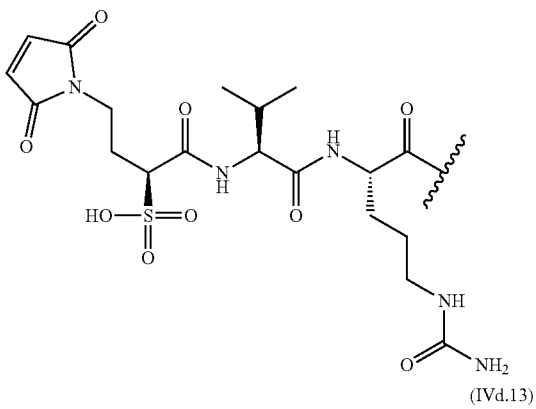

(IVd.12)

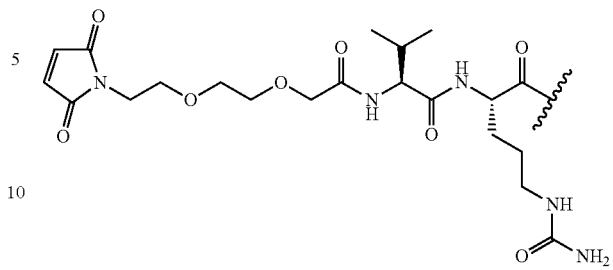

(IVd.17)

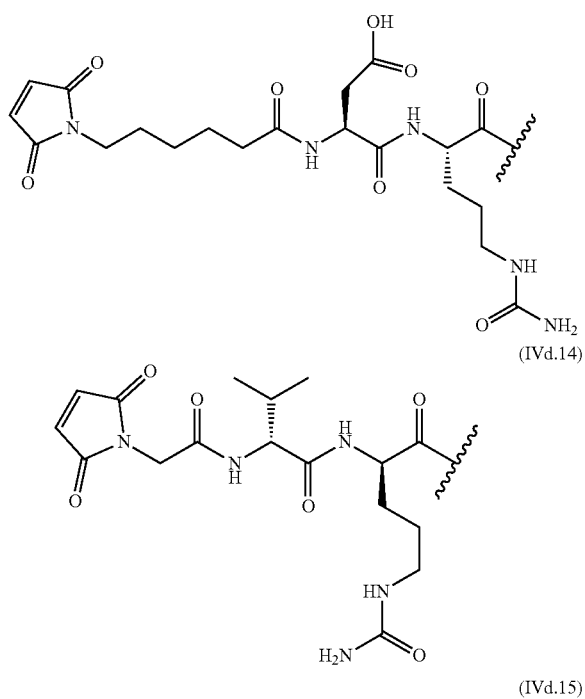

(IVd.13)

(IVd.14)

(IVd.15)

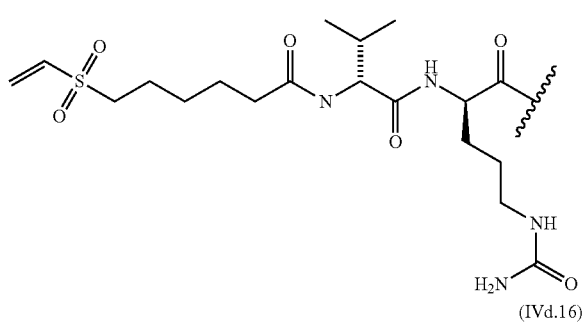

(IVd.16)

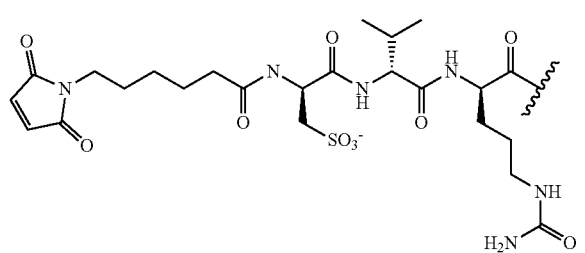

In certain embodiments, the linker comprising structural formula (IVa), (IVb), (IVc), or (IVd) further comprises a carbonate moiety cleavable by exposure to an acidic medium. In particular embodiments, the linker is attached through an oxygen to a cytotoxic and/or cytostatic agent.

7.5.2.2. Non-Cleavable Linkers

Although cleavable linkers may provide certain advantages, the linkers comprising the ADC described herein need not be cleavable. For noncleavable linkers, the release of drug does not depend on the differential properties between the plasma and some cytoplasmic compartments. The release of the drug is postulated to occur after internalization of the ADC via antigen-mediated endocytosis and delivery to lysosomal compartment, where the antibody is degraded to the level of amino acids through intracellular proteolytic degradation. This process releases a drug derivative, which is formed by the drug, the linker, and the amino acid residue to which the linker was covalently attached. The amino acid drug metabolites from conjugates with noncleavable linkers are more hydrophilic and generally less membrane permeable, which leads to less bystander effects and less nonspecific toxicities compared to conjugates with a cleavable linker. In general, ADCs with noncleavable linkers have greater stability in circulation than ADCs with cleavable linkers. Non-cleavable linkers may be alkylene chains, or maybe polymeric in natures, such as, for example, based upon polyalkylene glycol polymers, amide polymers, or may include segments of alkylene chains, polyalkylene glocols and/or amide polymers.

A variety of non-cleavable linkers used to link drugs to antibodies have been described. See, Jeffrey et al., 2006, *Bioconjug. Chem.* 17; 831-840; Jeffrey et al., 2007, *Bioorg. Med. Chem. Lett.* 17:2278-2280; and Jiang et al., 2005, *J. Am. Chem. Soc.* 127:11254-11255, each of which is incorporated herein by reference. All of these linkers may be included in the ADCs described herein.

In certain embodiments, the linker is non-cleavable in vivo, for example a linker according to structural formula (VIa), (VIb), (VIc) or (VId) (as illustrated, the linkers include a group suitable for covalently linking the linker to an antibody:

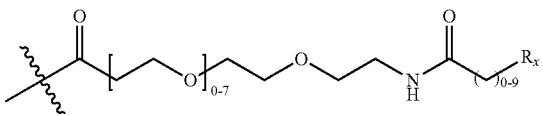

(VIa)

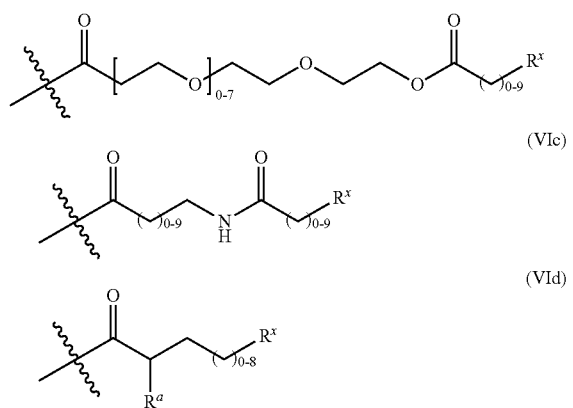

or salts thereof, wherein:

$R^a$ is selected from hydrogen, alkyl, sulfonate and methyl sulfonate;

$R^x$ is a moiety including a functional group capable of covalently linking the linker to an antibody; and / represents the point of attachment of the linker to a cytotoxic and/or cytostatic agent.

Specific exemplary embodiments of linkers according to structural formula (VIa)-(VId) that may be included in the ADCs described herein include the linkers illustrated below (as illustrated, the linkers include a group suitable for covalently linking the linker to an antibody, and "/" represents the point of attachment to a cytotoxic and/or cytostatic agent):

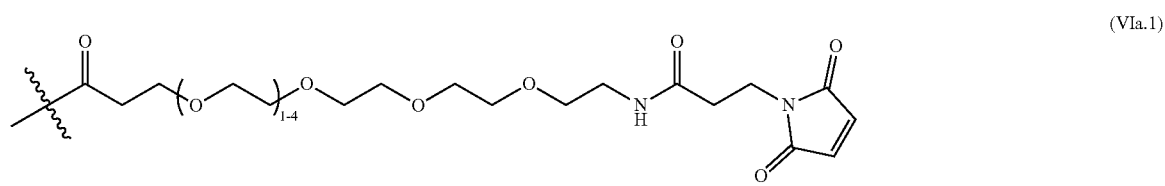

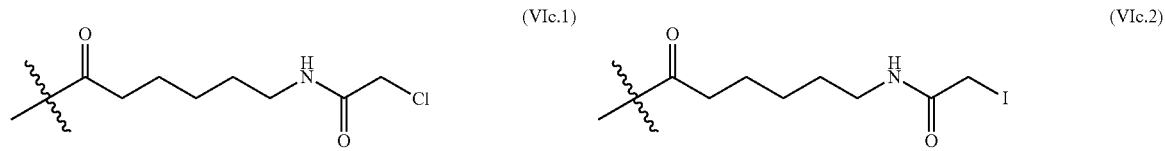

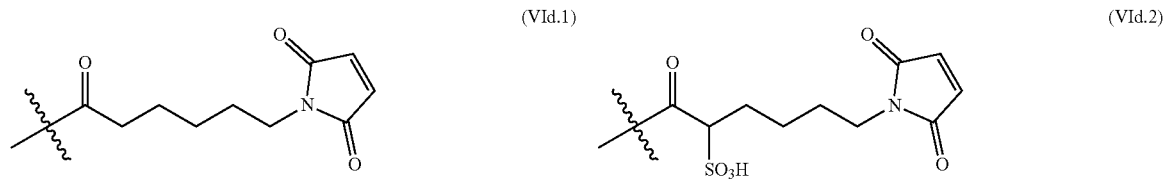

7.5.2.3. Groups Used to Attach Linkers to Antibodies

A variety of groups may be used to attach linker-drug synthons to antibodies to yield ADCs. Attachment groups can be electrophilic in nature and include: maleimide groups, activated disulfides, active esters such as NHS esters and HOBt esters, haloformates, acid halides, alkyl and benzyl halides such as haloacetamides. As discussed below, there are also emerging technologies related to "self-stabilizing" maleimides and "bridging disulfides" that can be used in accordance with the disclosure. The specific group used will depend, in part, on the site of attachment to the antibody.

One example of a "self-stabilizing" maleimide group that hydrolyzes spontaneously under antibody conjugation conditions to give an ADC species with improved stability is depicted in the schematic below. See US20130309256 A1; also Lyon et al., Nature Biotech published online, doi: 10.1038/nbt.2968.

Normal system:

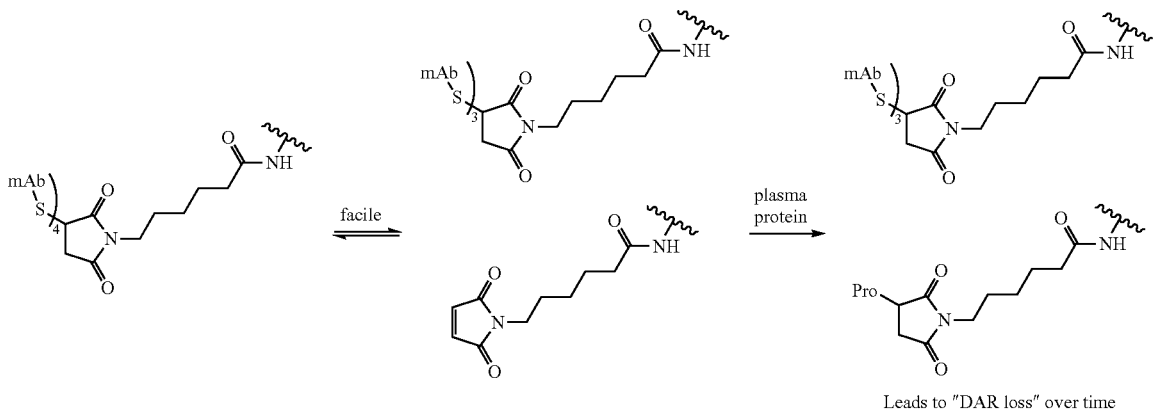

Leads to "DAR loss" over time

SGN MalDPR (maleimido dipropylamino) system:

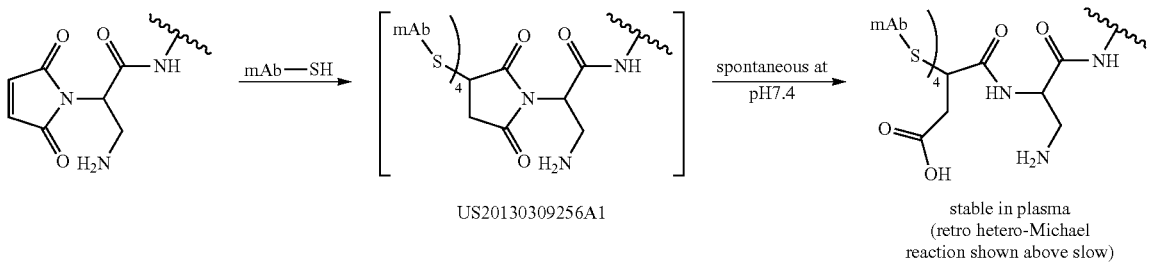

US20130309256A1 stable in plasma
(retro hetero-Michael
reaction shown above slow)

Polytherics has disclosed a method for bridging a pair of sulfhydryl groups derived from reduction of a native hinge disulfide bond. See, Badescu et al., 2014, Bioconjugate Chem. 25:1124-1136. The reaction is depicted in the schematic below. An advantage of this methodology is the ability to synthesize enriched DAR4 ADCs by full reduction of IgGs (to give 4 pairs of sulfhydryls) followed by reaction with 4 equivalents of the alkylating agent. ADCs containing "bridged disulfides" are also claimed to have increased stability.

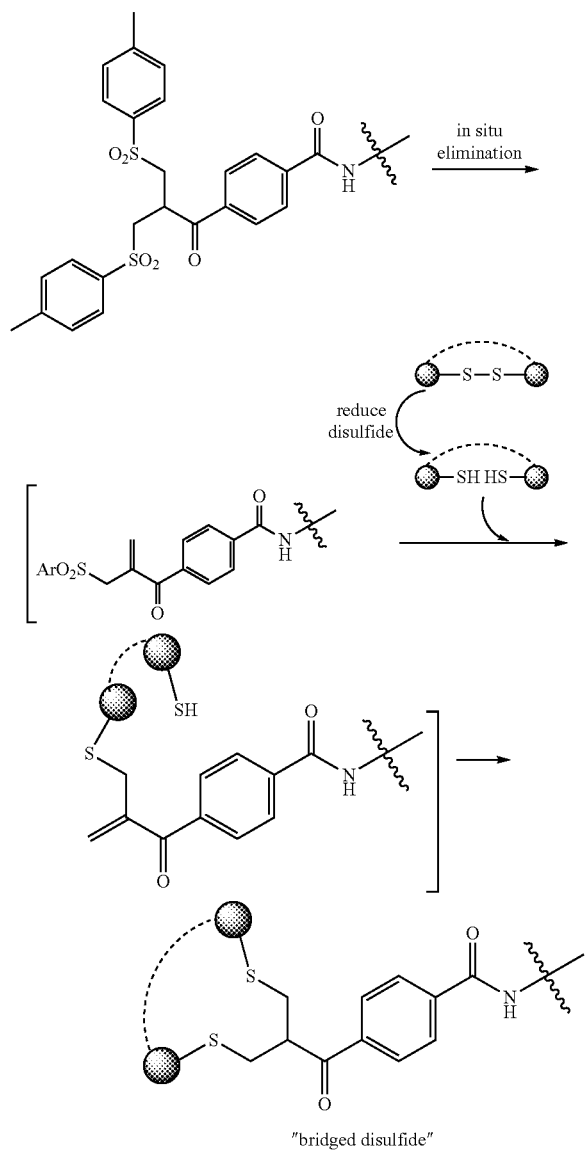

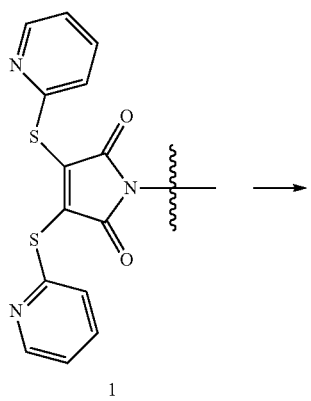

Similarly, as depicted below, a maleimide derivative (1, below) that is capable of bridging a pair of sulfhydryl groups has been developed. See WO2013/085925.

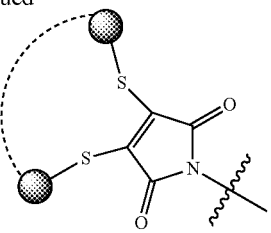

7.5.2.4. Linker Selection Considerations

As is known by skilled artisans, the linker selected for a particular ADC may be influenced by a variety of factors, including but not limited to, the site of attachment to the antibody (e.g., lys, cys or other amino acid residues), structural constraints of the drug pharmacophore and the lipophilicity of the drug. The specific linker selected for an ADC should seek to balance these different factors for the specific antibody/drug combination. For a review of the factors that are influenced by choice of linkers in ADCs, see Nolting, Chapter 5 "Linker Technology in Antibody-Drug Conjugates," In: *Antibody-Drug Conjugates: Methods in Molecular Biology*, vol. 1045, pp. 71-100, Laurent Ducry (Ed.), Springer Science & Business Medica, LLC, 2013.

For example, ADCs have been observed to effect killing of bystander antigen-negative cells present in the vicinity of the antigen-positive tumor cells. The mechanism of bystander cell killing by ADCs has indicated that metabolic products formed during intracellular processing of the ADCs may play a role. Neutral cytotoxic metabolites generated by metabolism of the ADCs in antigen-positive cells appear to play a role in bystander cell killing while charged metabolites may be prevented from diffusing across the membrane into the medium and therefore cannot affect bystander killing. In certain embodiments, the linker is selected to attenuate the bystander killing effect caused by cellular metabolites of the ADC. In certain embodiments, the linker is selected to increase the bystander killing effect.

The properties of the linker may also impact aggregation of the ADC under conditions of use and/or storage. Typically, ADCs reported in the literature contain no more than 3-4 drug molecules per antibody molecule (see, e.g., Chari, 2008, *Acc Chem Res* 41:98-107). Attempts to obtain higher drug-to-antibody ratios ("DAR") often failed, particularly if both the drug and the linker were hydrophobic, due to aggregation of the ADC (King et al., 2002, *J Med Chem* 45:4336-4343; Hollander et al., 2008, *Bioconjugate Chem* 19:358-361; Burke et al., 2009 *Bioconjugate Chem* 20:1242-1250). In many instances, DARs higher than 3-4 could be beneficial as a means of increasing potency. In instances where the cytotoxic and/or cytostatic agent is hydrophobic in nature, it may be desirable to select linkers that are relatively hydrophilic as a means of reducing ADC aggregation, especially in instances where DARS greater than 3-4 are desired. Thus, in certain embodiments, the linker incorporates chemical moieties that reduce aggregation of the ADCs during storage and/or use. A linker may incorporate polar or hydrophilic groups such as charged groups or groups that become charged under physiological pH to reduce the aggregation of the ADCs. For example, a linker may incorporate charged groups such as salts or groups that deprotonate, e.g., carboxylates, or protonate, e.g., amines, at physiological pH.

Exemplary polyvalent linkers that have been reported to yield DARs as high as 20 that may be used to link numerous cytotoxic and/or cytostatic agents to an antibody are described in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the content of which are incorporated herein by reference in their entireties.

In particular embodiments, the aggregation of the ADCs during storage or use is less than about 10% as determined by size-exclusion chromatography (SEC). In particular embodiments, the aggregation of the ADCs during storage or use is less than 10%, such as less than about 5%, less than about 4%, less than about 3%, less than about 2%, less than about 1%, less than about 0.5%, less than about 0.1%, or even lower, as determined by size-exclusion chromatography (SEC).

7.6. Methods of Making Anti-CS1 Antibody Drug Conjugates

The ADCs described herein may be synthesized using chemistries that are well-known. The chemistries selected will depend upon, among other things, the identity of the cytotoxic and/or cytostatic agent(s), the linker and the groups used to attach linker to the antibody. Generally, ADCs according to formula (I) may be prepared according to the following scheme:

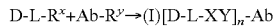

where D, L, Ab, XY and n are as previously defined, and $R^x$ and $R^y$ represent complementary groups capable of forming a covalent linkages with one another, as discussed above.

The identities of groups $R^x$ and $R^y$ will depend upon the chemistry used to link synthon D-L-W to the antibody. Generally, the chemistry used should not alter the integrity of the antibody, for example its ability to bind its target. Preferably, the binding properties of the conjugated antibody will closely resemble those of the unconjugated antibody. A variety of chemistries and techniques for conjugating molecules to biological molecules such as antibodies are known in the art and in particular to antibodies, are well-known. See, e.g., Amon et al., "Monoclonal Antibodies For Immunotargeting Of Drugs In Cancer Therapy," in: *Monoclonal Antibodies And Cancer Therapy*, Reisfeld et al. Eds., Alan R. Liss, Inc., 1985; Hellstrom et al., "Antibodies For Drug Delivery," in: *Controlled Drug Delivery*, Robinson et al. Eds., Marcel Dekker, Inc., 2nd Ed. 1987; Thorpe, "Antibody Carriers Of Cytotoxic Agents In Cancer Therapy: A Review," in: *Monoclonal Antibodies '84: Biological And Clinical Applications*, Pinchera et al., Eds., 1985; "Analysis, Results, and Future Prospective of the Therapeutic Use of Radiolabeled Antibody In Cancer Therapy," in: *Monoclonal Antibodies For Cancer Detection And Therapy*, Baldwin et al., Eds., Academic Press, 1985; Thorpe et al., 1982, *Immunol. Rev.* 62:119-58; PCT publication WO 89/12624. Any of these chemistries may be used to link the synthons to an antibody.

A number of functional groups $R^x$ and chemistries useful for linking synthons to accessible lysine residues are known, and include by way of example and not limitation NHS-esters and isothiocyanates.

A number of functional groups $R^x$ and chemistries useful for linking synthons to accessible free sulfhydryl groups of cysteine residues are known, and include by way of example and not limitation haloacetyls and maleimides.

However, conjugation chemistries are not limited to available side chain groups. Side chains such as amines may be converted to other useful groups, such as hydroxyls, by linking an appropriate small molecule to the amine. This strategy can be used to increase the number of available linking sites on the antibody by conjugating multifunctional small molecules to side chains of accessible amino acid residues of the antibody. Functional groups $R^x$ suitable for covalently linking the synthons to these "converted" functional groups are then included in the synthons.

The antibody may also be engineered to include amino acid residues for conjugation. An approach for engineering antibodies to include non-genetically encoded amino acid residues useful for conjugating drugs in the context of ADCs is described by Axup et al., 2012, *Proc Natl Acad Sci USA*. 109(40):16101-16106, as are chemistries and functional group useful for linking synthons to the non-encoded amino acids.

Typically, the synthons are linked to the side chains of amino acid residues of the antibody, including, for example, the primary amino group of accessible lysine residues or the sulfhydryl group of accessible cysteine residues. Free sulfhydryl groups may be obtained by reducing interchain disulfide bonds.

For linkages where $R^y$ is a sulfhydryl group (for example, when $R^x$ is a maleimide), the antibody is generally first fully or partially reduced to disrupt interchain disulfide bridges between cysteine residues. Specific cysteine residues and interchain disulfide bridges that may be reduced for attachment of drug-linker synthons including a group suitable for conjugation to a sulfhydryl group for exemplary humanized anti-CS1 antibody Hu34C3 are the interchain disulfide bridges at Cys220 (Eu numbering system) in the light chain; and Cys220, Cys226, and Cys229 (Eu numbering system; Cys233, Cys239, and Cys242, respectively, by Kabat numbering) in the human IgG$_1$ heavy chain as illustrated in FIGS. 3A-3C.

Cysteine residues that do not participate in disulfide bridges may engineered into an antibody by mutation of one or more codons. Reducing these unpaired cysteines yields a sulfhydryl group suitable for conjugation. Preferred positions for incorporating engineered cysteines include, by way of example and not limitation, positions S112C, S113C, A114C, S115C, A176C, S180C, S252C, V286C, V292C, S357C, A359C, S398C, S428C (Kabat numbering) on the human IgG$_1$ heavy chain and positions V110C, S114C, S121C, S127C, S168C, V205C (Kabat numbering) on the human Ig kappa light chain (see, e.g., U.S. Pat. Nos. 7,521,541, 7,855,275 and 8,455,622).

As will appreciated by skilled artisans, the number of cytotoxic and/or cytostatic agents linked to an antibody molecule may vary, such that a collection of ADCs may be heterogeneous in nature, where some antibodies contain one linked agent, some two, some three, etc. (and some none). The degree of heterogeneity will depend upon, among other things, the chemistries used for linking the cytostoxic and/or cytostatic agents. For example, where the antibodies are reduced to yield sulfhydryl groups for attachment, heterogenous mixtures of antibodies having zero, 2, 4, 6 or 8 linked agents per molecule are often produced. Furthermore, by limiting the molar ratio of attachment compound, antibodies having zero, 1, 2, 3, 4, 5, 6, 7 or 8 linked agents per molecule are often produced. Thus, it will be understood that depending upon context, stated DARs may be averages for a collection of antibodies. For example, "DAR4" can refer to an ADC preparation that has not been subjected to purification to isolate specific DAR peaks and can comprise a heterogeneous mixture of ADC molecules having different numbers of cytostatic and/or cytotoxic agents attached per antibody (e.g., 0, 2, 4, 6, 8 agents per antibody), but has an average drug-to-antibody ratio of 4. Similarly, in some embodiments, "DAR2" refers to a heterogeneous ADC preparation in which the average drug-to-antibody ratio is 2.

When enriched preparations are desired, antibodies having defined numbers of linked cytotoxic and/or cytostatic agents may be obtained via purification of heterogeneous mixtures, for example, via column chromatography, e.g., hydrophobic interaction chromatography.

Heterogeneous ADC preparations may be processed, for example, by hydrophobic interaction chromatography ("HIC") to yield preparations enriched in an ADC having a specified DAR of interest (or a mixture of two or more specified DARS). Such enriched preparations are designed herein as "EX," where "E" indicates the ADC preparation has been processed and is enriched in an ADC having a specific DAR and "X" represents the number of cytostatic and/or cytotoxic agents linked per ADC molecule. Preparations enriched in a mixture of ADCs having two specific DARs are designed "EXEY," three specific DARs "EXEYEZ" etc., where "E" indicates the ADC preparation has been purified to enrich the specified DARs and "X," "Y" and "Z" represent the DARs enriched. As specific examples, "E2" refers to an ADC preparation that has been enriched to contain primarily ADCs having two cytostatic and/or cytotoxic agents linked per ADC molecule. "E4" refers to an ADC preparation that has been enriched to contain primarily ADCs having four cytostatic and/or cytotoxic agents linked per ADC molecule. "E2E4" refers to an ADC preparation that has been enriched to contain primarily two ADC populations, one having two cytostatic and/or cytotoxic agents linked per ADC molecule and another having four cytostatic and/or cytotoxic agents linked per ADC molecule.

As used herein, enriched "E" preparations will generally be at least about 80% pure in the stated DAR ADCs, although higher levels of purity, such as purities of at least about 85%, 90%, 95%, 98%, or even higher, may be obtainable and desirable. For example, an "EX" preparation will generally be at least about 80% pure in ADCs having X cytostatic and/or cytotoxic agents linked per ADC molecule. For "higher order" enriched preparations, such as, for example, "EXEY" preparations, the sum total of ADCs having X and Y cytostatic and/or cytotoxic agents linked per ADC molecule will generally comprise at least about 80% of the total ADCs in the preparation. Similarly, in an enriched "EXEYEZ" preparation, the sum total of ADCs having X, Y and Z cytostatic and/or cytotoxic agents linked per ADC molecule will comprise at least about 80% of the total ADCs in the preparation.

In some embodiments, enriched or highly purified ADC preparations from heterogeneous mixtures of ADCs comprising the humanized antibody Hu34C3 are contemplated. For example, mixtures of ADCs of Hu34C3 that have undergone chromatography purification, e.g., HIC, can have an enriched distribution of drug and linker attached per antibody. Hu34C3 E2 refers to an enriched ADC population that primarily contains 2 drug molecules per antibody. Hu34C3 E4 refers to an enriched ADC population that primarily contains 4 drug molecules per antibody. Hu34C3 E2E4 is an enriched ADC population that primarily contains 2 and 4 drug molecules per antibody. In some embodiments, the Hu34C3 ADC is enriched to Hu34C3 E2, Hu34C3 E4, or Hu34C3 E2E4. In a specific embodiment, the Hu34C3 E2 is Hu34C3-MMAE E2, a preparation of Hu34C3 with two MMAE molecules per antibody. In another specific embodiment, the Hu34C3 E4 is Hu34C3-MMAE E4, a preparation of Hu34C3 with four MMAE molecules per antibody.

Purity may be assessed by a variety of methods, as is known in the art. As a specific example, an ADC preparation may be analyzed via HPLC or other chromatography and the purity assessed by analyzing areas under the curves of the resultant peaks.

Specific methods for obtaining heterogenous mixtures of ADCs comprising humanized antibody Hu34C3 having an average DAR of 4, as well as highly purified or enriched preparations containing 2 and 4 linked agents are provided in the Examples section. These specific methods may be modified using routine skill to obtain heterogeneous and/or enriched ADCs comprising other anti-CS1 antibodies, linkers and/or cytotoxic and/or cytostatic agents.

7.7. Compositions

The antibodies and/or ADCs described herein may be in the form of compositions comprising the antibody and/or ADC and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the antibody and/or ADC and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody and/or ADC, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an antibody and/or ADC described herein per dose. The quantity of antibody and/or ADC included in a unit dose will depend on the disease being treated, as well as other factors as are well known in the art. Such unit dosages may be in the form of a lyophilized dry powder containing an amount of antibody and/or ADC suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of antibody and/or ADC suitable for a single administration.

The pharmaceutical compositions may also be supplied in bulk from containing quantities of ADC suitable for multiple administrations.

Pharmaceutical compositions may be prepared for storage as lyophilized formulations or aqueous solutions by mixing an antibody and/or ADC having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 wt % per wt of ADC.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

A specific embodiment of an aqueous composition suitable for administration via intravenous infusion comprises 20 mg/mL Hu34C3 antibody and/or ADC, e.g., Hu34C3 E2. The Hu34C3 antibody and/or ADC composition may be in the form of a lyophilized powder, e.g., in a vial containing 50 mg, 100 mg, or 200 mg of Hu34C3 antibody and/or ADC, that, upon reconstitution with sterile water or other solution suitable for injection or infusion (for example, 0.9% saline, Ringer's solution, lactated Ringer's solution, etc.) provides the above aqueous composition. The specific embodiment, or other embodiments of compositions, may also be in the form of a syringe or other device suitable for injection and/or infusion pre-filled with a quantity of composition suitable for a single administration of Hu34C3 antibody and/or ADC.

7.8. Methods of Use

Pharmaceutical compositions comprising the antibodies and/or ADCs described herein are used to treat a plasma cell neoplasm, e.g., MM. Typically, the pharmaceutical compositions can be used to treat Monoclonal Gammopathy of Undetermined Significance (MGUS), plasmacytoma, smoldering-asymptomatic MM, and symptomatic MM, ranging from newly diagnosed to relapsed, and relapsed and refractory.

The pharmaceutical compositions can be combined with other treatment strategies, such as radiation therapy, surgery, chemotherapy, stem cell transplantation, and supportive therapy to develop an effective treatment strategy based on the stage of myeloma being treated.

The staging system most widely used since 1975 has been the Durie-Salmon system, in which the clinical stage of disease (Stage I, II, or III) is based on four measurements (see, e.g., Durie and Salmon, 1975, Cancer, 36:842-854). These four measurements are: (1) levels of monoclonal (M) protein (also known as paraprotein) in the serum and/or the urine; (2) the number of lytic bone lesions; (3) hemoglobin values; and, (4) serum calcium levels. These three stages can be further divided according to renal function, classified as A (relatively normal renal function, serum creatinine value <2.0 mg/dL) and B (abnormal renal function, creatinine value ≥2.0 mg/dL). A new, simpler alternative is the International Staging System (ISS) (see, e.g., Greipp et al., 2003, "Development of an international prognostic index (IPI) for myeloma: report of the international myeloma working group", The Hematology). The ISS is based on the assessment of two blood test results, beta$_2$-microglobulin ($\beta_2$-M) and albumin, which separates patients into three prognostic groups irrespective of type of therapy.

Administration of the pharmaceutical compositions at selected dosage ranges and routes typically elicits a beneficial response as defined by the European Group for Blood and Marrow transplantation (EBMT). EBMT criteria for response are listed below.

| EBMT/IBMTR/ABMTR[1] Criteria for Response | |
|---|---|
| Complete Response | No M-protein detected in serum or urine by immunofixation for a minimum of 6 weeks and fewer than 5% plasma cells in bone marrow |
| Partial Response | >50% reduction in serum M-protein level and/or 90% reduction in urine free light chain excretion or reduction to <200 mg/24 hrs for 6 weeks[2] |
| Minimal Response | 25-49% reduction in serum M-protein level and/or 50-89% reduction in urine free light chain excretion which still exceeds 200 mg/24 hrs for 6 weeks[3] |
| No Change | Not meeting the criteria or either minimal response or progressive disease |
| Plateau | No evidence of continuing myeloma-related organ or tissue damage, <25% change in M-protein levels and light chain excretion for 3 months |
| Progressive Disease | Myeloma-related organ or tissue damage continuing despite therapy or its reappearance in plateau phase, >25% increase in serum M-protein level (>5 g/L) and/or >25% increase in urine M-protein level (>200 mg/24 hrs) and/or >25% increase in bone marrow plasma cells (at least 10% in absolute terms)[2] |
| Relapse | Reappearance of disease in patients previously in complete response, including detection of paraprotein by immunofixation |

[1]EBMT: European Group for Blood and Marrow transplantation; IBMTR: International Bone Marrow Transplant Registry; ABMTR: Autologous Blood and Marrow Transplant Registry.
[2]For patients with non-secretory myeloma only, reduction of plasma cells in the bone marrow by >50% of initial number (partial response) or 25-49% of initial number (minimal response) is required.
[3]In non-secretory myeloma, bone marrow plasma cells should increase by >25% and at least 10% in absolute terms; MRI examination may be helpful in selected patients.

Additional criteria that can be used to measure the outcome of a treatment include "near complete response" and "very good partial response". A "near complete response" is defined as the criteria for a "complete response" (CR), but with a positive immunofixation test. A "very good partial response" is defined as a greater than 90% decrease in M protein (see, e.g., Multiple Myeloma Research Foundation, Multiple Myeloma: Treatment Overview 9 (2005)).

The degree to which administration of the compositions elicits a response in an individual clinically manifesting at least one symptom associated with MM, depends in part, on the severity of disease, e.g., Stage I, II, or III, and in part, on whether the patient is newly diagnosed or has relapsed, or relapsed and refractory MM. Thus, in some embodiments, administration of the pharmaceutical composition elicits a complete response.

In other embodiments, administration of the pharmaceutical composition elicits a very good partial response or a partial response.

In other embodiments, administration of the pharmaceutical composition elicits a minimal response.

In other embodiments, administration of the pharmaceutical composition prevents the disease from progressing, resulting in a response classified as "no change" or "plateau" by the EBMT.

Anti-CS1 ADCs may be administered alone (monotherapy) or adjunctive to, or with, other anti-cancer therapies and/or targeted or non-targeted anti-cancer agents. When administered as monotherapy, one or more anti-CS1 ADCs may be used. Whether administered as monotherapy or adjunctive to, or with, other therapies or agents, an amount of anti-CS1 ADC is administered such that the overall treatment regimen provides therapeutic benefit.

Therapeutic agents that can be used in combination with the antibodies and/or ADCs described herein include, but are not limited to, targeted agents, conventional chemotherapy agents, and supportive care agents. One or more therapeutic agents from the different classes, e.g., targeted, conventional chemotherapeutic, and supportive care, and/or subclasses can be combined in the compositions described herein. By way of example, targeted agents can be separated into a number of different subclasses depending on their mechanism of action. As will be apparent to those of skill in the art, the agents can have more than one mechanism of action, and thus, could be classified into one or more subclasses. For purposes of the compositions and methods described herein, the following subclasses have been identified: anti-angiogenic, inhibitors of growth factor signaling, immunomodulators, inhibitors of protein synthesis, folding and/or degradation, inhibitors of gene expression, pro-apoptotic agents, agents that inhibit signal transduction and agents with "other" mechanisms of action. Typically, the mechanism of action for agents falling into the "other" subclass is unknown or poorly characterized.

For example, in some embodiments, targeted agents, such as bevacizumab, sunitinib, sorafenib, vandetanib, aflibercept, etaracizumab (MEDI-522), cilengitide, TKI258, CP-751,871, atacicept, rituximab, alemtuzumab, aldesleukine, atlizumab, tocilizumab, siltuximab, temsirolimus, everolimus, NPI-1387, MLNM3897, HCD 122, SGN-40, HLL1, huN901-DM1, atiprimod, natalizumab, bortezomib, NPI-0052, tanespimycin, belinostat, panobinostat, mapatumumab, lexatumumab, AMG951, oblimersen, plitidepsin, SCIO-469, P276-00, enzastaurin, tipifarnib, perifosine, imatinib, dasatinib, daratumumab, SAR650984, MOR202, nivolumab, pembrolizumab, pomalidomide, lenalidomide, and thalidomide, can be combined with the antibodies and/or ADCs described herein and used to treat MM patients.

In other embodiments, agents that enhance ADCC (such as anti-KIR or anti-CD137), enhance immune activation such as checkpoint inhibitors (including anti-PD 1, anti-PDL1, anti-TIM3, anti-AG3, anti-CTLA4), BTK inhibitors (such as ibrutinib and CC-292), T-cell agonists (such as anti-OX40, anti-GITR) or non T-cell agonists (such as anti-CD40) can be combined with the antibodies and/or ADCs described herein and used to treat MM patients.

By way of another example, conventional chemotherapy agents, such as alklyating agents (e.g., oxaliplatin, carboplatin, cisplatin, cyclophosphamide, melphalan, ifosfamide, uramustine, chlorambucil, carmustine, mechloethamine, thiotepa, busulfan, temozolomide, dacarbazine), anti-metabolic agents (e.g., gemcitabine, cytosine arabinoside, Ara-C, capecitabine, 5FU (5-fluorouracil), azathioprine, mercaptopurine (6-MP), 6-thioguanine, aminopterin, pemetrexed, methotrexate), plant alkaloid and terpenoids (e.g., docetaxel, paclitaxel, vincristine, vinblastin, vinorelbine, vindesine, etoposide, VP-16, teniposide, irinotecan, topotecan), anti-tumor antibiotics (e.g., dactinomycin, doxorubicin, liposomal doxorubicin, daunorubicin, daunomycin, epirubicin, mitoxantrone, adriamycin, bleomycin, plicamycin, mitomycin C, carminomycin, esperamicins), and other agents (e.g., darinaparsin) can be combined with the antibodies and/or ADCs described herein and used to treat MM patients.

By way of another example, infusion reactions in patients receiving an anti-CS1 antibody or ADC can be managed by administering intravenous corticosteroids and/or premedications, including acetaminophen/paracetamol, diphenhydramine, H2-blockers, or steroids (such as dexamethasone, prednisone, and prednisolone). The corticosteroids and/or premedications will be administered prior to dosing with the anti-CS1 antibody or ADC using well established guidelines for the prevention of infusion reactions (Lonial, et al., 2012, J Clin Oncol 30:1953-1959).

In some embodiments, the antibodies and/or ADCs described herein are combined with dexamethasone and used to treat MM patients. In other embodiments, the antibodies and/or ADCs described herein are combined with pomalidomide, or pomalidomide and dexamethasone, and used to treat MM patients. In other aspects, the antibodies and/or ADCs described herein are combined with lenalidomide, or lenalidomide and dexamethasone, and used to treat MM patients. In other embodiments, the antibodies and/or ADCs described herein are combined with thalidomide, or thalidomide and dexamethasone, and used to treat MM patients. In yet other embodiments, the antibodies and/or ADCs described herein are combined with bortezomib, bortezomib and dexamethasone, or panobinostat, panobinostat and bortezomib, panobinostat with bortezomib and dexamethasone and used to treat MM. In yet other embodiments, the antibodies and/or ADCs described herein are combined with melphalan, melphalan and prednisone (MP), MP and thalidomide (MPT), or MP and bortezomib (VMP) and used to treat MM. In yet other embodiments, the antibodies and/or ADCs described herein are combined with cyclophosphamide, cyclophosphamide and thalidomide and dexamethasone (CTD), or cyclophosphamide and bortezomib and dexamethasone (CyBorD) and used to treat MM.

By way of another example, supportive care agents such as bisphosphonates (e.g., pamidronate, zoledronic acid), ibandronate, gallium nitrate, denosumab, darbepotin alpha, epoetin alpha, eltrombopag, and pegfilgrastim can be combined with the antibodies and/or ADCs described herein and used to treat MM patients.

In some embodiments, Hu34C3 E2 is combined with dexamethasone and used to treat MM patients. In other embodiments, Hu34C3 E2 is combined with pomalidomide, or pomalidomide and dexamethasone, and used to treat MM patients. In other aspects, Hu34C3 E2 is combined with lenalidomide, or lenalidomide and dexamethasone, and used to treat MM patients. In yet other embodiments, Hu34C3 E2 is combined with bortezomib, and optionally with dexamethasone, and used to treat MM. In yet other aspects, Hu34C3 E2 is combined with bortezomib and with an IMiD (e.g., thalidomide, pomalidomide, lenalidomide) and optionally with dexamethasone and used to treat MM. In yet other embodiments, Hu34C3 E2 is combined with melphalan, melphalan and prednisone (MP), MP and thalidomide (MPT), or MP and bortezomib (VMP) and used to treat MM. In yet other embodiments, Hu34C3 E2 is combined with cyclophosphamide, cyclophosphamide and thalidomide and dexamethasone (CTD), or cyclophosphamide and bortezomib and dexamethasone (CyBorD) and used to treat MM.

7.9. Dosages and Administration Regimens

The amount of antibody and/or ADC administered will depend upon a variety of factors, including but not limited to, the particular disease being treated, the mode of administration, the desired therapeutic benefit, the stage or severity of the disease, the age, weight and other characteristics of the patient, etc. Determination of effective dosages is within the capabilities of those skilled in the art.

Effective dosages may be estimated initially from in vivo animal models or clinical. Suitable animal models for a wide variety of diseases are known in the art. Initial dosages may also be estimated from clinical data with other anti-CS1 antibodies, such as, for example, clinical data obtained with elotuzumab.

In one embodiment, an anti-CS1 antibody and/or ADC composition described herein is further diluted with saline and administered via intravenous infusion once every 7 days, once every 14 days, once every 21 days, or once every 28 days. In certain embodiments, for the first cycle, the infusion occurs over 180 minutes. In some embodiments, subsequent infusions occur over 90 minutes.

When administered as monotherapy, doses of anti-CS1 antibodies used in the methods described herein typically range between 0.5 mg/kg to 20 mg/kg when administered every 7, 14, 21, or 28 days via intravenous injection or infusion. In some embodiments, an anti-CS1 antibody, e.g., Hu34C3, is present in a pharmaceutical composition at a concentration, or in a weight/volume percentage, or in a weight amount, suitable for intravenous administration at a dosage rate at least about 0.5 mg/kg, at least about 0.75 mg/kg, at least about 1 mg/kg, at least about 2 mg/kg, at least about 2.5 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, and at least about 20 mg/kg. In some embodiments, Hu34C3 antibody is administered once every 21 days at 0.6 mg/kg, 0.9 mg/kg, 1.4 mg/kg, 2 mg/kg, 3 mg/kg, 4 mg/kg, 5 mg/kg, 6 mg/kg, 7 mg/kg, or 8 mg/kg. For example, Hu34C3 antibody can be administered once every 21 days at 4 mg/kg. In certain embodiments, Hu34C3 antibody is administered once every 21 days at 5 mg/kg. In certain embodiments, Hu34C3 antibody is administered once every 21 days at 6 mg/kg. In certain embodiments, Hu34C3 antibody is administered once every 21 days at 7 mg/kg. In some embodiments, Hu34C3 antibody is administered once every 14 days at 0.4 mg/kg, 0.6 mg/kg, 1 mg/kg, 1.3 mg/kg, 2 mg/kg, 2.6 mg/kg, 3.3 mg/kg, 4 mg/kg, 4.6 mg/kg, or 5.3 mg/kg. For example, Hu34C3 antibody can be administered once every 14 days at 2.6 mg/kg. In certain embodiments, Hu34C3 antibody is administered once every 14 days at 3.3 mg/kg. In certain embodiments, Hu34C3 antibody is administered once every 14 days at 4 mg/kg. In certain embodiments, Hu34C3 antibody is administered once every 14 days at 4.6 mg/kg. In some embodiments, Hu34C3 antibody is administered once every 7 days at 0.2 mg/kg, 0.3 mg/kg, 0.5 mg/kg, 0.7 mg/kg, 1 mg/kg, 1.3 mg/kg, 1.7 mg/kg, 2 mg/kg, 2.3 mg/kg, or 2.6 mg/kg. For example, Hu34C3 antibody can be administered once every 7 days at 1.3 mg/kg. In certain embodiments, Hu34C3 antibody is administered once every 7 days at 1.7 mg/kg.

Monotherapy doses of ADCs used in the methods described herein typically range between 0.15 mg/kg to 10 mg/kg. In some embodiments, Hu34C3 E2 is used at dosage range between 0.6 mg/kg to 6 mg/kg. In some embodiments, an ADC such as Hu34C3 E2 is present in a pharmaceutical composition at a concentration, or in a weight/volume percentage, or in a weight amount, suitable for intravenous administration at a dosage rate at least about 0.15 mg/kg, 0.3 mg/kg, 0.6 mg/kg, at least about 1.2 mg/kg, at least about 2 mg/kg, at least about 2.4 mg/kg, at least about 3.6 mg/kg, at least about 4.8 mg/kg, at least about 5.4 mg/kg, and at least about 6.0 mg/kg, at least about 7.0 mg/kg, at least about 8 mg/kg, at least about 9 mg/kg, at least about 10 mg/kg. In some embodiments, Hu34C3 E2 is administered once every 21 days at 0.6 mg/kg, 0.9 mg/kg, 1.4 mg/kg, 2 mg/kg, 3 mg/kg, 4 mg/kg, 5 mg/kg, 6 mg/kg, 7 mg/kg, or 8 mg/kg. For example, Hu34C3 E2 can be administered once every 21 days at 4 mg/kg. In certain embodiments, Hu34C3 E2 is administered once every 21 days at 5 mg/kg. In certain embodiments, Hu34C3 E2 is administered once every 21 days at 6 mg/kg. In certain embodiments, Hu34C3 E2 is administered once every 21 days at 7 mg/kg. In some embodiments, Hu34C3 E2 is administered once every 14 days at 0.4 mg/kg, 0.6 mg/kg, 1 mg/kg, 1.3 mg/kg, 2 mg/kg, 2.6 mg/kg, 3.3 mg/kg, 4 mg/kg, 4.6 mg/kg, or 5.3 mg/kg. For example, Hu34C3 E2 can be administered once every 14 days at 2.6 mg/kg. In certain embodiments, Hu34C3 E2 is administered once every 14 days at 3.3 mg/kg. In certain embodiments, Hu34C3 E2 is administered once every 14 days at 4 mg/kg. In certain embodiments, Hu34C3 E2 is administered once every 14 days at 4.6 mg/kg. In some embodiments, Hu34C3 E2 is administered once every 7 days at 0.2 mg/kg, 0.3 mg/kg, 0.5 mg/kg, 0.7 mg/kg, 1 mg/kg, 1.3 mg/kg, 1.7 mg/kg, 2 mg/kg, 2.3 mg/kg, or 2.6 mg/kg. For example, Hu34C3 E2 can be administered once every 7 days at 1.3 mg/kg. In certain embodiments, Hu34C3 E2 is administered once every 7 days at 1.7 mg/kg.

When administered adjunctive to, or with, other agents, such as other chemotherapeutic agents, the antibodies and/or ADCs may be administered on the same schedule with the other agents, or on a different schedule. When administered on the same schedule, the antibodies and/or ADC may be administered before, after, or concurrently with the other agent. In some embodiments where the antibody and/or ADC is administered adjunctive to, or with, standards of care, the antibody and/or ADC may be initiated prior to commencement of the standard therapy, for example a day, several days, a week, several weeks, a month, or even several months before commencement of standard of care therapy.

In some embodiments, the antibodies and/or ADCs may be administered in combination with dexamethasone. For example, Hu34C3 E2 can be administered weekly, every 2 weeks, every 3 weeks or monthly between 0.15 mg/kg to 10 mg/kg in combination with low-dose dexamethasone provided as an oral tablet at 20 mg/week or 40 mg/week on a 28-day cycle. In other embodiments, Hu34C3 E2 can be administered weekly, every 2 weeks, every 3 weeks or monthly between 0.15 mg/kg to 10 mg/kg in combination with high-dose dexamethasone provided orally as 40 mg on days 1-4, 9-12, and 17-20 of a 28-day cycle. In other embodiments, Hu34C3 E2 can be administered weekly, every 2 weeks, every 3 weeks or monthly between 0.15 mg/kg to 10 mg/kg in combination with dexamethasone to inhibit infusion related reactions. Dexamethasone may be provided orally or intravenously at 8 mg, 32 mg or 40 mg, 1-24 hrs prior to dosing of Hu34C3 E2.

In other embodiments, the antibodies and/or ADCs may be administered in combination with pomalidomide with or without low-dose dexamethasone. For example, Hu34C3 E2 can be administered weekly, every 2 weeks, every 3 weeks or monthly between 0.15 mg/kg to 10 mg/kg in combination with low-dose dexamethasone provided as an oral tablet at 20 mg/week or 40 mg/week on a 28-day cycle and with pomalidomide at 4 mg/day oral every day for 21 days plus 7 days with no drug on repeated 28 day cycles.

In other embodiments, the antibodies and/or ADCs may be administered in combination with lenalidomide with or without low-dose dexamethasone. For example, Hu34C3 E2 can be administered weekly, every 2 weeks, every 3 weeks or monthly between 0.15 mg/kg to 10 mg/kg in combination with low-dose dexamethasone provided as an oral tablet at 20 mg/week or 40 mg/week on a 28-day cycle and with lenalidomide 25 mg orally on days 1 to 21.

In some embodiments, the antibodies and/or ADCs may be administered in combination with bortezomib with or without low-dose dexamethasone. For example, Hu34C3 E2 can be administered weekly, every 2 weeks, every 3 weeks or monthly between 0.15 mg/kg to 10 mg/kg in combination with bortezomib at 1.3 mg/m$^2$ IV or subcutaneously on Days 1, 4, 8, and 11 for the first 8 cycles, and then on Days 1, 8, and 15 until progression. In other embodiments, Hu34C3 E2 can be administered weekly, every 2 weeks, every 3 weeks or monthly between 0.15 mg/kg to 10 mg/kg in combination with bortezomib at 1.3 mg/m$^2$ IV or subcutaneously on Days 1, 4, 8, and 11 for the first 8 cycles, and then on Days 1, 8, and 15 (until disease progression) and low dose dexamethasone orally or intravenously at 8 mg on days 1, 8, 15 (first two cycles), days 1 &11 (for cycles 3-8), and days 1 and 15 (for all additional cycles). As will be appreciated by a person of skill in the art, other doses of bortezomib may also be used, including 1.3, 1.0, or 0.7 mg/m$^2$/day. Additional dosing regimen may also include dosing once per week.

8. EXAMPLES

The following Examples, which highlight certain features and properties of the exemplary embodiments of the antibodies and ADCs described herein are provided for purposes of illustration, and not limitation.

Example 1. Generation of Anti-CS1 Antibodies that Bind Novel Epitopes

The methodology used to generate and identify various anti-CS1 antibodies is described below.

1.1. Preparation of Plasmid Encoding Full Length Human CS1

Full length human CS1 (FL-HuCS1) cDNA was isolated from Raji cells using primers flanking the CS1 gene. The PCR product was gel purified and ligated into a vector allowing for stable expression of FL-HuCS1. The plasmid encoding FL-HuCS1 was purified on a large scale and confirmed by DNA sequencing.

1.2. Preparation of Plasmid Encoding the Extracellular Domain of Cynomolgus CS1

DNA encoding the extracellular domain (ECD) of cynomolgus CS1 (CmCS1) was isolated from activated PBMC cells using primers flanking the ECD of CmCS1. The PCR product was gel purified and ligated into a vector encoding the constant region of human IgG1 (human Fc-γ1). The plasmid encoding CmCS1 ECD-huIgG1 was purified on a large scale and confirmed by DNA sequencing.

1.3. Preparation of NS0 Cells Stably Expressing Full Length hCS1

50 μg of plasmid encoding FL-HuCS1 was linearized, precipitated in ethanol, washed, and resuspended in 500 μL of sterile PBS. NS0 cells (ECACC Catalog #85110503) were washed twice in cold PBS and resuspended at 2×10$^7$ cells/mL in PBS. 500 μL of the NS0 cell suspension (corresponding to 1×10$^7$ cells) was mixed with the resuspended linearized FL-HuCS1 plasmid. Cells were electroporated at 1.5V and 3 µF using a BioRad Gene pulser. Following electroporation, cells were added to 100 mL of DMEM complete media and plated into T75 flask. G418 was added to the DMEM complete media at 1 µg/mL 24 hours after the transfection. Positive transfectants were identified by flow cytometry on day 10 and expanded into 48- and 24-well plates. Positive transfectants were re-screened, and high FL-HuCS1 expressing clones were expanded and used for immunization.

1.4. Preparation of HEK-293 Cells Stably Expressing the Extracellular Domain of Cynomolgus CS1

The CmCS1 ECD-HuIgG1 plasmid was used to stably transfect HEK-293 cells. Transfection was performed using Lipofectamine (Invitrogen) as recommended according to the manufacturers instructions. Briefly, HEK-293 cells were grown on 10 cm plates, washed twice in cold PBS, and covered with Opti-MEM media. Lipofectamine (10 µL) was mixed with the CmCS1 ECD-huIgG1 plasmid (2 µg) for 10 minutes then added to the prepared HEK-293 cells. G418 was added to the DMEM complete media at 1 µg/mL 24 hours after the transfection. G418 resistant cells were subcloned into 96-well plates, and high CmCS1 ECD-huIgG1 expressing clones were identified by ELISA.

1.5. Purification of cmCS1 ECD-huIgG1

Stable transfectants expressing the CmCS1 ECD-huIgG1 fusion protein were expanded into 600 mL of DMEM complete media with glucose additives for five days. The fusion protein was purified on a protein A Sepharose column and dialyzed against 1×PBS. Reduced and non-reduced forms of CmCS1 ECD-huIgG1 were analyzed by Coomassie staining. CmCS1 ECD-huIgG1 was also analyzed by Western blot using anti-HuIgG, and confirmed by N-terminal sequencing.

1.6. Immunization Strategy

Irradiated NS0 cells expressing FL-huCS1 or purified recombinant CmCS1 ECD-huIgG1 fusion protein were used to immunize BALB/c and SJL mice via footpads. Briefly, mice were immunized in the hind footpads with 10 µg of CmCS1 ECD-huIgG1 protein or 5 million irradiated NS0-huCS1 cells with an equal volume of GerbuMM adjuvant in a total volume of 25 µL. Footpad immunizations were performed 4 times at 3- or 4-day intervals. The NS0-HuCS1 cells were used for the first 2 immunizations and CmCS1 ECD-huIgG1 fusion proteins were used for subsequent boosts.

1.7. Preparation of Hybridomas

Three mice immunized with NSO-HuCS1 and CmCS1 ECD-huIgG1 were sacrificed. The popliteal lymph nodes were removed from the mice. Lymphocytes were isolated from the lymph nodes, and hybridomas were generated by fusing lymphocytes with the murine myeloma cells line NS0 using an electrofusion (BTX ECM2001) machine. Fused cells were plated into 96-well plates at a density of 2×10$^6$ cells per plate. Selection of successfully fused cells was accomplished using media containing hypoxanthine, aminopterin, and thymidine (HAT).

1.8. Identification of Anti-CS1 Antibodies

Specificity of antibodies secreted by hybridomas was determined by binding to human CS1 ECD-huIgG1 and CmCS1 ECD-huIgG1, and not to negative control CLL1 ECD-huIgG1 by ELISA. Human CS1-ECD-huIgG1, CmCS1 ECD-huIgG1, or CLL1 ECD-huIgG1 was captured onto plates that had been pre-coated with goat anti-human IgG (Fc specific) antibody. Hybridoma supernatants were allowed to bind to the proteins and detected with an HRP conjugated donkey anti mouse IgG (H+L) antibody. Hybridomas that recognized both human and cynomolgus but not CLL fusion proteins were further tested for binding to the huCS1 molecule on an endogenously expressing OPM-2 cells using standard flow cytometry protocols. Briefly, OPM-2 cells were incubated with hybridoma supernatants for 30 minutes on ice. After extensive washing, cells were incubated with phycoerythrin conjugated goat anti mouse IgG specific antibodies for 30 minutes on ice. Cells were washed again and analyzed on a Becton Dickinson FACSCalibur for the presence of cell surface bound antibodies. A summary of the parameters of the immunizations strategy and the numbers of clones identified is provided in Table 4, below. The vast majority of human/cyno CS1 cross-reactive antibodies were generated in SJL strain (N=28), while similar immunization in BALB/c mice resulted in a single human/cyno CS1 cross-reactive antibody.

TABLE 4

Summary of Immunization Strategies for Anti-CS1 Antibodies

|  | AD158 | AD159 | AD176 |
| --- | --- | --- | --- |
| Study | Cage 7 | Cage 8 | Cage 8 |
| Strain | BALB/c | SJL | SJL |
| Immunization | NS0-CS1 with CmCS1-Fc boosts | NS0-CS1 with CmCS1-Fc boosts | 3T12-CmCS1 with HuCS1-Fc boosts |
| Mouse # | 1, 3 | 2, 4, 5 | 2, 3 |
| # plates | 15 | 35 | 25 |
| 1ry screen (HuCS1Fc+, CmCS1+, CLL1Fc−) | 2 | 197 | 17 |
| 2ry screen (OPM-2+) | 1 | 13 | 15 |

Example 2. The New Anti-CS1 Antibodies Bind to Epitopes Different from the Epitope Bound by PDL241

Exemplary anti-CS1 antibodies were tested in flow-cytometry-based competition assays with known anti-CS1 antibody PDL241. The competition assays confirm that the antibodies described herein bind an epitope different from that bound by PDL241.

2.1. Methods 293s cells transfected with human CS1 (300,000 cells per data point) were incubated at various concentrations with an AF488-labeled PDL241 antibody. The concentration at which 80% of maximal binding occurred was identified (6 µg/mL) and used for the subsequent competition assays.

For the competition assays, transfected 293s cells (300,000 cells per data point) were incubated for 30 min (on ice) with a tenfold excess of unlabeled test antibody (60 µg/mL). After the incubation, 6 µg/mL of AF488-labeled PDL241 was added to the cells and incubated on ice for 30 minutes. After this incubation, the cells were washed with PBS+1% FBS, and binding of AF488-labeled PDL241 was determine by flow cytometry. Any antibody that did not inhibit AF488-labeled PDL241 binding by 20% is considered not to compete with PDL241, and to bind an epitope different from that bound by PDL241. Antibody MSL109 was run as a negative control, and elotuzumab, which has previously been demonstrated to bind an epitope different from PDL241 (see, Woo, 2013, *Arthritis Res Ther* 15(6):R207) was run as a positive control.

2.2. Results

The results are shown in FIG. 4. Only antibody Mu4F2 competes with, and binds the same epitope as, PDL241. All other antibodies tested, including Mu12D10, Mu14C11, Mu27A12, Mu27H1, Mu28A6, Mu31D2, Mu34C3 and Mu30C1, do not compete with PDL241, and bind epitopes distinct from that bound by PDL241.

Example 3. Antibody Drug Conjugates Including the Exemplary Antibodies Inhibit Proliferation of L-363 Cells In Vitro Antibodies that bound HuCS1 and CmCS1 and that did not compete for binding with PDL241 were tested for their ability to inhibit proliferation of cells when conjugated as ADCs.

3.1. Methods

All antibodies were conjugated to each of monomethyl auristatin E ("MMAE"; auristatin microtubule inhibitor), monomethyl auristatin F ("MMAF"; auristatin microtubule inhibitor) and duocarmycin (DNA damaging drug) using previously described methods (Doronina et al., 2003, *Nat Biotechnology* 21(7):778-784; Polson et al., 2007, *Blood* 1102:616-623). Drug loading for each ADC was similar. 10,000-20,000 cells (L-363 human multiple myeloma cells) expressing HuCS1 were plated into 96-well plates, and different amounts of ADCs added to the cells. Four days post addition of ADC, cell viability was measured using the CellTiter-Blue® Cell Viability Assay (Promega), and $IC_{50}$ values were calculated.

3.2. Results

The $IC_{50}$ values of all ADCs tested are provided in TABLE 5, below. All ADCs tested inhibited proliferation of cells.

TABLE 5

| $IC_{50}$ (nM) of Various Exemplary ADCs | | | |
|---|---|---|---|
| Antibody | MMAE ADC | MMAF ADC | Duo ADC |
| Mu34C3 | 1.3 | 0.08 | 0.25 |
| Mu31D2 | 3.5 | 0.12 | 0.2 |
| Mu27A12 | 3.5 | 0.11 | 0.19 |
| Mu12D10 | Not available | 0.15 | 0.2 |
| Mu14C11 | Not available | 0.25 | 0.31 |
| Mu28A6 | Not available | 0.39 | 1 |
| Mu30C1 | Not available | 0.18 | 0.36 |

Example 4. Humanization of Exemplary Anti-CS1 Antibodies

Antibodies that formed the basis of the three most potent inhibitors of proliferation, as ADCs, including antibodies Mu34C3, Mu31D2 and Mu27A12, were selected for humanization, and were humanized using standard methods.

4.1. Summary of Humanization Process

The humanization process used is summarized in the flow-chart shown in FIG. 31.

The various steps were as follows:
1. Determine framework and CDR residues of the murine sequences (donor sequences)
2. Create a VH-VL structure model based on homology to existing antibodies by MOE software
3. Identify residues within 5 Å of CDRs or nearing VH/VL interface that are important for CDR loop structures and VH/VL interface including Vernier zone residues
4. Assign residues according to the Kabat numbering scheme
5. Determine canonical structures of heavy and light chain CDRs
6. Identify human VH and VL framework sequences that has the same CDR canonical structures as potential acceptor frameworks
7. Identify human junction region sequences (JH and Jk) that has the best identity and highest similarity to the murine donor sequences
8. Align murine donor sequence with potential human acceptor sequences having the same (or most similar) CDR canonical structures. This is done separately for VH and VL sequences by comparing:
    a. Overall V region identity and similarity
    b. Overall V region identity and similarity excluding CDR residues
    c. Framework residues important for CDR loop structure and VH/VL interface
    d. CDR sequences and framework residues important for CDR loop structure and VH/VL interface
9. Consider residues from all alignments and identify one or two best human framework sequences for VH and one to two for VL as acceptor sequences. The two selected VH or VL sequences should be from different subgroups.
10. Graft donor murine CDR sequences onto selected human framework sequences to create humanized antibody VH and VL sequences
    a. Check to confirm no N-linked glycosylation sites (N{P}S/T)
    b. Consider changing N-terminal Gln to Glu
    c. Screen for potential deamidation (NG, NS, NN), isomerization (DG, DS, DH), proteolysis (DP) sites and flag for further liability engineering
11. Compare humanized and murine donor sequence to identify framework residues that are different between the two and are important for CDR loop structure or VH/VL interface. These are back-mutation candidates.

4.2. Human Germline Sequence Selections for Constructing CDR-Grafted, Humanized Anti-CS1 Antibodies By applying the aforementioned method, the CDR sequences of $V_H$ and $V_L$ chains of monoclonal antibodies Mu34C3, Mu27A12 and Mu31D2 were grafted onto different human heavy and light chain acceptor sequences.

4.2.1. Humanization of Mu34C3

Based on the alignments with the $V_H$ and $V_L$ sequences of monoclonal antibody Mu34C3, the following known human sequences were selected:
1. IGHV3-7*01 and IGHJ6*01 for constructing heavy chain acceptor sequences
2. IGKV2-29*02 and IGKJ4*01 for constructing light chain acceptor sequences By grafting the corresponding $V_H$ and $V_L$ CDRs of Mu34C3 into said acceptor sequences, CDR-grafted, humanized, and modified $V_H$ and $V_L$ sequences were prepared. $V_H$ sequences prepared are show in FIG. 2A; $V_L$ sequences prepared are shown in FIG. 2B.

Hu34C3$V_H$.1 (SEQ ID NO:7) is a CDR-grafted, humanized Mu34C3/Mu27A12 $V_H$ containing IGHV3-7*01 and IGHJ6*01 framework sequences.

Hu34C3$V_H$.1b (SEQ ID NO:8) is a design based on Hu34C3$V_H$.1 (SEQ ID NO:7) and has three CDR human germline changes, L60V, L63V and S65G.

Hu34C3$V_L$.1 (SEQ ID NO:9) is a CDR-grafted humanized Mu34C3/Mu27A12 $V_L$ containing IGKV2-29*02 and IGKJ4*01 framework sequences.

Hu34C3$V_L$.1a (SEQ ID NO:10) is a humanized design based on Hu34C3$V_L$.1 (SEQ ID NO:9) with two framework back-mutations, I2V and Y87F.

Hu34C3$V_L$.1b (SEQ ID NO:11) is an intermediate design between Hu34C3$V_L$.1 (SEQ ID NO:9) and Hu34C3$V_L$.1a (SEQ ID NO:10) with one framework back-mutation (I2V).

4.2.2. Humanization of Mu27A12

Based on the alignments with the $V_H$ and $V_L$ sequences of monoclonal antibody Mu27A12, the following known human sequences were selected:
1. IGHV3-7*01 and IGHJ6*01 for constructing heavy chain acceptor sequences
2. IGKV2-29*02 and IGKJ4*01 for constructing light chain acceptor sequences By grafting the corresponding $V_H$ and $V_L$ CDRs of Mu27A12 into said acceptor sequences, CDR-grafted, humanized, and modified $V_H$ and $V_L$ sequences were prepared. $V_H$ sequences prepared are shown in FIG. 2A; $V_L$ sequences prepared are shown in FIG. 2B.

Hu27A12$V_H$.1 (SEQ ID NO:23) is a CDR-grafted, humanized Mu34C3/Mu27A12 $V_H$ containing IGHV3-7*01 and IGHJ6*01 framework sequences.

Hu27A12$V_H$.1b (SEQ ID NO:24) is design based on Hu27A12$V_H$.1 and has three CDR human germline changes L60V, L63V and S65G.

Hu27A12$V_L$.1 (SEQ ID NO:25) is a CDR-grafted humanized Mu34C3/Mu27A12 $V_L$ containing IGKV2-29*02 and IGKJ4*01 framework sequences.

Hu27A12$V_L$.1a (SEQ ID NO:26) is a humanized design based on Hu27A12$V_L$.1 (SEQ ID NO:25) with two framework back-mutations, I2V and Y87F.

Hu27A12$V_L$.1b (SEQ ID NO:27) is an intermediate design between Hu27A12$V_L$.1 (SEQ ID NO:25) and Hu27A12$V_L$.1a (SEQ ID NO:26) with one framework back-mutation, I2V.

4.2.3. Humanization of Mu31D2

Based on the alignments with the $V_H$ and $V_L$ sequences of monoclonal antibody Mu31D2, the following known human sequences were selected:
1. IGHV3-7*01 and IGHJ4*01 for constructing heavy chain acceptor sequences
2. IGKV2-28*01 and IGKJ4*01 for constructing light chain acceptor sequences By grafting the corresponding $V_H$ and $V_L$ CDRs of Mu31D2 into said acceptor sequences, CDR-grafted, humanized, and modified $V_H$ and $V_L$ sequences were prepared. $V_H$ sequences prepared are show in FIG. 2A; $V_L$ sequences prepared are shown in FIG. 2B.

Hu31D2$V_H$.1 (SEQ ID NO:16) is a CDR-grafted, humanized Mu31D2 $V_H$ containing IGHV3-7*01 and IGHJ4*01 framework sequences. No back-mutation is present.

Hu31D2$V_H$.1a (SEQ ID NO:17) is a humanized design based on Hu31D2$V_H$.1 and contains three CDR human germline changes L60V, L63V and S65G. No back-mutations are present.

Hu31D2$V_L$.1 (SEQ ID NO:18) is a CDR-grafted humanized Mu31D2 $V_L$ containing IGKV2-28*01 and IGKJ4*01 framework sequences.

Hu31D2$V_L$.1a (SEQ ID NO:19) is a humanized design based on Hu31D2$V_L$.1 (SEQ ID NO:18) with two framework back-mutations, I2V and Y87F.

Hu31D2$V_L$.1b (SEQ ID NO:20) is an intermediate design between Hu31D2$V_L$.1 (SEQ ID NO:18) and Hu31D2$V_L$.1a (SEQ ID NO:19) with one framework back-mutation, I2V.

Example 5. The Humanized Antibodies Bind Epitopes Different from the Epitopes Bound by PDL241, Elotuzumab and Luc34.3.8

Humanized antibodies Hu34C3, Hu31D2 and Hu27A12 were tested in flow-cytometry-based competition assays with known anti-CS1 antibodies PDL241, elotuzumab and Luc34.3.8. The competition assays confirm that antibodies Hu34C3, Hu31D2 and Hu27A12 bind epitopes different from those bound by PDL241, elotuzumab and Luc34.3.8.

5.1. Methodology for PDL241 Competition Assay 293s cells transfected with human CS1 were incubated at various concentrations with an AF488 labeled PDL241 antibody. The concentration at which 80% of maximal binding occurred was identified (5 µg/mL). Transfected 293s cells (300,000 cells per data point) were incubated for 30 min (on ice) with a tenfold excess of unlabeled test antibody (50 µg/mL). After the incubation, 5 µg/mL of AF488-labeled PDL241 was added to the cells and incubated on ice for 30 minutes. After this incubation, the cells were washed with PBS+1% FBS and binding of AF488-labeled PDL241 was determine by flow cytometry. Any antibody that did not inhibit AF488-labeled PDL241 binding by 20% is considered not to compete with PDL241, and to bind an epitope different from that bound by PDL241. Antibody MSL109 was run as a negative control, and elotuzumab, which has previously been demonstrated to bind an epitope different from PDL241 (see, Woo, 2013, Arthritis Res Ther 15(6): R207) was run as a positive control.

5.2. Results of PDL241 Competition Assay

The results of the assay are provided in FIG. 5. Hu27A12, Hu34C3 and Hu31D2 do not compete with, and bind different epitopes than, PDL241.

5.3. Methodology for Elotuzumab Competition Assay

A similar experiment was conducted with AF488-labeled elotuzumab at 10 µg/mL. Transfected 293s cells (300,000 cells per data point) were incubated for 30 min (on ice) with a tenfold excess of unlabeled antibody (100 µg/mL). After the incubation, 10 µg/mL of AF488-labeled elotuzumab was added to the cells and incubated on ice for 30 minutes. After this incubation, the cells were washed with PBS+1% FBS and binding of AF488-labeled elotuzumab determined by flow cytometry. Any antibody that did not inhibit AF488-labeled elotuzumab binding by 20% is considered not to compete with elotuzumab, and to bind an epitope different from that bound by elotuzumab. Antibody MSL109 was run as a negative control, and PDL241, which has previously been demonstrated to bind an epitope different from elotuzumab (see, Woo, 2013, *Arthritis Res Ther* 15(6):R207) was run as a positive control.

5.4. Results of Elotuzumab Competition Assay

The results of the assay are provided in FIG. 6. Hu27A12, Hu34C3 and Hu31D2 do not compete with, and bind different epitopes than, elotuzumab.

5.5. Methodology for Luc34.3.8 Competition Assay

A similar experiment was conducted with AF488-labeled Luc34.3.8 at 2 µg/mL. L-363 cells (human multiple myeloma cell line) expressing HuCS1 (300,000 cells per data point) was incubated for 30 min (on ice) with a tenfold excess of unlabeled test antibody (20 µg/mL). After the incubation, 2 µg/mL of AF488-labeled Luc34.3.8 was added to the cells and incubated on ice for 30 minutes. After this incubation, the cells were washed with PBS+1% FBS, and binding of AF488-labeled PDL241 determined by flow cytometry. Any antibody that did not inhibit AF488-labeled Luc34.3.8 binding by 20% is considered not to compete with Luc34.3.8, and to bind an epitope different from that bound by Luc34.3.8. Antibody MSL109 was run as a negative control, and elotuzumab, which has previously been demonstrated to bind an epitope different from Luc34.3.8 (see, U.S. Pat. No. 8,455,646 to Williams et al.) was run as a positive control.

5.6. Results of Luc34.3.8 Competition Assay

The results of the assay are provided in FIG. 7. Hu27A12, Hu34C3 and Hu31D2 do not compete with, and bind different epitopes than, Luc34.3.8.

Example 6. Antibody Hu34C3 Binds to a Distinct Epitope

Flow-cytometry-based competition experiments conducted with various exemplary anti-CS1 antibodies described herein demonstrate that Hu34C3, in addition to binding an epitope different from the epitopes bound by PDL241, elotuzumab and Luc34.3.8, binds an epitope that is unique.

6.1. Method 293s cells transfected with human CS1 were incubated at various concentrations with an AF488 labeled Hu34C3 antibody. The concentration at which 80% of maximal binding occurred was identified (10 µg/mL). For the competition assays, transfected 293s cells (300,000 cells per data point) were incubated for 30 min (on ice) with a tenfold excess of unlabeled test antibody (100 µg/mL). After the incubation, 10 µg/mL of AF488-labeled Hu34C3 was added to the cells and incubated on ice for 30 minutes. After this incubation, the cells were washed with PBS+1% FBS, and binding of AF488-labeled Hu34C3 was determine by flow cytometry. Any antibody that did not inhibit AF488-labeled Hu34C3 binding by 20% is considered not to compete with Hu34C3, and to bind an epitope different from that bound by Hu34C3. Antibody MSL109 was run as a negative control, and elotuzumab, which has been shown herein to bind an epitope different from Hu34C3, was run as a positive control.

6.2. Results

The results of the competition assay are shown in FIG. 8. None of the anti-CS1 antibodies tested (including Hu27A12 and Hu31D2) compete with Hu34C3, demonstrating that Hu34C3 binds a unique epitope.

Example 7. Antibody Hu34C3 has Superior Binding Properties

The binding affinities of the three exemplary humanized antibodies Hu27A12, Hu34C3 and Hu31D2 were evaluated by flow cytometry and compared to that of elotuzumab.

7.1. Method

L-363 cells were incubated with different amounts of test antibody on ice for 30 min. Cells were washed three times with PBS+1% FBS. A PE-conjugated goat anti-human Fc antibody was added to the cells and incubated for 30 min on ice. Cells were washed three times with PBS+1% FBS, and binding was quantitated by flow cytometry.

7.2. Results

The results are provided in TABLE 6, below.

TABLE 6

| Binding Properties of Humanized Antibodies | | | |
|---|---|---|---|
| Antibody | $EC_{50}$ (nM) | GeoMean (max)[a] | % of Elotuzumab |
| Elotuzumab | 35.9 | 17.5 | 100 |
| Hu34C3 | 2.5 | 43.5 | 249 |
| Hu31D2 | 3.1 | 28 | 160 |
| Hu27A12 | 4.7 | 24.8 | 142 |

[a]GeoMean (max) = maximum fluorescent value obtained by an antibody at any of the tested concentrations.

All antibodies tested exhibit superior binding affinity compared to elotuzumab, and antibody Hu34C3 displays superior maximal binding compared to the other antibodies tested.

Example 8. Preparation of Hu34C3-MMAE ADCs Having an Average DAR4

Hu34C3-MMAE ADC having an average DAR4 was prepared by a two-step chemical process-disulfide reduction of Hu34C3 followed by alkylation (conjugation) with maleimidocaproyl valine-citrulline para-aminobenzyl alcohol ("PABA") monomethyl auristatin ("vcMMAE"), illustrated below:

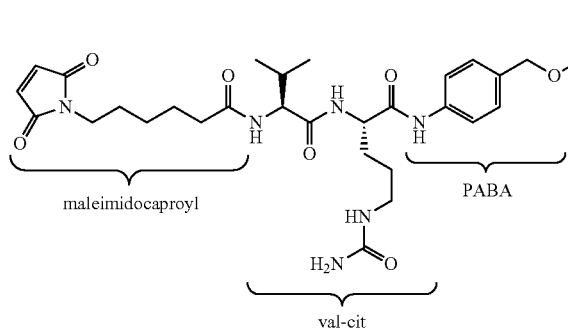
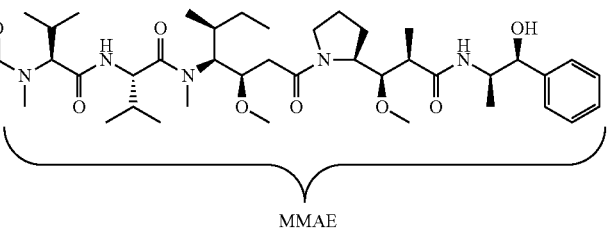

In the first step, a limited number of interchain disulfide bonds of Hu34C3 are reduced with tris(2-carboxyethyl) phosphine ("TCEP") (≥0.8 equiv). Partially-reduced Hu34C3 is then conjugated to vcMMAE (≥1.8 equiv) in DMSO. Residual unreacted vcMMAE is quenched with N-acetyl-L-cysteine.

Referring to FIG. 21, which shows a chromatographic resolution of the resultant ADC preparation, the ADC is a heterogenous mixture containing antibodies having zero MMAE molecules attached ("E0" peak), two MMAE molecules attached ("E2" peak), four MMAE molecules attached ("E4" peak), six MMAE molecules attached ("E6" peak) and eight MMAE molecules attached ("E8" peak), depending upon the number of interchain disulfide bridges reduced.

Methods of chromatographically separating and isolating the enriched E2 and E4 peaks are described by Hamblett et al., Clin Cancer Res 2004; 10:7063-7070.

Example 9. Preparation of MMAF ADCs Having an Average DAR4

Hu34C3-MMAF ADC having an average DAR4 was prepared by the method of Example 8, using maleimidocaproyl monomethyl auristatin F in the conjugation step.

Example 10. MMAE ADCs Including Hu34C3, but not Hu31D2 and Hu27A12, Exhibit Anti-Tumor Properties in an In Vivo Model of Multiple Myeloma Antibodies Hu34C3, Hu31D2 and Hu27A12 were each conjugated with MMAE using the procedure of Example 8 to an average DAR4. These ADCs were tested in the U266 multiple myeloma in vivo model described by Miyakawa et al., 2004, Biochemical and Biophysical Research Communications 313:258-262. MSL109 and MSL109 conjugated with MMAE to DAR4 (prepared as above) were run as controls.

Briefly, 2×10$^6$ U266 human multiple myeloma cells were injected in NOD/Scid/γc null (NSG) mice intravenously. The U266 cells infiltrate bone marrow cavity forming tumor mass which replaced normal bone marrow. Positive HuCS1 staining is detected on U266 tumor cells in mouse bone marrow tissues. The growth of tumor cells in the bone narrow leads to osteolytic lesions in bones and the loss of trabecular bones that results in physical symptoms of hind leg paralysis and ruffled fur.

28 Days after U266 cell inoculation, mice were randomized into the indicted groups and treated with 5 mg/kg of ADC every four days for 3 doses (q4d×3). The mice were scored for clinical symptoms and the number of HuCS1-positive U266 cells in the bone marrow (femur) was determined. Clinical symptoms were scored on a level of severity ranging from 0 (no detrimental physical symptoms) to 5 (severe detrimental physical symptoms). The researchers involved in this study were blinded to avoid bias. Treatment with Hu34C3 MMAE DAR4 significantly reduced both clinical symptoms (FIG. 9A) and U266 cell number (FIG. 9B) compared to isotype control. Surprisingly, Hu27A12 MMAE DAR4 and Hu31D2 MMAE DAR4 were ineffective in this model. Hu27A12 and Hu31D2 do not compete with Hu34C3 and bind to an epitope on CS1 different from that of Hu34C3. This difference may contribute to the lack of efficacy observed in vivo.

Example 11. ADCs Comprising Exemplary New Anti-CS1 Antibodies Inhibit Proliferation of Multiple Myeloma Cells In Vitro Several exemplary new anti-CS1 antibodies were conjugated with MMAE to an average DAR4 as described in Example 8 and tested against the human multiple myeloma cell line, MOLP-8, in vitro and in vivo. MSL109 MMAE DAR4 was run as a control. The in vitro proliferation assay was performed as described as in Example 3. Hu34C3 MMAE DAR4 and Mu176.1.1 MMAE DAR4 showed similar in vitro potency, and both were superior to the six other antibodies tested in vitro (FIG. 10).

FIG. 10 depicts percent survival of multiple myeloma cells ("% survival") relative to the nanomolar concentration of administered antibody-drug conjugate ("Test ADC (nM)"). Solid circle, solid line depicts cell survival after administration of Mu176.1.1 MMAE DAR4; hollow square, dashed line depicts cell survival after administration of Mu176.2.3 MMAE DAR4; hollow triangle, dotted line depicts cell survival after administration of Mu176.3.3 MMAE DAR4; hollow inverted triangle, dash-dot line depicts cell survival after administration of Mu176.4.1 MMAE DAR4; hollow diamond, dashed line depicts cell survival after administration of Mu176.7.1 MMAE DAR4; hollow circle, dotted line depicts cell survival after administration of Mu176.8.1 MMAE DAR4; solid square, solid line depicts cell survival after administration of Mu176.9.1 MMAE DAR4; solid triangle, dashed line depicts cell survival after administration of Hu34C3 MMAE DAR4; solid inverted triangle, solid line depicts cell survival after administration of MSL109 MMAE DAR4.

Example 12. ADCs Comprising Antibody Hu34C3 Inhibit Proliferation of Multiple Myeloma Cells In Vivo The same panel of antibodies tested in Example 11, above, was tested in vivo on MOLP-8 derived xenografts.

SCID mice were inoculated subcutaneously into the right flank with 10×10⁶ viable human multiple myeloma derived MOLP-8 cells. The injection volume was 0.1 mL, composed of a 1:1 mixture of serum-free media and Matrigel (BD, Franklin Lakes, N.J.). Tumor-bearing mice were sorted into groups with equivalent mean tumor volumes when tumor volumes were approximately 160 mm³. Therapy began immediately following randomization and size matching of tumors into required cohorts. Mice weighed approximately 25 g at the onset of therapy. Tumor volume was estimated two to three times weekly. Tumor dimensions were measured with electronic calipers, and tumor volumes calculated using the formula: $V=\frac{1}{2}\times length \times width \times height$. Study day 0 was defined as the day of cell inoculation. Mice were treated with the indicated ADC at 3 mg/kg q4d×3 (once every 4 days for a total of 3 doses). Surprisingly, Hu34C3 MMAE DAR4 was the only ADC to show significant in vivo activity. Mu176.1.1 MMAE DAR4 had comparable activity to Hu34C3 in vitro but was significantly inferior in vivo. Clone 176.1.1 does not compete with Hu34C3 and binds to a different epitope on CS1. This difference may contribute to the lack of efficacy observed in vivo (FIG. 11).

FIG. 11 depicts xenograft tumor volume in cubic millimeters ("Tumor Volume (mm³)") relative to time in days after administration of indicated antibody-drug conjugate ("Days Post Cell Inoculation"). Hollow right-pointing triangle, dashed line depicts volume after administration of MSL109 MMAE DAR4; hollow circle, dotted line depicts volume after administration of Mu176.1.1 MMAE DAR4; solid right-pointing triangle, dash-dot line depicts volume after administration of Mu176.2.3 MMAE DAR4; solid triangle, solid line depicts volume after administration of Mu176.3.3 MMAE DAR4; shaded right-pointing triangle, dashed line depicts volume after administration of Mu176.4.1 MMAE DAR4; solid circle, dotted line depicts volume after administration of Mu176.7.1 MMAE DAR4; hollow square, solid line depicts volume after administration of Mu176.8.1 MMAE DAR4; solid square, dotted line depicts volume after administration of Mu176.9.1 MMAE DAR4; hollow left-pointing triangle, solid line depicts volume after administration of Hu34C3 MMAE DAR4.

12.1. Generation of Higher Affinity Mutants of Hu34C3

A number of mutants of Hu34C3 having higher binding affinity for HuCS1 than Hu34C3 were identified by systematically mutating each residue of the CDRs in the $V_H$ and $V_L$ chains of Hu34C3. The sequences of the $V_H$, and $V_L$ regions and the respective CDRs of the mutants are provided in FIG. 2 as sequences Hu34C3 S55E (SEQ ID NO:12) and Hu34C3 N30L (SEQ ID NO:13). Their binding affinities (relative as compared to Hu34C3 as determined by FACS) as provided in TABLE 7, below:

TABLE 7

| Antibody | % Binding |
|---|---|
| Hu34C3 | 100% |
| Hu34C3 N30L | 128% |
| Hu34C3 S55E | 125% |
| Hu34C3 N30L/S55E | 134% |

Example 13. ADCs Including Higher Affinity Mutants of Hu34C3 Inhibit Proliferation of Multiple Myeloma Cells In Vitro The N30L, S55E and N30L/S55E mutants of Hu34C3 were produced in HEK293 cells using standard methods, conjugated to MMAE to DAR4, and compared to Hu34C3-MMAE DAR4 in an in vitro proliferation assay with L-363 cells. The S55E, N30L and the S55E/N30L mutants all displayed enhance activity compared to wild-type (FIG. 12).

FIG. 12 depicts percentage of cell survival of multiple myeloma cells ("% Survival") after administration of nanomolar concentration of the indicated antibody-drug conjugate ("Antibody Conc. (nM)"). Solid circle, dotted line depicts effects of MSL109 MMAE DAR4; solid diamond, dashed line depicts effects of Hu34C3 MMAE DAR4; hollow circle, dash-dot line depicts effects of Hu34C3 with single mutation N30L MMAE DAR4; hollow square, solid line depicts effects of Hu34C3 with single mutation S55E MMAE DAR4; hollow triangle, solid line depicts effects of Hu34C3 with double mutation S55E/N30L MMAE DAR4.

Example 14. ADCs Including Higher Affinity Mutants of Hu34C3 Inhibit Tumor Proliferation In Vivo SCID mice were inoculated subcutaneously into the right flank with 10×10⁶ viable human multiple myeloma derived L-363 cells. The injection volume was 0.1 mL, composed of a 1:1 mixture of serum-free media and Matrigel (BD, Franklin Lakes, N.J.). Tumor-bearing mice were sorted into groups with equivalent mean tumor volumes when tumor volumes were approximately 100 mm³. Therapy began immediately following randomization and size matching of tumors into required cohorts. Mice weighed approximately 25 g at the onset of therapy. Tumor volume was estimated two to three times weekly. Tumor dimensions were measured with electronic calipers, and tumor volumes calculated using the formula: $V=\frac{1}{2}\times length \times width \times height$. Study day 0 was defined as the day of cell inoculation. Mice were treated with either MSL109 MMAE DAR4 (control), Hu34C3 MMAE DAR4, Hu34C3 N30L MMAE DAR4, or Hu34C3 S55E/N30L MMAE DAR4 at 3 mg/kg q4d×4 (once every 4 days for a total of 4 doses). All ADCs tested were effective. Interestingly, ADCs including mutants with enhanced affinity for HuCS1 were not more effective in the in vivo assay than an ADC comprising wild-type Hu34C3. (FIG. 13).

FIG. 13 depicts xenograft tumor volume in cubic millimeters ("Tumor Volume (mm³)") after administration of the indicated antibody-drug conjugate of several days ("Days Post Cell Implantation") with multiple administered doses (as indicated with the hollow star). Solid square, dashed line depicts MSL109 MMAE DAR4; hollow circle, dotted line depicts Hu34C3 MMAE DAR4; hollow square, solid line depicts Hu34C3 with single mutation N30L MMAE DAR4; hollow triangle, solid line depicts Hu34C3 with double mutation S55E/N30L MMAE DAR4.

Example 15. ADCs of Hu34C3 and Pyrrolobenzodiazepines Inhibit Proliferation of Multiple Myeloma Cells In Vitro Hu34C3 and an isotype control antibody, AB095, were conjugated with PBD (pyrrolobenzodiazepine SGD-1882) to an average DAR2 by a two-step chemical process: disulfide reduction followed by alkylation (conjugation) with maleimidocaproyl valine-alanine ("val-ala") pyrrolobenzodiazepine ("PBD").

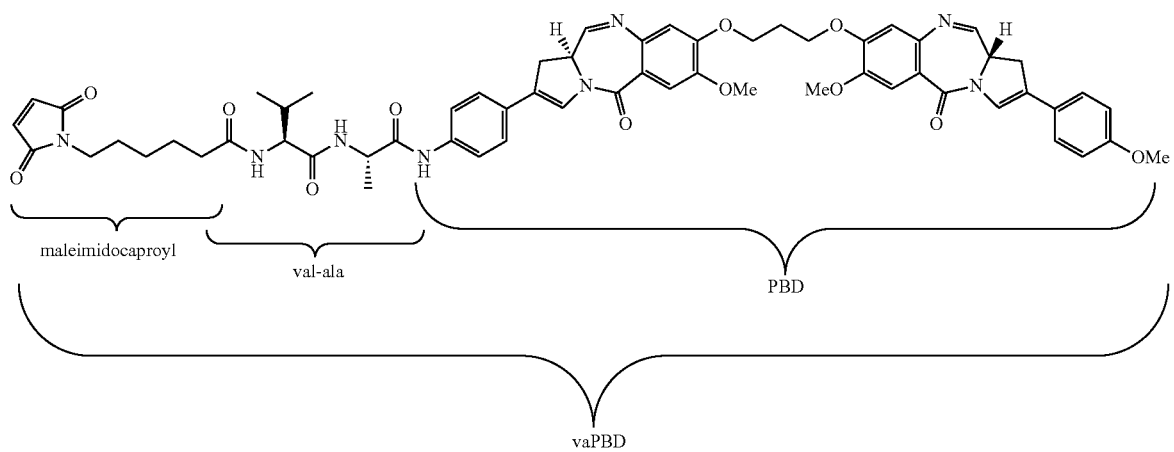 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1 ; "PBD" ; "vaPBD"]

(vaPBD, maleimidocaproyl, val-ala, PBD)

In the first step, a limited number of interchain disulfide bonds are reduced with tris(2-carboxyethyl) phosphine ("TCEP") (≥2 equiv). Partially-reduced antibody is then conjugated to vaPBD (≥5 equiv) in DMSO. Residual unreacted vaPBD is quenched with N-acetyl-L-cysteine. The resulting reaction mixture was run over a preparative S300 size exclusion chromatography column and the resulting ADCs—Hu34C3-PBD DAR2 and AB095-PBD DAR2— were tested against the human multiple myeloma cell lines, OPM-2, L-363, MM1.S and MOLP-8 in vitro. The in vitro proliferation assay was performed as described in Example 3. Hu34C3-PBD DAR2 showed superior in vitro potency, than the isotype control antibody (AB095-PBD DAR2). FIGS. 14A, 14B, 14C, and 14D depict the results for OPM-2, L-363, MM1.S, and MOLP-8 cells, respectively.

Example 16. ADCs of Hu34C3 and Pyrrolobenzodiazepines Inhibit Tumor Proliferation In Vivo OPM-2 xenografts were prepared and conducted as previously described. NSG mice (NOD.Cg-Prkdcscid Il2rgtm1Wj1/SzJ) from The Jackson Laboratory (strain code 05557) were used. This strain lacks effector cells and eliminates the ADCC mechanism for all antibodies. AB095, an antibody that targets tetanus toxoid, was run as control. Dosing of test ADCs was normalized such that equal masses of the PBD component were delivered. Results are shown in FIG. 15. Hu34C3 PBD DAR2 did not demonstrate statistically greater anti-tumor activity than the isotype control (AB095 PBD DAR2) in the dose groups.

Example 17. ADCs of Mutant Hu34C3 and Pyrrolobenzodiazepines Inhibit Proliferation of Multiple Myeloma Cells In Vitro Hu34C3 and an isotype control antibody, AB095, were modified by mutating the position 239 serine into cysteine (S239C). These mutated antibodies (Hu34C3 S239C and AB095 S239C) were conjugated with PBD (Pyrrolobenzodiazepine) as described in Example 15 and tested against the human multiple myeloma cell lines L-363 and MM1.S in vitro. The in vitro proliferation assay was performed as described in Example 3. Hu34C3 S239C-PBD showed superior in vitro potency, than the isotype control antibody (AB095 S239C-PBD) in OPM-2 and L-363 cells (FIGS. 16A and 16B, respectively).

Example 18. ADCs of Hu34C3 and Topoisomerase I Inhibitors Inhibit Proliferation of Multiple Myeloma Cells In Vitro Hu34C3 and an isotype control antibody, AB095, were each conjugated individually with SN-38 by a two-step chemical process as described in Example 8 that produced a DAR4 material in each case. Conjugation was performed either with a linker-drug moiety with SN-38 attached via the phenolic OH of SN-38 ("SN-38 linker-drug"), or a linker-drug moiety with SN-38 attached via the tertiary OH of SN-38 ("CL-38 linker-drug").

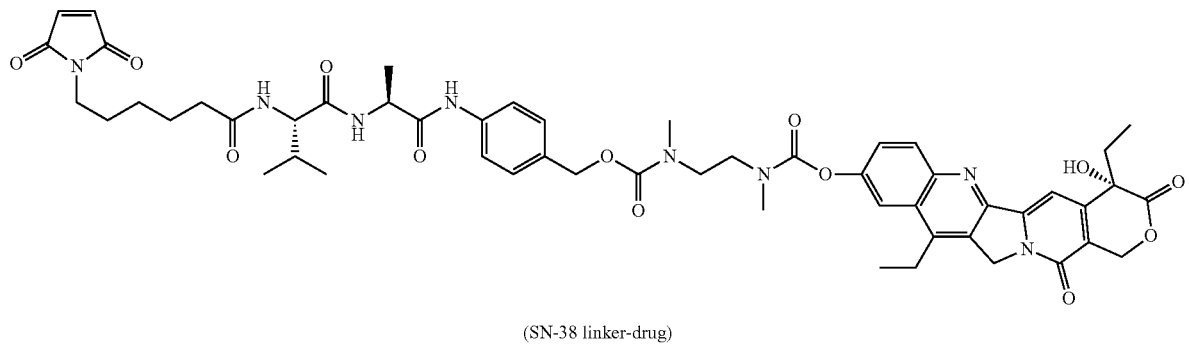

(SN-38 linker-drug)

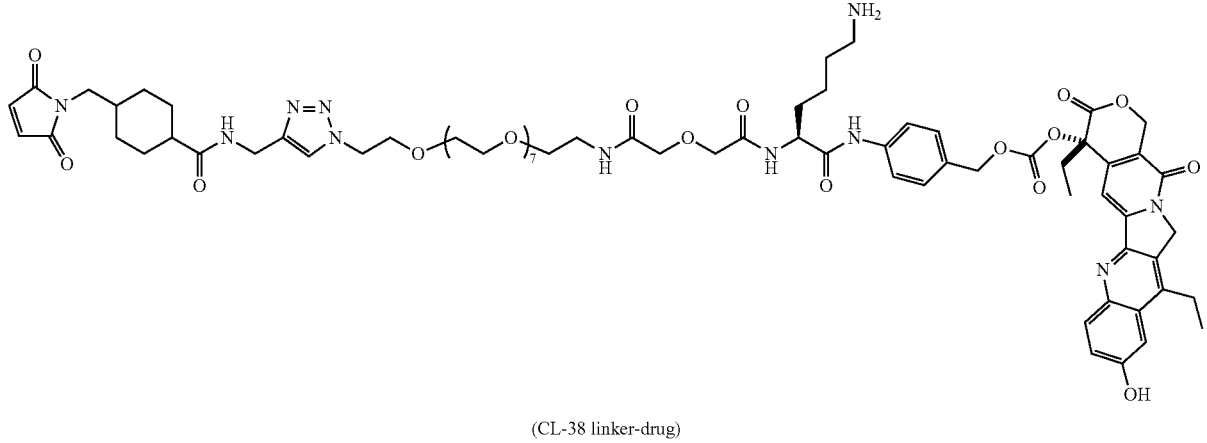

(CL-38 linker-drug)

Subsequent to reaction, the crude mixture was run over a G25 resin desalting column to remove excess reagents, and tested against the human multiple myeloma cell lines OPM-2 and L-363 in vitro. The in vitro proliferation assay was performed as described in Example 3. Hu34C3 conjugated to SN-38, attached via the phenolic OH of SN-38, as an average DAR4 ("Hu34C3-SN38 DAR4") and Hu34C3 conjugated to SN-38, attached via the tertiary OH of SN-38, as an average DAR4 ("Hu34C3-CL38 DAR4") did not demonstrate anti-proliferation activity that was statistically significantly greater than that observed for the isotype control (AB095 conjugated to SN-38, attached via the phenolic OH of SN-38, as an average DAR4 ("AB095-SN38 DAR4") and AB095 conjugated to SN-38, attached via the tertiary OH of SN-38, as an average DAR4 ("AB095-CL38 DAR4") (FIGS. 17A and 17B, respectively).

Example 19. ADCs of Hu34C3 and Topoisomerase I Inhibitors Inhibit Tumor Proliferation In Vivo OPM-2 xenografts were prepared and conducted as previously described. NSG mice (NOD.Cg-Prkdcscid Il2rgtm1Wj1/SzJ) from The Jackson Laboratory (strain code 05557) were used. This strain lacks effector cells and eliminates the ADCC mechanism for all antibodies. AB095, an antibody that targets tetanus toxoid was run as control. Dosing of test ADCs was normalized such that equal masses of the SN38 component were delivered.

Hu34C3-SN38 DAR4 did not demonstrate statistically significantly improved anti-tumor activity than the isotype control (AB095-SN38 DAR4) (FIG. 18).

Example 20. The Anti-Tumor Activity of Hu34C3 is not Dependent Upon ADCC

The Fc region of Hu34C3 was modified in an attempt to enhance anti-tumor activity. A number of mutations were made that altered ADCC activity, FcRn binding, and pinocytosis. MMAE DAR4 ADCs of these mutants were tested in vivo in an OPM-2 xenograft model in SCID mice as previously described (van Rhee, et al., 2009 Mol. Cancer Therapeutics 8: 2616-24). An MMAE ADC of AB095, an IgG$_1$ isotype antibody that targets tetanus toxoid, was run as a control. Results are shown in FIG. 19A. Antibody Hu34C3 mut1 is an IgG$_1$ isotype antibody containing a mutation that reduces binding to CD16 and significantly inhibits ADCC activity. Antibody Hu34C3 mut2 is an IgG$_2$ isotype antibody containing a similar mutation. Surprisingly, mutants that lost ADCC activity as compared to wild-type Hu34C3 maintained similar in vivo activity as wild-type Hu34C3. This suggests that the anti-tumor activity of antibody Hu34C3 is not dependent upon ADCC activity, but primarily due to its ability to deliver the MMAE payload. This is in contrast to other anti-CS1 antibodies, whose anti-tumor activity is ADCC dependent (see, e.g., Hsi et al., 2008, Clin Cancer Res 14(9):2775-2784; Woo, 2013, Arthritis Res Ther 15(6): R207).

FIG. 19A depicts xenograft tumor volume in cubic millimeters ("Tumor Volume (mm$^3$)") after administration of the indicated antibody-drug conjugate of several days ("Days Post Cell Implantation") with multiple administered doses (as indicated with the hollow star). Solid square, dashed line depicts MSL109 MMAE DAR4; solid star, solid line depicts Hu34C3 MMAE DAR4; hollow triangle, solid line depicts Hu34C3 mut1 MMAE DAR4; hollow circle, dotted line depicts Hu34C3 mut2 MMAE DAR4.

A similar experiment conducted with ADCs comprising Hu34C3 mutants with increased circulating in vivo half-life and reduced pinocytosis; these mutants significantly decreased the anti-tumor activity of Hu34C3-based ADCs. The results are shown in FIG. 19B. Antibody Hu34C3 mut3 is an IgG$_1$ isotype antibody containing mutations that alter ADCC and half-life. Antibody Hu34C3 mut4 is an IgG$_1$ isotype antibody containing mutations that alter ADCC, half-life and pinocytosis.

FIG. 19B depicts xenograft tumor volume in cubic millimeters ("Tumor Volume (mm$^3$)") after administration of the indicated antibody-drug conjugate of several days ("Days Post Cell Implantation") with multiple administered doses (as indicated with the hollow star). Solid square, dashed line depicts MSL109 MMAE DAR4; solid star, solid line depicts Hu34C3 MMAE DAR4; solid circle, solid line depicts Hu34C3 mut3 MMAE DAR4; hollow circle, dotted line depicts Hu34C3 mut4 MMAE DAR4.

Example 21. Hu34C3-MMAE DAR4 ADCs are More Effective In Vivo than Hu34C3-MMAF ADCs The antitumor activities of Hu34C-MMAE DAR4 ADCs were compared to Hu34C3-MMAF DAR4 ADCs in an MOLP-8 xenograft in vivo model as described in Example 12. Antibody MSL109 (dosed at 10 mg/kg). MSL109-MMAE (dosed at 6 mg/kg) and MSL109-MMAF (dosed at 6 mg/kg) were run as controls. Test ADCs were dosed at 6 mg/kg every 4 days for 3 doses. Published reports suggest that MMAF ADCs are more potent toxins (see, e.g., Doronina et al., 2006 *Biocon. Chem* 170(1):114-124). Surprisingly, in this MOLP-8 xenograft model, Hu34C3-MMAE ADC displayed significantly superior activity to Hu34C3-MMAF ADC (FIG. 20).

FIG. 20 depicts xenograft tumor volume in cubic millimeters ("Tumor Volume (mm$^3$)") after administration of the indicated antibody-drug conjugate of several days ("Days Post Cell Implantation"). Hollow circle, dashed line depicts MSL109 at 10 mg/kg dose; hollow triangle, solid line depicts MSL109 MMAE DAR4 at 6 mg/kg dose; solid inverted triangle, solid line depicts MSL109 MMAF DAR4 at 6 mg/kg dose; solid square, dotted line depicts Hu34C3 MMAE DAR4 at 6 mg/kg dose; hollow diamond, dashed line depicts Hu34C3 MMAF DAR4 at 6 mg/kg dose.

Example 22. Isolation of Enriched Hu34C3-MMAE DAR2 and Hu34C3-MMAE DAR4

Crude preparations of Hu34C3-MMAE DAR4 prepared as described in Example 8 results in a heterogeneous mixture having an average DAR4 that is comprised of antibodies having 0 MMAE molecules attached, antibodies having 2 MMAE molecules attached, antibodies having 4 MMAE molecules attached, having 6 MMAE molecules attached and antibodies having 8 MMAE molecules attached (see, e.g., FIG. 21). Enriched preparations of Hu34C3 ADCs having two molecules of MMAE attached (i.e., Hu34C3-MMAE E2, referred to as "Hu34C3 E2" in FIGS. 22-29) and four molecules of MMAE attached (i.e., Hu34C3-MMAE E4, referred to as "Hu34C3 E4" in FIGS. 22-24) were isolated from Hu34C3-MMAE DAR4 prepared as described in Example 8. Additionally, enriched preparations of Hu34C3 ADCs having two or four molecules of MMAE attached (i.e., Hu34C3-MMAE E2E4, referred to as "Hu34C3 E2E4" in FIG. 28) were isolated from Hu34C3-MMAE DAR4 preparations.

As depicted in FIG. 21, the antibody-drug conjugate preparations of Hu34C3-MMAE with different DAR can be separated by chromatography. The methods for separation are described by Hamblett et al., *Clin Cancer Res* 2004; 10:7063-7070.

For the isolation, the crude conjugation reaction mixture was adjusted to column binding salt conditions by the addition of ⅓ volume of 4.5M (NH$_4$)$_2$SO$_4$ to give 110 mS conductivity. This load material was pumped onto a 2.6×150 cm column packed with 70 mL GE Butyl-HP resin and equilibrated with Buffer A [1.5M (NH$_4$)$_2$SO$_4$, 20 mM PO$_4$, pH 7]. After loading and washing to baseline, unconjugated antibody Hu34C3 ("E0") was eluted with a 90 mS step gradient blend of Buffers A and B (Buffer B=20 mM PO$_4$ pH 7+25% IPA) (retention time=3 min). Hu34C3 E2 was eluted with a 60 mS step gradient blend of Buffers A and B (retention time=4 min). Finally, Hu34C3 E4 was eluted with a 30 mS step gradient of Buffers A+B (retention time=5 min). The eluted pool of Hu34C3 E2 was buffer exchanged and concentrated on a Pellicon® tangential-flow filtration system (membrane XL-30kD) using 15 mM MES buffer pH 6.0. Preparations of "E6" (enriched Hu34C3-MMAE containing 6 MMAE molecules) and "E8" (enriched Hu34C3-MMAE containing 8 MMAE molecules) can also be isolated with this gradient. Final material was quantified via UV/Vis (A-280), assessed for purity via HIC and % aggregation via size-exclusion chromatography ("SEC").

Example 23. Hu34C3-MMAE E2 and Hu34C3-MMAE E4 are Effective In Vivo in an LP-1 LMC Mouse Model of Multiple Myeloma A fusion construct of luc2 (Promega, Madison, Wis., USA) and mCherry (Clontech, Mountain View, Calif., USA) was cloned into the Lenti X lentiviral vector (Clontech). The human multiple myeloma cell line, LP-1, was transduced with lentiviral particles for 48 h and a pool of cells stably expressing the fusion construct were selected using 2 μg/mL puromycin for two weeks, subsequently referred to as LP-1 luc2-mCherry (LP-1-LMC). LP-1-LMC cells were grown to passage three in vitro. On Day −1, female SCID-Beige mice were irradiated with three Gray whole-body irradiation to enable increased tumor cell engraftment. On Day 0, five million LP-1-LMC cells per mouse were inoculated intravenously via the tail vein. Animals were size matched into treatment groups on Day 22 or Day 30 based on whole-body ROI analysis of bioluminescent signal. The mean bioluminescent signal at staging was approximately 5×10$^6$ photons/second. Data calculations were made using Living Image, Version 4.4.

Efficacy of Hu34C3-MMAE E2 and Hu34C3-MMAE E4 was assessed in systemic LP-1-LMC xenografts. The ADCs were dose-normalized, such that equal masses of the MMAE component were delivered, with 2-fold differences in the IgG component. A single dose was administered intraperitoneally across a range of dose levels. There were no detectable signs of any tumor cells in all mice treated with Hu34C3-MMAE E2 or Hu34C3-MMAE E4. There was no difference in efficacy between the E2 and E4 preparations in this model (FIG. 22).

FIG. 22A depicts bioluminescent signal ("Normalized Flux (p/s)") vs. days after animal size matching and administration of antibody-drug conjugate at the indicated dose ("Days Post Size Match"). Dashed line indicates untreated animals; shaded square, solid line indicates animals treated with Hu34C3-MMAE E2 ("Hu34C3 E2") at 3 mg/kg; solid square, solid line indicates animals treated with Hu34C3-MMAE E2 at 6 mg/kg; hollow square, dotted line indicates animals treated with Hu34C3-MMAE E2 at 9 mg/kg. Animals were dosed at Day 0 after size matching.

FIG. 22B depicts bioluminescent signal ("Normalized Flux (p/s)") vs. days after animal size matching and administration of antibody-drug conjugate at the indicated dose ("Days Post Size Match"). Dashed line indicates untreated animals; shaded square, solid line indicates animals treated with Hu34C3-MMAE E4 at 1.5 mg/kg; solid square, solid line indicates animals treated with Hu34C3-MMAE E4 at 3 mg/kg; hollow square, dotted line indicates animals treated with Hu34C3-MMAE E4 at 4.5 mg/kg. Animals were dosed at Day 0 after size matching.

Example 24. Hu34C3-MMAE E2 and Hu34C3-MMAE E4 are Effective in In Vivo in L-363, MM1.S and MOLP-8 Xenograft Models of Multiple Myeloma L-363, MM1.S and MOLP-8 xenografts were prepared and studies conducted as generally described in Example 12. NSG mice (NOD.Cg-Prkdcscid Il2rgtm1Wj1/SzJ) from The Jackson Laboratory (strain code 05557) were used. This strain lacks effector cells and eliminates the ADCC mechanism for all antibodies. Using this strain permits evaluation of Hu34C3-MMAE E2 and Hu34C3-MMAE E4 ADC activity independently of ADCC activity. Unconjugated antibody AB095, an antibody that targets tetanus toxoid (dosed at 10 mg/kg) and unconjugated Hu34C3 (dosed at 10 mg/kg) were run as controls. Dosing of test ADCs was normalized such that equal masses of the MMAE component were delivered, with 2-fold differences in the IgG component (i.e., Hu34C3-MMAE E2 was dosed at 10 mg/kg; Hu34C3-MMAE E4 was dosed at 5 mg/kg.) Results are shown in FIGS. 23A-23C. In the L-363 (FIG. 23A) and MM1.S (FIG. 23B) models, Hu34C3-MMAE E2 displayed significantly better anti-tumor activity than Hu34C3-MMAE E4 when compared on a normalized, mass of MMAE delivered, basis. Hu34C3-MMAE E2 and Hu34C3-MMAE E4 were similarly effective in the MOLP-8 model (FIG. 23C). Unconjugated Hu34C3 showed no activity in this model.

FIG. 23A depicts xenograft volume in cubic millimeters ("Tumor Volume (mm$^3$)") vs. days after cancer cell transplantation ("Days Post Cell Transplantation"). Intravenous dosing of antibody-drug conjugate is indicated at the arrow ("I.V. Dosing Day"). Results: hollow circle, dotted line indicates animals treated with 10 mg/kg AB095; hollow square, solid line indicates animals treated with 10 mg/kg Hu34C3; hollow inverted triangle, solid line indicates animals treated with Hu34C3-MMAE E2 at 10 mg/kg; solid square, dashed line indicates animals treated with Hu34C3-MMAE E4 at 5 mg/kg.

FIG. 23B depicts xenograft volume in cubic millimeters ("Tumor Volume (mm$^3$)") vs. days after cancer cell transplantation ("Days Post Cell Transplantation"). Intravenous dosing of antibody-drug conjugate is indicated at the arrow ("I.V. Dosing Day"). Results: hollow circle, dotted line indicates animals treated with 10 mg/kg AB095; hollow square, solid line indicates animals treated with 10 mg/kg Hu34C3; hollow inverted triangle, solid line indicates animals treated with Hu34C3-MMAE E2 at 10 mg/kg; solid square, dashed line indicates animals treated with Hu34C3-MMAE E4 at 5 mg/kg.

FIG. 23C depicts xenograft volume in cubic millimeters ("Tumor Volume (mm$^3$)") vs. days after cancer cell transplantation ("Days Post Cell Transplantation"). Intraperitoneal dosing of antibody-drug conjugate is indicated at the arrow ("Dosing Days i.p."). Results: hollow circle, dotted line indicates animals treated with 10 mg/kg AB095; hollow square, solid line indicates animals treated with 10 mg/kg Hu34C3; hollow triangle, solid line indicates animals treated with Hu34C3-MMAE E2 at 10 mg/kg; solid circle, dashed line indicates animals treated with Hu34C3-MMAE E4 at 5 mg/kg.

In all in vivo models tested, Hu34C3-MMAE E2 had similar or superior anti-tumor activity than Hu34C3-MMAE E4, normalized by MMAE component.

Example 25. Hu34C3-MMAE E2 is Less Toxic than Hu34C3-MMAE E4 in Rats

Sprague-Dawley rats were given a single dose of crude Hu34C3-MMAE DAR4 (30 mg/kg), Hu34C3-MMAE E4 (40 mg/kg) or Hu34C3-MMAE E2 (80 mg/kg) intravenously. Rats were observed daily for signs of distress (ruffled fur, responsiveness and weight loss) and were euthanized according to established protocols. Blood samples were taken 5 and 10 days post injection of ADCs. These samples were analyzed for changes in cell count and blood chemistry using VetScan and Hemavet instruments.

Results are shown in FIGS. 24A-24D. Significant toxicity was observed in rats dosed with Hu34C3-MMAE DAR4 and Hu34C3-MMAE E4, eventually resulting in the death of all animals in these treatment groups (FIG. 24A). Since the Hu34C3 antibody does not bind to rat CS1, it can be surmised that the toxicity observed was due to the conjugated MMAE, or to unconjugated MMAE that can be released upon metabolism and clearance of the ADC.

FIG. 24A shows percent survival of animals ("Percent Survival") vs. number of days post-administration of antibody-drug conjugate ("Days"). Bold solid line depicts heterogenous Hu34C3 MMAE mixture having an average DAR4 at 30 mg/kg dose; dashed line depicts Hu34C3-MMAE E4 at 40 mg/kg dose; thin solid line depicts Hu34C3-MMAE E2 at 80 mg/kg dose.

Interestingly, when an equivalent dose of MMAE was delivered via Hu34C3-MMAE E2, all animals survived. Further investigation revealed that animals treated with Hu34C3-MMAE E2 also had more platelets, more neutrophils (FIGS. 24B & 24C), and less liver damage (measured by ALT levels) than animals treated with Hu34C3-MMAE E4 (FIG. 24D). In FIGS. 24B and 24C, three out of the four rats treated with Hu34C3-MMAE DAR4 died prior to hematological assessments.

FIG. 24B shows concentration of platelets ("Platelets (1000 s/μL)") in animals vs. antibody-drug conjugate. Exposure to MMAE is indicated in μmol/m$^2$ on the x-axis. Shaded circle indicates an animal treated with vehicle; shaded triangle indicates an animal treated with Hu34C3 MMAE DAR4 at 30 mg/kg; solid triangle indicates an animal treated with Hu34C3-MMAE E4 at 30 mg/kg; solid circle indicates an animal treated with Hu34C3-MMAE E4 at 40 mg/kg; hollow triangle indicates an animal treated with Hu34C3-MMAE E2 at 60 mg/kg; hollow circle indicates an animal treated with Hu34C3-MMAE E2 at 80 mg/kg; hollow square indicates an animal treated with Hu34C3-MMAE E2 at 100 mg/kg.

FIG. 24C shows concentration of neutrophils ("Neutrophils (1000 s/μL)") in animals vs. antibody-drug conjugate. Exposure to MMAE is indicated in μmol/m$^2$ on the x-axis. Shaded circle indicates an animal treated with vehicle; shaded triangle indicates an animal treated with Hu34C3 MMAE DAR4 at 30 mg/kg; solid triangle indicates an animal treated with Hu34C3-MMAE E4 at 30 mg/kg; solid circle indicates an animal treated with Hu34C3-MMAE E4 at 40 mg/kg; hollow triangle indicates an animal treated with Hu34C3-MMAE E2 at 60 mg/kg; hollow circle indicates an animal treated with Hu34C3-MMAE E2 at 80 mg/kg; hollow square indicates an animal treated with Hu34C3-MMAE E2 at 100 mg/kg.

FIG. 24D shows ALT levels (in units/L) in animals on the y-axis vs. antibody-drug conjugate. Exposure to MMAE is indicated in μmol/m$^2$ on the x-axis. Shaded circle indicates an animal treated with vehicle; shaded triangle indicates an animal treated with Hu34C3 MMAE DAR4 at 30 mg/kg; solid triangle indicates an animal treated with Hu34C3-MMAE E4 at 30 mg/kg; solid circle indicates an animal treated with Hu34C3-MMAE E4 at 40 mg/kg; hollow triangle indicates an animal treated with Hu34C3-MMAE E2 at 60 mg/kg; hollow circle indicates an animal treated with Hu34C3-MMAE E2 at 80 mg/kg; hollow square indicates an animal treated with Hu34C3-MMAE E2 at 100 mg/kg.

These data indicate that Hu34C3-MMAE E2 is less toxic in rats than Hu34C3-MMAE E4 when doses are compared on a normalized (mass of MMAE delivered) basis.

Example 26. Hu34C3-MMAE E2 is Better Tolerated in Cynomolgus Monkeys than Hu34C3-MMAE E4

In a non-GLP dose range-finding study, Hu34C3-MMAE E2 was administered to cynomolgus monkeys via 30-minute IV infusion at every 3 week (Q3W) dose interval for a total of 2 doses (Day 1 and Day 22), with necropsy on Day 29. The test material used in this study included a comparison of Hu34C3-MMAE E2, Hu34C3-MMAE E4, Hu34C3-MMAE DAR4 and unconjugated Hu34C3 antibody.

Results are summarized in TABLE 8, below:

TABLE 8

Summary of Non-GLP Dose Range-Finding Cynomolgus Studies

| | Dose (mg/kg) | Summary Observations |
|---|---|---|
| Vehicle control | 0 | No remarkable changes |
| Hu34C3 (unconjugated) | 24 | No remarkable changes |
| Hu34C3-MMAE E2 | 6 | ↓Lymphocytes (non-adverse) |
| Hu34C3-MMAE E2 | 12 | ↓Neutrophils (non-adverse), ↓Lymphocytes (non-adverse) |
| Hu34C3-MMAE E4 | 6 | ↓Neutrophils (adverse), ↓Lymphocytes (non-adverse), ↓Monocytes (non-adverse), ↓RBC mass & reticulocytes (non-adverse) |
| Hu34C3-MMAE E2 | 24 | ↓Neutrophils (adverse), ↓Lymphocytes (non-adverse), ↓Monocytes (non-adverse), ↓RBC mass & reticulocytes (non-adverse) |
| Hu34C3-MMAE E4 | 12 | ↓Neutrophils (adverse), ↓Lymphocytes (non-adverse), ↓Monocytes (non-adverse), ↓RBC mass & reticulocytes (non-adverse) |
| Hu34C3-MMAE DAR4 | 12 | ↓Neutrophils (adverse), ↓Lymphocytes (non-adverse), ↓Monocytes (non-adverse), ↓RBC mass & reticulocytes (non-adverse) |

Adverse decreases in neutrophils correlated histopathologically with minimal to moderate bone marrow hypocellularity In general, the magnitude of effects observed at an Hu34C3-MMAE E2 dose of 24 mg/kg was similar to the magnitude of effects observed at ≥6 mg/kg of Hu34C3-MMAE E4 or 12 mg/kg Hu34C3-MMAE DAR4. Furthermore, effects at doses of 6 and 12 mg/kg of Hu34C3-MMAE E4 and of 12 mg/kg Hu34C3-MMAE DAR4 were adverse in magnitude (<1000 cells/μL), whereas effects at these same doses of Hu34C3-MMAE E2 were not adverse in magnitude. The differences in magnitude of effects at different drug-to-antibody ratios indicate that the Hu34C3-MMAE E2 results in better tolerability at higher doses.

Example 27. Activity of Hu34C3-MMAE E2 with Bortezomib on Inhibition of OPM-2 Xenografts in Effector-Cell-Negative Mice Efficacy of Hu34C3-MMAE E2 in combination with bortezomib ((also known as [(1R)-3-methyl-1-[[(2S)-1-oxo-3-phenyl-2-[(pyrazinylcarbonyl) amino]propyl]amino]butyl] boronic acid; marketed under the tradename VELCADE by Millennium Pharmaceuticals, Inc., Cambridge, Mass. 02139) was determined in subcutaneous xenografts of OPM-2 (van Rhee, et al., 2009 Mol. Cancer Therapeutics 8: 2616-24). Effector-cell-negative mice were used (NSG strain) in this experiment. Treatment with Hu34C3-MMAE E2 or bortezomib resulted in significant tumor growth inhibition (TGImax values of 54% and 58%, respectively) (FIG. 25). The combination of Hu34C3-MMAE E2 plus bortezomib showed significant enhancement of inhibition of tumor growth (TGImax 93%) as compared to Hu34C3-MMAE E2 or bortezomib alone.

FIG. 25 depicts xenograft tumor volume in cubic millimeters ("Tumor Volume (mm$^3$)") vs. time after introduction of cancer cells in mice ("Days Post Cell Inoculation"). Bortezomib dosing is indicated at days with the shaded inverted triangle, antibody-drug conjugate dosing ("ADC Dosing") is indicated at days with the solid inverted triangle. Results: solid circle, dotted line indicates effect of AB095-MMAE E2 ("AB095 E2") at 3 mg/kg; hollow square, solid line indicates effect of bortezomib at 1 mg/kg; hollow triangle, dashed line indicates effect of Hu34C3-MMAE E2 at 3 mg/kg; solid inverted triangle, solid line indicates effect of bortezomib at 1 mg/kg in combination with Hu34C3-MMAE E2 at 3 mg/kg.

Example 28. Activity of Hu34C3-MMAE E2 with Carfilzomib on Inhibition of OPM-2 Xenografts in Effector-Cell-Negative Mice Efficacy of Hu34C3-MMAE E2 in combination with carfilzomib ((also known as (S)-4-Methyl-N—((S)-1-(((S)-4-methyl-1-((R)-2-methyloxiran-2-yl)-1-oxopentan-2-yl) amino)-1-oxo-3-phenylpropan-2-yl)-2-((S)-2-(2-morpholinoacetamido)-4-phenylbutanamido)pentanamide; marketed under the tradename Kyprolis by Onyx Pharmaceuticals, Inc., South San Francisco, Calif.) was determined in subcutaneous xenografts of OPM-2. Effector-cell-negative mice were used (NSG strain) in this experiment. Treatment with Hu34C3-MMAE E2 resulted in significant tumor growth inhibition (TGImax values of 45%). Treatment with carfilzomib did not significantly affect tumor size (<10% TGImax) (FIGS. 26A and 26B). The combination of Hu34C3-MMAE E2 plus carfilzomib inhibited tumor growth (TGImax 43% (FIG. 26A) and TGImax 59% (FIG. 26B)) at similar levels to Hu34C3-MMAE E2 alone.

Example 29. Hu34C3-MMAE E2 is Effective as Monotherapy on Inhibition of OPM-2 Xenografts in Effector-Cell-Negative Mice, and is Effective in Combination with Pomalidomide and/or Dexamethasone Efficacy of Hu34C3-MMAE E2 in combination with pomalidomide ((also known as 4-Amino-2-(2,6-dioxopiperidin-3-yl)isoindole-1,3-dione; marketed under the tradename POMALYST by Celgene Corporation, Summit, N.J. 07901) and/or dexamethasone ((also known as 8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one) was determined in subcutaneous xenografts of OPM-2 cells (van Rhee et al., 2009 Mol. Cancer Therapeutics 8: 2616-24). Effector-cell-negative mice were used (NSG strain) in this experiment. Vehicle (PBS/DMSO) was run as a control. ADCs were dosed at 3 or 6 mg/kg i.p.; pomalidomide was dosed at 20 mg/kg i.p. and dexamethasone was dosed at 10 mg/kg i.p.

Treatment with Hu34C3-MMAE E2 as a single agent resulted in significant tumor growth inhibition at low (3 mg/kg) and moderate (6 mg/kg) dose levels, with TGImax values of 70% and 97%, respectively. Five of eight mice treated with Hu34C3-MMAE E2 at 6 mg/kg showed a complete response. The combination of low-dose Hu34C3-MMAE E2 plus dexamethasone showed little improvement (TGImax 73%) over single-agent Hu34C3-MMAE E2 (TGImax 70%), but did show enhanced tumor growth inhibition compared to dexamethasone alone (TGImax 25%). The combination of low-dose Hu34C3-MMAE E2 plus pomalidomide showed enhanced tumor growth inhibition (TGImax 94%) compared to Hu34C3-MMAE E2 alone (TGImax 70%) or pomalidomide alone (TGImax 34%), and also induced a complete response in three of eight mice (FIG. 27).

FIG. 27 shows xenograft tumor volume in cubic millimeters ("Tumor Volume (mm$^3$)") vs. time after cancer cells were introduced ("Days Post Cell Inoculation"). Solid inverted triangle indicates antibody-drug conjugate dosing days ("ADC Dosing: 3 or 6 mg/kg"); shaded inverted triangle indicates pomalidomide dosing days at 20 mg/kg; hollow triangle indicates dexamethasone dosing days at 10 mg/kg. Results: solid circle, dotted line indicates effect of AB095-MMAE E2 at 6 mg/kg; solid triangle, dashed line indicates effect of dexamethasone only; hollow inverted triangle, solid line indicates effect of pomalidomide only; solid inverted triangle, solid line indicates effect of pomalidomide with dexamethasone; hollow circle, dotted line indicates effect of Hu34C3-MMAE E2 at 3 mg/kg; hollow square, solid line indicates effect of Hu34C3-MMAE E2 at 3 mg/kg and dexamethasone; hollow diamond, dotted line indicates effect of Hu34C3-MMAE E2 at 3 mg/kg, dexamethasone, and pomalidomide; hollow triangle, dashed line indicates effect of Hu34C3-MMAE E2 at 3 mg/kg and pomalidomide; solid circle, dashed line indicates effect of Hu34C3-MMAE E2 at 6 mg/kg.

Example 30. Hu34C3-MMAE E2 is More Effective than Elotuzumab/Lenalidomide in L-363 Xenografts in Effector-Cell-Positive Mice Efficacy of Hu34C3-MMAE E2 was determined in subcutaneous xenografts of L-363 cells (Tai et al., 2008 *Blood* 112(4): 1329-37). These xenografts were treated with elotuzumab (10 mg/kg) and lenalidomide (50 mg/kg) for two weeks. Elotuzumab was administered twice a week; lenalidomide was administered 5 times a week. At the end of this two week treatment, the elotuzumab/lenalidomide-treated group had a 52% TGImax. These tumors were re-randomized and either continued on with elotuzumab/lenalidomide treatment or received Hu34C3-MMAE E2E4 (a 50:50 mixture of Hu34C3-MMAE E2 and Hu34C3-MMAE E4). Treatment with Hu34C3MMAE E2E4 induced a significant delay in tumor growth (TGImax=75%), whereas elotuzumab/lenalidomide treatment showed a minor delay in growth (FIG. 28).

FIG. 28 shows xenograft tumor volume in cubic millimeters ("Tumor Volume (mm$^3$)") vs. time after cancer cells were introduced ("Days Post Implantation"). Solid triangle indicates lenalidomide dosing days ("Len Dosing"); solid square indicates elotuzumab dosing days ("Elo Dosing"), and shaded triangle indicates antibody-drug conjugate dosing days ("ADC Dosing"). Results: solid circle, solid line indicates effect of vehicle dosing ("PBS Control"); hollow inverted triangle with dash-dot line indicates effect of AB095-MMAE E2E4 dosing at 10 mg/kg; hollow triangle with dashed line indicates effect of elotuzumab dosing at 10 mg/kg in combination with lenalidomide at 50 mg/kg; solid triangle, dashed line indicates effect of Hu34C3-MMAE E2E4 dosing at 10 mg/kg; solid inverted triangle, solid line indicates effect of Hu34C3-MMAE E2E4 at 3 mg/kg.

Example 31. Growth Inhibition of OPM-2 Xenografts by Hu34C3-MMAE E2 Pre-Treated with Bortezomib in Effector-Cell-Negative Mice Efficacy of Hu34C3-MMAE E2 was determined in subcutaneous xenografts of OPM-2 cells (van Rhee et al., 2009 *Mol. Cancer Therapeutics* 8: 2616-24). These xenografts were treated with bortezomib twice a week for two weeks. At the end of this two week treatment, a moderate response was seen in this bortezomib-treated group (66% TGImax). These tumors were re-randomized and either continued with bortezomib treatment or were switched to lenalidomide plus dexamethasone, pomalidomide, Hu34C3-MMAE E2, or Hu34C3-MMAE E2 plus pomalidomide treatments. The combination of Hu34C3-MMAE E2 (5 mg/kg) plus pomalidomide (90% TGImax) demonstrated significantly greater efficacy compared to treatment with Hu34C3-MMAE E2 or pomalidomide alone. Hu34C3-MMAE E2, when dosed at twice the level (10 mg/kg), showed similar efficacy as moderate-dose Hu34C3-MMAE E2 (5 mg/kg) in combination with pomalidomide (FIG. 29).

FIG. 29 shows xenograft tumor volume in cubic millimeters ("Tumor Volume (mm$^3$)") vs. time after cancer cells were introduced ("Days Post Cell Inoculation"). Solid diamond indicates bortezomib dosing day; solid circle indicates pomalidomide dosing day; solid star indicates lenalidomide dosing day; shaded triangle indicates dexamethasone dosing day; and solid inverted triangle indicates antibody-drug conjugate dosing day ("ADC Dosing"). Results: hollow circle, dashed line indicates vehicle dosing ("PBS Control"); solid square, solid line indicates effect of bortezomib dosing at 1 mg/kg; hollow inverted triangle, dash-dot line indicates effect of lenalidomide at 50 mg/kg in combination with dexamethasone at 10 mg/kg; bold hollow inverted triangle, dashed line indicates effect of pomalidomide dosing at 20 mg/kg; shaded circle, dotted line indicates effect of Hu34C3-MMAE E2 at 5 mg/kg; hollow triangle, dashed line indicates effect of Hu34C3-MMAE E2 at 5 mg/kg in combination with pomalidomide at 20 mg/kg; solid circle, solid line indicates effect of Hu34C3-MMAE E2 dosing at 10 mg/kg.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An antibody drug conjugate ("ADC") comprising a cytotoxic and/or cytostatic agent linked to an antibody by way of a linker, wherein the antibody comprises six CDRs in which:
   $V_H$ CDR#1 has an amino acid sequence DYYMA (SEQ ID NO:100),
   $V_H$ CDR#2 has an amino acid sequence SINY-DGSSTYYVDSVKG (SEQ ID NO:104),
   $V_H$ CDR#3 has an amino acid sequence DRGYYFDY (SEQ ID NO:111),
   $V_L$ CDR#1 has an amino acid sequence RSSQSLVH-SNGNTYLH (SEQ ID NO:114),
   $V_L$ CDR#2 has an amino acid sequence KVSNRFS (SEQ ID NO:121), and
   $V_L$ CDR#3 has an amino acid sequence SQSTHVPPFT (SEQ ID NO:123).

2. The ADC of claim 1, wherein the antibody comprises a $V_H$ chain corresponding in sequence to SEQ ID NO:8 and a $V_L$ chain corresponding in sequence to SEQ ID NO:10.

3. The ADC of claim 1, wherein the antibody comprises a heavy chain corresponding in sequence to SEQ ID NO:34 and a light chain corresponding in sequence to SEQ ID NO:35.

4. The ADC of claim 1, wherein the antibody is an $IgG_1$.

5. The ADC of claim 1 which has an average drug-to-antibody ratio in the range of 1-10.

6. The ADC of claim 1 which has an average drug-to-antibody ratio in the range of 2-4.

7. The ADC of claim 1 in which the cytotoxic and/or cytostatic agent is selected from the group consisting of calicheamicin, a maytansinoid, an auristatin and doxorubicin.

8. The ADC of claim 1 in which the cytotoxic and/or cytostatic agent is an auristatin.

9. The ADC of claim 1 in which the cytotoxic and/or cytostatic agent is monomethyl auristatin E or monomethyl auristatin F.

10. An antibody drug conjugate ("ADC") comprising a cytotoxic and/or cytostatic agent linked to an antibody by way of a linker, wherein the ADC has a structure according to formula (I):

$$[D-L-XY-]_n-Ab \qquad (I)$$

or a salt thereof, wherein:
D is the antineoplastic drug;
L is the linker;
Ab is the antibody;
XY represents a covalent linkage linking linker L to antibody Ab; and
n is an integer ranging from 2 to 8;
and wherein Ab comprises six CDRs in which:
   $V_H$ CDR#1 has an amino acid sequence DYYMA (SEQ ID NO:100),
   $V_H$ CDR#2 has an amino acid sequence SINY-DGSSTYYVDSVKG (SEQ ID NO:104),
   $V_H$ CDR#3 has an amino acid sequence DRGYYFDY (SEQ ID NO:111),
   $V_L$ CDR#1 has an amino acid sequence RSSQSLVH-SNGNTYLH (SEQ ID NO:114),
   $V_L$ CDR#2 has an amino acid sequence KVSNRFS (SEQ ID NO:121), and
   $V_L$ CDR#3 has an amino acid sequence SQSTHVPPFT (SEQ ID NO:123).

11. The ADC of claim 10 in which n is 2, 3 or 4.

12. The ADC of claim 10 in which XY is a linkage formed with a sulfydryl group on antibody Ab.

13. The ADC of claim 10 in which the compound according to structural formula (I) has the structure of formula (IIa):

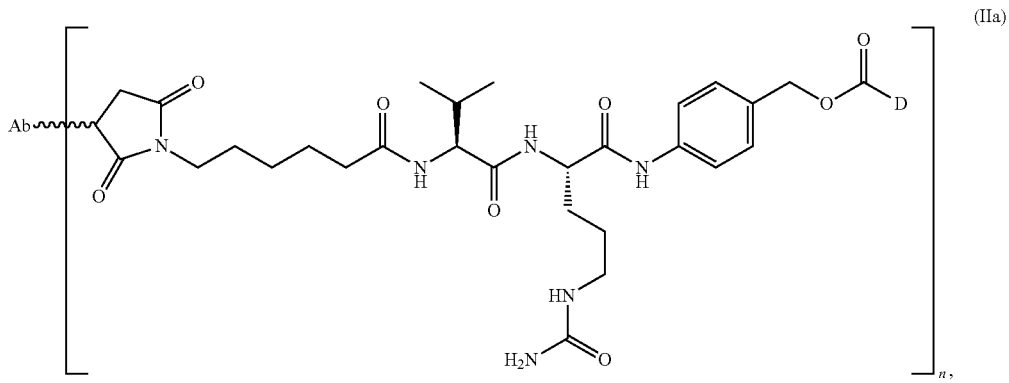

where Ab is an antibody having a $V_H$ chain corresponding in sequence to SEQ ID NO:8 and a $V_L$ chain corresponding in sequence to SEQ ID NO:10.

14. The ADC of claim 13 in which n is 2 or 4.

15. The ADC of claim 13 in which D is an auristatin.

16. The ADC of claim 10 which has the structure:

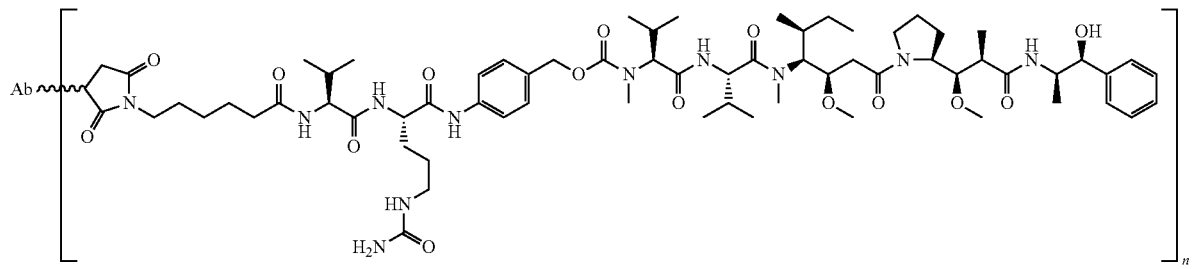

where Ab is an antibody having a $V_H$ chain corresponding in sequence to SEQ ID NO:8 and a $V_L$ chain corresponding in sequence to SEQ ID NO:10, and n is 2 or 4.

17. The ADC of claim 16, wherein n is 2.

18. The ADC of claim 16, wherein Ab is an antibody having a heavy chain corresponding in sequence to SEQ ID NO:34 and a light chain corresponding in sequence to SEQ ID NO:35.

19. The ADC of claim 18, wherein n is 2.

20. A composition comprising an antibody-drug conjugate ("ADC") and a carrier, excipient or diluent,
   wherein the ADC comprises a cytotoxic and/or cytostatic agent linked to an antibody by way of a linker, the antibody comprising six CDRs in which:

$V_H$ CDR#1 has an amino acid sequence DYYMA (SEQ ID NO:100), $V_H$ CDR#2 has an amino acid sequence SINY-DGSSTYYVDSVKG (SEQ ID NO:104), $V_H$ CDR#3 has an amino acid sequence DRGYYFDY (SEQ ID NO:111), $V_L$ CDR#1 has an amino acid sequence RSSQSLVH-SNGNTYLH (SEQ ID NO:114), $V_L$ CDR#2 has an amino acid sequence KVSNRFS (SEQ ID NO:121), and $V_L$ CDR#3 has an amino acid sequence SQSTHVPPFT (SEQ ID NO:123).

* * * * *

SEQUENCE LISTING

```
<160> NUMBER OF SEQ ID NOS: 133

<210> SEQ ID NO 1
<211> LENGTH: 335
<212> TYPE: PRT
<213> ORGANISM: Homo sapiens

<400> SEQUENCE: 1
```

```
Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
            35                  40                  45

Asp Ser Ile Val Trp Thr Phe Asn Thr Thr Pro Leu Val Thr Ile Gln
        50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
            115                 120                 125

Ser Lys Pro Lys Val Thr Met Gly Leu Gln Ser Asn Lys Asn Gly Thr
        130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
            195                 200                 205

Ile Leu Ala Arg Lys Leu Cys Glu Gly Ala Ala Asp Asp Pro Asp Ser
        210                 215                 220

Ser Met Val Leu Leu Cys Leu Leu Val Pro Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
            275                 280                 285

His Thr Asn Arg Thr Ile Leu Lys Glu Asp Pro Ala Asn Thr Val Tyr
        290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 2
<211> LENGTH: 1008
<212> TYPE: DNA
<213> ORGANISM: Homo sapiens
<220> FEATURE:
<221> NAME/KEY: CDS
<222> LOCATION: (1)..(1005)

<400> SEQUENCE: 2 atg gct ggt tcc cca aca tgc ctc acc ctc atc tat atc ctt tgg cag    48
Met Ala Gly Ser Pro Thr Cys Leu Thr Leu Ile Tyr Ile Leu Trp Gln
1               5                   10                  15
```

| | | |
|---|---|---|
| ctc aca ggg tca gca gcc tct gga ccc gtg aaa gag ctg gtc ggt tcc<br>Leu Thr Gly Ser Ala Ala Ser Gly Pro Val Lys Glu Leu Val Gly Ser<br>        20                      25                  30 | | 96 |
| gtt ggt ggg gcc gtg act ttc ccc ctg aag tcc aaa gta aag caa gtt<br>Val Gly Gly Ala Val Thr Phe Pro Leu Lys Ser Lys Val Lys Gln Val<br>      35                    40                45 | | 144 |
| gac tct att gtc tgg acc ttc aac aca acc cct ctt gtc acc ata cag<br>Asp Ser Ile Val Trp Thr Phe Asn Thr Thr Pro Leu Val Thr Ile Gln<br>    50                  55                60 | | 192 |
| cca gaa ggg ggc act atc ata gtg acc caa aat cgt aat agg gag aga<br>Pro Glu Gly Gly Thr Ile Ile Val Thr Gln Asn Arg Asn Arg Glu Arg<br>65                    70                75                80 | | 240 |
| gta gac ttc cca gat gga ggc tac tcc ctg aag ctc agc aaa ctg aag<br>Val Asp Phe Pro Asp Gly Gly Tyr Ser Leu Lys Leu Ser Lys Leu Lys<br>                  85                90              95 | | 288 |
| aag aat gac tca ggg atc tac tat gtg ggg ata tac agc tca tca ctc<br>Lys Asn Asp Ser Gly Ile Tyr Tyr Val Gly Ile Tyr Ser Ser Ser Leu<br>            100                 105             110 | | 336 |
| cag cag ccc tcc acc cag gag tac gtg ctg cat gtc tac gag cac ctg<br>Gln Gln Pro Ser Thr Gln Glu Tyr Val Leu His Val Tyr Glu His Leu<br>        115                 120               125 | | 384 |
| tca aag cct aaa gtc acc atg ggt ctg cag agc aat aag aat ggc acc<br>Ser Lys Pro Lys Val Thr Met Gly Leu Gln Ser Asn Lys Asn Gly Thr<br>130                   135               140 | | 432 |
| tgt gtg acc aat ctg aca tgc tgc atg gaa cat ggg gaa gag gat gtg<br>Cys Val Thr Asn Leu Thr Cys Cys Met Glu His Gly Glu Glu Asp Val<br>145                   150               155               160 | | 480 |
| att tat acc tgg aag gcc ctg ggg caa gca gcc aat gag tcc cat aat<br>Ile Tyr Thr Trp Lys Ala Leu Gly Gln Ala Ala Asn Glu Ser His Asn<br>                 165               170              175 | | 528 |
| ggg tcc atc ctc ccc atc tcc tgg aga tgg gga gaa agt gat atg acc<br>Gly Ser Ile Leu Pro Ile Ser Trp Arg Trp Gly Glu Ser Asp Met Thr<br>        180                 185               190 | | 576 |
| ttc atc tgc gtt gcc agg aac cct gtc agc aga aac ttc tca agc ccc<br>Phe Ile Cys Val Ala Arg Asn Pro Val Ser Arg Asn Phe Ser Ser Pro<br>            195               200              205 | | 624 |
| atc ctt gcc agg aag ctc tgt gaa ggt gct gct gat gac cca gat tcc<br>Ile Leu Ala Arg Lys Leu Cys Glu Gly Ala Ala Asp Asp Pro Asp Ser<br>210                   215               220 | | 672 |
| tcc atg gtc ctc ctg tgt ctc ctg ttg gtg ccc ctc ctc agt ctc<br>Ser Met Val Leu Leu Cys Leu Leu Leu Val Pro Leu Leu Leu Ser Leu<br>225                   230               235              240 | | 720 |
| ttt gta ctg ggg cta ttt ctt tgg ttt ctg aag aga gag aga caa gaa<br>Phe Val Leu Gly Leu Phe Leu Trp Phe Leu Lys Arg Glu Arg Gln Glu<br>                 245               250              255 | | 768 |
| gag tac att gaa gag aag aag aga gtg gac att tgt cgg gaa act cct<br>Glu Tyr Ile Glu Glu Lys Lys Arg Val Asp Ile Cys Arg Glu Thr Pro<br>            260               265              270 | | 816 |
| aac ata tgc ccc cat tct gga gag aac aca gag tac gac aca atc cct<br>Asn Ile Cys Pro His Ser Gly Glu Asn Thr Glu Tyr Asp Thr Ile Pro<br>        275               280               285 | | 864 |
| cac act aat aga aca atc cta aag gaa gat cca gca aat acg gtt tac<br>His Thr Asn Arg Thr Ile Leu Lys Glu Asp Pro Ala Asn Thr Val Tyr<br>290                   295               300 | | 912 |
| tcc act gtg gaa ata ccg aaa aag atg gaa aat ccc cac tca ctg ctc<br>Ser Thr Val Glu Ile Pro Lys Lys Met Glu Asn Pro His Ser Leu Leu<br>305                   310               315              320 | | 960 |
| acg atg cca gac aca cca agg cta ttt gcc tat gag aat gtt atc tag<br>Thr Met Pro Asp Thr Pro Arg Leu Phe Ala Tyr Glu Asn Val Ile<br>                 325               330              335 | | 1008 |

<210> SEQ ID NO 3
<211> LENGTH: 335
<212> TYPE: PRT
<213> ORGANISM: Macaca fascicularis

<400> SEQUENCE: 3

| Met | Ala | Gly | Ser | Pro | Thr | Cys | Phe | Thr | Phe | Ile | Tyr | Ile | Leu | Trp | Gln |
|---|---|---|---|---|---|---|---|---|---|---|---|---|---|---|---|
| 1 | | | | 5 | | | | | 10 | | | | | 15 | |

| Leu | Thr | Gly | Ser | Thr | Ala | Ser | Gly | Ser | Val | Lys | Glu | Leu | Val | Gly | Ser |
| | | | 20 | | | | | 25 | | | | | 30 | | |

| Ile | Gly | Gly | Ala | Val | Thr | Phe | Pro | Leu | Lys | Ser | Glu | Val | Lys | Gln | Val |
| | | | 35 | | | | | 40 | | | | | 45 | | |

| Asp | Ser | Ile | Val | Trp | Thr | Phe | Asn | Thr | Thr | Leu | Val | Thr | Ile | Gln |
| | 50 | | | | | 55 | | | | | 60 | | | |

| Pro | Glu | Gly | Gly | Pro | Met | Ile | Val | Thr | Gln | Asn | Arg | Asn | Lys | Glu | Arg |
| 65 | | | | | 70 | | | | | 75 | | | | | 80 |

| Val | His | Phe | Pro | Asp | Gly | Gly | Tyr | Ser | Leu | Lys | Leu | Ser | Lys | Leu | Lys |
| | | | | 85 | | | | | 90 | | | | | 95 | |

| Lys | Asn | Asp | Ser | Gly | Ile | Tyr | Asn | Val | Glu | Ile | Tyr | Ser | Ser | Ser | Leu |
| | | | 100 | | | | | 105 | | | | | 110 | | |

| Gln | Asp | Pro | Phe | Thr | Arg | Lys | Tyr | Val | Leu | Arg | Val | Tyr | Glu | His | Leu |
| | | | 115 | | | | | 120 | | | | | 125 | | |

| Ser | Lys | Pro | Lys | Val | Thr | Met | Gly | Leu | Gln | Ser | Asn | Lys | Asn | Gly | Thr |
| | 130 | | | | | 135 | | | | | 140 | | | | |

| Cys | Val | Thr | Asn | Leu | Thr | Cys | Cys | Met | Glu | His | Gly | Glu | Glu | Asp | Val |
| 145 | | | | | 150 | | | | | 155 | | | | | 160 |

| Ile | Tyr | Thr | Trp | Lys | Ala | Leu | Gly | Gln | Ala | Val | Asn | Glu | Ser | His | Asn |
| | | | | 165 | | | | | 170 | | | | | 175 | |

| Gly | Ser | Ile | Leu | Pro | Ile | Ser | Trp | Arg | Trp | Gly | Glu | Ser | Asp | Met | Thr |
| | | | 180 | | | | | 185 | | | | | 190 | | |

| Phe | Ile | Cys | Thr | Val | Arg | Asn | Pro | Val | Ser | Ser | Asn | Ser | Ser | Ser | Pro |
| | | | 195 | | | | | 200 | | | | | 205 | | |

| Ile | Leu | Ala | Arg | Lys | Leu | Cys | Glu | Gly | Ala | Ala | Asp | Asp | Ser | Asp | Ser |
| | 210 | | | | | 215 | | | | | 220 | | | | |

| Ser | Met | Val | Leu | Leu | Cys | Leu | Leu | Val | Pro | Leu | Leu | Ser | Leu |
| 225 | | | | | 230 | | | | | 235 | | | | 240 |

| Phe | Val | Leu | Gly | Leu | Phe | Leu | Trp | Phe | Leu | Lys | Arg | Glu | Thr | Gln | Glu |
| | | | | 245 | | | | | 250 | | | | | 255 | |

| Glu | Ser | Ile | Glu | Gly | Lys | Lys | Arg | Ala | Asp | Ile | Cys | Arg | Glu | Thr | Pro |
| | | | 260 | | | | | 265 | | | | | 270 | | |

| Asn | Ile | Cys | Pro | Tyr | Ser | Gly | Glu | Asn | Thr | Glu | Tyr | Asp | Thr | Ile | Pro |
| | | | 275 | | | | | 280 | | | | | 285 | | |

| Tyr | Thr | Asn | Arg | Thr | Ile | Pro | Met | Glu | Asp | Ala | Ala | Asn | Thr | Leu | Tyr |
| | 290 | | | | | 295 | | | | | 300 | | | | |

| Ser | Thr | Val | Glu | Ile | Pro | Lys | Lys | Ile | Glu | Asn | Pro | His | Ser | Leu | Leu |
| 305 | | | | | 310 | | | | | 315 | | | | | 320 |

| Thr | Met | Pro | Asp | Thr | Pro | Arg | Leu | Phe | Ala | Tyr | Glu | Asn | Val | Ile |
| | | | | 325 | | | | | 330 | | | | | 335 |

<210> SEQ ID NO 4
<211> LENGTH: 1008
<212> TYPE: DNA
<213> ORGANISM: Macaca fascicularis
<220> FEATURE:
<221> NAME/KEY: CDS

<222> LOCATION: (1)..(1005)

<400> SEQUENCE: 4

| | | | | | | | | | | | | | | | | |
|---|---|---|---|---|---|---|---|---|---|---|---|---|---|---|---|---|
| atg | gct | ggt | tcc | cca | aca | tgc | ttc | acc | ttc | atc | tat | atc | ctt | tgg | cag | 48 |
| Met | Ala | Gly | Ser | Pro | Thr | Cys | Phe | Thr | Phe | Ile | Tyr | Ile | Leu | Trp | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctc | aca | ggg | tca | aca | gcc | tct | gga | tcc | gtg | aaa | gag | ctg | gtc | ggt | tcc | 96 |
| Leu | Thr | Gly | Ser | Thr | Ala | Ser | Gly | Ser | Val | Lys | Glu | Leu | Val | Gly | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| att | ggt | ggg | gct | gtg | act | ttc | ccc | ctg | aag | tct | gaa | gta | aag | caa | gtt | 144 |
| Ile | Gly | Gly | Ala | Val | Thr | Phe | Pro | Leu | Lys | Ser | Glu | Val | Lys | Gln | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gac | tct | att | gtc | tgg | acc | ttc | aac | aca | acc | act | ctt | gtc | acc | ata | cag | 192 |
| Asp | Ser | Ile | Val | Trp | Thr | Phe | Asn | Thr | Thr | Thr | Leu | Val | Thr | Ile | Gln | |
| | 50 | | | | | 55 | | | | | 60 | | | | | |

| | | | | | | | | | | | | | | | | |
|---|---|---|---|---|---|---|---|---|---|---|---|---|---|---|---|---|
| cca | gaa | ggg | ggc | cct | atg | ata | gtg | acc | caa | aat | cgt | aat | aag | gag | aga | 240 |
| Pro | Glu | Gly | Gly | Pro | Met | Ile | Val | Thr | Gln | Asn | Arg | Asn | Lys | Glu | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gta | cac | ttc | cca | gat | gga | ggc | tat | tcc | ctg | aag | ctc | agc | aaa | ctg | aag | 288 |
| Val | His | Phe | Pro | Asp | Gly | Gly | Tyr | Ser | Leu | Lys | Leu | Ser | Lys | Leu | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | aat | gac | tca | ggg | atc | tac | aat | gtg | gag | ata | tac | agc | tca | tcc | ctc | 336 |
| Lys | Asn | Asp | Ser | Gly | Ile | Tyr | Asn | Val | Glu | Ile | Tyr | Ser | Ser | Ser | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| cag | gat | ccc | ttc | acc | cgg | aag | tat | gtg | ctg | cgt | gtc | tac | gag | cac | ctg | 384 |
| Gln | Asp | Pro | Phe | Thr | Arg | Lys | Tyr | Val | Leu | Arg | Val | Tyr | Glu | His | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| tca | aag | cct | aaa | gtc | acc | atg | ggt | cta | cag | agt | aat | aag | aat | ggc | acc | 432 |
| Ser | Lys | Pro | Lys | Val | Thr | Met | Gly | Leu | Gln | Ser | Asn | Lys | Asn | Gly | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| tgt | gtg | acc | aat | ctg | aca | tgc | tgc | atg | gaa | cat | ggg | gaa | gag | gat | gtg | 480 |
| Cys | Val | Thr | Asn | Leu | Thr | Cys | Cys | Met | Glu | His | Gly | Glu | Glu | Asp | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| att | tat | acc | tgg | aag | gcc | ctg | ggg | caa | gca | gtc | aat | gag | tcc | cat | aat | 528 |
| Ile | Tyr | Thr | Trp | Lys | Ala | Leu | Gly | Gln | Ala | Val | Asn | Glu | Ser | His | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| ggg | tcc | atc | cta | ccc | atc | tcc | tgg | aga | tgg | gga | gaa | agt | gat | atg | acc | 576 |
| Gly | Ser | Ile | Leu | Pro | Ile | Ser | Trp | Arg | Trp | Gly | Glu | Ser | Asp | Met | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| ttc | atc | tgc | act | gtc | agg | aac | cct | gtc | agc | agc | aac | tcc | tca | agc | ccc | 624 |
| Phe | Ile | Cys | Thr | Val | Arg | Asn | Pro | Val | Ser | Ser | Asn | Ser | Ser | Ser | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| atc | ctt | gcc | agg | aag | ctc | tgt | gaa | ggt | gct | gct | gat | gac | tca | gat | tcc | 672 |
| Ile | Leu | Ala | Arg | Lys | Leu | Cys | Glu | Gly | Ala | Ala | Asp | Asp | Ser | Asp | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| tcc | atg | gtc | ctc | ctg | tgt | ctc | ctg | ttg | gtg | ccc | ctc | ctg | ctc | agt | ctc | 720 |
| Ser | Met | Val | Leu | Leu | Cys | Leu | Leu | Leu | Val | Pro | Leu | Leu | Leu | Ser | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ttt | gta | ctg | ggg | cta | ttt | ctt | tgg | ttt | ctg | aag | aga | gag | aca | caa | gaa | 768 |
| Phe | Val | Leu | Gly | Leu | Phe | Leu | Trp | Phe | Leu | Lys | Arg | Glu | Thr | Gln | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| gag | tcc | att | gaa | ggg | aag | aag | aga | gcg | gac | att | tgt | cgg | gaa | act | cct | 816 |
| Glu | Ser | Ile | Glu | Gly | Lys | Lys | Arg | Ala | Asp | Ile | Cys | Arg | Glu | Thr | Pro | |
| | | | 260 | | | | | 265 | | | | | 270 | | | |

| | | | | | | | | | | | | | | | | |
|---|---|---|---|---|---|---|---|---|---|---|---|---|---|---|---|---|
| aac | ata | tgc | ccc | tat | tct | gga | gag | aac | aca | gag | tat | gac | aca | atc | cct | 864 |
| Asn | Ile | Cys | Pro | Tyr | Ser | Gly | Glu | Asn | Thr | Glu | Tyr | Asp | Thr | Ile | Pro | |
| | | 275 | | | | | 280 | | | | | 285 | | | | |

| | | | | | | | | | | | | | | | | |
|---|---|---|---|---|---|---|---|---|---|---|---|---|---|---|---|---|
| tac | act | aat | aga | act | atc | cca | atg | gaa | gat | gca | gca | aat | aca | ctt | tat | 912 |
| Tyr | Thr | Asn | Arg | Thr | Ile | Pro | Met | Glu | Asp | Ala | Ala | Asn | Thr | Leu | Tyr | |
| | 290 | | | | | 295 | | | | | 300 | | | | | |

```
tcc act gtg gaa ata cca aaa aag att gaa aat ccc cac tca ctg ctc    960
Ser Thr Val Glu Ile Pro Lys Lys Ile Glu Asn Pro His Ser Leu Leu
305                 310                 315                 320 acg atg cca gac aca cca agg cta ttt gcc tat gag aat gtt atc tag   1008
Thr Met Pro Asp Thr Pro Arg Leu Phe Ala Tyr Glu Asn Val Ile
                325                 330                 335
```

<210> SEQ ID NO 5
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 5

```
Glu Val Lys Leu Val Glu Ser Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Ser Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Phe
65                  70                  75                  80

Leu Gln Met Asn Ser Leu Lys Ser Glu Asp Thr Ala Thr Tyr Tyr Cys
                85                  90                  95

Ala Arg Asp Arg Gly Tyr Tyr Phe Asp Tyr Trp Gly Gln Gly Thr Thr
            100                 105                 110

Leu Thr Val Ser Ser
        115
```

<210> SEQ ID NO 6
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Phe Thr Phe Gly Gly Gly Thr Lys Leu Glu Ile
            100                 105                 110

Lys
```

```
<210> SEQ ID NO 7
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Phe Asp Tyr Trp Gly Gln Gly Thr Thr
            100                 105                 110

Val Thr Val Ser Ser
        115

<210> SEQ ID NO 8
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Tyr Asp Gly Ser Ser Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Phe Asp Tyr Trp Gly Gln Gly Thr Thr
            100                 105                 110

Val Thr Val Ser Ser
        115

<210> SEQ ID NO 9
<211> LENGTH: 113
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 9

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Phe Thr Phe Gly Gly Gly Thr Lys Val Glu Ile
            100                 105                 110

Lys

<210> SEQ ID NO 10
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Pro Phe Thr Phe Gly Gly Gly Thr Lys Val Glu Ile
            100                 105                 110

Lys

<210> SEQ ID NO 11
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Phe Thr Phe Gly Gly Gly Thr Lys Val Glu Ile
            100                 105                 110

Lys

<210> SEQ ID NO 12
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Tyr Asp Gly Glu Ser Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Phe Asp Tyr Trp Gly Gln Gly Thr Thr
            100                 105                 110

Val Thr Val Ser Ser
        115

<210> SEQ ID NO 13
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Leu Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Pro Phe Thr Phe Gly Gly Gly Thr Lys Val Glu Ile
            100                 105                 110

Lys

<210> SEQ ID NO 14
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
                20                  25                  30

Tyr Met Ala Trp Val Arg Gln Val Pro Glu Lys Gly Leu Glu Trp Val
            35                  40                  45

Ala Asp Ile Asn Tyr Asp Gly Ser Thr Tyr Tyr Leu Asp Ser Leu
        50                  55                  60

Lys Ser Arg Phe Ile Ile Ser Arg Asp Asn Ala Lys Asn Ile Leu Cys
65                  70                  75                  80

Leu Gln Met Ser Ser Leu Lys Ser Glu Asp Thr Ala Thr Tyr Tyr Cys
                85                  90                  95

Ala Arg Asp Arg Gly Tyr Tyr Phe Asp Tyr Trp Gly Gln Gly Thr Thr
            100                 105                 110

Leu Thr Val Ser Ser
        115

<210> SEQ ID NO 15
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Phe Thr Phe Gly Gly Gly Thr Lys Leu Glu Ile

Lys

<210> SEQ ID NO 16
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asp Ile Asn Tyr Asp Gly Gly Ser Thr Tyr Tyr Leu Asp Ser Leu
    50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Phe Asp Tyr Trp Gly Gln Gly Thr Leu
            100                 105                 110

Val Thr Val Ser Ser
        115

<210> SEQ ID NO 17
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asp Ile Asn Tyr Asp Gly Gly Ser Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Phe Asp Tyr Trp Gly Gln Gly Thr Leu
            100                 105                 110

Val Thr Val Ser Ser
        115

<210> SEQ ID NO 18
<211> LENGTH: 113

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Phe Thr Phe Gly Gly Gly Thr Lys Val Glu Ile
            100                 105                 110

Lys

<210> SEQ ID NO 19
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Pro Phe Thr Phe Gly Gly Gly Thr Lys Val Glu Ile
            100                 105                 110

Lys

<210> SEQ ID NO 20
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20
```

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Phe Thr Phe Gly Gly Gly Thr Lys Val Glu Ile
            100                 105                 110

Lys

<210> SEQ ID NO 21
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
            35                  40                  45

Ala Glu Ile Asn Tyr Asp Gly Ser Ser Thr Tyr Tyr Leu Asp Ser Leu
        50                  55                  60

Lys Ser Arg Phe Ile Ile Ser Arg Asp Asn Ala Lys Asn Ile Leu Tyr
65                  70                  75                  80

Leu Gln Met Ser Asn Leu Lys Ser Glu Asp Thr Ala Thr Tyr Tyr Cys
                85                  90                  95

Ala Arg Asp Arg Gly Phe Tyr Phe Asp Tyr Trp Gly Gln Gly Thr Thr
            100                 105                 110

Leu Thr Val Ser Ser
        115

<210> SEQ ID NO 22
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asn Thr Tyr Leu His Trp Tyr Leu Gln Lys Pro Gly Gln Ser
            35                  40                  45
```

-continued

```
Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Tyr Thr Phe Gly Gly Gly Thr Lys Leu Glu Ile
            100                 105                 110

Lys

<210> SEQ ID NO 23
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Glu Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Phe Tyr Phe Asp Tyr Trp Gly Gln Gly Thr Thr
            100                 105                 110

Val Thr Val Ser Ser
        115

<210> SEQ ID NO 24
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Glu Ile Asn Tyr Asp Gly Ser Ser Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

85                  90                  95

Ala Arg Asp Arg Gly Phe Tyr Phe Asp Tyr Trp Gly Gln Gly Thr Thr
            100                 105                 110

Val Thr Val Ser Ser
        115

<210> SEQ ID NO 25
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Asn
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Tyr Thr Phe Gly Gly Gly Thr Lys Val Glu Ile
            100                 105                 110

Lys

<210> SEQ ID NO 26
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Asn
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Pro Tyr Thr Phe Gly Gly Gly Thr Lys Val Glu Ile
            100                 105                 110

Lys

```
<210> SEQ ID NO 27
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Asn
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Tyr Thr Phe Gly Gly Gly Thr Lys Val Glu Ile
            100                 105                 110

Lys

<210> SEQ ID NO 28
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Phe Met Ala Trp Val Arg Gln Val Pro Glu Lys Gly Leu Glu Trp Val
        35                  40                  45

Ala Ser Ile Asn Tyr Asp Gly Asn Ser Thr Tyr Phe Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Asp Arg Gly Phe Tyr Phe Asp Tyr Trp Gly Gln Gly Thr Thr
            100                 105                 110

Leu Thr Val Ser Ser
        115

<210> SEQ ID NO 29
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 29

Asp Val Val Met Thr Gln Thr Pro Leu Ser Leu Pro Val Ser Leu Gly
1               5                   10                  15

Asp Gln Ala Ser Ile Ser Cys Arg Phe Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Ser
                85                  90                  95

Thr His Val Arg Pro Tyr Thr Phe Gly Gly Gly Thr Lys Leu Glu Ile
            100                 105                 110

Arg

<210> SEQ ID NO 30
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Ser Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Tyr
65              70                  75                  80

Leu Gln Met Ser Gly Leu Lys Ser Glu Asp Thr Ala Thr Tyr Ser Cys
                85                  90                  95

Ala Arg Asp Arg Gly Phe Tyr Phe Asp Tyr Trp Gly Gln Gly Thr Thr
            100                 105                 110

Leu Thr Val Ser Ser
        115

<210> SEQ ID NO 31
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Pro Tyr Thr Phe Gly Gly Gly Thr Lys Leu Glu Ile
            100                 105                 110

Lys

<210> SEQ ID NO 32
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gln Val Gln Leu Gln Gln Ser Gly Pro Glu Leu Val Lys Pro Gly Thr
 1               5                  10                  15

Ser Val Asn Ile Ser Cys Lys Ala Ser Gly Tyr Thr Phe Thr Asp His
                 20                  25                  30

Tyr Ile Asn Trp Val Lys Gln Arg Pro Gly Gln Gly Leu Glu Trp Ile
             35                  40                  45

Gly Trp Ile Phe Pro Gly Thr Gly Ile Thr Tyr Tyr Asn Glu Asn Phe
 50                  55                  60

Lys Gly Lys Ala Thr Leu Thr Val Asp Lys Ser Ser Ser Thr Ala Tyr
 65                  70                  75                  80

Met Leu Leu Ser Ser Leu Thr Ser Glu Asp Ser Ala Val Tyr Phe Cys
                 85                  90                  95

Ala Arg Arg Gly Tyr Gly Ser Phe Asp Tyr Trp Gly Gln Gly Thr Thr
            100                 105                 110

Leu Thr Val Ser Ser
        115

<210> SEQ ID NO 33
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Val Met Thr Gln Ser Pro Ser Ser Leu Ala Met Ser Val Gly
 1               5                  10                  15

Gln Lys Val Thr Met Ser Cys Lys Ser Ser Gln Ser Leu Leu Asn Ser
                 20                  25                  30

Ser Asn Gln Lys Asn Tyr Leu Ala Trp Tyr Leu Gln Lys Pro Gly Gln
             35                  40                  45

Ser Leu Lys Leu Met Val Tyr Phe Ala Tyr Thr Arg Glu Ser Gly Val
 50                  55                  60

Pro Asp Arg Phe Ile Gly Ser Gly Ser Gly Thr Asp Phe Thr Leu Thr

```
                65                  70                  75                  80
Ile Ser Ser Val Gln Ala Glu Asp Pro Ala Asp Tyr Phe Cys Gln Gln
                    85                  90                  95

His Tyr Ser Ser Pro Tyr Thr Phe Gly Gly Gly Thr Lys Leu Glu Ile
                    100                 105                 110

Lys

<210> SEQ ID NO 34
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Tyr Asp Gly Ser Ser Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 35
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Pro Phe Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
```

<210> SEQ ID NO 36
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser
        115

<210> SEQ ID NO 37
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys Arg
            100                 105

<210> SEQ ID NO 38
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 38

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ala Phe Ser Ser Ser
            20                  25                  30
Trp Met Asn Trp Val Arg Gln Ala Pro Gly Gln Gly Leu Glu Trp Ile
        35                  40                  45
Gly Arg Ile Tyr Pro Gly Asp Gly Asp Thr Lys Tyr Asn Gly Lys Phe
    50                  55                  60
Lys Gly Lys Ala Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Thr Met Ile Ala Thr Gly Ala Met Asp Tyr Trp Gly Gln
            100                 105                 110
Gly Thr Leu Val Thr Val Ser Ser
        115                 120
```

<210> SEQ ID NO 39
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Asp Arg Phe Thr Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Ser Thr Pro Pro
                85                  90                  95
Tyr Thr Phe Gly Gly Gly Thr Lys Val Glu Ile Lys Arg
            100                 105
```

<210> SEQ ID NO 40
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

```
Gln Val Gln Leu Gln Gln Ser Gly Ala Glu Leu Ala Arg Pro Gly Ala
1               5                   10                  15
Ser Val Lys Leu Ser Cys Lys Ala Ser Gly Tyr Thr Phe Thr Ser Tyr
            20                  25                  30
```

```
Trp Met Gln Trp Val Lys Gln Arg Pro Gly Gln Gly Leu Glu Trp Ile
            35                  40                  45

Gly Ala Ile Tyr Pro Gly Asp Gly Asp Thr Arg Tyr Thr Gln Lys Phe
 50                  55                  60

Lys Gly Lys Ala Thr Leu Thr Ala Asp Lys Ser Ser Ser Thr Ala Tyr
 65                  70                  75                  80

Met Gln Leu Ser Ser Leu Ala Ser Glu Asp Ser Ala Val Tyr Tyr Cys
                 85                  90                  95

Ala Arg Gly Lys Val Tyr Tyr Gly Ser Asn Pro Phe Ala Tyr Trp Gly
                100                 105                 110

Gln Gly Thr Leu Val Thr Val Ser Ala
            115                 120
```

<210> SEQ ID NO 41
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

```
Asp Ile Gln Met Thr Gln Ser Ser Ser Tyr Leu Ser Val Ser Leu Gly
 1               5                  10                  15

Gly Arg Val Thr Ile Thr Cys Lys Ala Ser Asp His Ile Asn Asn Trp
                 20                  25                  30

Leu Ala Trp Tyr Gln Gly Lys Pro Gly Asn Ala Pro Arg Leu Leu Ile
             35                  40                  45

Ser Gly Ala Thr Ser Leu Glu Thr Gly Val Pro Ser Arg Phe Ser Gly
 50                  55                  60

Ser Gly Ser Gly Lys Asp Tyr Thr Leu Ser Ile Thr Ser Leu Gln Thr
 65                  70                  75                  80

Glu Asp Val Ala Thr Tyr Tyr Cys Gln Gln Tyr Trp Ser Thr Pro Trp
                 85                  90                  95

Thr Phe Gly Gly Gly Thr Lys Leu Glu Ile Lys Arg
                100                 105
```

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any aromatic residue

<400> SEQUENCE: 50

Asp Tyr Xaa Met Ala
1               5

<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any polar or acid residue
<220> FEATURE:
<221> NAME/KEY: MOD_RES
<222> LOCATION: (7)..(7)
<223> OTHER INFORMATION: Any polar, non-polar or acidic residue
<220> FEATURE:
<221> NAME/KEY: MOD_RES
<222> LOCATION: (11)..(11)
<223> OTHER INFORMATION: Any aromatic residue
<220> FEATURE:
<221> NAME/KEY: MOD_RES
<222> LOCATION: (12)..(12)
<223> OTHER INFORMATION: Any aliphatic residue
<220> FEATURE:
<221> NAME/KEY: MOD_RES
<222> LOCATION: (15)..(15)
<223> OTHER INFORMATION: Any aliphatic residue
<220> FEATURE:
<221> NAME/KEY: MOD_RES
<222> LOCATION: (17)..(17)

<223> OTHER INFORMATION: Any small residue

<400> SEQUENCE: 51

Xaa Ile Asn Tyr Asp Gly Xaa Ser Thr Tyr Xaa Xaa Asp Ser Xaa Lys
1               5                   10                  15

Xaa

<210> SEQ ID NO 52
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: Any aromatic residue

<400> SEQUENCE: 52

Asp Arg Gly Xaa Tyr Phe Asp Tyr
1               5

<210> SEQ ID NO 53
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any polar or aromatic residue
<220> FEATURE:
<221> NAME/KEY: MOD_RES
<222> LOCATION: (9)..(9)
<223> OTHER INFORMATION: Any polar or basic residue
<220> FEATURE:
<221> NAME/KEY: MOD_RES
<222> LOCATION: (12)..(12)
<223> OTHER INFORMATION: Any polar or aliphatic residue

<400> SEQUENCE: 53

Arg Xaa Ser Gln Ser Leu Val His Xaa Asn Gly Xaa Thr Tyr Leu His
1               5                   10                  15

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: Any aromatic residue

<400> SEQUENCE: 54

Ser Gln Ser Thr His Val Pro Pro Xaa Thr
1               5                   10

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78

```
<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89
```

000

<210> SEQ ID NO 90
<400> SEQUENCE: 90

000

<210> SEQ ID NO 91
<400> SEQUENCE: 91

000

<210> SEQ ID NO 92
<400> SEQUENCE: 92

000

<210> SEQ ID NO 93
<400> SEQUENCE: 93

000

<210> SEQ ID NO 94
<400> SEQUENCE: 94

000

<210> SEQ ID NO 95
<400> SEQUENCE: 95

000

<210> SEQ ID NO 96
<400> SEQUENCE: 96

000

<210> SEQ ID NO 97
<400> SEQUENCE: 97

000

<210> SEQ ID NO 98
<400> SEQUENCE: 98

000

<210> SEQ ID NO 99
<400> SEQUENCE: 99

000

<210> SEQ ID NO 100
<211> LENGTH: 5
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 100

Asp Tyr Tyr Met Ala
1               5

<210> SEQ ID NO 101
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Asp Tyr Phe Met Ala
1               5

<210> SEQ ID NO 102
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Asp His Tyr Ile Asn
1               5

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ser Ile Asn Tyr Asp Gly Ser Ser Thr Tyr Tyr Leu Asp Ser Leu Lys
1               5                   10                  15

Ser

<210> SEQ ID NO 104
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Ser Ile Asn Tyr Asp Gly Ser Ser Thr Tyr Tyr Val Asp Ser Val Lys
1               5                   10                  15

Gly

<210> SEQ ID NO 105
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 105

Ser Ile Asn Tyr Asp Gly Glu Ser Thr Tyr Tyr Val Asp Ser Val Lys
1               5                   10                  15

Gly

<210> SEQ ID NO 106
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Asp Ile Asn Tyr Asp Gly Gly Ser Thr Tyr Tyr Leu Asp Ser Leu Lys
1               5                   10                  15

Ser

<210> SEQ ID NO 107
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Glu Ile Asn Tyr Asp Gly Ser Ser Thr Tyr Tyr Leu Asp Ser Leu Lys
1               5                   10                  15

Ser

<210> SEQ ID NO 108
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Glu Ile Asn Tyr Asp Gly Ser Ser Thr Tyr Tyr Val Asp Ser Val Lys
1               5                   10                  15

Gly

<210> SEQ ID NO 109
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Ser Ile Asn Tyr Asp Gly Asn Ser Thr Tyr Phe Leu Asp Ser Leu Lys
1               5                   10                  15

Ser
```

```
<210> SEQ ID NO 110
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Trp Ile Phe Pro Gly Thr Gly Ile Thr Tyr Tyr Asn Glu Asn Phe Lys
1               5                   10                  15
Gly

<210> SEQ ID NO 111
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Asp Arg Gly Tyr Tyr Phe Asp Tyr
1               5

<210> SEQ ID NO 112
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Asp Arg Gly Phe Tyr Phe Asp Tyr
1               5

<210> SEQ ID NO 113
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Arg Gly Tyr Gly Ser Phe Asp Tyr
1               5

<210> SEQ ID NO 114
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Arg Ser Ser Gln Ser Leu Val His Ser Asn Gly Asn Thr Tyr Leu His
1               5                   10                  15

<210> SEQ ID NO 115
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Arg Ser Ser Gln Ser Leu Val His Ser Asn Gly Leu Thr Tyr Leu His
1               5                   10                  15

<210> SEQ ID NO 116
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Arg Ser Ser Gln Ser Leu Val His Ser Asn Gly Asn Thr Tyr Leu His
1               5                   10                  15

<210> SEQ ID NO 117
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Arg Ser Ser Gln Ser Leu Val His Asn Asn Gly Asn Thr Tyr Leu His
1               5                   10                  15

<210> SEQ ID NO 118
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Arg Phe Ser Gln Ser Leu Val His Arg Asn Gly Asn Thr Tyr Leu His
1               5                   10                  15

<210> SEQ ID NO 119
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Arg Ser Ser Gln Ser Leu Val His Arg Asn Gly Asn Thr Tyr Leu His
1               5                   10                  15

<210> SEQ ID NO 120
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 120

Lys Ser Ser Gln Ser Leu Leu Asn Ser Ser Asn Gln Lys Asn Tyr Leu
1               5                   10                  15

Ala

<210> SEQ ID NO 121
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Lys Val Ser Asn Arg Phe Ser
1               5

<210> SEQ ID NO 122
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Phe Ala Tyr Thr Arg Glu Ser
1               5

<210> SEQ ID NO 123
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Ser Gln Ser Thr His Val Pro Pro Phe Thr
1               5                   10

<210> SEQ ID NO 124
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Ser Gln Ser Thr His Val Pro Pro Tyr Thr
1               5                   10

<210> SEQ ID NO 125
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                          Synthetic peptide"

<400> SEQUENCE: 125

Ser Gln Ser Thr His Val Arg Pro Tyr Thr
1               5                   10

<210> SEQ ID NO 126
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Gln Gln His Tyr Ser Ser Pro Tyr Thr
1               5

<210> SEQ ID NO 127
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Gly Gly Gly Gly Ser Gly Gly Gly Gly Ser Gly Gly Gly Gly Ser
1               5                   10                  15

<210> SEQ ID NO 128
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Gly Phe Leu Gly
1

<210> SEQ ID NO 129
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Ala Leu Ala Leu
1

<210> SEQ ID NO 130
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
```

```
<223> OTHER INFORMATION: /replace="Asp" or "Glu"
<220> FEATURE:
<221> NAME/KEY: VARIANT
<222> LOCATION: (7)..(7)
<223> OTHER INFORMATION: /replace="Glu" or "Gly" or "Asn"
<220> FEATURE:
<221> NAME/KEY: VARIANT
<222> LOCATION: (11)..(11)
<223> OTHER INFORMATION: /replace="Phe"
<220> FEATURE:
<221> NAME/KEY: VARIANT
<222> LOCATION: (12)..(12)
<223> OTHER INFORMATION: /replace="Leu"
<220> FEATURE:
<221> NAME/KEY: VARIANT
<222> LOCATION: (15)..(15)
<223> OTHER INFORMATION: /replace="Leu"
<220> FEATURE:
<221> NAME/KEY: VARIANT
<222> LOCATION: (17)..(17)
<223> OTHER INFORMATION: /replace="Ser"
<220> FEATURE:
<221> NAME/KEY: misc_feature
<222> LOCATION: (1)..(17)
<223> OTHER INFORMATION: /note="Variant residues given in the sequence
      have no preference with respect to those in the annotations
      for variant positions"

<400> SEQUENCE: 130

Ser Ile Asn Tyr Asp Gly Ser Ser Thr Tyr Tyr Val Asp Ser Val Lys
1               5                   10                  15

Gly

<210> SEQ ID NO 131
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Phe"
<220> FEATURE:
<221> NAME/KEY: misc_feature
<222> LOCATION: (1)..(8)
<223> OTHER INFORMATION: /note="Variant residues given in the sequence
      have no preference with respect to those in the annotations
      for variant positions"

<400> SEQUENCE: 131

Asp Arg Gly Tyr Tyr Phe Asp Tyr
1               5

<210> SEQ ID NO 132
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Phe"
<220> FEATURE:
<221> NAME/KEY: VARIANT
<222> LOCATION: (9)..(9)
<223> OTHER INFORMATION: /replace="Asn" or "Arg"
<220> FEATURE:
<221> NAME/KEY: VARIANT
```

```
<222> LOCATION: (12)..(12)
<223> OTHER INFORMATION: /replace="Leu"
<220> FEATURE:
<221> NAME/KEY: misc_feature
<222> LOCATION: (1)..(16)
<223> OTHER INFORMATION: /note="Variant residues given in the sequence
      have no preference with respect to those in the annotations
      for variant positions"

<400> SEQUENCE: 132

Arg Ser Ser Gln Ser Leu Val His Ser Asn Gly Asn Thr Tyr Leu His
1               5                   10                  15

<210> SEQ ID NO 133
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (9)..(9)
<223> OTHER INFORMATION: /replace="Tyr"
<220> FEATURE:
<221> NAME/KEY: misc_feature
<222> LOCATION: (1)..(10)
<223> OTHER INFORMATION: /note="Variant residues given in the sequence
      have no preference with respect to those in the annotations
      for variant positions"

<400> SEQUENCE: 133

Ser Gln Ser Thr His Val Pro Pro Phe Thr
1               5                   10
```